United States Patent
Jung et al.

(10) Patent No.: US 8,283,056 B2
(45) Date of Patent: Oct. 9, 2012

(54) ORGANIC COMPOUND, AND ORGANIC PHOTOELECTRIC DEVICE INCLUDING THE SAME

(75) Inventors: Sung-Hyun Jung, Gunpo-si (KR); Hyung-Sun Kim, Uiwang-si (KR); Ho-Jae Lee, Yongin-si (KR); Eun-Sun Yu, Anyang-si (KR); Mi-Young Chae, Yongin-si (KR)

(73) Assignee: Cheil Industries, Inc., Gumi-si, Kyeongsangbuk-do (KR)

( * ) Notice: Subject to any disclaimer, the term of this patent is extended or adjusted under 35 U.S.C. 154(b) by 384 days.

(21) Appl. No.: 12/659,580

(22) Filed: Mar. 12, 2010

(65) Prior Publication Data

US 2010/0276673 A1 Nov. 4, 2010

Related U.S. Application Data

(63) Continuation-in-part of application No. PCT/KR2008/005411, filed on Sep. 12, 2008.

(30) Foreign Application Priority Data

Sep. 14, 2007 (KR) .................. 10-2007-0093866

(51) Int. Cl.
 *H01L 51/54* (2006.01)
(52) U.S. Cl. ........ 428/690; 428/917; 313/504; 313/505; 313/506; 257/40; 257/E51.032; 548/440
(58) Field of Classification Search .............. 428/690, 428/917; 313/504, 505, 506; 257/40, E51.032; 548/440

See application file for complete search history.

(56) References Cited

U.S. PATENT DOCUMENTS 6,670,054 B1 12/2003 Hu et al.

FOREIGN PATENT DOCUMENTS

| CN | 1 769 269 A | 5/2006 |
|---|---|---|
| JP | 2004-281296 A | 10/2004 |
| JP | 2005-183345 A | 7/2005 |

OTHER PUBLICATIONS

Sonntag, Martin, et al., "Novel Star-Shaped Triphenylamine-Based Molecular Glasses and Their Uses in OFETs", Chem. Mater. 17:3031-3039 (2005).

*Primary Examiner* — Jennifer Chriss
*Assistant Examiner* — Gregory Clark
(74) *Attorney, Agent, or Firm* — Lee & Morse, P.C.

(57) ABSTRACT

Disclosed is an organic compound that easily dissolves in an organic solvent, and that is applicable as a host material of an emission layer of an organic photoelectric device since it emits fluorescence and phosphorescence at a red wavelength through a blue wavelength. The organic compound according to one embodiment of the present invention is represented by Chemical Formula 1.

[Chemical Formula 1]

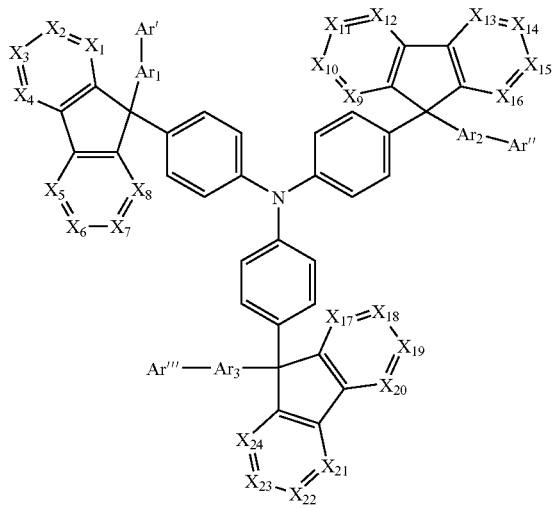

In the above Chemical Formula 1, $X_1$ to $X_{24}$, $Ar_1$ to $Ar_3$, and Ar' to Ar''', and Chemical Formulae 2 to 5, are as described in the specification. The organic compound easily dissolves in an organic solvent, and is applicable as a host material of an emission layer of an organic photoelectric device since it emits fluorescence and phosphorescence at a red wavelength through a blue wavelength.

14 Claims, 13 Drawing Sheets

Topography image

Topography image

ORGANIC COMPOUND, AND ORGANIC PHOTOELECTRIC DEVICE INCLUDING THE SAME

CROSS-REFERENCE TO RELATED APPLICATIONS

This application is a continuation-in-part of pending International Application No. PCT/KR2008/005411, entitled "ORGANIC COMPOUND, AND ORGANIC PHOTOELECTRIC DEVICE INCLUDING THE SAME," which was filed on Sep. 12, 2008, the entire contents of which are hereby incorporated by reference.

This application claims priority to and the benefit of Korean Patent Application No. 10-2007-0093866 filed in the Korean Intellectual Property Office on Sep. 14, 2007, the entire contents of which are incorporated herein by reference.

BACKGROUND OF THE INVENTION (a) Field of the Invention

The present invention relates to an organic compound and an organic photoelectric device including the same. More particularly, the present invention relates to an organic compound that easily dissolves in an organic solvent, and is applicable as a host material of an emission layer of an organic photoelectric device since it emits fluorescence and phosphorescence at a red wavelength through a blue wavelength, and an organic photoelectric device including the same.

(b) Description of the Related Art

An organic photoelectric device includes an organic light emitting material between a rear plate including ITO transparent electrode patterns as an anode on a transparent glass substrate and an upper plate including a metal electrode as a cathode on a substrate. When a predetermined voltage is applied between the transparent electrode and metal electrode, current flows through the organic light emitting material to emit light.

Such an organic light emitting material for an organic photoelectric device was firstly developed by Eastman Kodak, Inc., in 1987. The material is a low molecular aromatic diamine and aluminum complex as an emission-layer-forming material (Applied Physics Letters. 51, 913, 1987). C. W Tang et al. firstly disclosed a practicable device as an organic photoelectric device in 1987 (Applied Physics Letters, 51 12, 913-915, 1987).

According to the reference, the organic layer has a structure in which a thin film (hole transport layer (HTL)) of a diamine derivative and a thin film of tris(8-hydroxy-quinolate)aluminum ($Alq_3$) are laminated. The $Alq_3$ thin film functions as an emission layer for transporting electrons.

Generally, the organic photoelectric device is composed of an anode of a transparent electrode, an organic thin layer of a light emitting region, and a metal electrode (cathode) formed on a glass substrate, in that order. The organic thin layer may includes an emission layer, a hole injection layer (HIL), a hole transport layer (HTL), an electron transport layer (ETL), or an electron injection layer (EIL). It may further include an electron blocking layer or a hole blocking layer due to the emission characteristics of the emission layer.

When the organic photoelectric device is applied with an electric field, holes and electrons are injected from the anode and the cathode, respectively. The injected holes and electrons are recombined on the emission layer though the hole transport layer (HTL) and the electron transport layer (ETL) to provide light emitting excitons.

The provided light emitting excitons emit light by transiting to the ground state.

The light emitting may be classified as a fluorescent material including singlet excitons and a phosphorescent material including triplet excitons.

Recently, it has become known that the phosphorescent light emitting material can be used for a light emitting material in addition to the fluorescent light emitting material (D. F. O'Brien et al., Applied Physics Letters, 74 3, 442-444, 1999; M. A. Baldo et al., Applied Physics letters, 75 1, 4-6, 1999). Such phosphorescent emission occurs by transiting electrons from the ground state to the exited state, non-radiative transiting of a singlet exciton to a triplet exciton through intersystem crossing, and transiting the triplet exciton to the ground state to emit light.

When the triplet exciton is transited, it cannot directly transit to the ground state. Therefore, the electron spin is flipped, and then it is transited to the ground state so that it provides a characteristic of extending the lifetime (emission duration) to more than that of fluorescent.

In other words, the duration of fluorescent emission is extremely short at several nanoseconds, but the duration of phosphorescent emission is relatively long such as at several microseconds, so that it provides a characteristic of extending the lifetime (emission duration) to more than that of the fluorescent emission.

In addition, evaluating quantum mechanically, when holes injected from the anode are recombined with electrons injected from the cathode to provide light emitting excitons, the singlet and the triplet are produced in a ratio of 1:3, in which the triplet light emitting excitons are produced at three times the amount of the singlet light emitting excitons in the organic photoelectric device.

Accordingly, the percentage of the singlet exited state is 25% (the triplet is 75%) in the case of a fluorescent material, so it has limits in luminous efficiency. On the other hand, in the case of a phosphorescent material, it can utilize 75% of the triplet exited state and 25% of the singlet exited state, so theoretically the internal quantum efficiency can reach up to 100%. When a phosphorescent light emitting material is used, it has advantages in an increase in luminous efficiency of around four times that of the fluorescent light emitting material.

In the above-mentioned organic light emitting diode, a light emitting colorant (dopant) may be added in an emission layer (host) in order to increase the efficiency and stability in the emission state.

In this structure, the efficiency and properties of the light emission diodes are dependent on the host material in the emission layer. According to studies regarding the emission layer (host), the organic host material can be exemplified by a material including naphthalene, anthracene, phenanthrene, tetracene, pyrene, benzopyrene, chrysene, pycene, carbazole, fluorene, biphenyl, terphenyl, triphenylene oxide, dihalobiphenyl, trans-stilbene group, and 1,4-diphenylbutadiene.

Generally, the host material includes 4,4-N,N-dicarbazolebiphenyl (CBP) having a glass transition temperature of 110° C. or less and a thermal decomposition temperature of 400° C. or less, in which the thermal stability is low and the symmetry is excessively high. Thereby, it tends to crystallize and cause problems such as a short and a pixel defect according to results of thermal resistance tests of the devices.

In addition, most host materials including CBP are materials in which the hole transporting property is greater than the electron transporting property. In other words, as the injected hole transportation is faster than the injected electron transportation, the excitons are ineffectively formed in the emission layer. Therefore, the resultant device has deteriorated luminous efficiency.

Accordingly, in order to realize a highly efficient and long lifetime organic light emitting device, it is required to develop a phosphorescent host material having high electrical and thermal stability and that is capable of transporting both holes and electrons.

SUMMARY OF THE INVENTION

One embodiment of the present invention provides an organic compound represented by the following Chemical Formulae 1, A, 4, and 5.

[Chemical Formula 1]

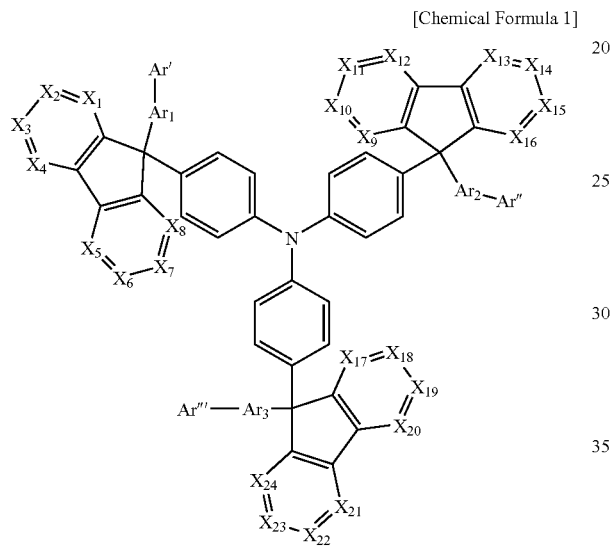

[Chemical Formula A]

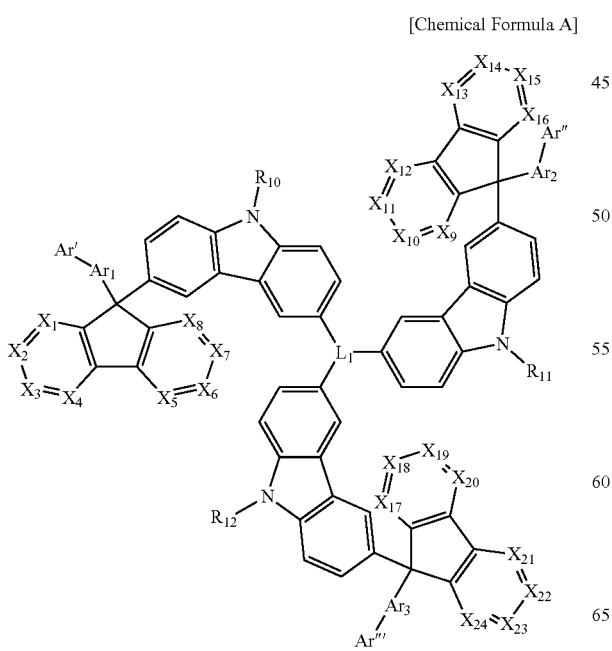

[Chemical Formula 4]

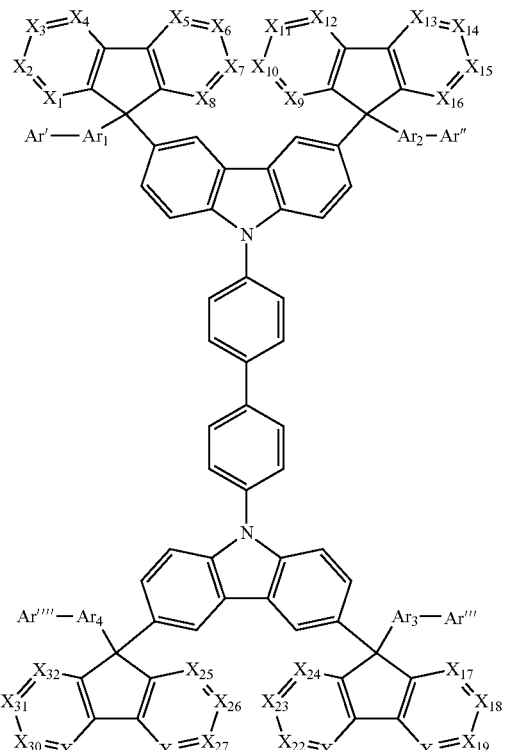

[Chemical Formula 5]

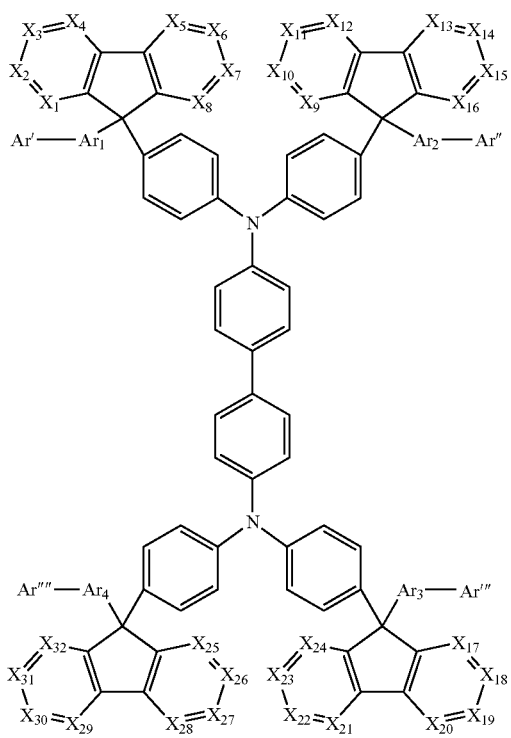

In the above Chemical Formulae 1, A, 4, and 5, $X_1$ to $X_{32}$ are the same or different, and are independently selected from CR' or N, $Ar_1$ to $Ar_4$ are the same or different, and are independently selected from a single bond, a substituted or unsubstituted C6 to C30 arylene group, and a substituted or unsubstituted C2 to C30 heteroarylene group, Ar' to Ar'''' are the same or different, and are independently selected from a substituted or unsubstituted C6 to C30 aryl group and a substituted or unsubstituted C2 to C30 heteroaryl group, and $L_1$ is a substituent represented by the following Chemical Formulae A-1 or A-2,

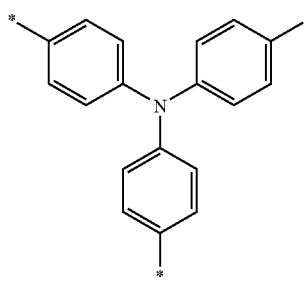
[Chemical Formula A-1]

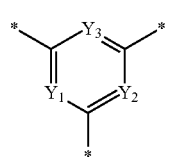
[Chemical Formula A-2]

wherein $Y_1$ to $Y_3$ are the same or different, and are independently selected from CR" or N, and R', R", and $R_{10}$ to $R_{12}$ are the same or different, and are independently selected from hydrogen, a halogen, a cyano group, a hydroxyl group, an amino group, a nitro group, a carboxyl group, a substituted or unsubstituted C1 to C20 alkyl group, a substituted or unsubstituted C2 to C20 alkenyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C2 to C20 heterooxy group, a substituted or unsubstituted C3 to C40 silyloxy group, a substituted or unsubstituted C1 to C20 acyl group, a substituted or unsubstituted C2 to C20 alkoxy carbonyl group, a substituted or unsubstituted C2 to C20 acyloxy group, a substituted or unsubstituted C2 to C20 acylamino group, a substituted or unsubstituted C2 to C20 alkoxy carbonyl amino group, a substituted or unsubstituted C7 to C20 acyloxy carbonyl amino group, a substituted or unsubstituted C1 to C20 sulfamoyl amino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocycloalkyl thiol group, a substituted or unsubstituted C1 to C20 ureide group, a substituted or unsubstituted C1 to C20 phosphoric acid amide group, and a substituted or unsubstituted C3 to C40 silyl group, $Ar_1$ to $Ar_4$ are the same or different, and may be independently selected from a substituted or unsubstituted carbazolyl group, a substituted or unsubstituted arylamine group, a substituted or unsubstituted phenyl group, a substituted or unsubstituted tolyl group, a substituted or unsubstituted naphthyl group, a substituted or unsubstituted stilbene group, a substituted or unsubstituted fluorenyl group, a substituted or unsubstituted anthracenyl group, a substituted or unsubstituted terphenyl group, a substituted or unsubstituted pyrenyl group, a substituted or unsubstituted diphenyl anthracenyl group, a substituted or unsubstituted dinaphthylanthracenyl group, a substituted or unsubstituted pentacenyl group, a substituted or unsubstituted bromophenyl group, a substituted or unsubstituted hydroxyphenyl group, a substituted or unsubstituted thienyl group, a substituted or unsubstituted pyridyl group, a substituted or unsubstituted azobenzenyl group, and a substituted or unsubstituted ferrocenyl group, and Ar' to Ar'''' are the same or different, and are independently selected from a substituted or unsubstituted carbazolyl group, a substituted or unsubstituted arylamine group, a substituted or unsubstituted phenyl group, a substituted or unsubstituted naphthyl group, a substituted or unsubstituted anthracenyl group, a substituted or unsubstituted fluorene group, a substituted or unsubstituted thiophene group, a substituted or unsubstituted pyrrole group, a substituted or unsubstituted pyridine group, a substituted or unsubstituted aryloxadiazole group, a substituted or unsubstituted triazole group, and a substituted or unsubstituted arylsilane group.

Ar' to Ar'''' are the same or different, and are independently selected from the substituents represented by the following Chemical Formulae 6 to 35.

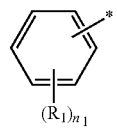
[Chemical Formula 6]

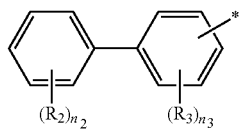
[Chemical Formula 7]

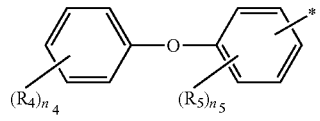
[Chemical Formula 8]

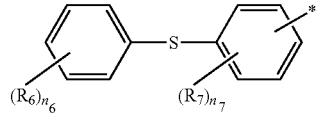
[Chemical Formula 9]

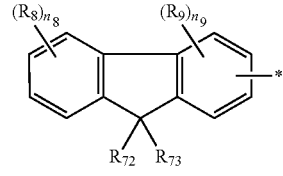
[Chemical Formula 10]

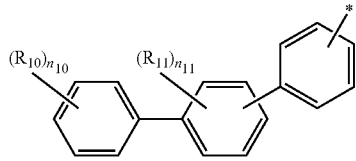
[Chemical Formula 11]

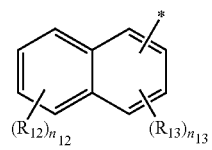
[Chemical Formula 12]

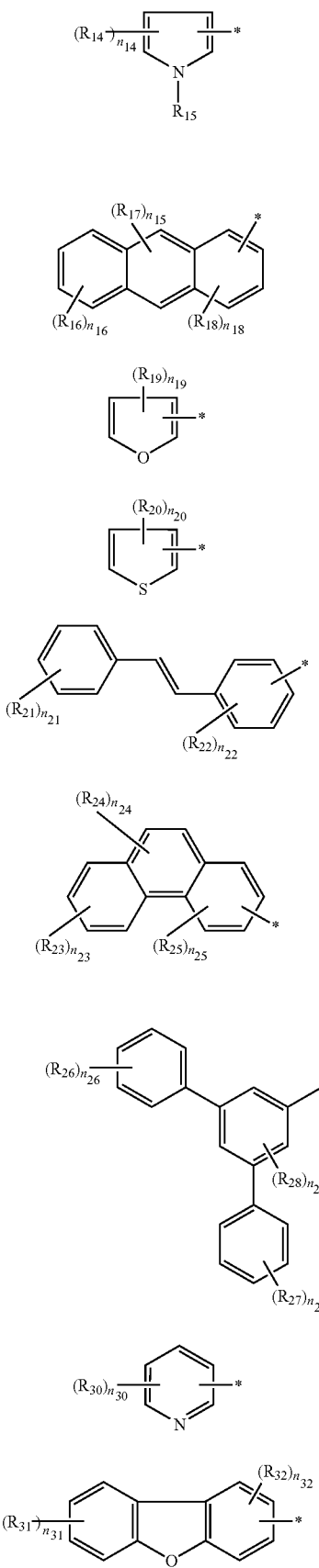

-continued

[Chemical Formula 30]

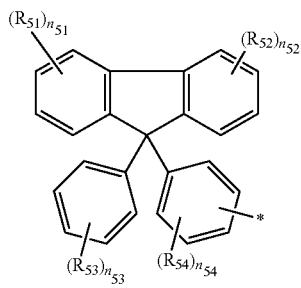

[Chemical Formula 31]

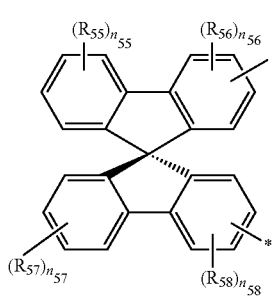

[Chemical Formula 32]

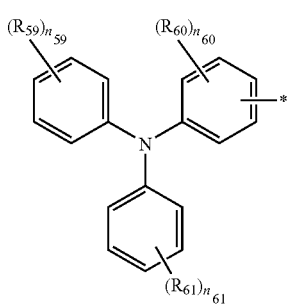

[Chemical Formula 33]

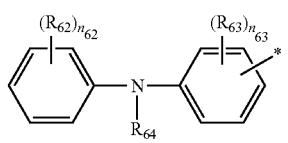

[Chemical Formula 34]

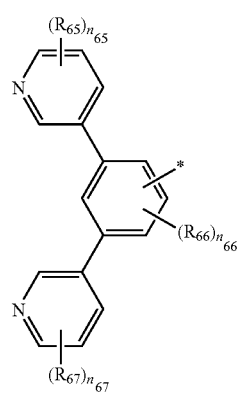

[Chemical Formula 35]

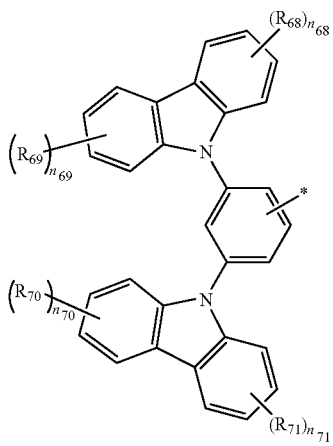

In the above Chemical Formulae 6 to 35, $R_1$ to $R_{76}$ are the same or different, and are independently selected from a halogen, a cyano group, a hydroxyl group, an amino group, a nitro group, a carboxyl group, a substituted or unsubstituted C1 to C20 alkyl group, a substituted or unsubstituted C2 to C20 alkenyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C2 to C20 heterooxy group, a substituted or unsubstituted C3 to C40 silyloxy group, a substituted or unsubstituted C1 to C20 acyl group, a substituted or unsubstituted C2 to C20 alkoxy carbonyl group, a substituted or unsubstituted C2 to C20 acyloxy group, a substituted or unsubstituted C2 to C20 acylamino group, a substituted or unsubstituted C2 to C20 alkoxy carbonyl amino group, a substituted or unsubstituted C7 to C20 acyloxy carbonyl amino group, a substituted or unsubstituted C1 to C20 sulfamoyl amino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocycloalkyl thiol group, a substituted or unsubstituted C1 to C20 ureide group, a substituted or unsubstituted C1 to C20 phosphoric acid amide group, and a substituted or unsubstituted C3 to C40 silyl group, $n_1$, $n_2$, $n_4$, $n_6$, $n_{10}$, $n_{21}$, $n_{26}$, $n_{27}$, $n_{35}$, $n_{39}$, $n_{46}$, $n_{47}$, $n_{49}$, $n_{53}$, $n_{59}$, $n_{61}$, and $n_{62}$ are integers ranging from 0 to 5, $n_3$, $n_5$, $n_7$, $n_8$, $n_{11}$, $n_{12}$, $n_{16}$, $n_{22}$, $n_{23}$, $n_{29}$, $n_{30}$, $n_{31}$, $n_{33}$, $n_{36}$, $n_{37}$, $n_{40}$, $n_{41}$ to $n_{44}$, $n_{48}$, $n_{50}$ to $n_{52}$, $n_{54}$, $n_{55}$, $n_{57}$, $n_{60}$, $n_{63}$, $n_{65}$, $n_{67}$, $n_{68}$, $n_{69}$, $n_{70}$, and $n_{71}$ are integers ranging from 0 to 4, $n_9$, $n_{13}$, $n_{14}$, $n_{18}$, $n_{19}$, $n_{20}$, $n_{25}$, $n_{28}$, $n_{32}$, $n_{34}$, $n_{38}$, $n_{45}$, $n_{56}$, $n_{58}$, and $n_{66}$ are integers ranging from 0 to 3, and $n_{15}$ and $n_{24}$ are integers ranging from 0 to 2.

Ar' to Ar'''' are the same or different, and are independently selected from the substituents represented by the following Chemical Formulae B-1 to B-9.

[Chemical Formula B-1]

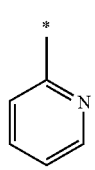

[Chemical Formula B-2]
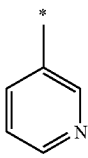
[Chemical Formula B-3]
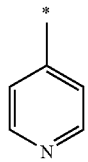
[Chemical Formula B-4]
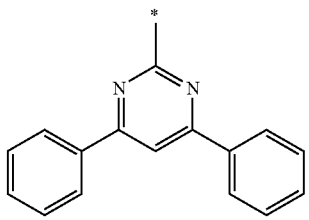
[Chemical Formula B-5]
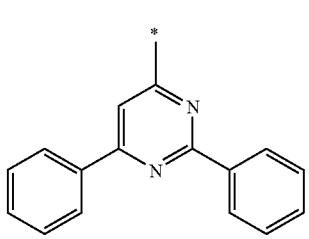
[Chemical Formula B-6]
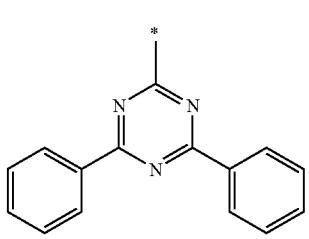
[Chemical Formula B-7]
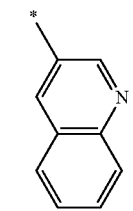
[Chemical Formula B-8]
[Chemical Formula B-9]
At least one of $X_4$, $X_5$, $X_{12}$, $X_{13}$, $X_{20}$, $X_{21}$, $X_{28}$, and $X_{29}$ may be N.
In another embodiment of the present invention, an organic compound represented by the following Chemical Formula 2 or 3 is provided.
[Chemical Formula 2]
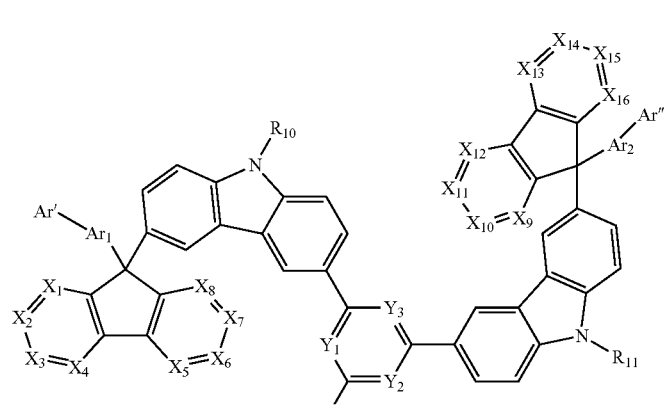

-continued

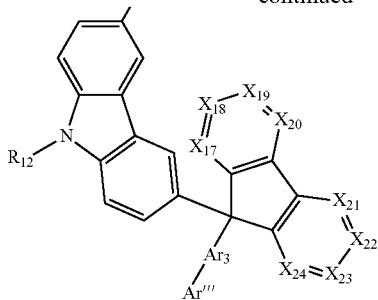

[Chemical Formula 3]

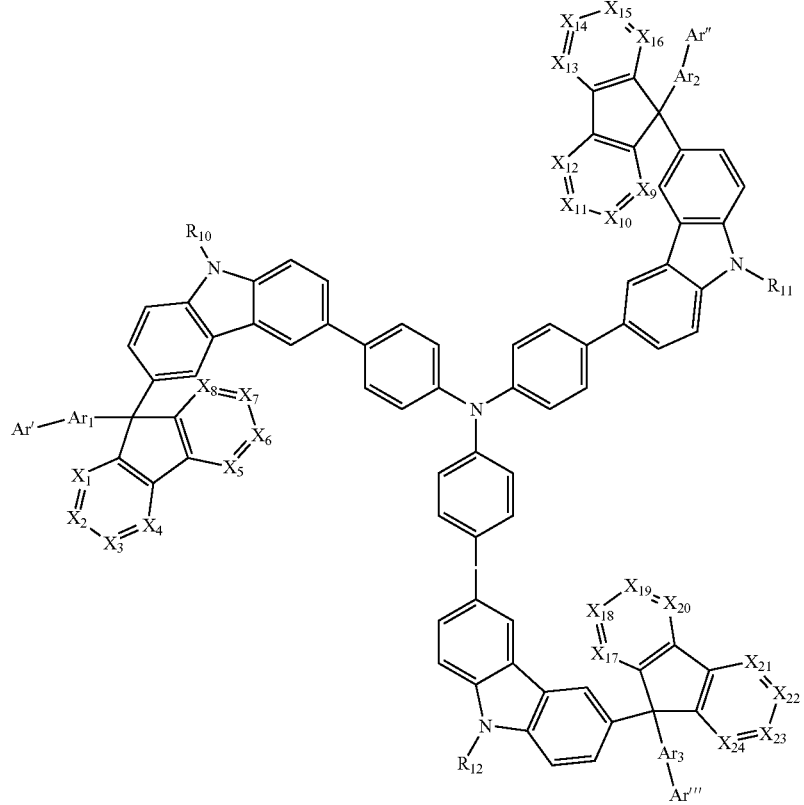

In the above Chemical Formulae 2 and 3, $X_1$ to $X_{24}$ are the same or different, and are independently selected from CR' and N, $Y_1$ to $Y_3$ are the same or different, and are independently selected from CR" and N, $Ar_1$ to $Ar_3$ are the same or different, and are independently selected from a single bond, a substituted or unsubstituted C6 to C30 arylene group, and a substituted or unsubstituted C2 to C30 heteroarylene group, Ar' to Ar''' are the same or different, and are independently selected from a substituted or unsubstituted C6 to C30 aryl group and a substituted or unsubstituted C2 to C30 heteroaryl group, and R', R", and $R_{10}$ to $R_{12}$ are the same or different, and are independently selected from hydrogen, a halogen, a cyano group, a hydroxyl group, an amino group, a nitro group, a carboxyl group, a substituted or unsubstituted C1 to C20 alkyl group, a substituted or unsubstituted C2 to C20 alkenyl group, a substituted or unsubstituted C6 to 030 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C2 to C20 heterooxy group, a substituted or unsubstituted C3 to C40 silyloxy group, a substituted or unsubstituted C1 to C20 acyl group, a substituted or unsubstituted C2 to C20 alkoxy carbonyl group, a substituted or unsubstituted C2 to C20 acyloxy group, a substituted or unsubstituted C2 to C20 acyl amino group, a substituted or unsubstituted C2 to C20 alkoxy carbonyl amino group, a substituted or unsubstituted C7 to C20 aryloxy carbonyl amino group, a substituted or unsubstituted C1 to C20 sulfamoyl amino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocycloalkyl thiol group, a substituted or unsubstituted C1 to C20 ureide group, a substituted or unsubstituted C1 to C20 phosphoric acid amide group, and a substituted or unsubstituted C3 to C40 silyl group.

In one embodiment, $Ar_1$ to $Ar_3$ are the same or different, and are independently selected from a single bond, a substituted or unsubstituted carbazolyl group, a substituted or unsubstituted arylamine group, a substituted or unsubstituted phenyl group, a substituted or unsubstituted tolyl group, a substituted or unsubstituted naphthyl group, a substituted or unsubstituted stilbene group, a substituted or unsubstituted fluorene group, a substituted or unsubstituted anthracenyl group, a substituted or unsubstituted terphenyl group, a substituted or unsubstituted pyrenyl group, a substituted or unsubstituted diphenyl anthracenyl group, a substituted or unsubstituted dinaphthyl anthracenyl group, a substituted or unsubstituted pentacenyl group, a substituted or unsubstituted bromophenyl group, a substituted or unsubstituted hydroxyphenyl group, a substituted or unsubstituted thienyl group, a substituted or unsubstituted pyridyl group, a substituted or unsubstituted azobenzenyl group, and a substituted or unsubstituted ferrocenyl group, and Ar' to Ar''' are the same or different, and are independently selected from a substituted or unsubstituted carbazolyl group, a substituted or unsubstituted arylamine group, a substituted or unsubstituted phenyl group, a substituted or unsubstituted naphthyl group, a substituted or unsubstituted anthracenyl group, a substituted or unsubstituted fluorene group, a substituted or unsubstituted thiophene group, a substituted or unsubstituted pyrrole group, a substituted or unsubstituted pyridine group, a substituted or unsubstituted aryloxadiazole group, a substituted or unsubstituted triazole group, and a substituted or unsubstituted arylsilane group.

In one embodiment, Ar' to Ar''' are the same or different, and are independently selected from the substituents represented by the following Chemical Formulae 6 to 35.

[Chemical Formula 6]
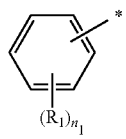

[Chemical Formula 7]
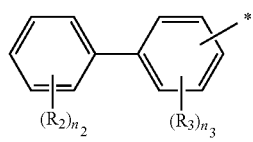

[Chemical Formula 8]
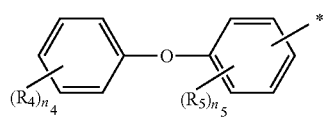

[Chemical Formula 9]
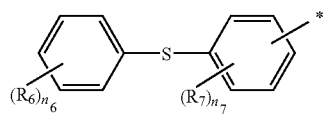

[Chemical Formula 10]
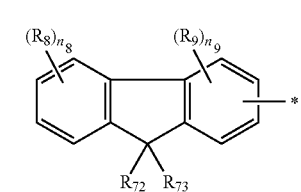

[Chemical Formula 11]
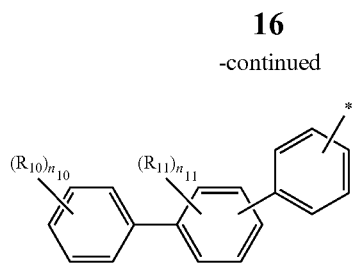

[Chemical Formula 12]
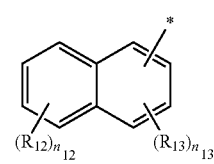

[Chemical Formula 13]
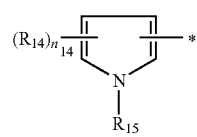

[Chemical Formula 14]
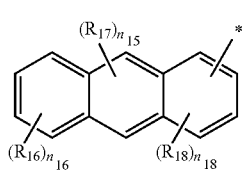

[Chemical Formula 15]
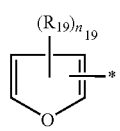

[Chemical Formula 16]
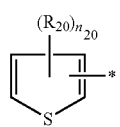

[Chemical Formula 17]
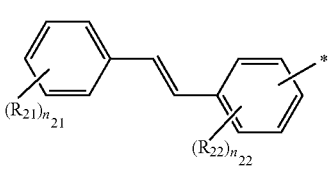

[Chemical Formula 18]
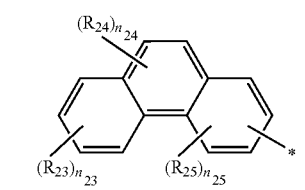

[Chemical Formula 19]
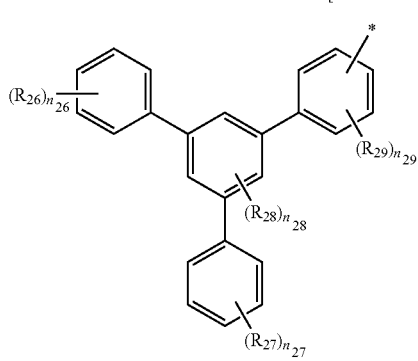
[Chemical Formula 20]
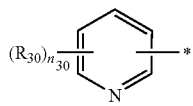
[Chemical Formula 21]
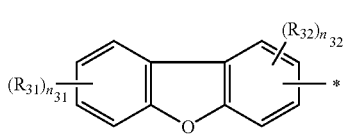
[Chemical Formula 22]
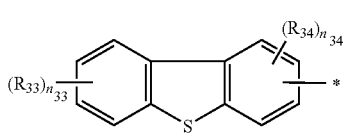
[Chemical Formula 23]
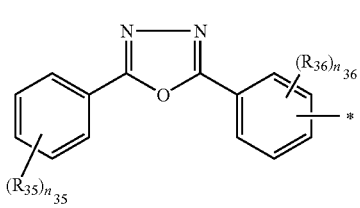
[Chemical Formula 24]
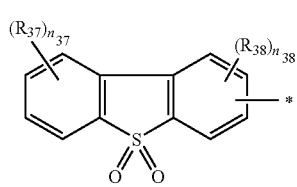
[Chemical Formula 25]
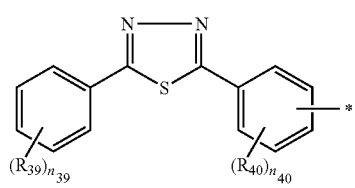
[Chemical Formula 26]
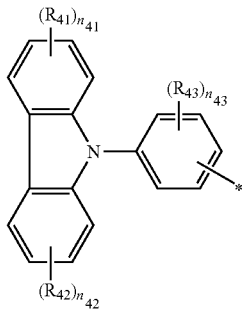
[Chemical Formula 27]
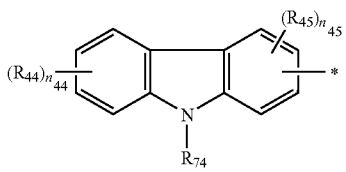
[Chemical Formula 28]
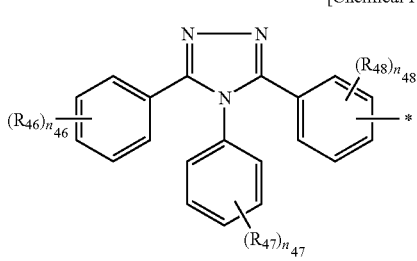
[Chemical Formula 29]
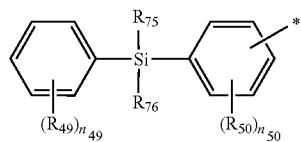
[Chemical Formula 30]
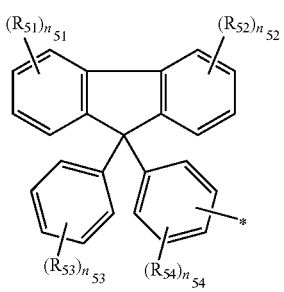
[Chemical Formula 31]
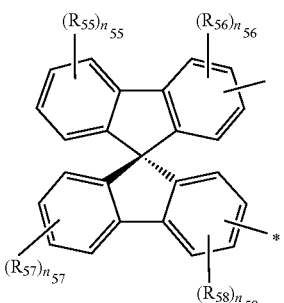

-continued

[Chemical Formula 32]

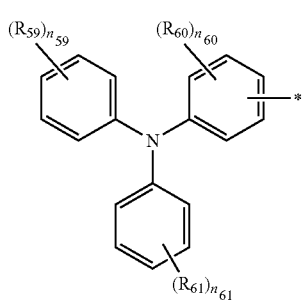

[Chemical Formula 33]

[Chemical Formula 34]

[Chemical Formula 35]

In the above Chemical Formulae 6 to 35, $R_1$ to $R_{76}$ are independently selected from hydrogen, a halogen, a cyano group, a hydroxyl group, an amino group, a nitro group, a carboxyl group, a substituted or unsubstituted C1 to C20 alkyl group, a substituted or unsubstituted C2 to C20 alkenyl, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C2 to C20 heterooxy group, a substituted or unsubstituted C3 to C40 silyloxy group, a substituted or unsubstituted C1 to C20 acyl group, a substituted or unsubstituted C2 to C20 alkoxy carbonyl group, a substituted or unsubstituted C2 to C20 acyloxy group, a substituted or unsubstituted C2 to C20 acylamino group, a substituted or unsubstituted C2 to C20 alkoxy carbonyl amino group, a substituted or unsubstituted C7 to C20 acyloxy carbonyl amino group, a substituted or unsubstituted C1 to C20 sulfamoyl amino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocycloalkyl thiol group, a substituted or unsubstituted C1 to C20 ureide group, a substituted or unsubstituted C1 to C20 phosphoric acid amide group, and a substituted or unsubstituted C3 to C40 silyl group, $n_1$, $n_2$, $n_4$, $n_6$, $n_{10}$, $n_{21}$, $n_{26}$, $n_{27}$, $n_{35}$, $n_{39}$, $n_{46}$, $n_{47}$, $n_{49}$, $n_{53}$, $n_{59}$, $n_{61}$, and $n_{62}$ are integers ranging from 0 to 5, $n_3$, $n_5$, $n_7$, $n_8$, $n_{11}$, $n_{12}$, $n_{16}$, $n_{22}$, $n_{23}$, $n_{29}$, $n_{30}$, $n_{31}$, $n_{33}$, $n_{36}$, $n_{37}$, $n_{40}$, $n_{41}$ to $n_{44}$, $n_{48}$, $n_{50}$ to $n_{52}$, $n_{54}$, $n_{55}$, $n_{57}$, $n_{60}$, $n_{63}$, $n_{65}$, $n_{67}$, $n_{68}$, $n_{69}$, $n_{70}$, and $n_{71}$ are integers ranging from 0 to 4, $n_9$, $n_{13}$, $n_{14}$, $n_{18}$, $n_{19}$, $n_{20}$, $n_{25}$, $n_{28}$, $n_{32}$, $n_{34}$, $n_{38}$, $n_{45}$, $n_{56}$, $n_{58}$, and $n_{66}$ are integers ranging from 0 to 3, and $n_{15}$ and $n_{24}$ are integers ranging from 0 to 2.

Ar' to Ar'" are the same or different, and are independently selected from the substituents represented by the following Chemical Formulae B-1 to B-9.

[Chemical Formula B-1]

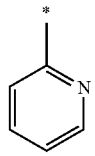

[Chemical Formula B-2]

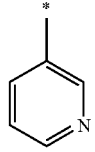

[Chemical Formula B-3]

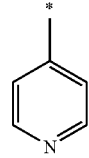

[Chemical Formula B-4]

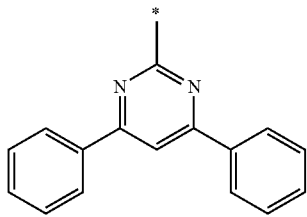

[Chemical Formula B-5]

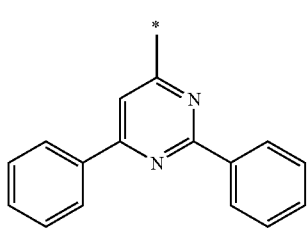

[Chemical Formula B-6]

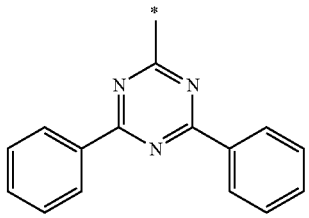

[Chemical Formula B-7]

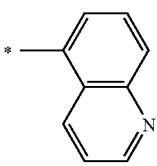

[Chemical Formula B-8]

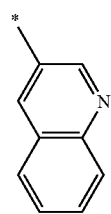

[Chemical Formula B-9]

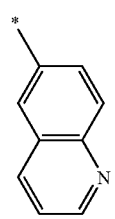

At least one of $X_4$, $X_5$, $X_{12}$, $X_{13}$, $X_{20}$, $X_{21}$, $X_{28}$, and $X_{29}$ may be N.

According to another embodiment of the present invention, provided is an organic photoelectric device that includes an organic layer disposed between a pair of electrodes. The organic layer includes the above organic compound.

The organic layer may be an emission layer.

The organic layer may be selected from a hole injection layer (HIL), a hole transport layer (HTL), a hole blocking film, and a combination thereof.

The organic layer is selected from an electron injection layer (EIL), an electron transport layer (ETL), an electron blocking film, and a combination thereof.

Hereinafter, other embodiments of the present invention will be described in detail.

The organic compound easily dissolves in an organic solvent, and is applicable as a host material of an emission layer of an organic photoelectric device since it emits fluorescence and phosphorescence at a red wavelength through a blue wavelength.

DESCRIPTION OF REFERENCE NUMERALS INDICATING PRIMARY ELEMENTS IN THE DRAWINGS

Figure 1:
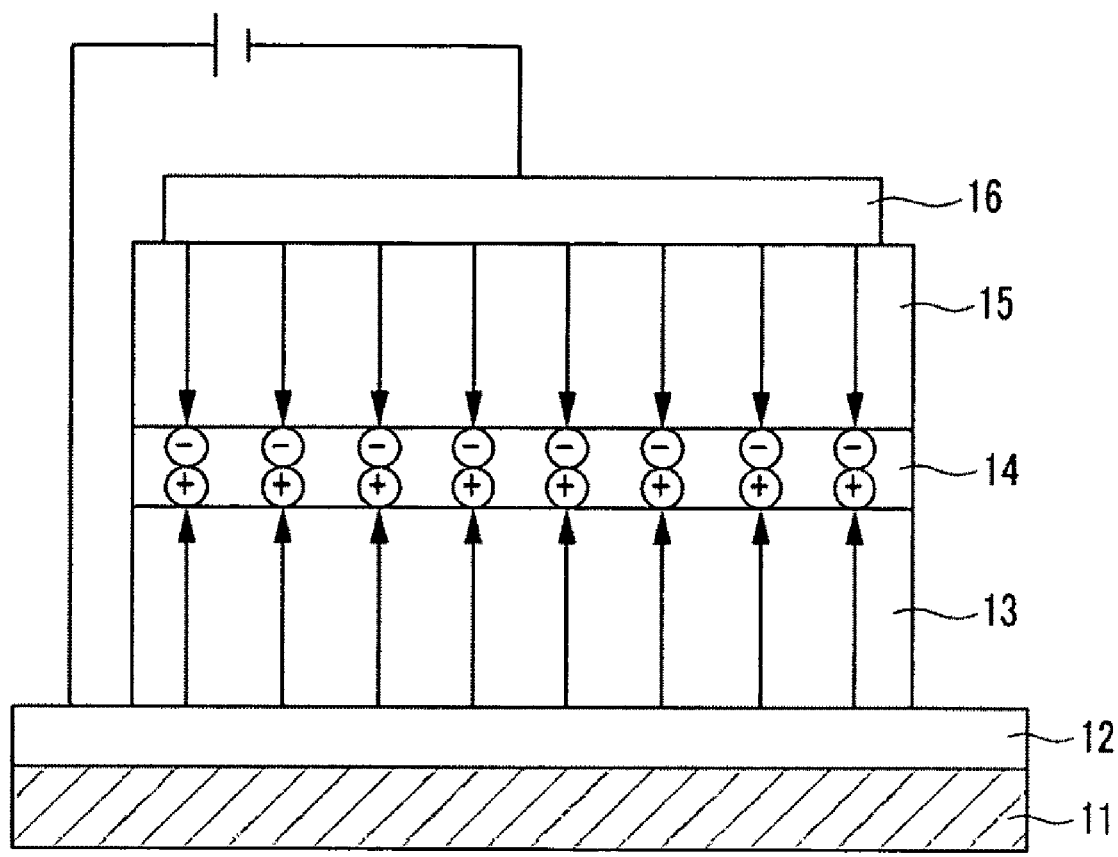
FIG. 1 is a cross-sectional view showing an organic photoelectric device according to one embodiment of the present invention.

| 11: substrate | 12: anode |
| 13: hole transport layer (HTL) | 14: organic emission layer |
| 15: electron transport layer (ETL) | 16: cathode |

DETAILED DESCRIPTION OF THE EMBODIMENTS

Exemplary embodiments of the present invention will hereinafter be described in detail. However, these embodiments are only exemplary, and the present invention is not limited thereto but rather is defined by scope of the appended claims.

According to one embodiment of the present invention, an organic compound represented by the following Chemical Formulae 1, A, 4, and 5 is provided.

[Chemical Formula 1]

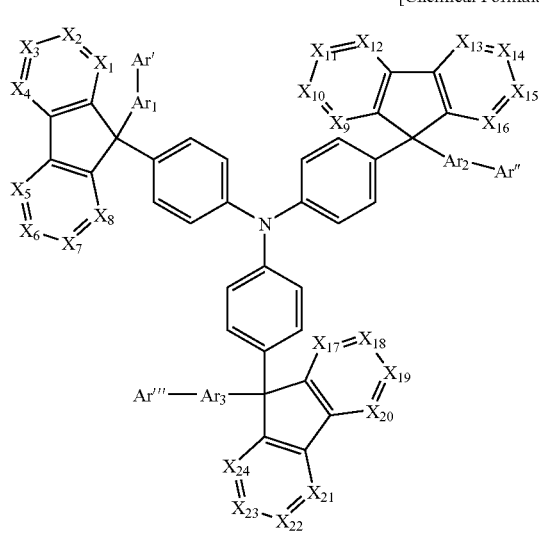

[Chemical Formula A]

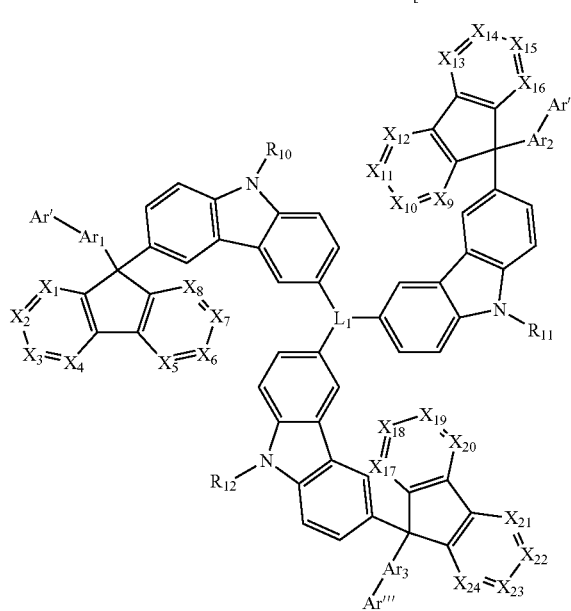

[Chemical Formula 4]

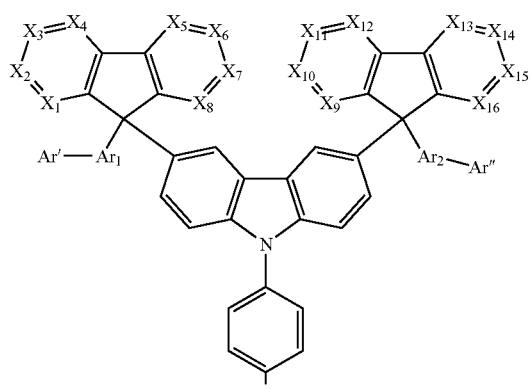

-continued

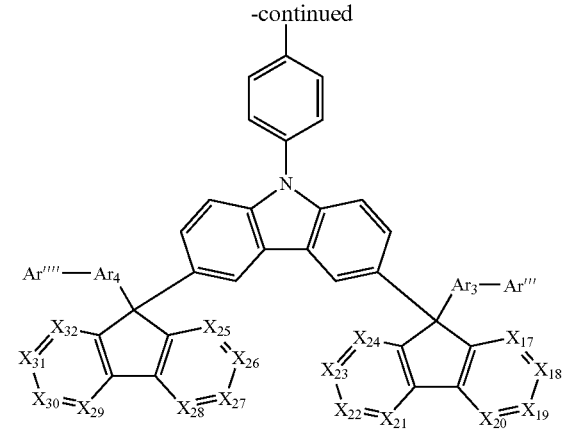

[Chemical Formula 5]

In the above Chemical Formulae 1, A, 4, and 5, $X_1$ to $X_{32}$ are the same or different, and are independently selected from CR' or N, $Ar_1$ to $Ar_4$ are the same or different, and are independently selected from a single bond, a substituted or unsubstituted C6 to C30 arylene group, and a substituted or unsubstituted C2 to C30 heteroarylene group, Ar' to Ar'''' are the same or different, and are independently selected from a substituted or unsubstituted C6 to C30 aryl group and a substituted or unsubstituted C2 to C30 heteroaryl group, and $L_1$ is a substituent represented by the following Chemical Formulae A-1 or A-2,

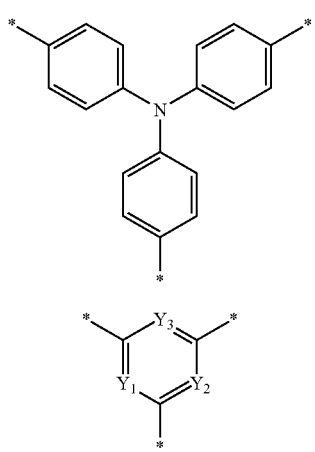

[Chemical Formula A-1]

[Chemical Formula A-2]

where $Y_1$ to $Y_3$ are the same or different, and are independently selected from CR" and N, and R', R", and $R_{10}$ to $R_{12}$ are the same or different, and are independently selected from hydrogen, a halogen, a cyano, a hydroxyl, an amino, a nitro, a carboxyl, a substituted or unsubstituted C1 to C20 alkyl group, a substituted or unsubstituted C2 to C20 alkenyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C2 to C20 heterooxy group, a substituted or unsubstituted C3 to C40 silyloxy group, a substituted or unsubstituted C1 to C20 acyl group, a substituted or unsubstituted C2 to C20 alkoxy carbonyl group, a substituted or unsubstituted C2 to C20 acyloxy group, a substituted or unsubstituted C2 to C20 acylamino group, a substituted or unsubstituted C2 to C20 alkoxy carbonyl amino group, a substituted or unsubstituted C7 to C20 acyloxy carbonyl amino group, a substituted or unsubstituted C1 to C20 sulfamoyl amino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocycloalkyl thiol group, a substituted or unsubstituted C1 to C20 ureide group, a substituted or unsubstituted C1 to C20 phosphoric acid amide group, and a substituted or unsubstituted C3 to C40 silyl group.

According to another embodiment of the present invention, an organic compound represented by the following Chemical Formula 2 or 3 is provided.

[Chemical Formula 2]

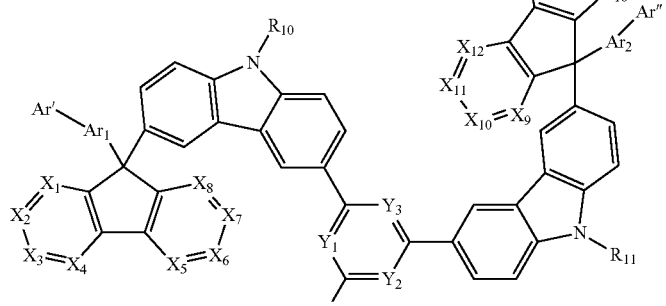

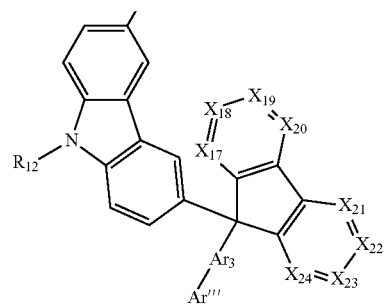

[Chemical Formula 3]

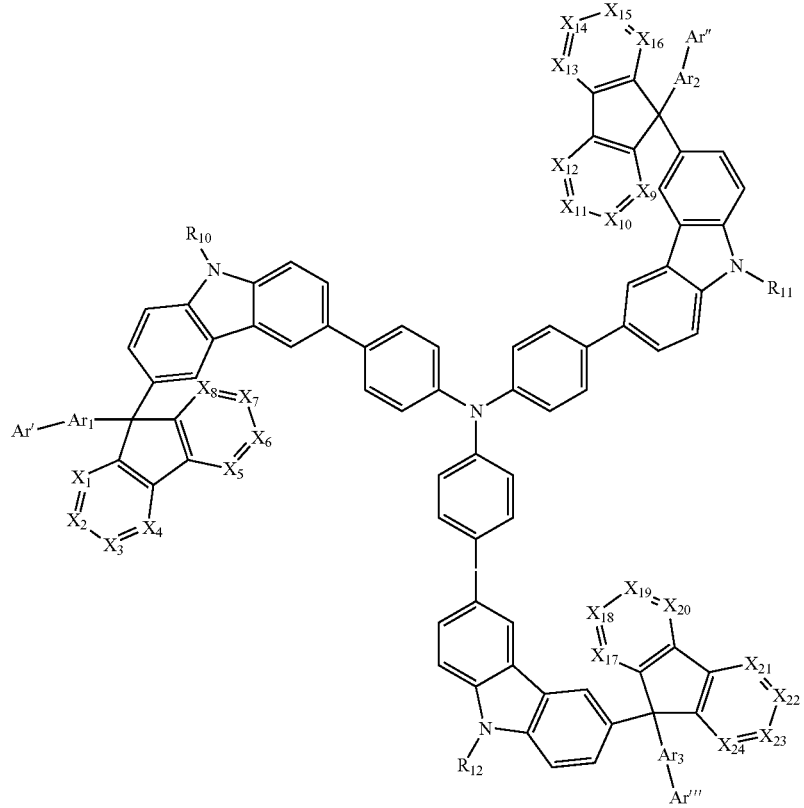

In the above Chemical Formulae 2 and 3, $X_1$ to $X_{24}$ are the same or different, and are independently selected from CR' and N, $Y_1$ to $Y_3$ are the same or different, and are independently selected from CR'' and N, $Ar_1$ to $Ar_3$ are the same or different, and are independently selected from a single bond, a substituted or unsubstituted C6 to C30 arylene group, and a substituted or unsubstituted C2 to C30 heteroarylene group, Ar' to Ar''' are the same or different, and are independently selected from a substituted or unsubstituted C6 to C30 aryl group and a substituted or unsubstituted C2 to C30 heteroaryl group, and R', R'', and $R_{10}$ to $R_{12}$ are the same or different, and are independently selected from hydrogen, a halogen, a cyano group, a hydroxyl group, an amino group, a nitro group, a carboxyl group, a substituted or unsubstituted C1 to C20 alkyl group, a substituted or unsubstituted C2 to C20 alkenyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C2 to C20 heterooxy group, a substituted or unsubstituted C3 to C40 silyloxy group, a substituted or unsubstituted C1 to C20 acyl group, a substituted or unsubstituted C2 to C20 alkoxy carbonyl group, a substituted or unsubstituted C2 to C20 acyloxy group, a substituted or unsubstituted C2 to C20 acyl amino group, a substituted or unsubstituted C2 to C20 alkoxy carbonyl amino group, a substituted or unsubstituted C7 to C20 aryloxy carbonyl amino group, a substituted or unsubstituted C1 to C20 sulfamoyl amino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocycloalkyl thiol group, a substituted or unsubstituted C1 to C20 ureide group, a substituted or unsubstituted C1 to C20 phosphoric acid amide group, and a substituted or unsubstituted C3 to C40 silyl group.

In one embodiment, $Ar_1$ to $Ar_4$ are the same or different, and are independently selected from a single bond, a substituted or unsubstituted carbazolyl group, a substituted or unsubstituted arylamine group, a substituted or unsubstituted phenyl group, a substituted or unsubstituted tolyl group, a substituted or unsubstituted naphthyl group, a substituted or unsubstituted stilbene group, a substituted or unsubstituted fluorenyl group, a substituted or unsubstituted anthracenyl group, a substituted or unsubstituted terphenyl group, a substituted or unsubstituted pyrenyl group, a substituted or unsubstituted diphenyl anthracenyl group, a substituted or unsubstituted dinaphthylanthracenyl group, a substituted or unsubstituted pentacenyl group, a substituted or unsubstituted bromophenyl group, a substituted or unsubstituted hydroxyphenyl group, a substituted or unsubstituted thienyl group, a substituted or unsubstituted pyridyl group, a substituted or unsubstituted azobenzenyl group, and a substituted or unsubstituted ferrocenyl group.

In one embodiment, Ar' to Ar'''' are the same or different, and are independently selected from a substituted or unsubstituted carbazolyl group, a substituted or unsubstituted arylamine group, a substituted or unsubstituted phenyl group, a substituted or unsubstituted naphthyl group, a substituted or unsubstituted anthracenyl group, a substituted or unsubstituted fluorenyl group, a substituted or unsubstituted thiophenyl group, a substituted or unsubstituted pyrrol, a substituted or unsubstituted pyridine group, a substituted or unsubstituted aryloxadiazole group, a substituted or unsubstituted triazole group, and a substituted or unsubstituted arylsilane group.

As used herein, the substituted arylene group and substituted heteroarylene group respectively refer to an arylene group and a heteroarylene group substituted with a C1 to C30 alkyl group, a halogen, a C1 to C30 haloalkyl group, a C6 to C30 aryl group, or a C2 to C30 heteroaryl group.

As used herein, the substituted alkyl group, substituted alkenyl group, substituted aryl group, substituted heteroaryl group, substituted alkoxy group substituted aryl oxy group, substituted hetero oxy group, substituted silyl oxy group, substituted acyl group, substituted alkoxy carbonyl group, substituted acyl oxy group, substituted acyl amino group, substituted alkoxy carbonyl amino group, substituted acyl oxycarbonylamino group, substituted sulfamoyl amino group, substituted sulfonyl group, substituted alkylthiol group, substituted aryl thiol group, a substituted heterocycloalkyl thiol group, substituted ureide group, substituted phosphoric acid amide group, and substituted silyl group respectively refer to an alkyl group, an alkenyl group, an aryl group, a heteroaryl group, an alkoxy group, an aryl oxy group, a heterooxy group, a silyl oxy group, an acyl group, an alkoxy carbonyl group, an acyl oxy group, an acyl amino group, an alkoxy carbonyl amino group, an acyl oxycarbonylamino group, a sulfamoyl amino group, a sulfonyl group, an alkylthiol group, an aryl thiol group, a heterocycloalkyl thiol group, a ureide group, a phosphoric acid amide group, and a silyl group substituted with a C1 to C30 alkyl group, a halogen, a C1 to C30 haloalkyl group, a C6 to C30 aryl group, or a C2 to C30 heteroaryl group.

As used herein, the substituted carbazolyl group, substituted arylamine group, substituted phenyl group, substituted tolyl group, substituted naphthyl group, substituted stilbene group, substituted fluorenyl group, substituted anthracenyl group, substituted terphenyl group, substituted pyrenyl group, substituted diphenylanthracenyl group, substituted dinaphthylanthracenyl group, substituted pentacenyl group, substituted bromophenyl group, substituted hydroxyphenyl group, substituted thienyl group, substituted pyridyl group, substituted azobenzenyl group, and substituted ferrocenyl group respectively refers to a carbazolyl group, an arylamine group, a phenyl group, a tolyl group, a naphthyl group, a stilbene group, a fluorenyl group, an anthracenyl group, a terphenyl group, a pyrenyl group, a diphenylanthracenyl group, a dinaphthylanthracenyl group, a pentacenyl group, a bromophenyl group, a hydroxyphenyl group, a thienyl group, a pyridyl group, an azobenzenyl group, and an ferrocenyl group substituted with a C1 to C30 alkyl group, a halogen, a C1 to C30 haloalkyl group, a C6 to C30 aryl group, or a C2 to C30 heteroaryl group.

As used herein, the substituted thiophene group, substituted pyrrole group, substituted pyridine group, substituted aryloxadiazole group, substituted triazole group, and substituted arylsilane group respectively refer to a thiophene group, a pyrrole group, a pyridine group, an aryloxadiazole group, a triazole group, and an arylsilane group substituted with a C1 to C30 alkyl group, a halogen, a C1 to C30 haloalkyl group, a C6 to C30 aryl group, or a C2 to C30 heteroaryl group.

In the present specification, the term "hetero" refers to one including 1 to 3 heteroatoms selected from nitrogen (N), oxygen (O), sulfur (S), or phosphorus (P), and the remainder being carbon.

Ar' to Ar'''' are the same or different, and are independently selected from substituents represented by the following Chemical Formulae 6 to 35.

[Chemical Formula 6]

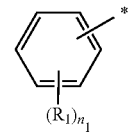

[Chemical Formula 7]

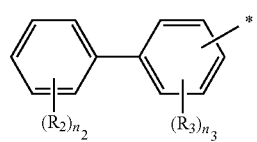

[Chemical Formula 8]

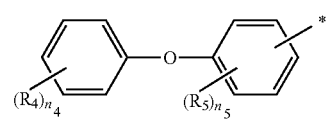

[Chemical Formula 9]

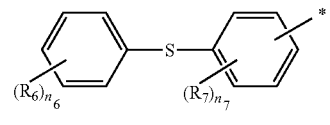

[Chemical Formula 10]

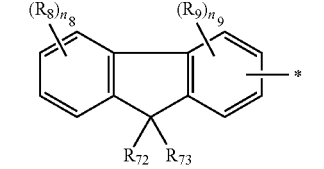

[Chemical Formula 11]

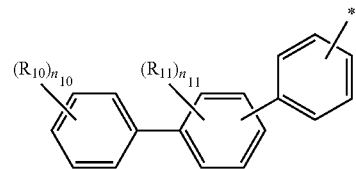

[Chemical Formula 12]

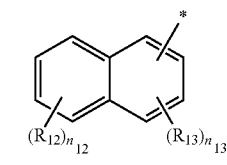

[Chemical Formula 13]

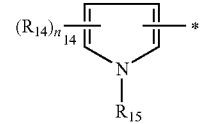

[Chemical Formula 14]

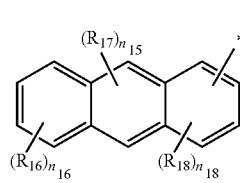

[Chemical Formula 15]

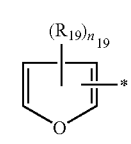

[Chemical Formula 16]
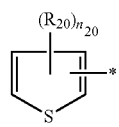
[Chemical Formula 17]
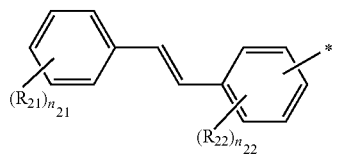
[Chemical Formula 18]
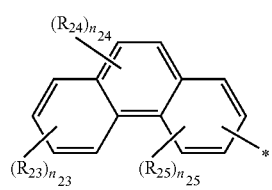
[Chemical Formula 19]
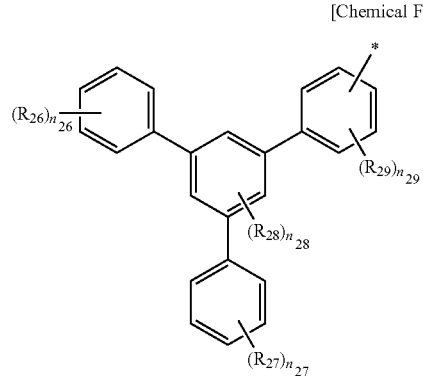
[Chemical Formula 20]
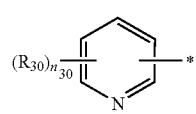
[Chemical Formula 21]
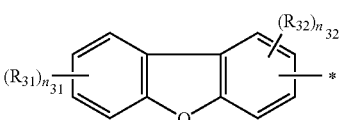
[Chemical Formula 22]
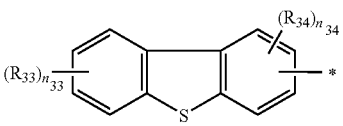
[Chemical Formula 23]
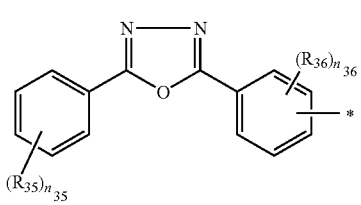
[Chemical Formula 24]
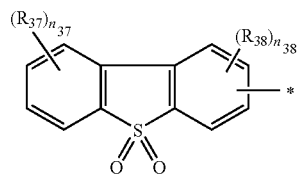
[Chemical Formula 25]
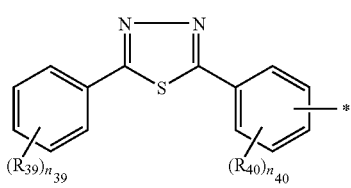
[Chemical Formula 26]
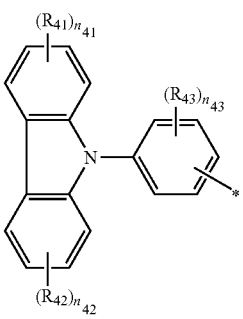
[Chemical Formula 27]
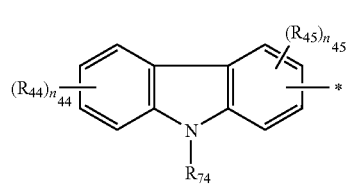
[Chemical Formula 28]
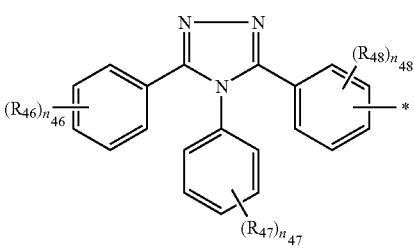
[Chemical Formula 29]
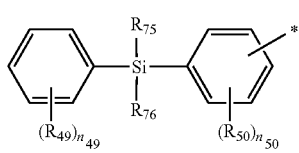
[Chemical Formula 30]
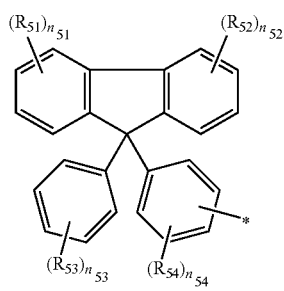

[Chemical Formula 31]

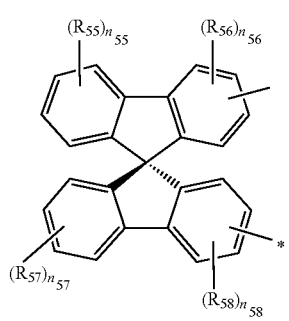

[Chemical Formula 32]

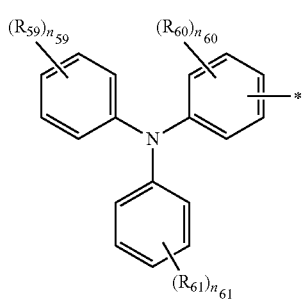

[Chemical Formula 33]

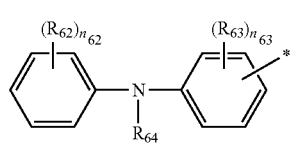

[Chemical Formula 34]

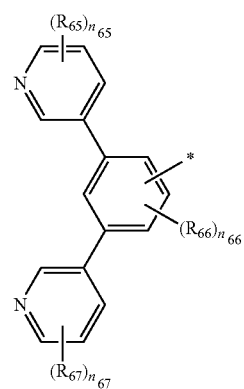

[Chemical Formula 35]

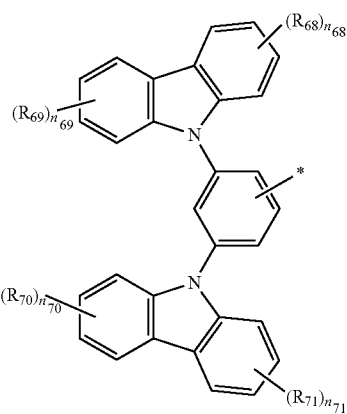

In the above Chemical Formulae 6 to 35, $R_1$ to $R_{76}$ are the same or different, and are independently selected from a halogen, a cyano group, a hydroxyl group, an amino group, a nitro group, a carboxyl group, a substituted or unsubstituted C1 to C20 alkyl group, a substituted or unsubstituted C2 to C20 alkenyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C2 to C20 heterooxy group, a substituted or unsubstituted C3 to C40 silyl oxy group, a substituted or unsubstituted C1 to C20 acyl group, a substituted or unsubstituted C2 to C20 alkoxy carbonyl group, a substituted or unsubstituted C2 to C20 acyl oxy group, a substituted or unsubstituted C2 to C20 acyl amino group, a substituted or unsubstituted C2 to C20 alkoxy carbonyl amino group, a substituted or unsubstituted C7 to C20 acyloxycarbonylamino group, a substituted or unsubstituted C1 to C20 sulfamoyl amino group, a substituted or unsubstituted C1 to C20 sulfonyl group, a substituted or unsubstituted C1 to C20 alkylthiol group, a substituted or unsubstituted C6 to C20 aryl thiol group, a substituted or unsubstituted C1 to C20 hetero cyclo alkyl thiol group, a substituted or unsubstituted C1 to C20 ureide group, a substituted or unsubstituted C1 to C20 phosphoric acid amide group, and a substituted or unsubstituted C3 to C40 silyl group, $n_1, n_2, n_4, n_6, n_{10}, n_{21}, n_{26}, n_{27}, n_{35}, n_{39}, n_{46}, n_{47}, n_{49}, n_{53}, n_{59}, n_{61}$, and $n_{62}$ are integers ranging from 0 to 5, $n_3, n_5, n_7, n_8, n_{11}, n_{12}, n_{16}, n_{22}, n_{23}, n_{29}, n_{30}, n_{31}, n_{33}, n_{36}, n_{37}, n_{40}, n_{41}$ to $n_{44}, n_{48}, n_{50}$ to $n_{52}, n_{54}, n_{55}, n_{57}, n_{60}, n_{63}, n_{65}, n_{67}, n_{68}, n_{69}, n_{70}$, and $n_{71}$ are integers ranging from 0 to 4, $n_9, n_{13}, n_{14}, n_{18}, n_{19}, n_{20}, n_{25}, n_{28}, n_{32}, n_{34}, n_{38}, n_{45}, n_{56}, n_{58}$, and $n_{66}$ are integers ranging from 0 to 3, and $n_{15}$ and $n_{24}$ are integers ranging from 0 to 2.

In one embodiment, Ar' to Ar'''' are the same or different, and are independently selected from the substituents represented by following Chemical Formulae B-1 to B-9.

[Chemical Formula B-1]

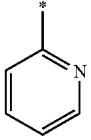

[Chemical Formula B-2]

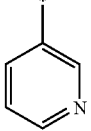

[Chemical Formula B-3]

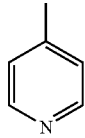

[Chemical Formula B-4]

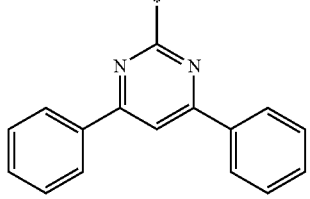

-continued
[Chemical Formula B-5]
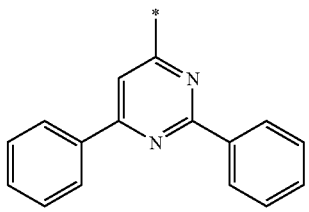
[Chemical Formula B-6]
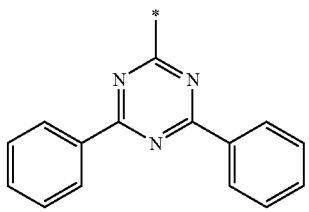
[Chemical Formula B-7]
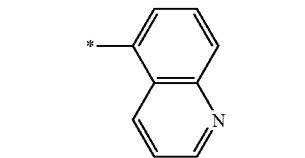
[Chemical Formula B-8]
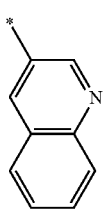
[Chemical Formula B-9]
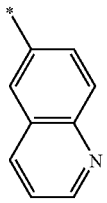
Particularly, at least one of $X_4$, $X_5$, $X_{12}$, $X_{13}$, $X_{20}$, $X_{21}$, $X_{28}$, and $X_{29}$ may be N.
The compound represented by the above Formula 1 may be compounds represented by the following Chemical Formulae 36 to 53.
[Chemical Formula 36]
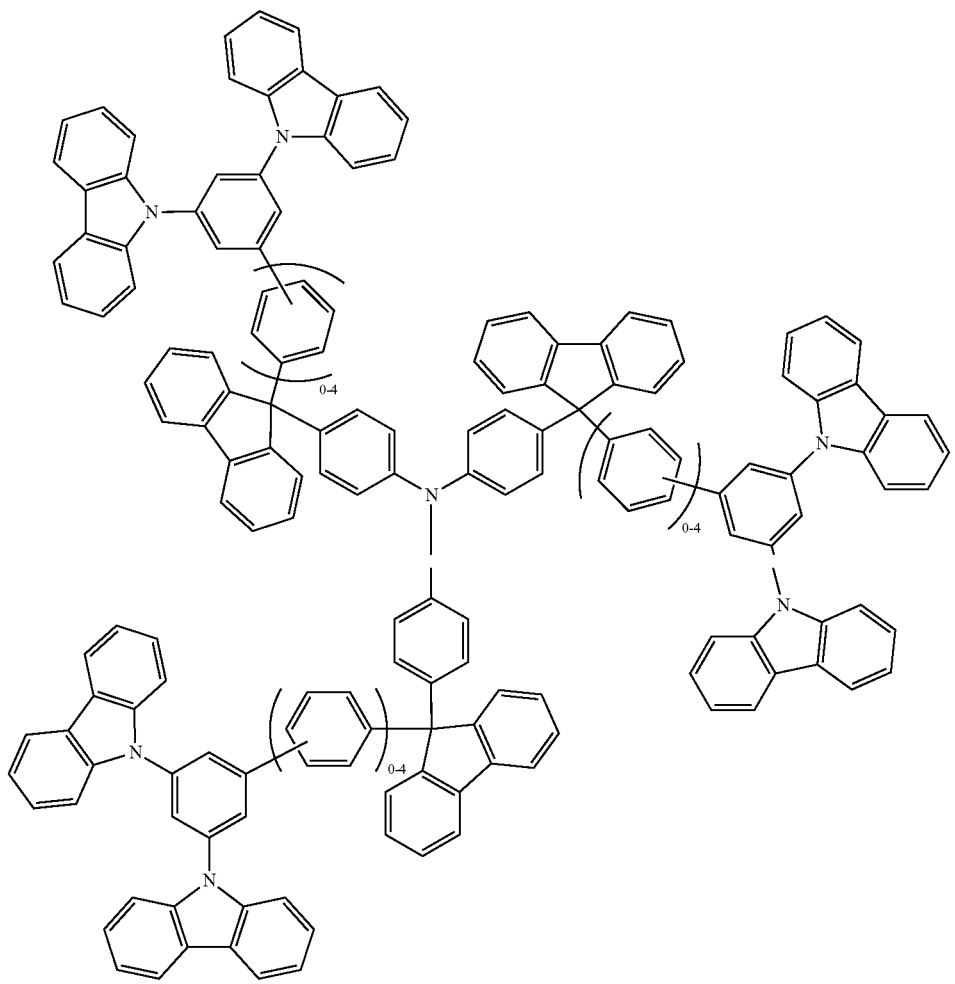

[Chemical Formula 37]
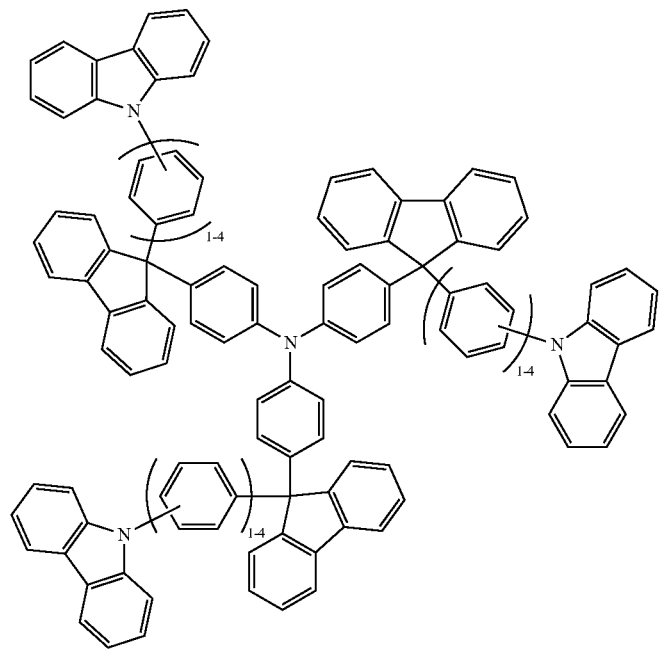
[Chemical Formula 38]
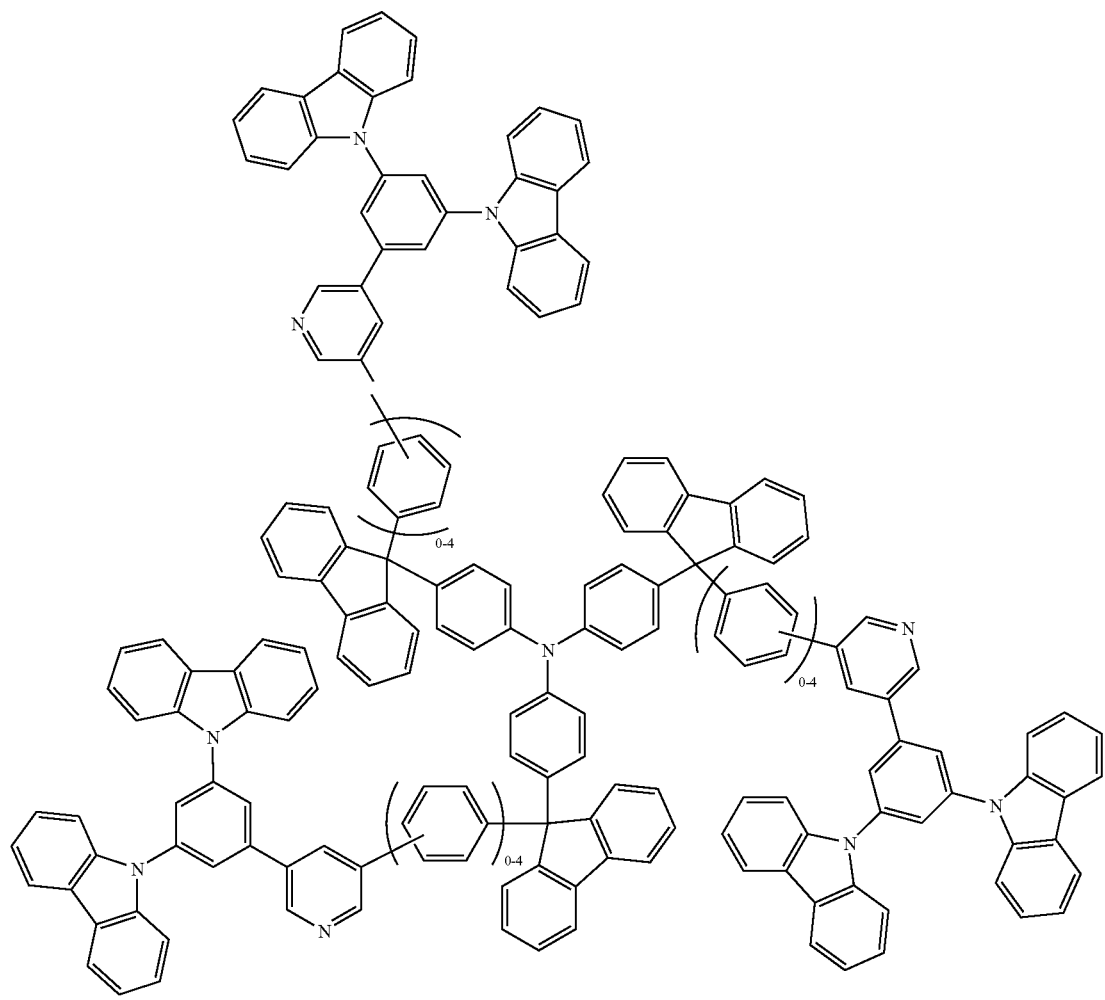

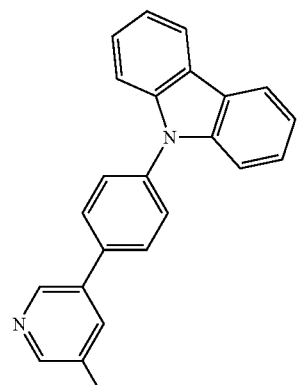
[Chemical Formula 39]
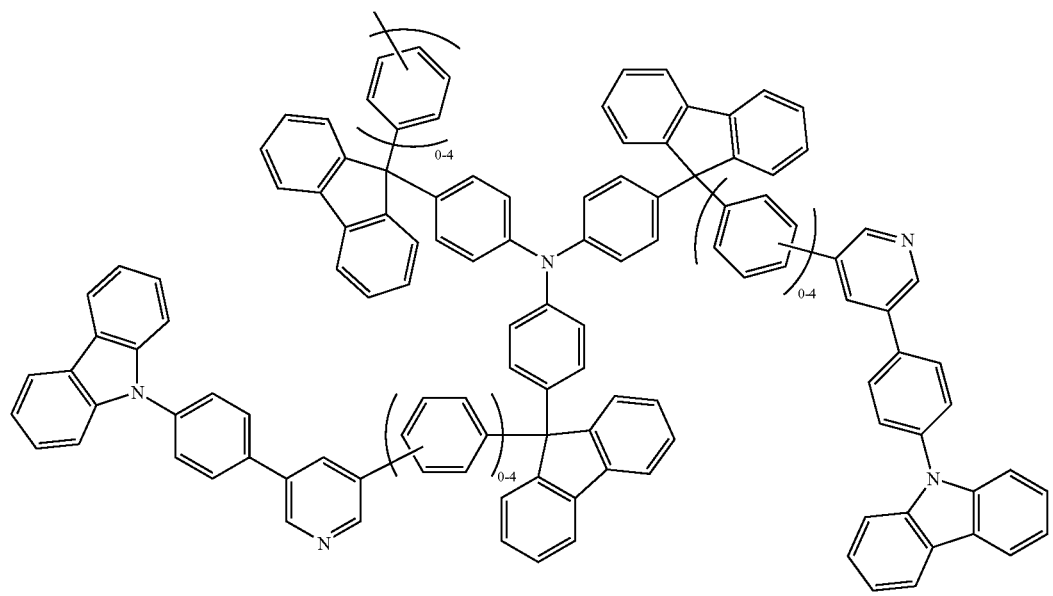
[Chemical Formula 40]
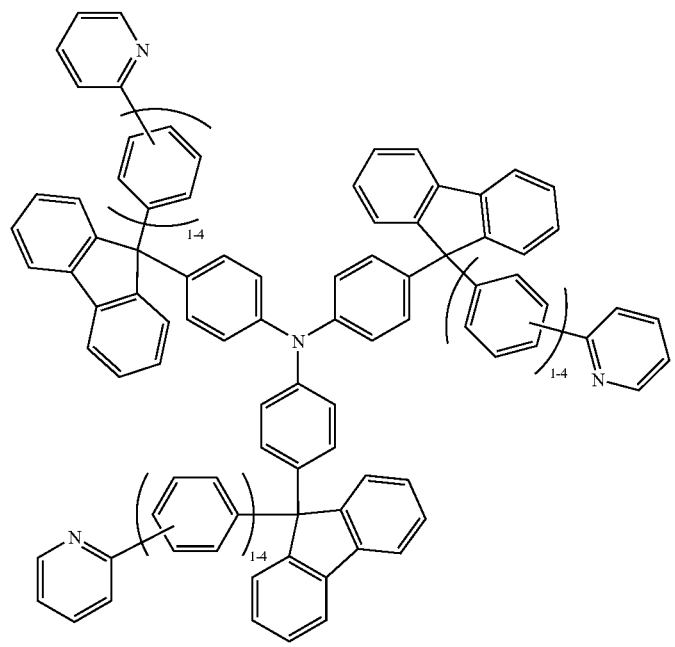

[Chemical Formula 41]
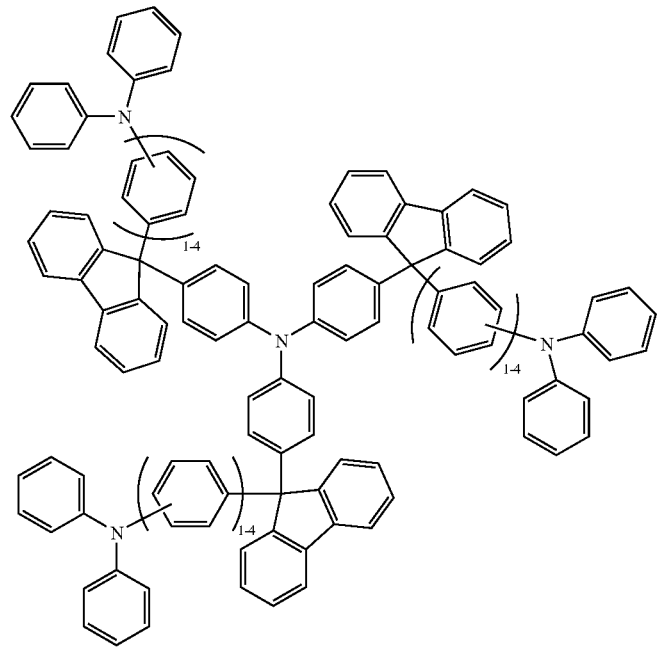
[Chemical Formula 42]
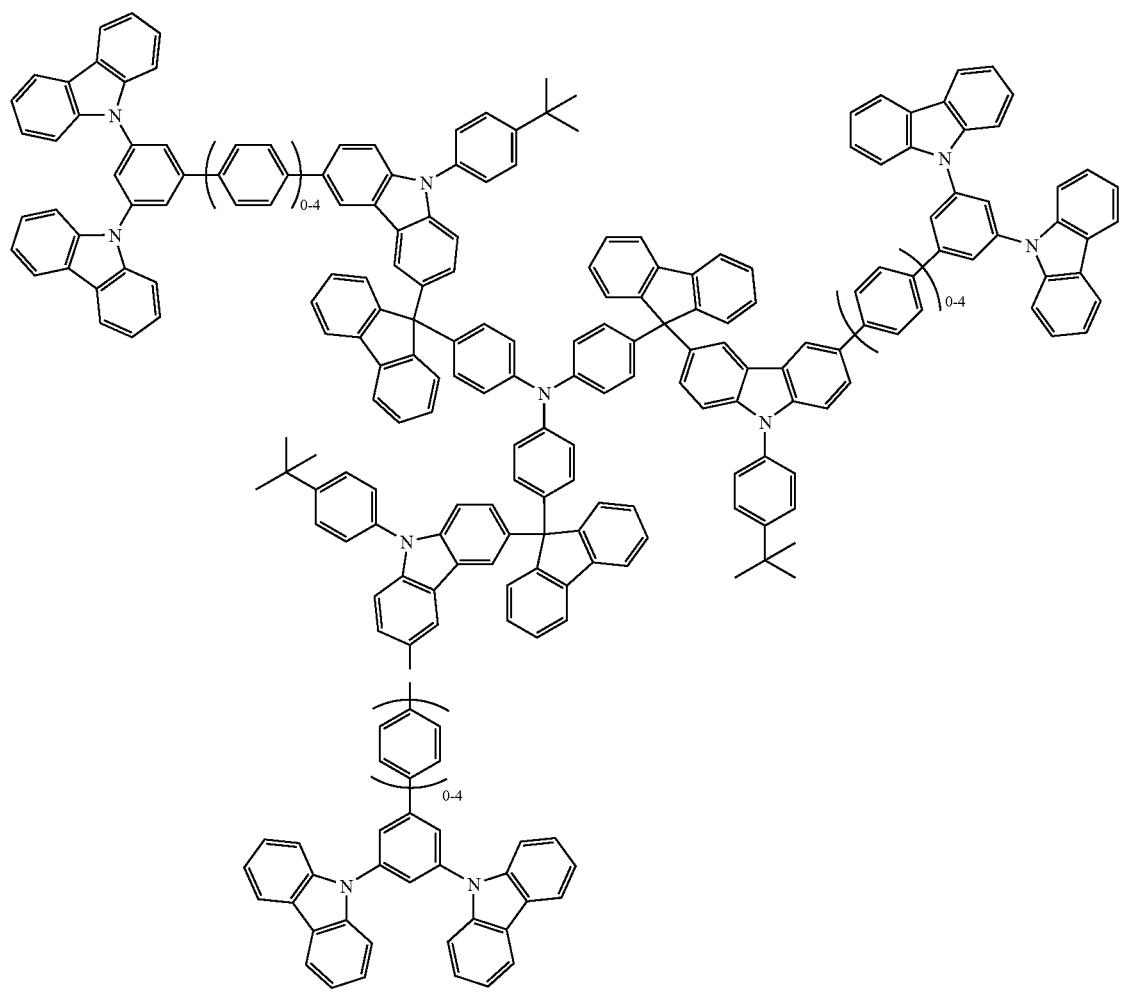

[Chemical Formula 43]
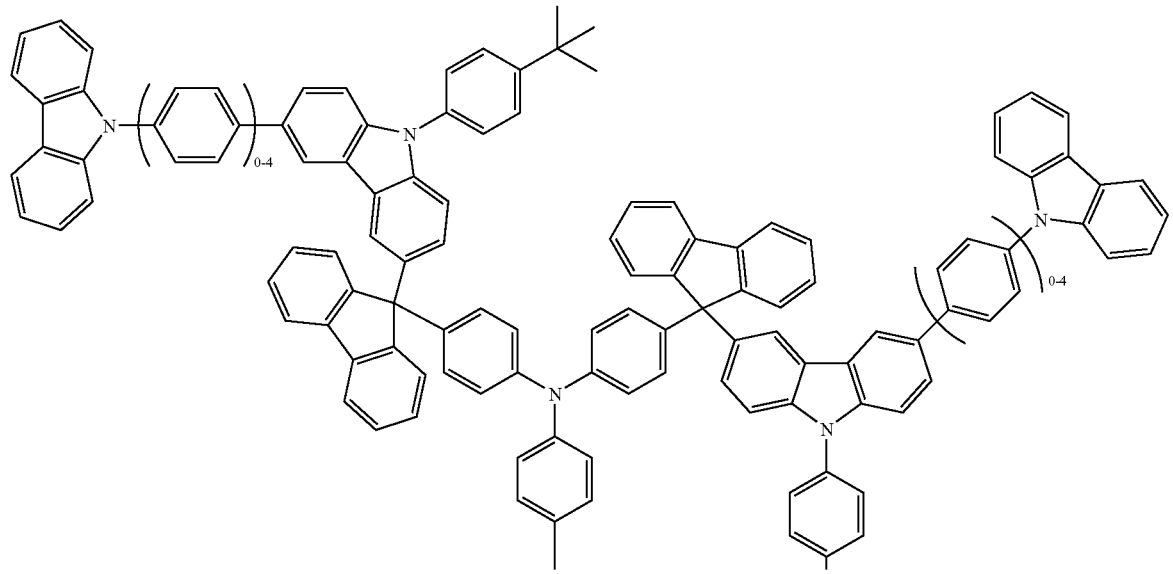
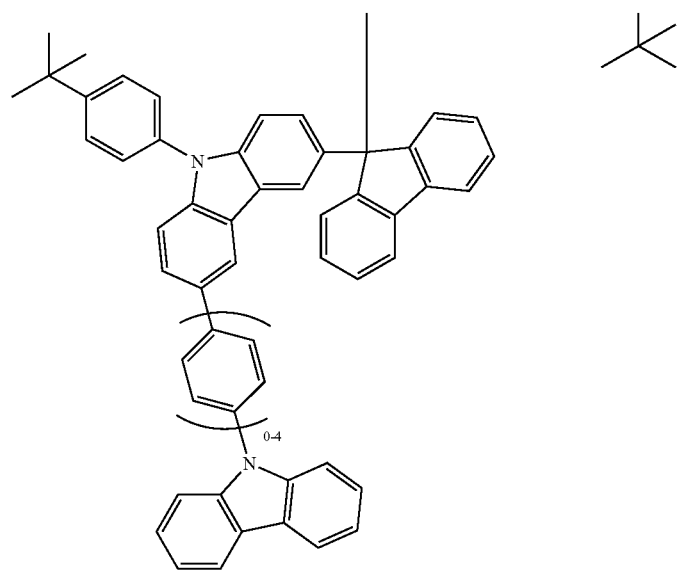

[Chemical Formula 44]
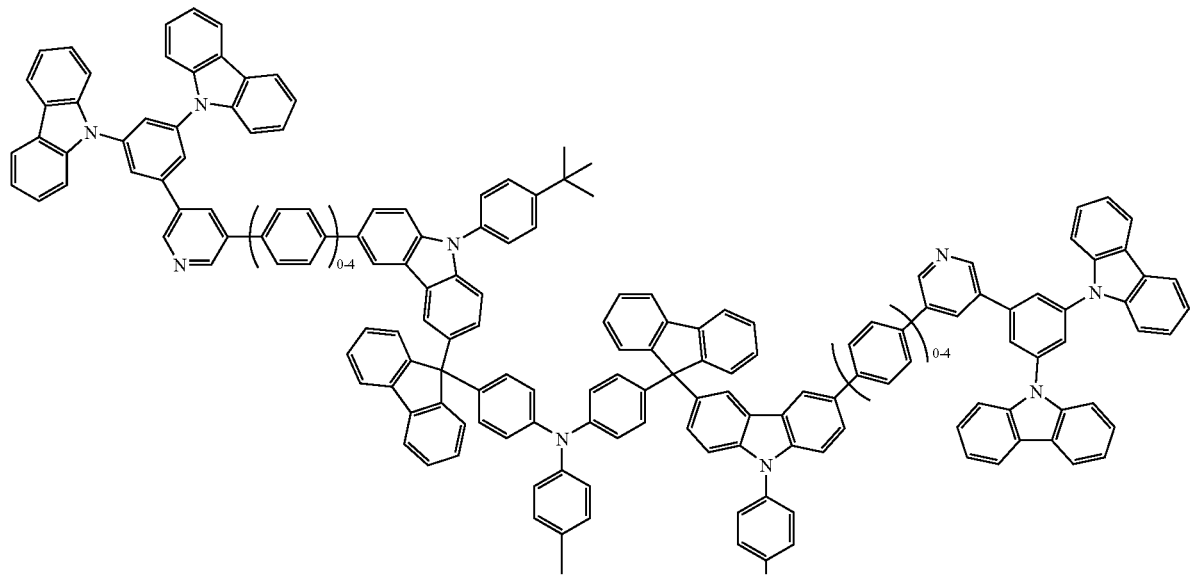
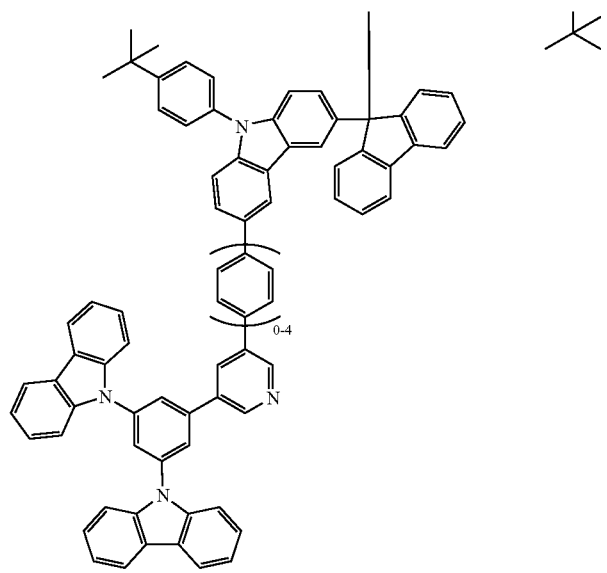

-continued
[Chemical Formula 45]
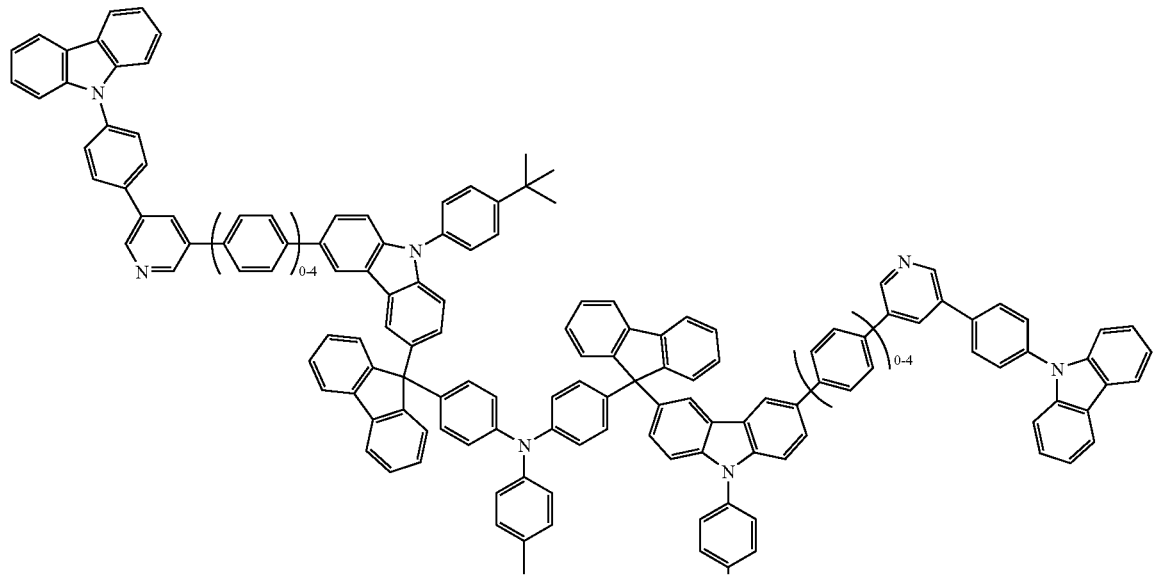
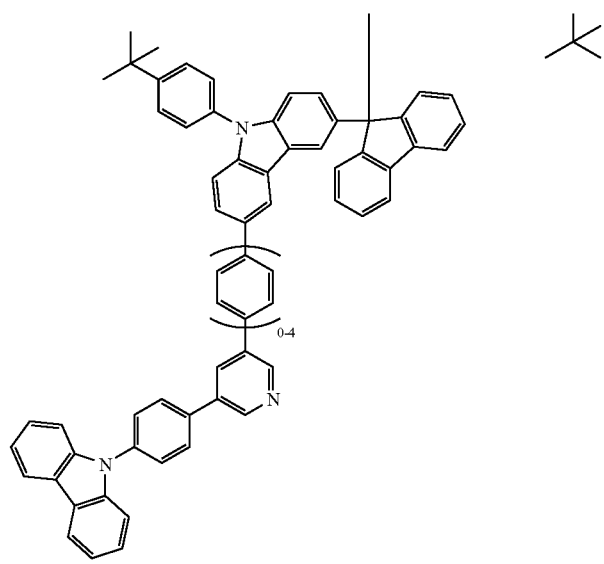

-continued
[Chemical Formula 46]
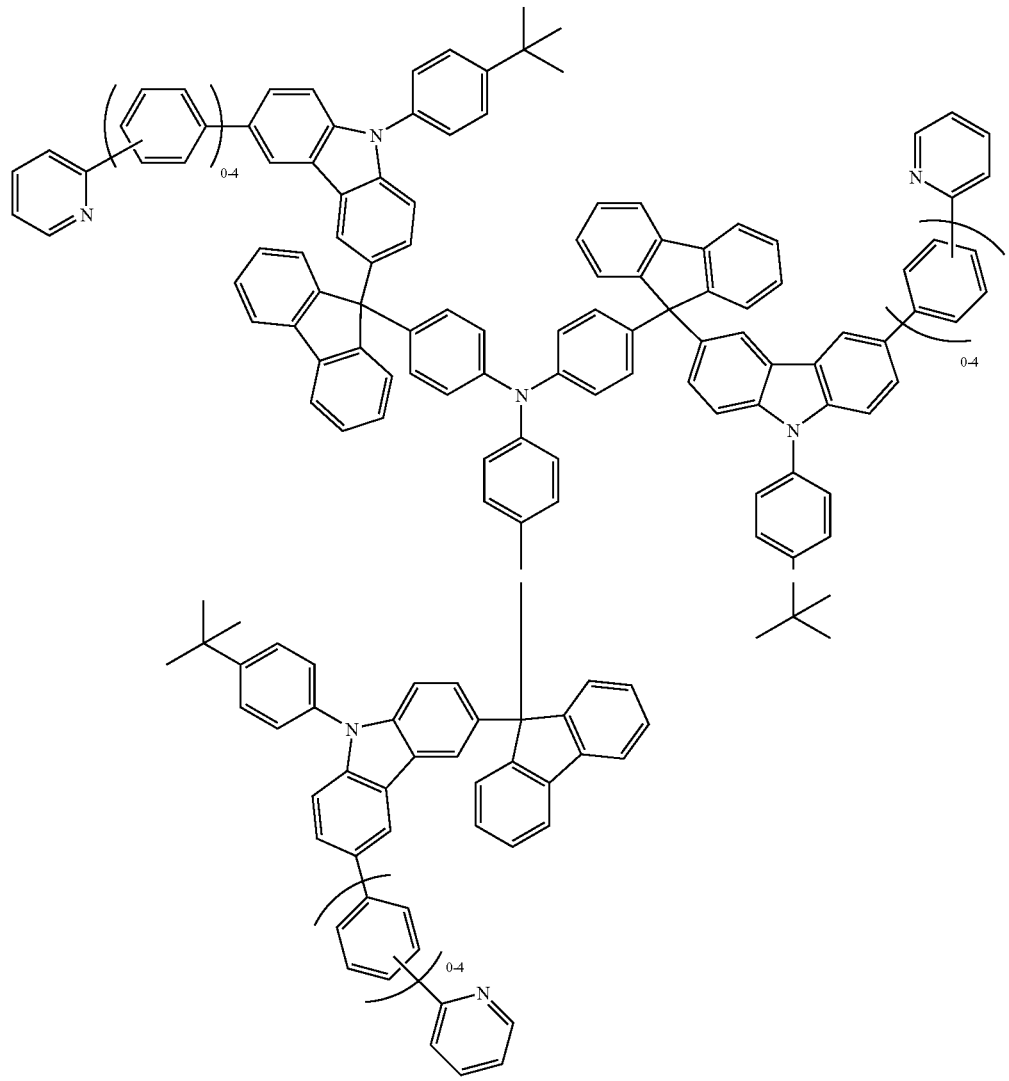
[Chemical Formula 47]
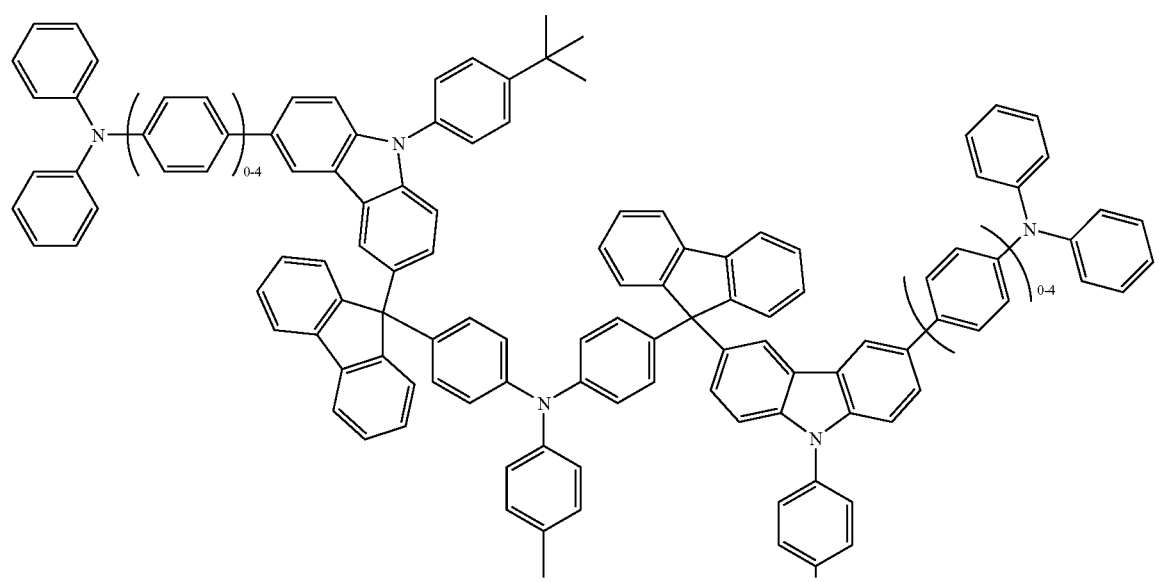

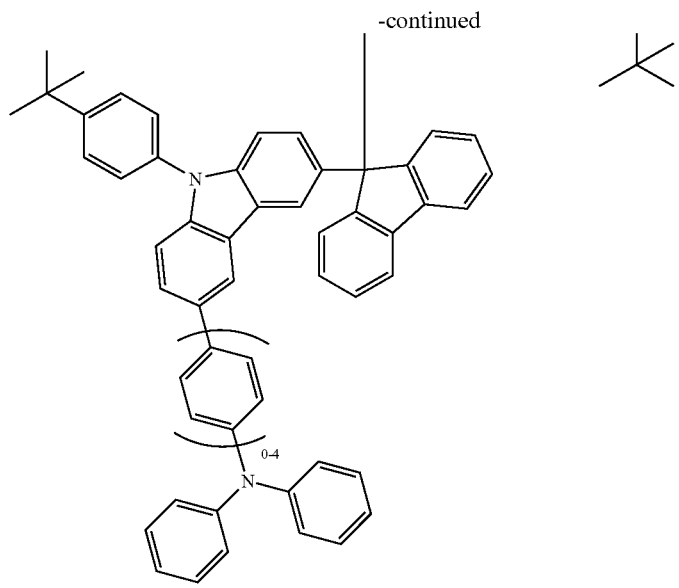
[Chemical Formula 48]
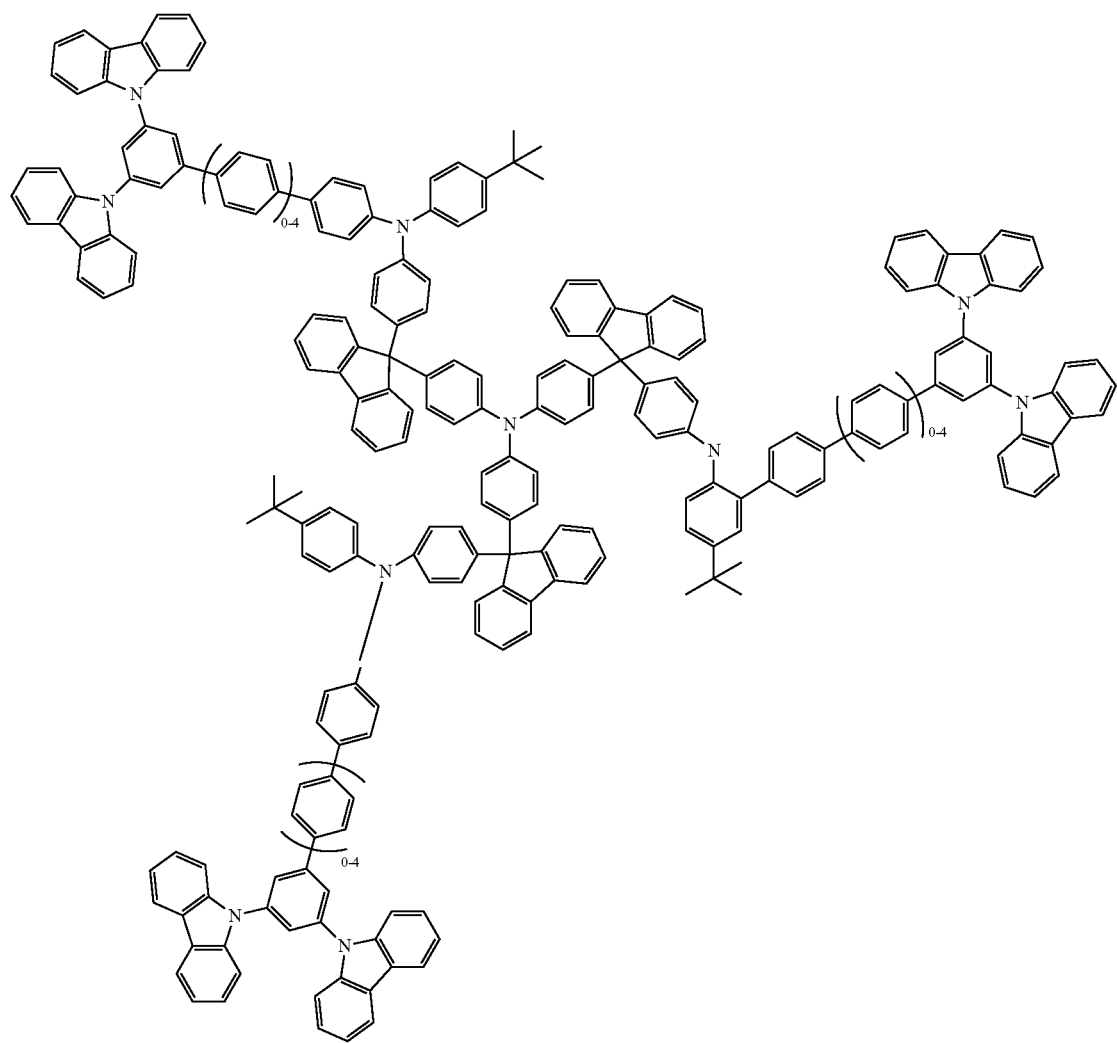

-continued
[Chemical Formula 49]
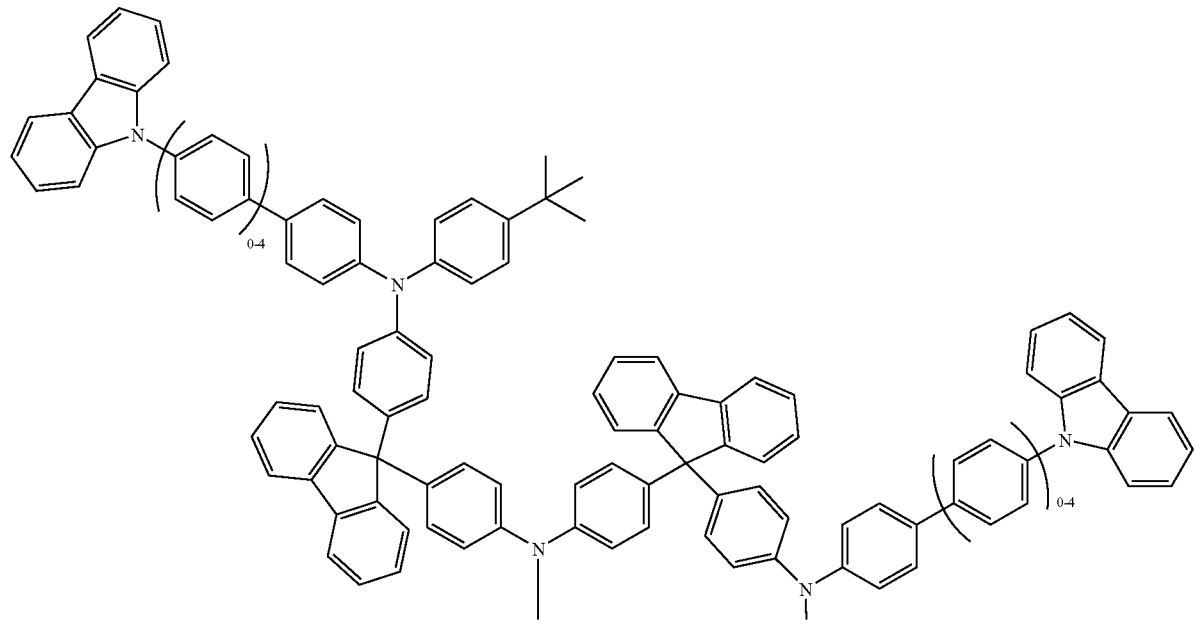
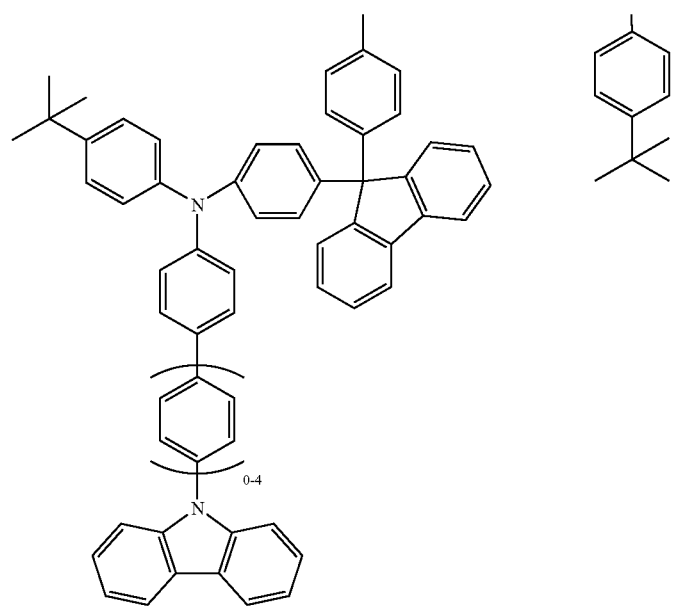

[Chemical Formula 50]
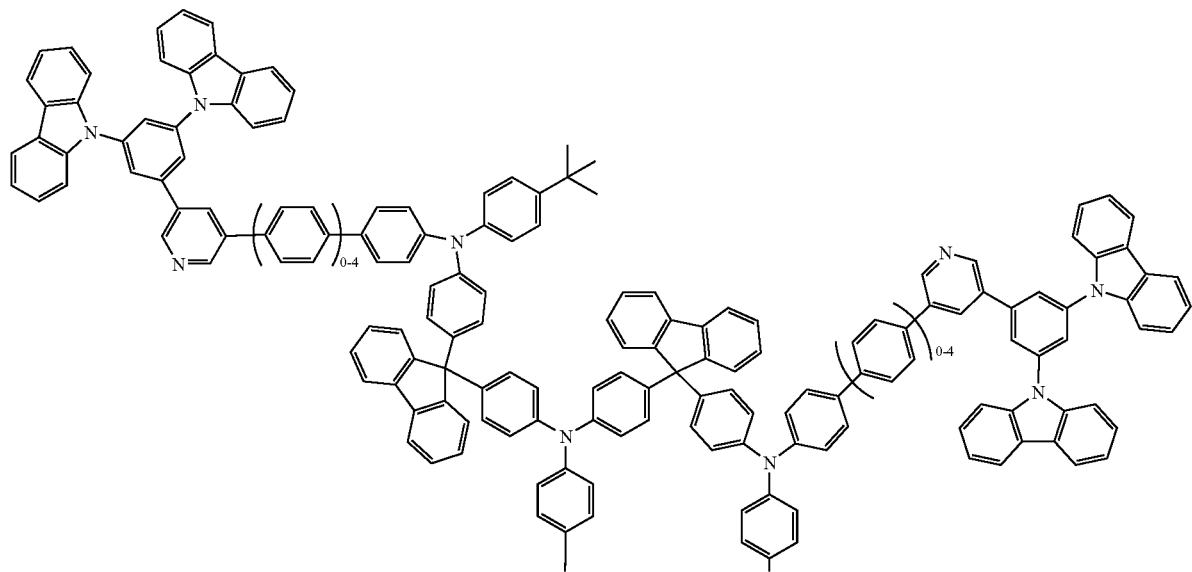
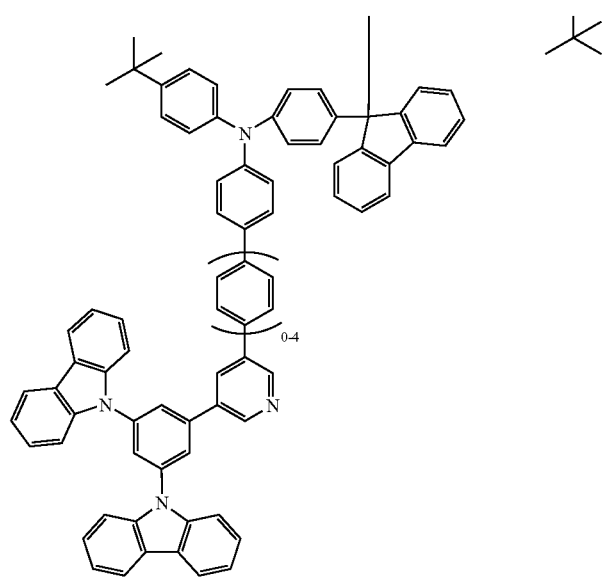

[Chemical Formula 51]
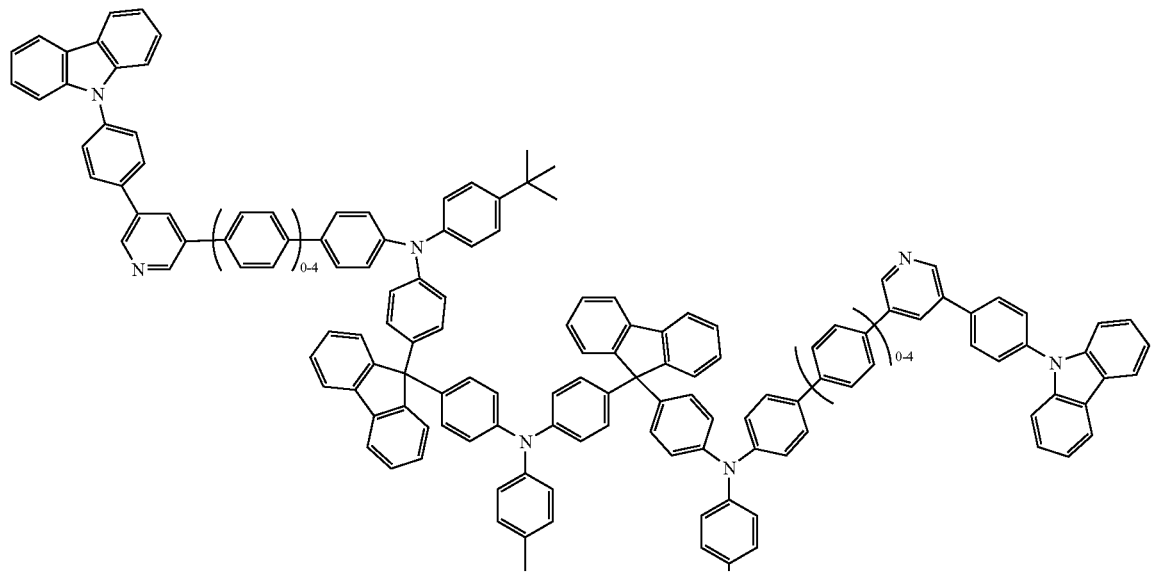
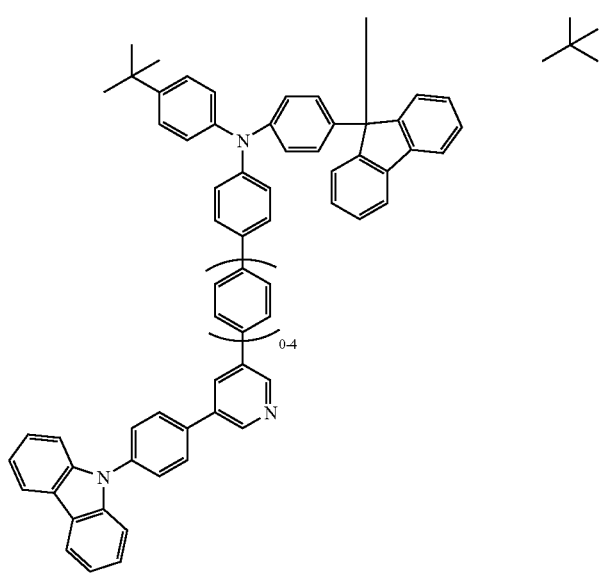

-continued
[Chemical Formula 52]
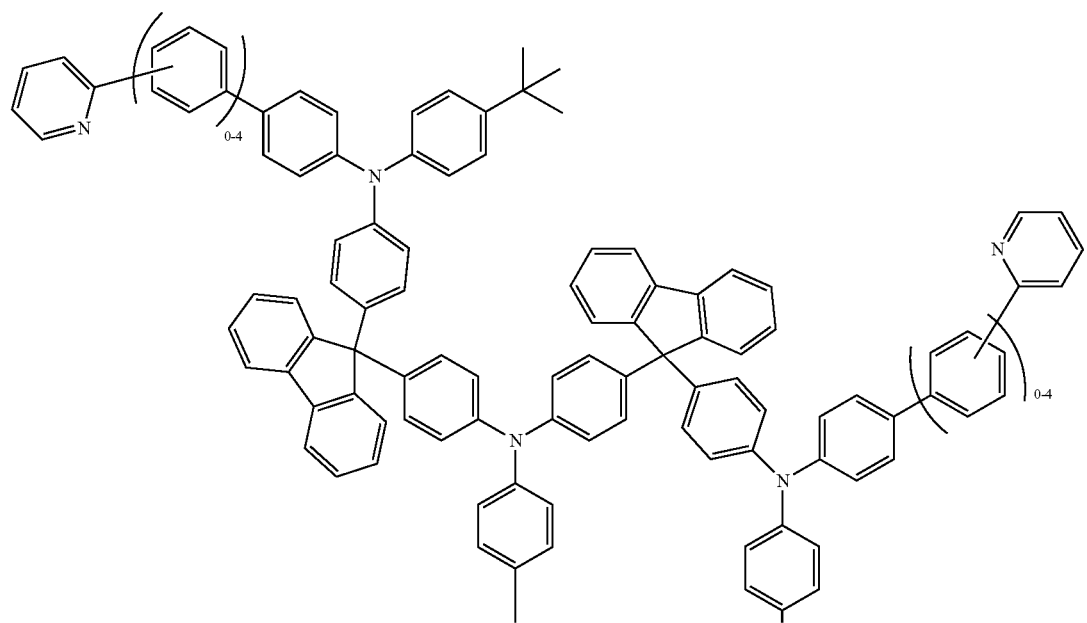
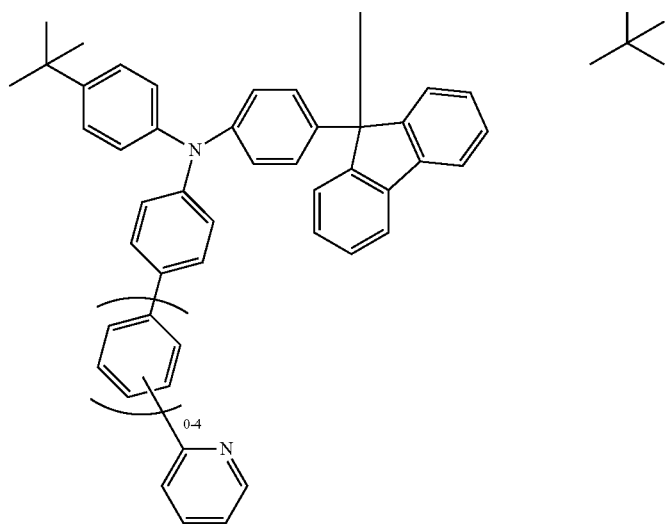

[Chemical Formula 53]
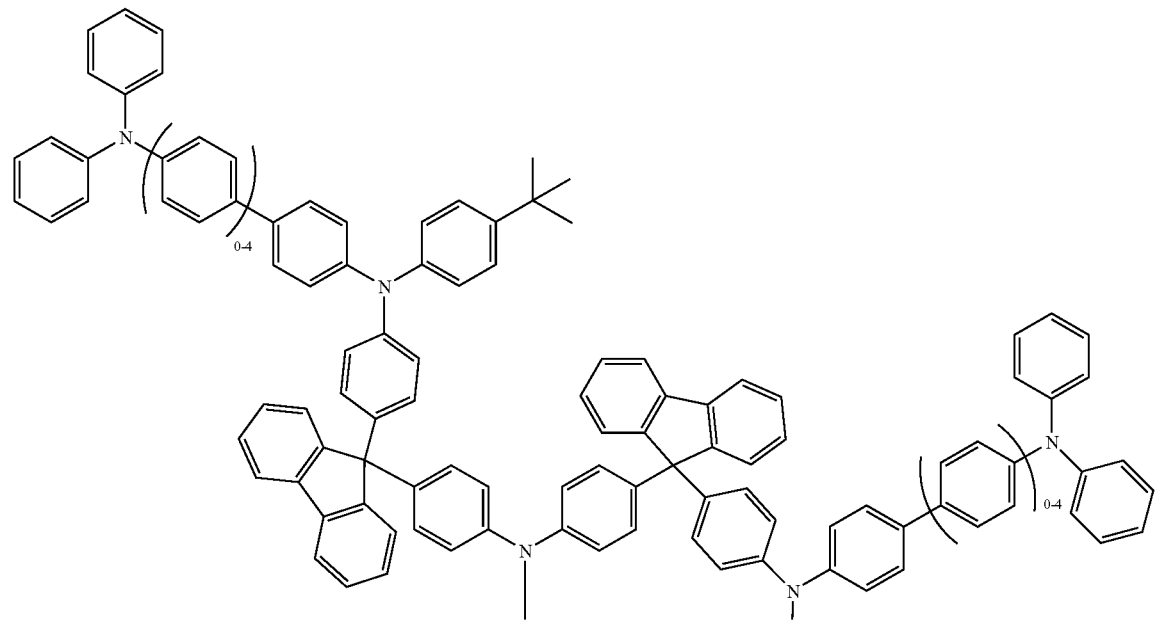
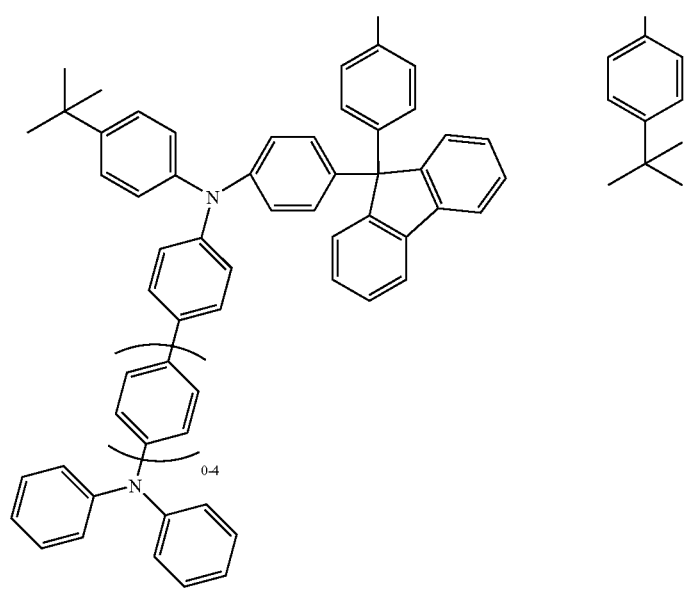

The compound represented by the above Formula 2 may be compounds represented by the following Chemical Formulae 54 to 71.
[Chemical Formula 54]
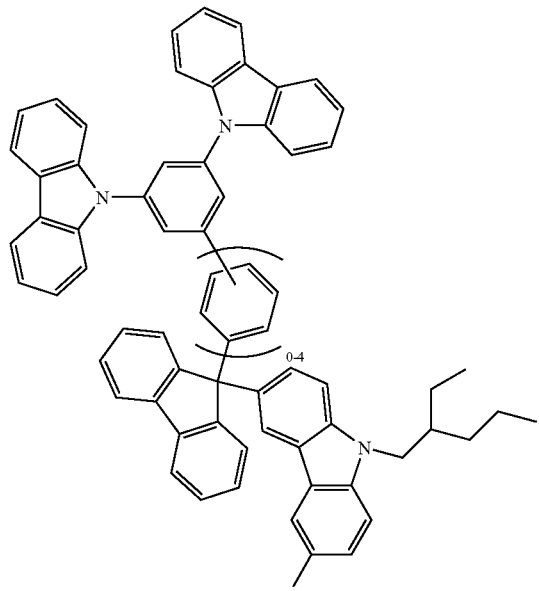
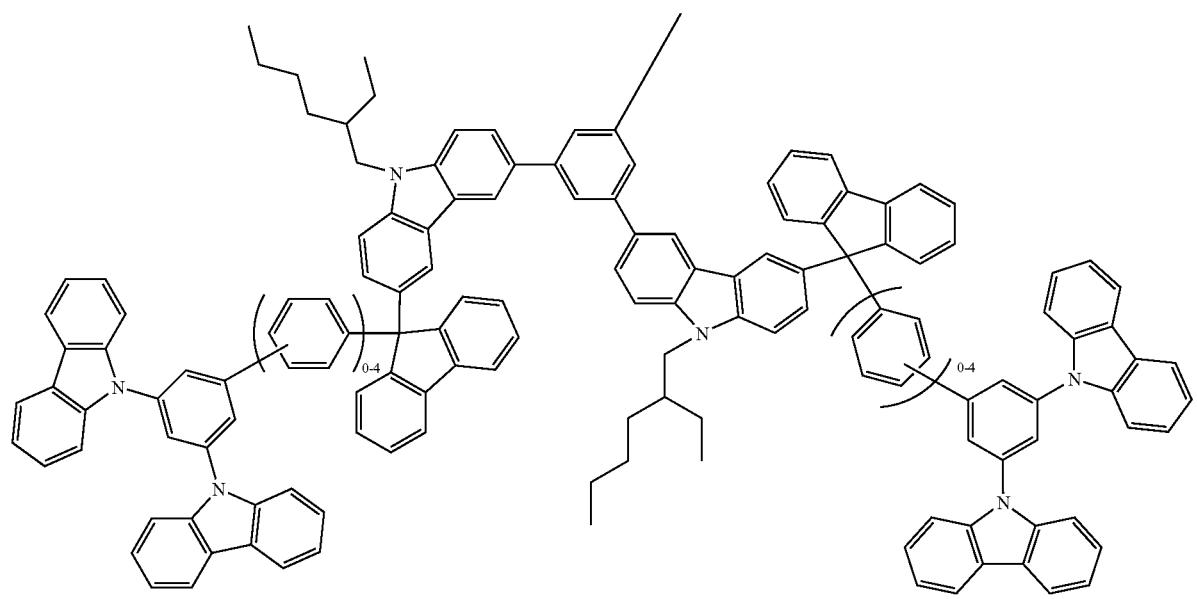

-continued
[Chemical Formula 55]
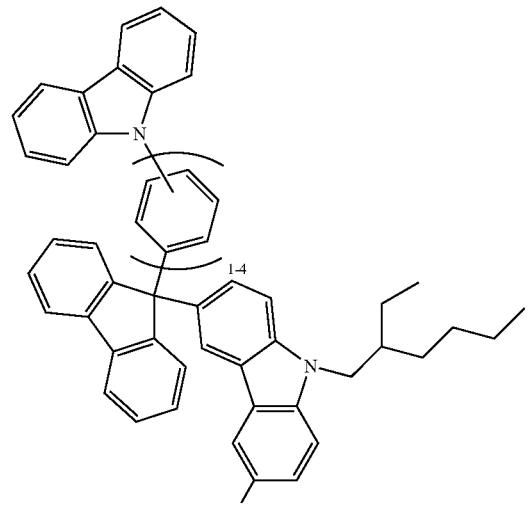
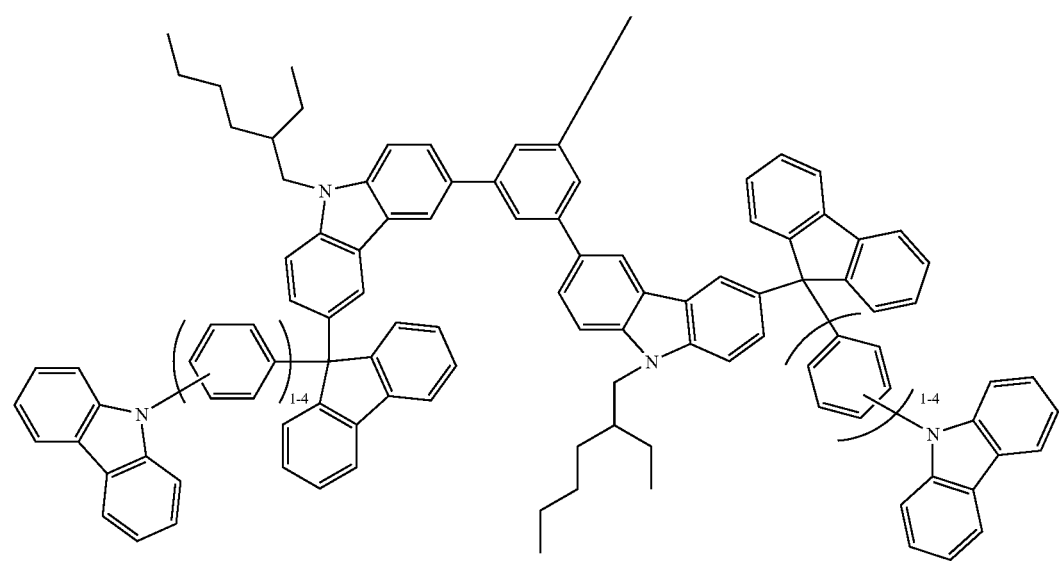

[Chemical Formula 56]
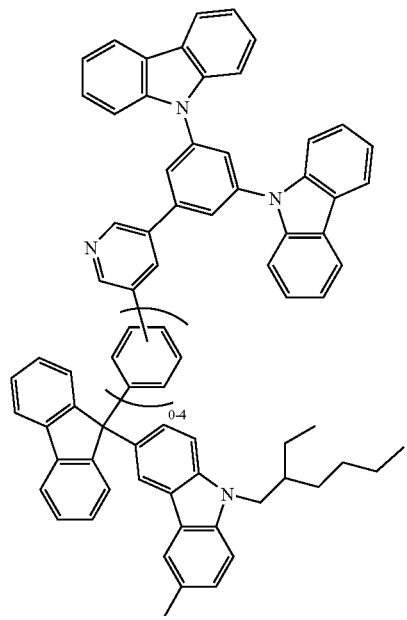
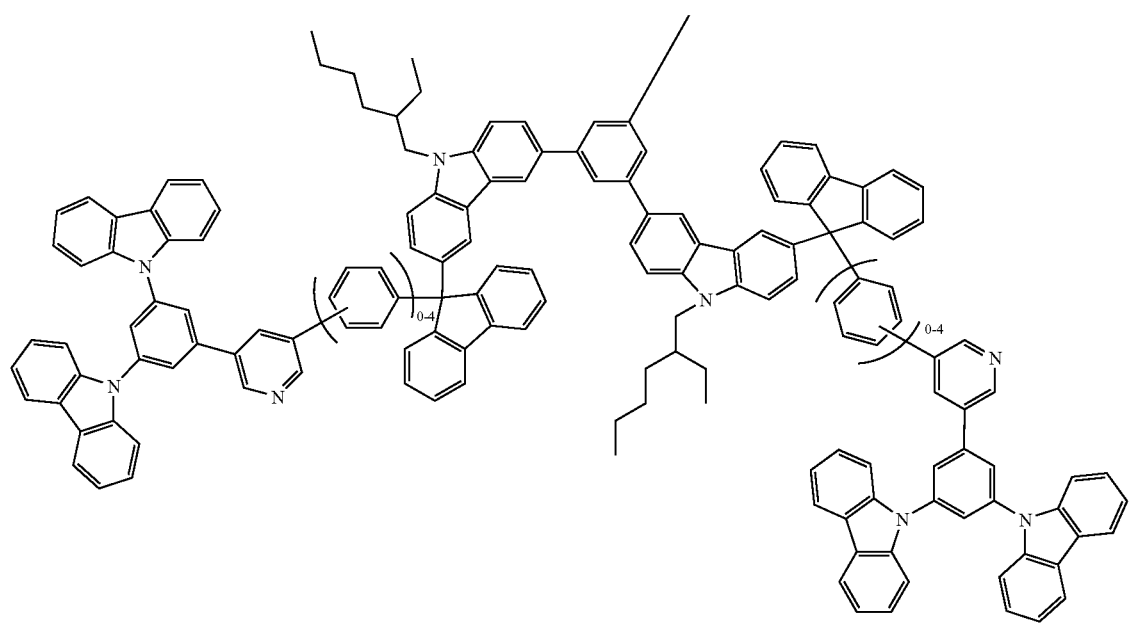

[Chemical Formula 57]
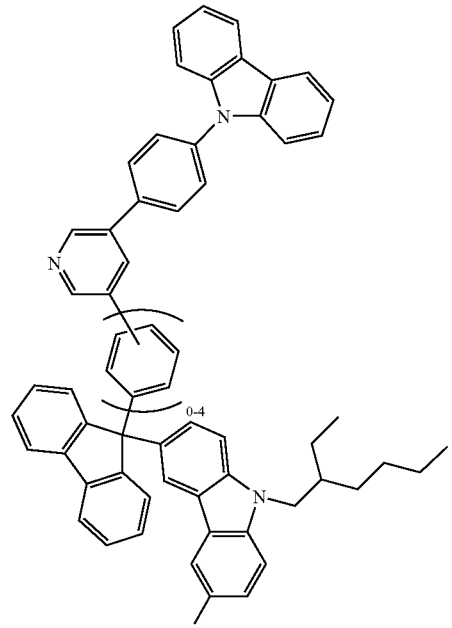
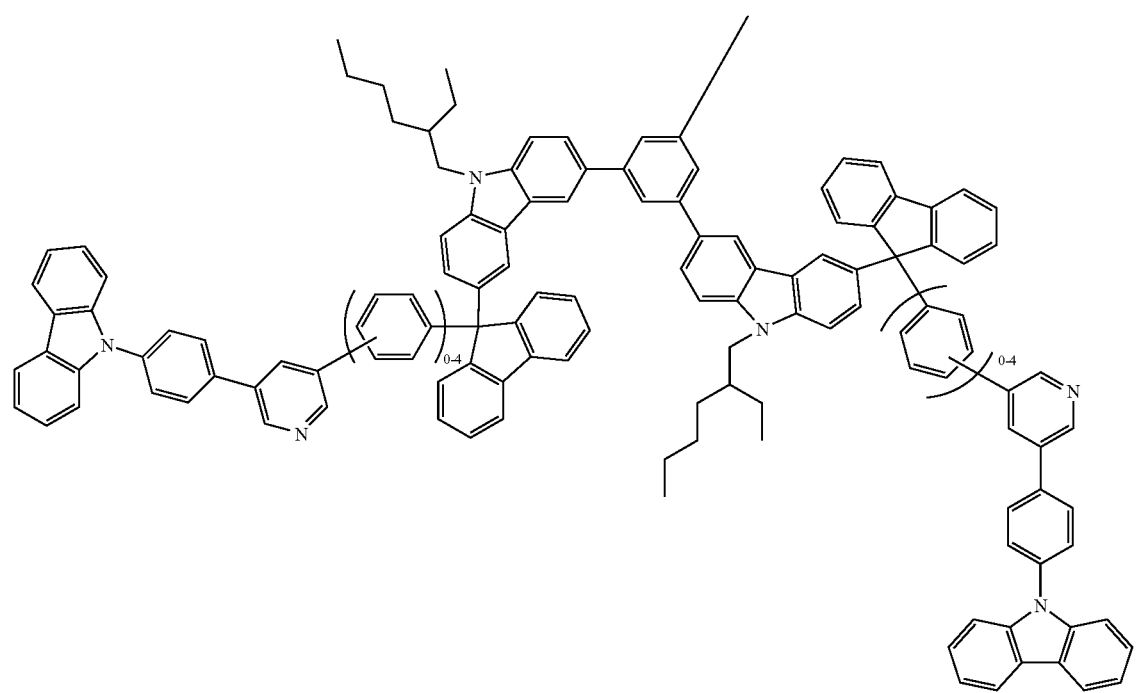

[Chemical Formula 58]
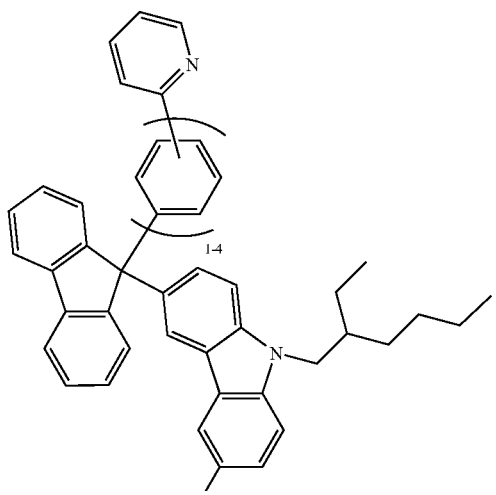
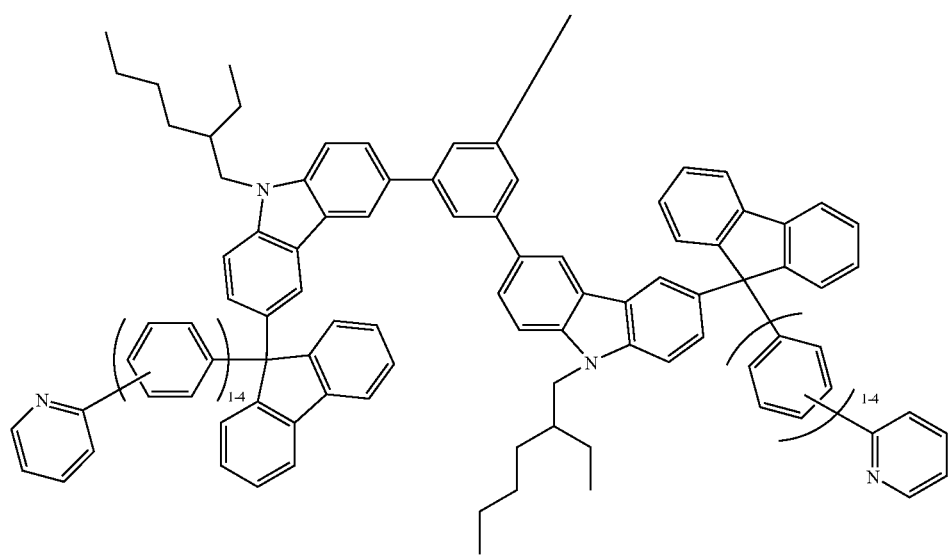
[Chemical Formula 59]
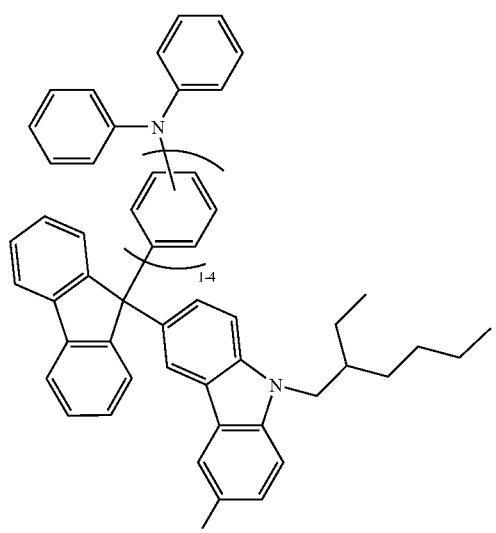

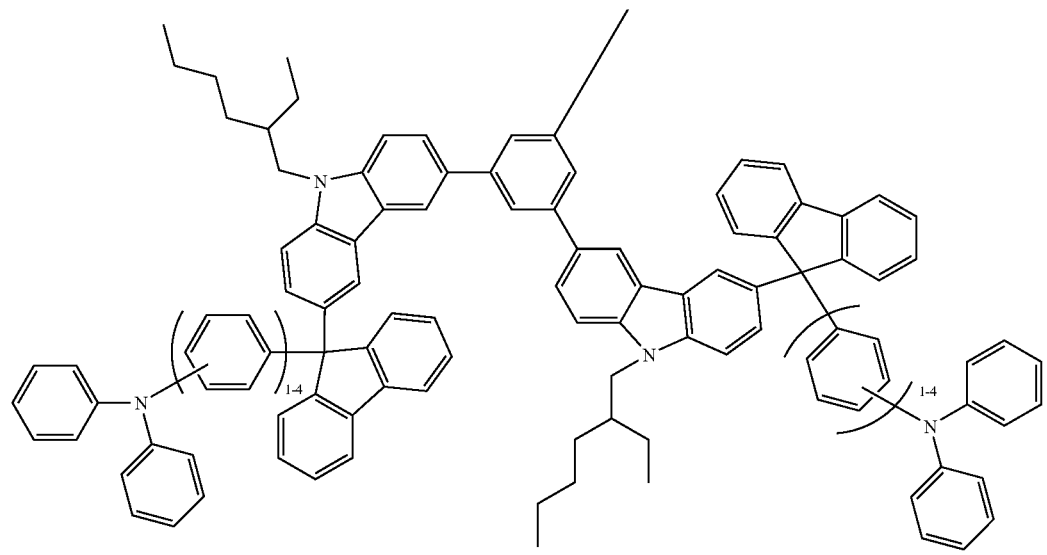
[Chemical Formula 60]
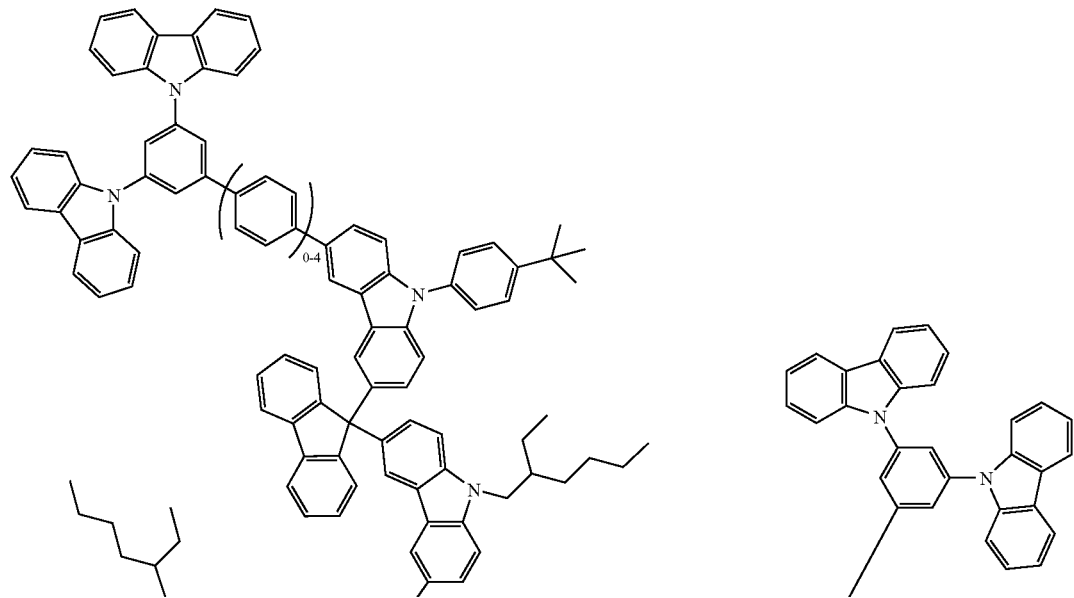

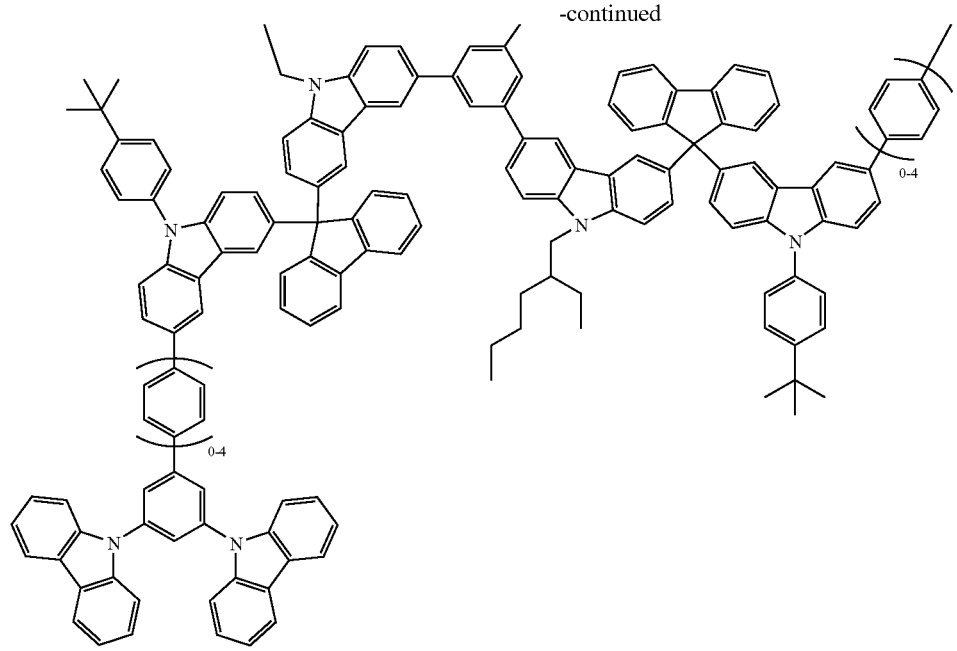
[Chemical Formula 61]
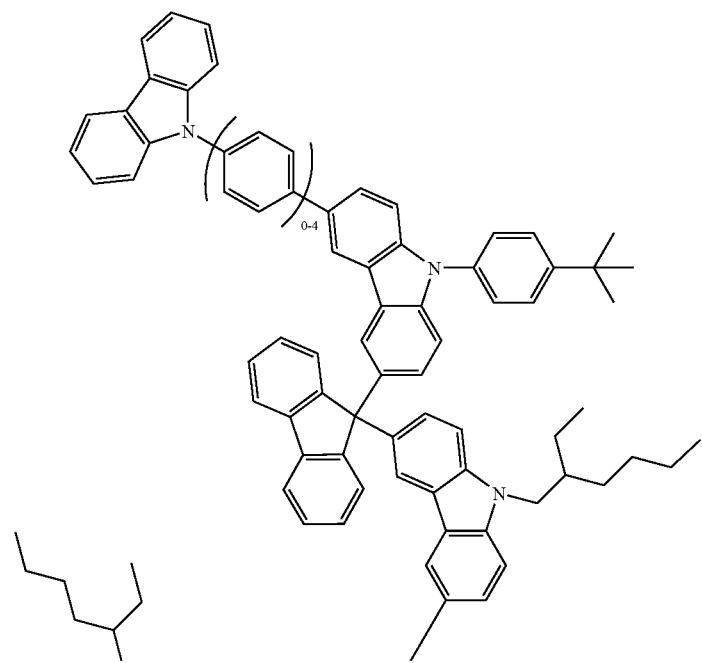

-continued
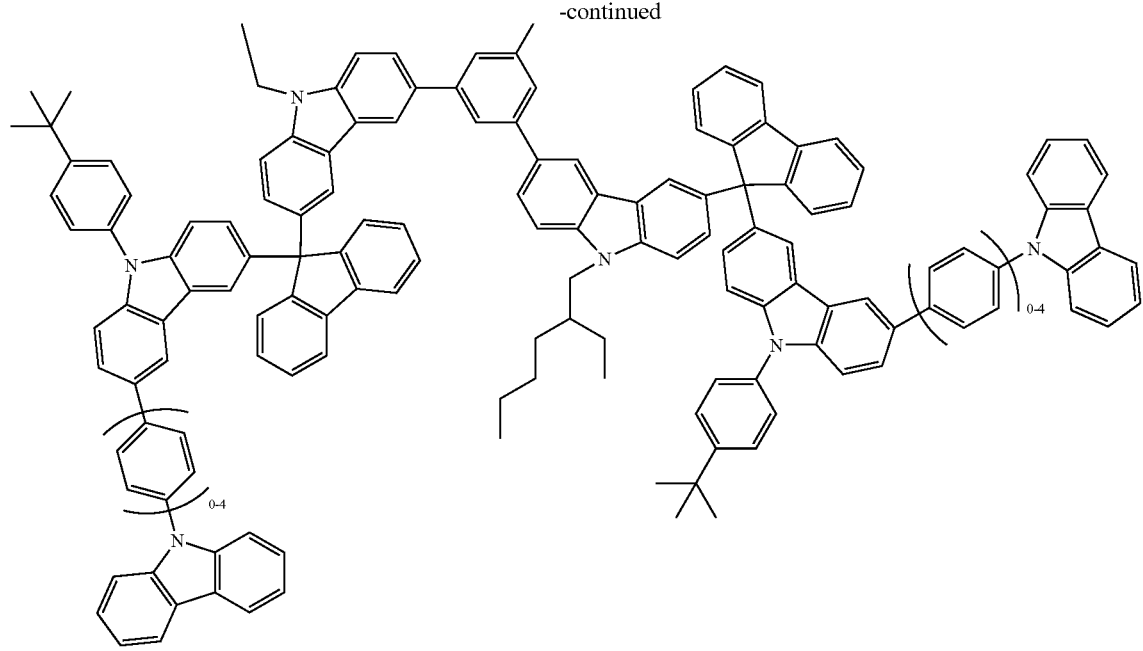
[Chemical Formula 62]
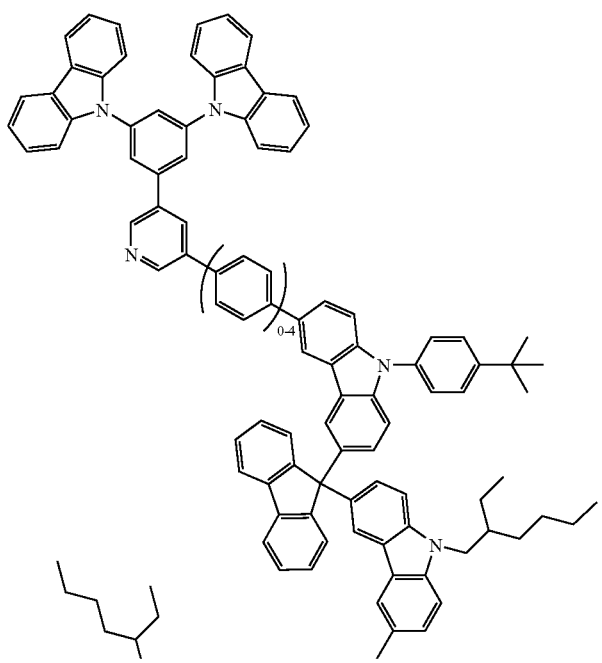

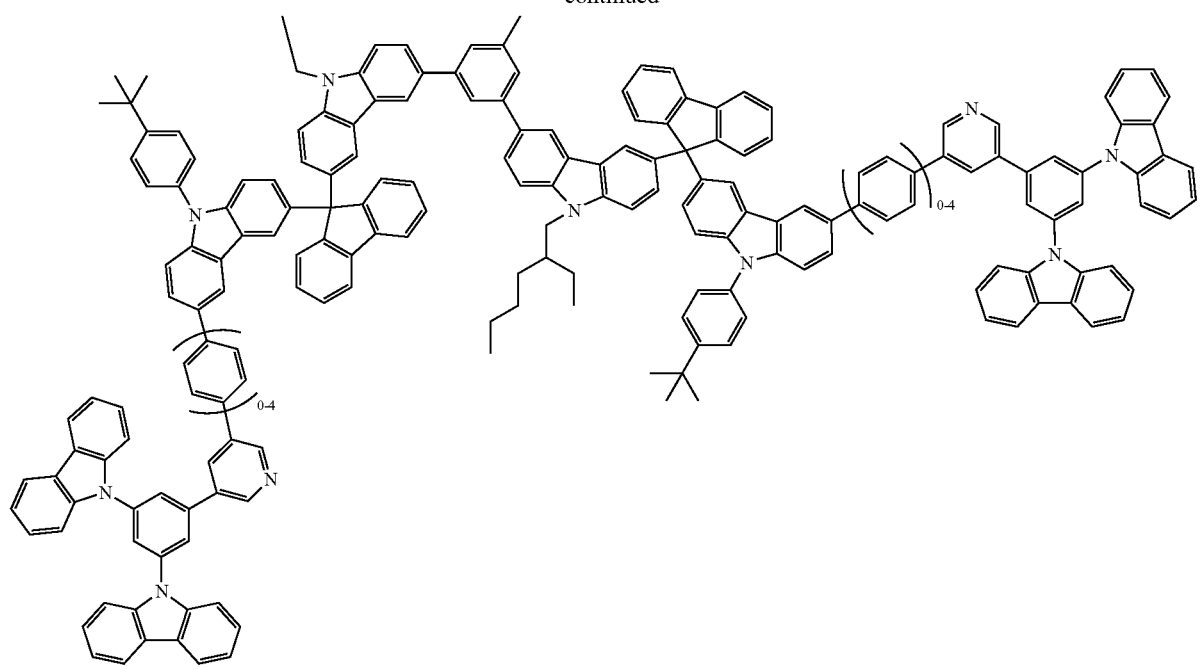
-continued
[Chemical Formula 63]
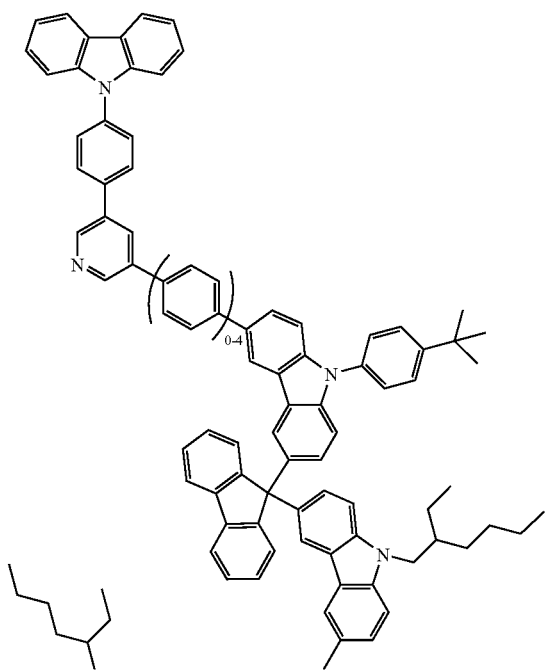

-continued
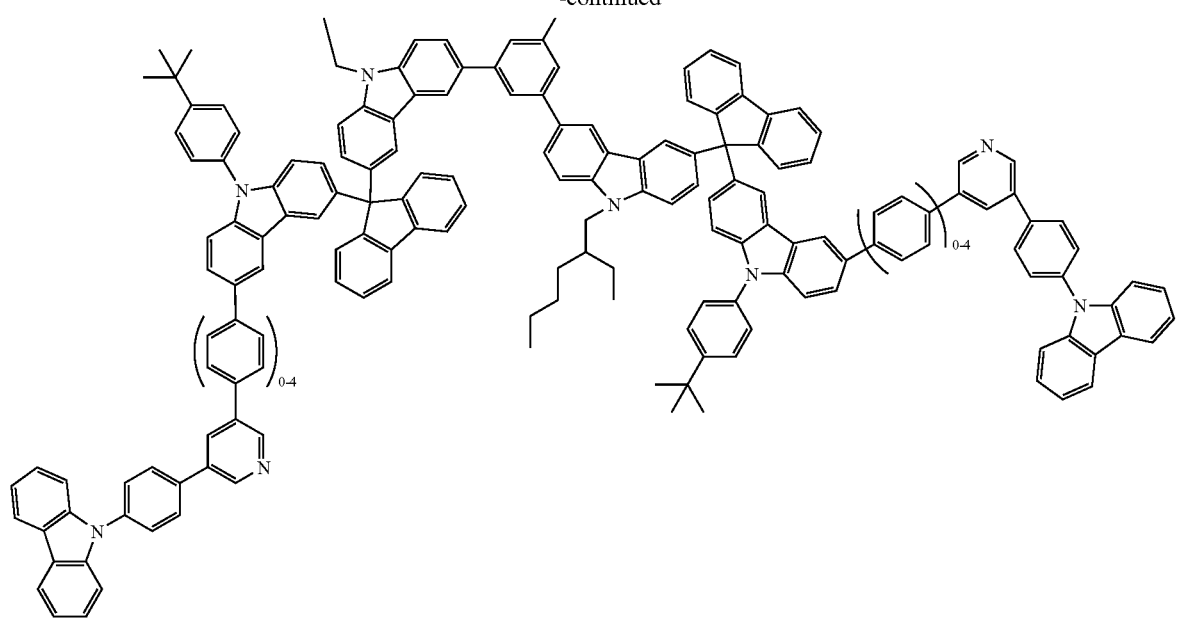
[Chemical Formula 64]
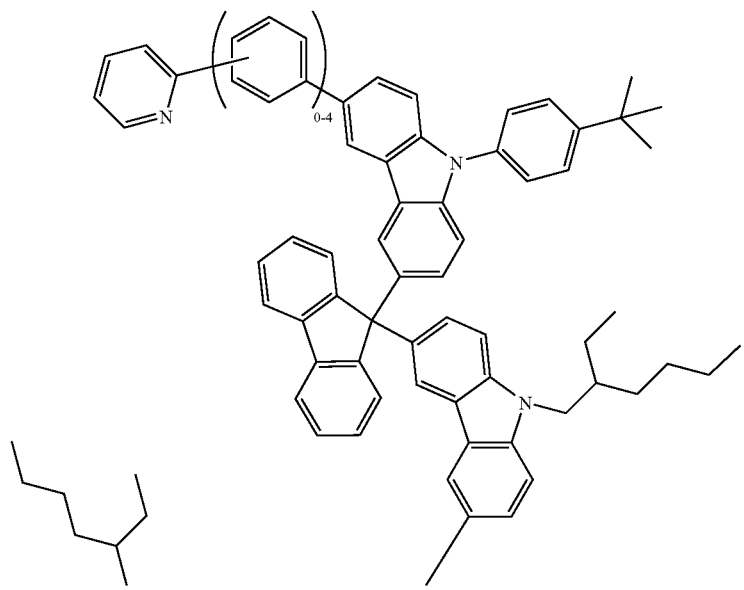

-continued
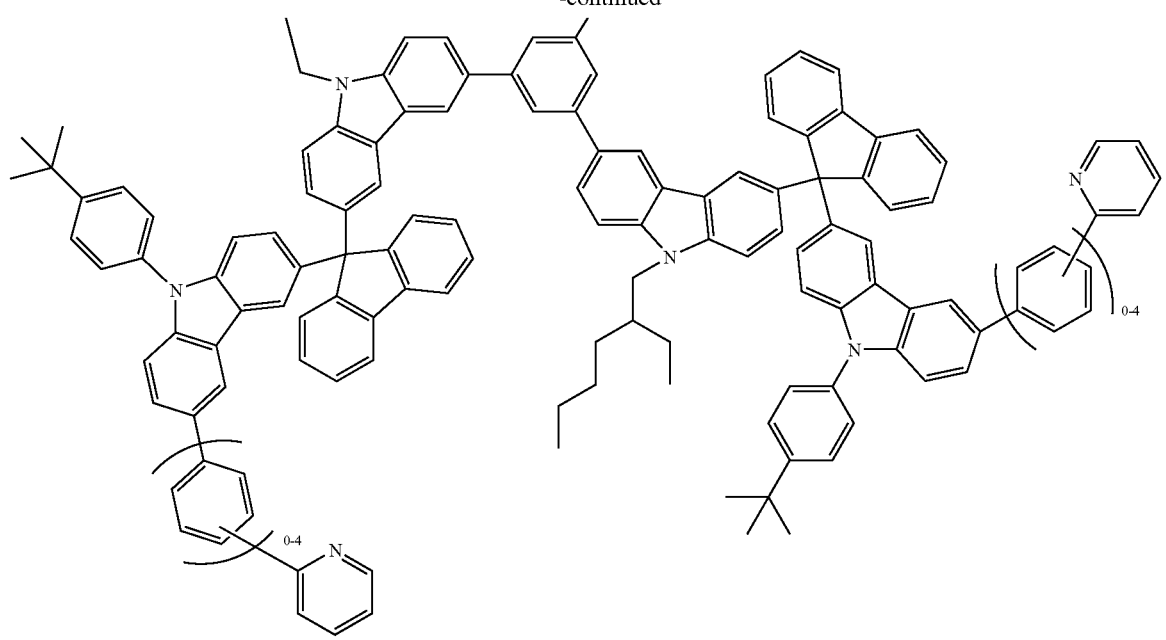
[Chemical Formula 65]
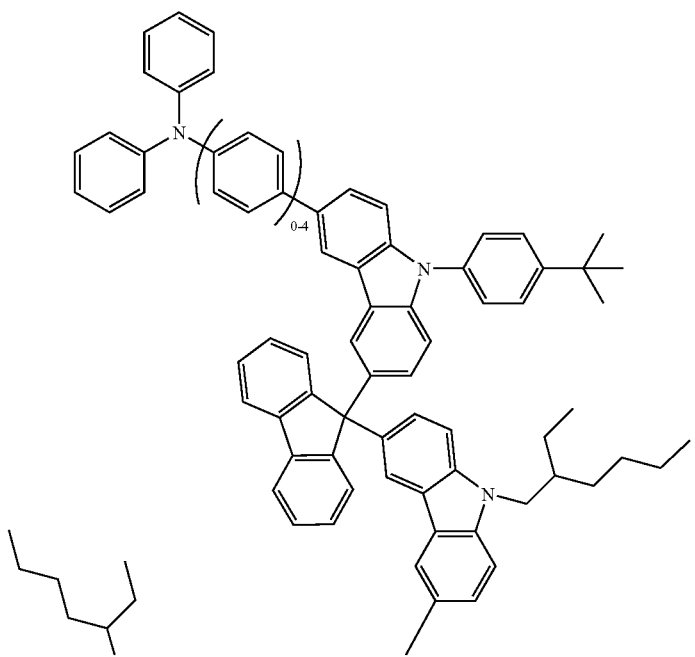

-continued
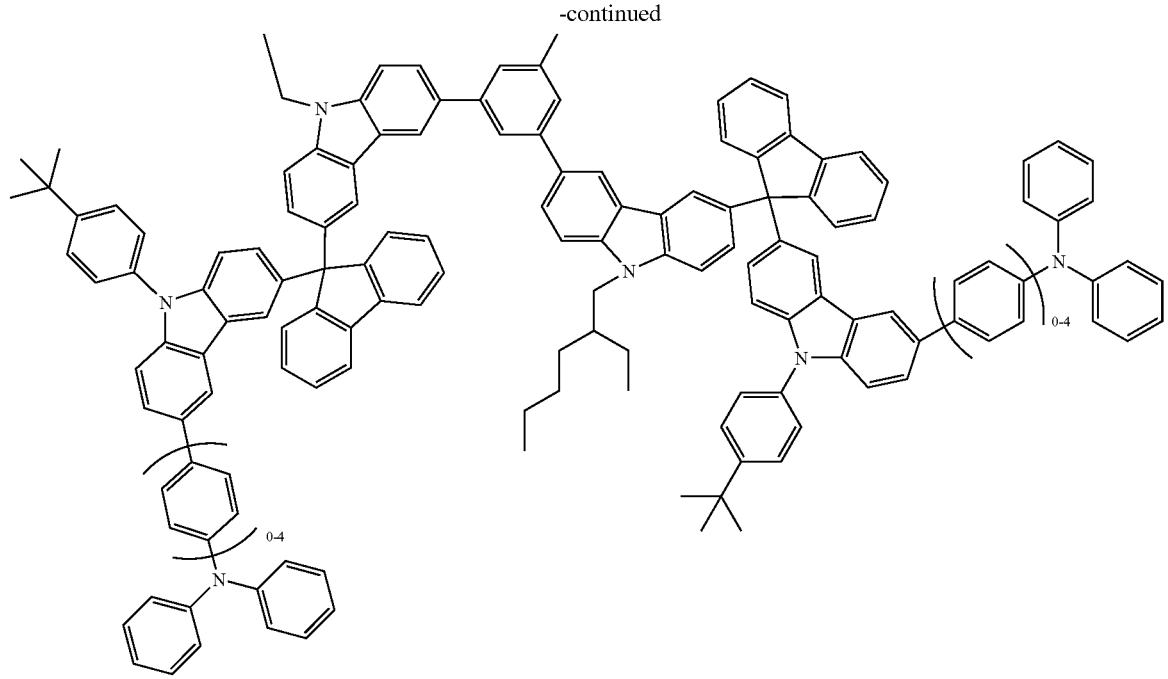
[Chemical Formula 66]
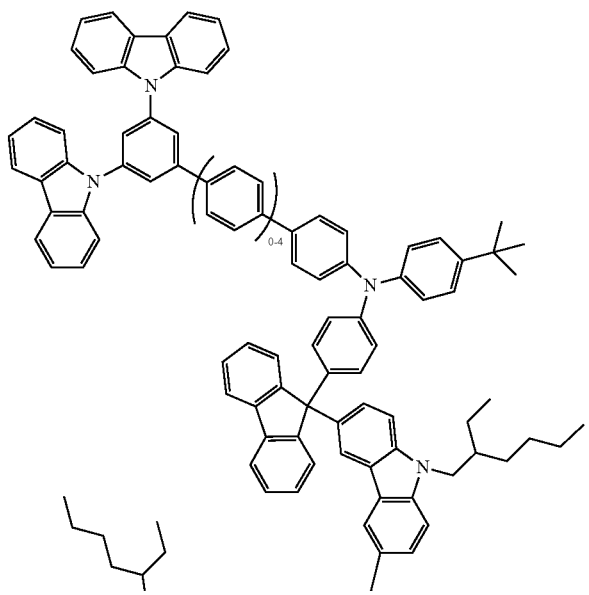

-continued
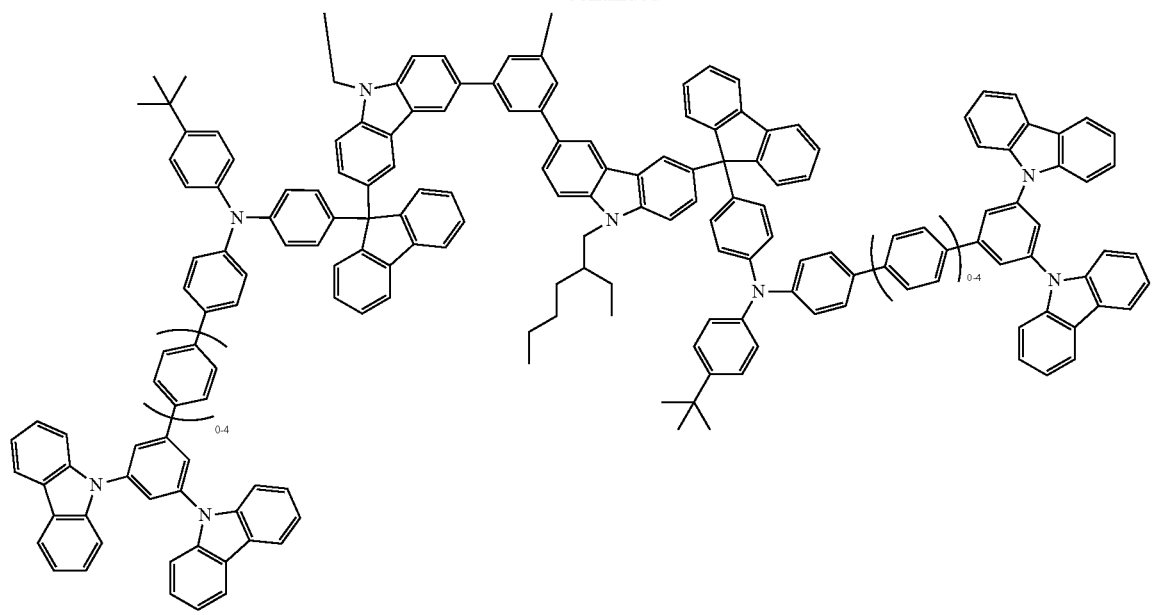
[Chemical Formula 67]
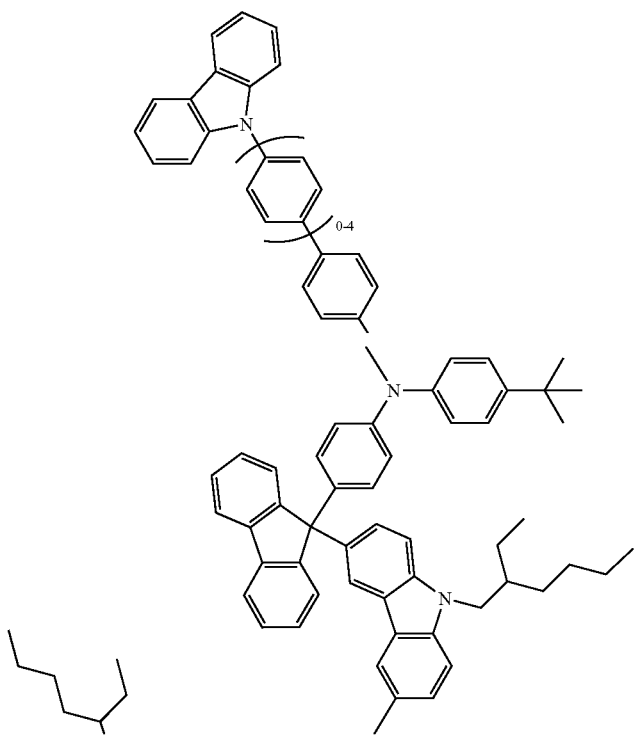

-continued
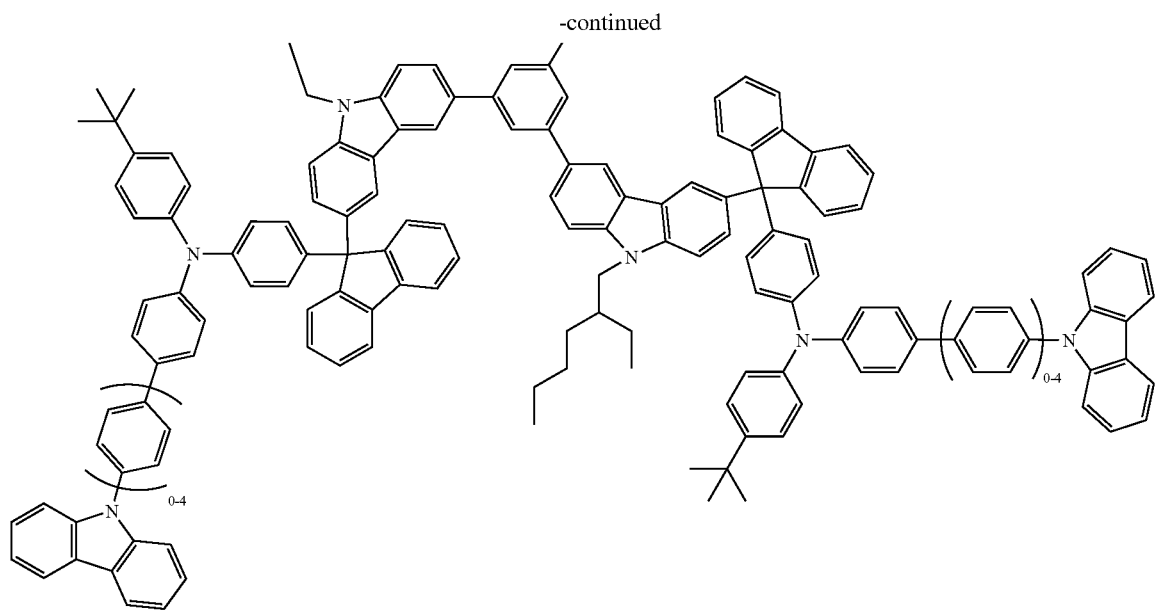
[Chemical Formula 68]
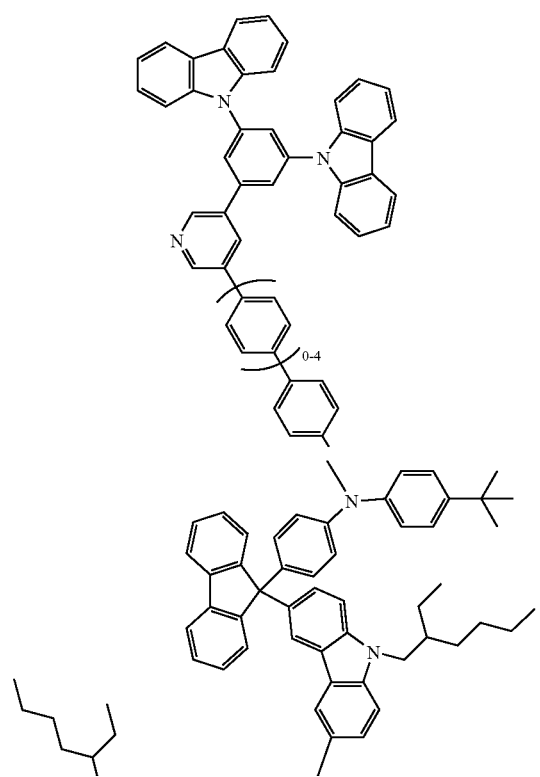

-continued
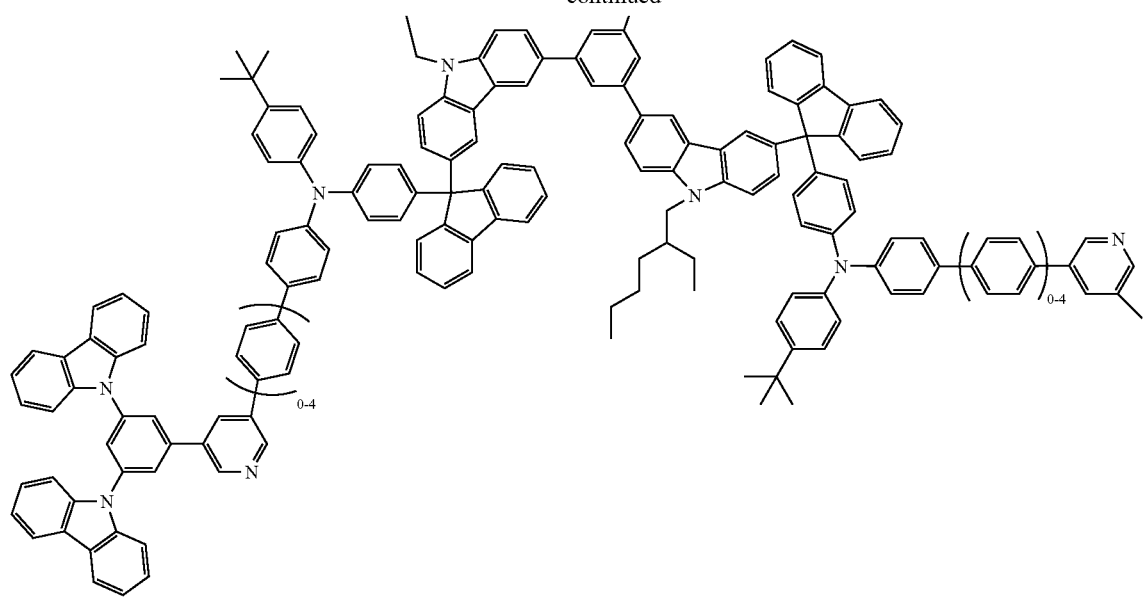
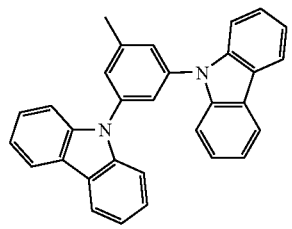
[Chemical Formula 69]
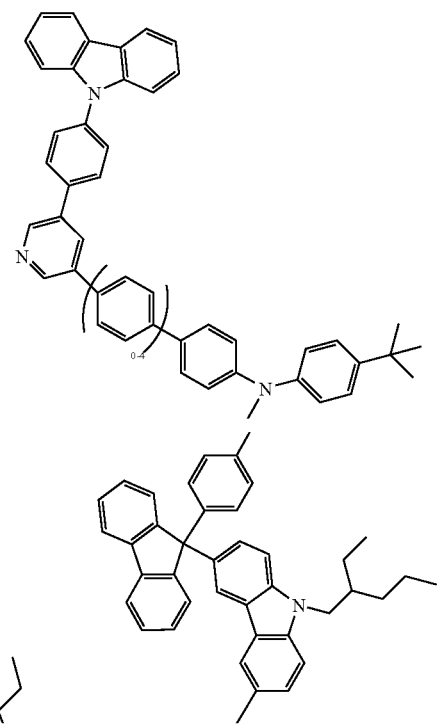

-continued
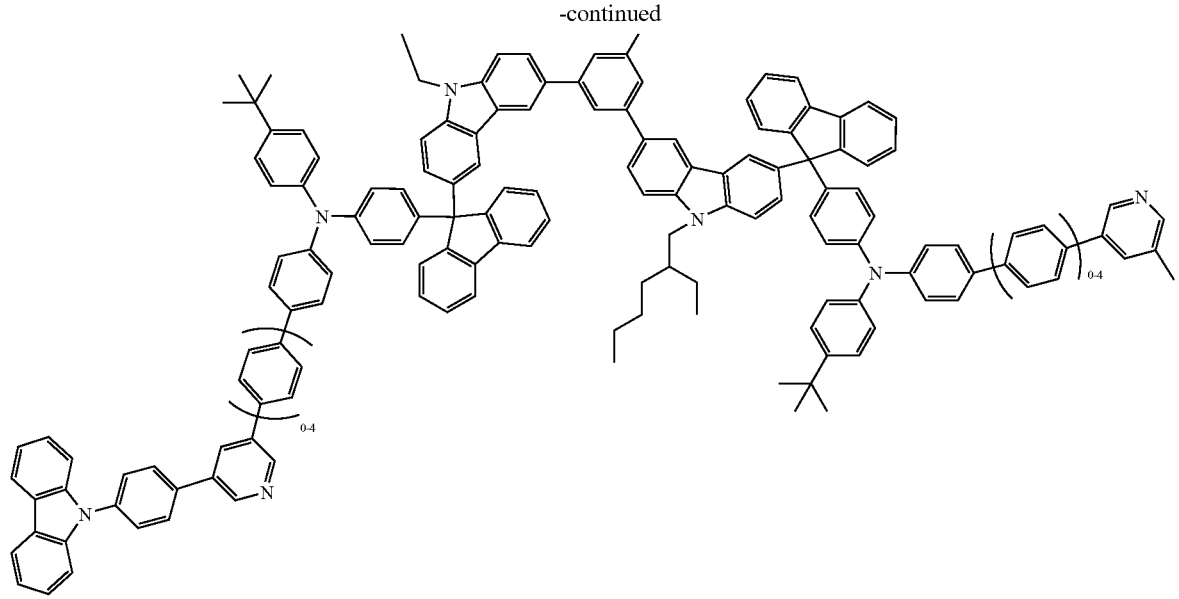
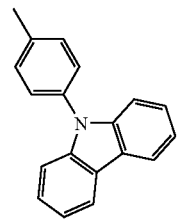
[Chemical Formula 70]
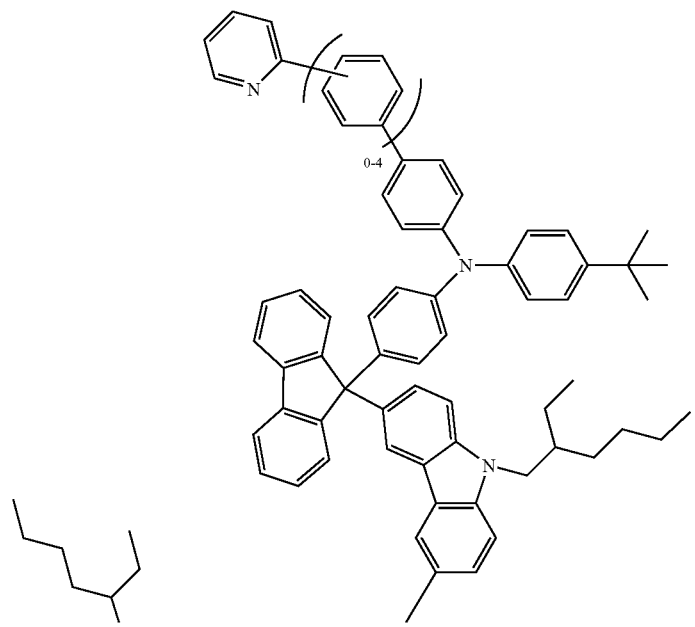

-continued
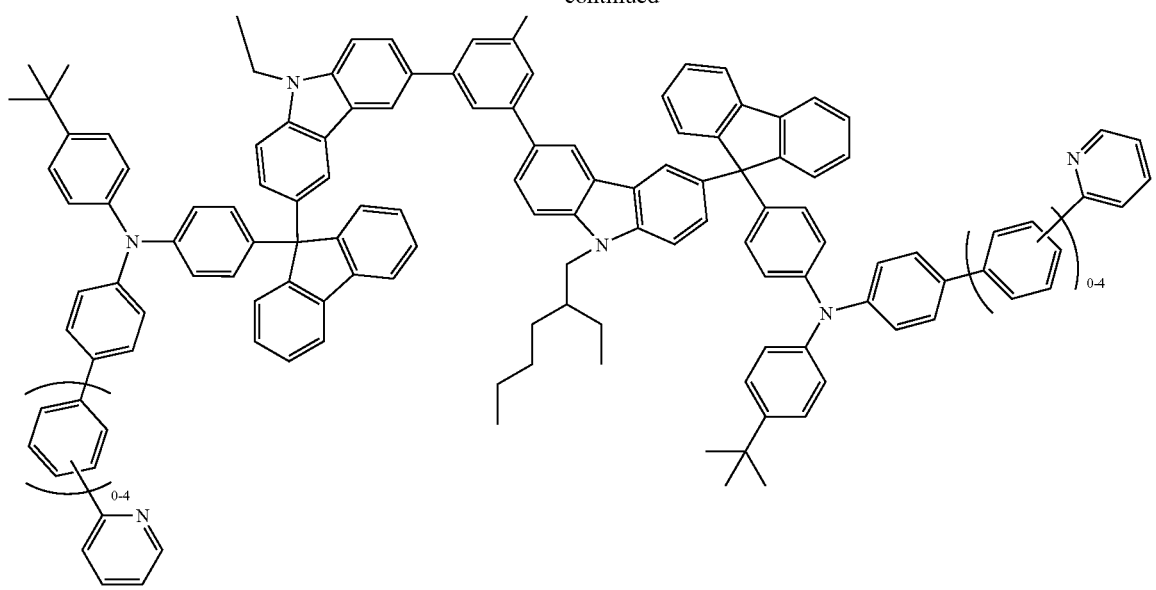
[Chemical Formula 71]
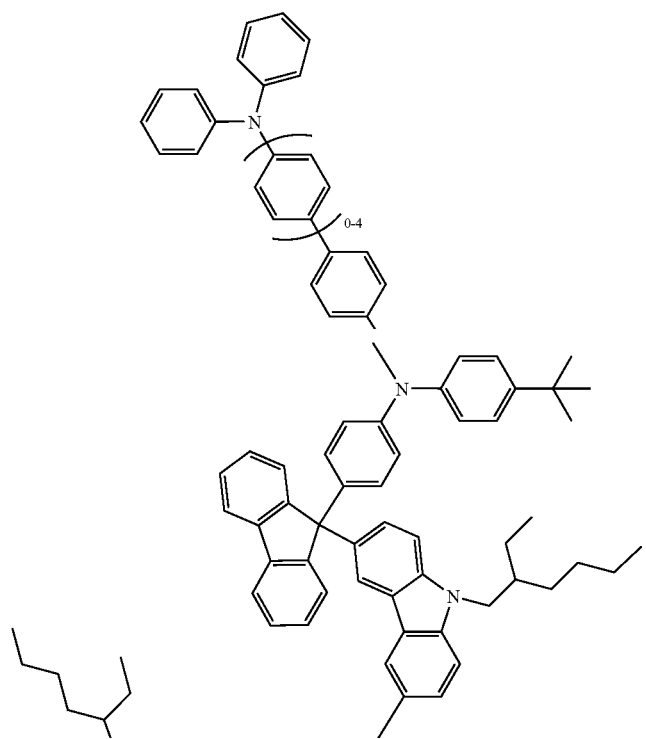

-continued
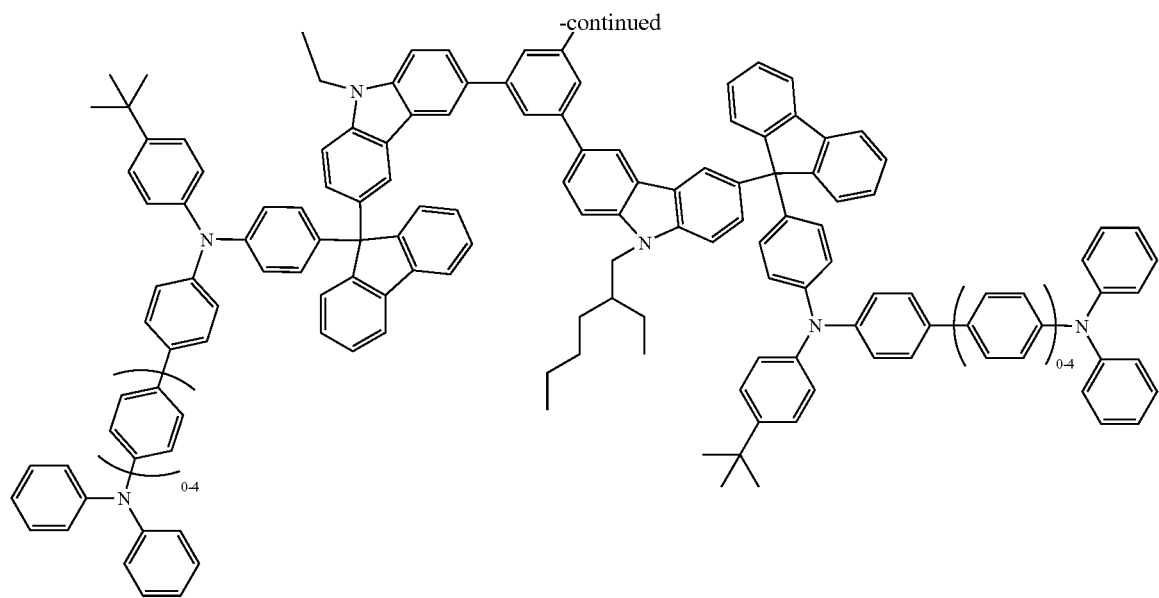
The compound represented by the above Formula 3 may be compounds represented by the following Chemical Formulae 72 to 89.
[Chemical Formula 72]
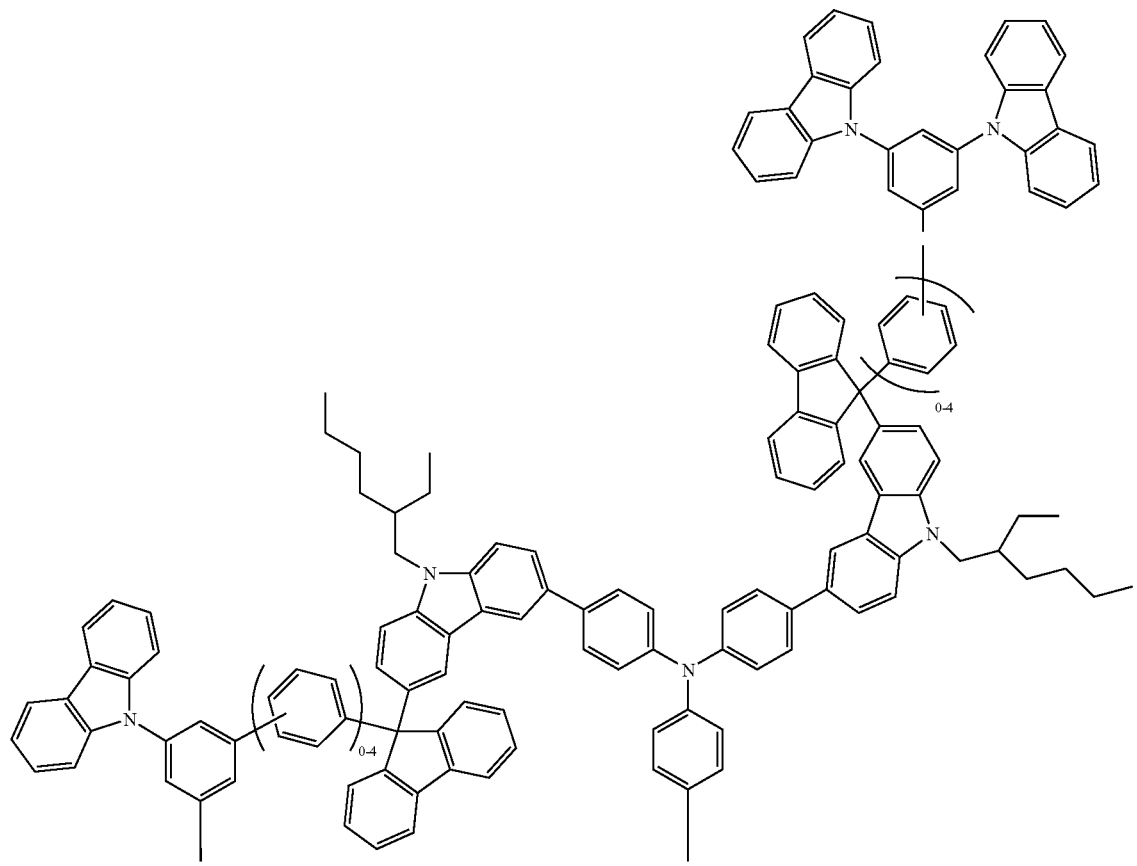

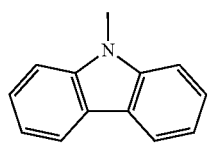
-continued
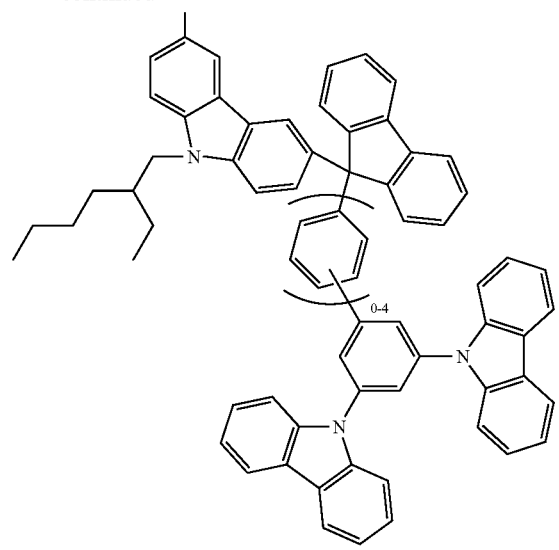
[Chemical Formula 73]
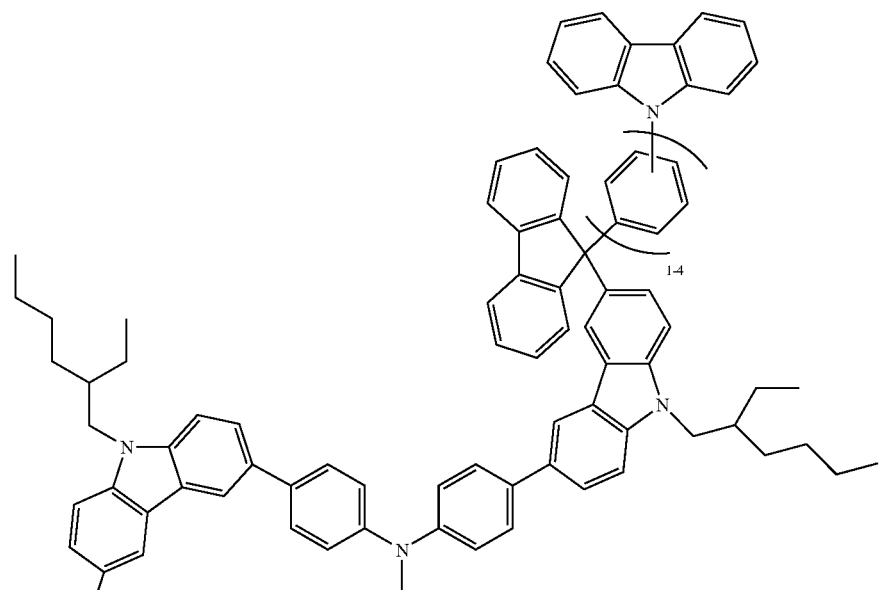

101
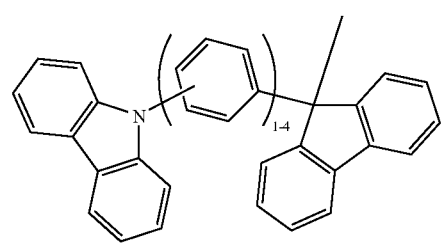
102
-continued
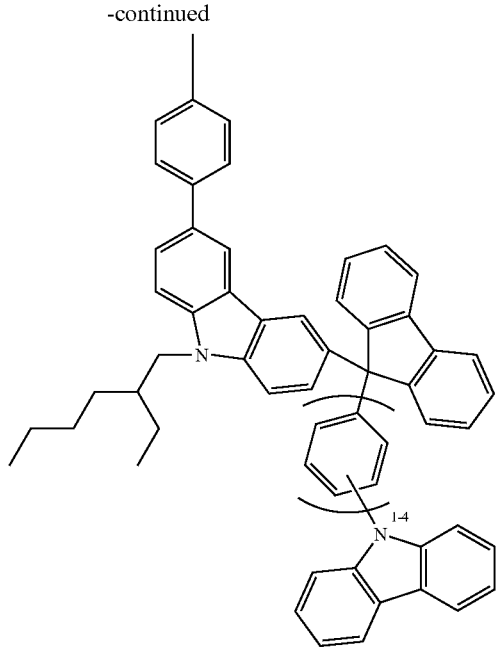
[Chemical Formula 74]
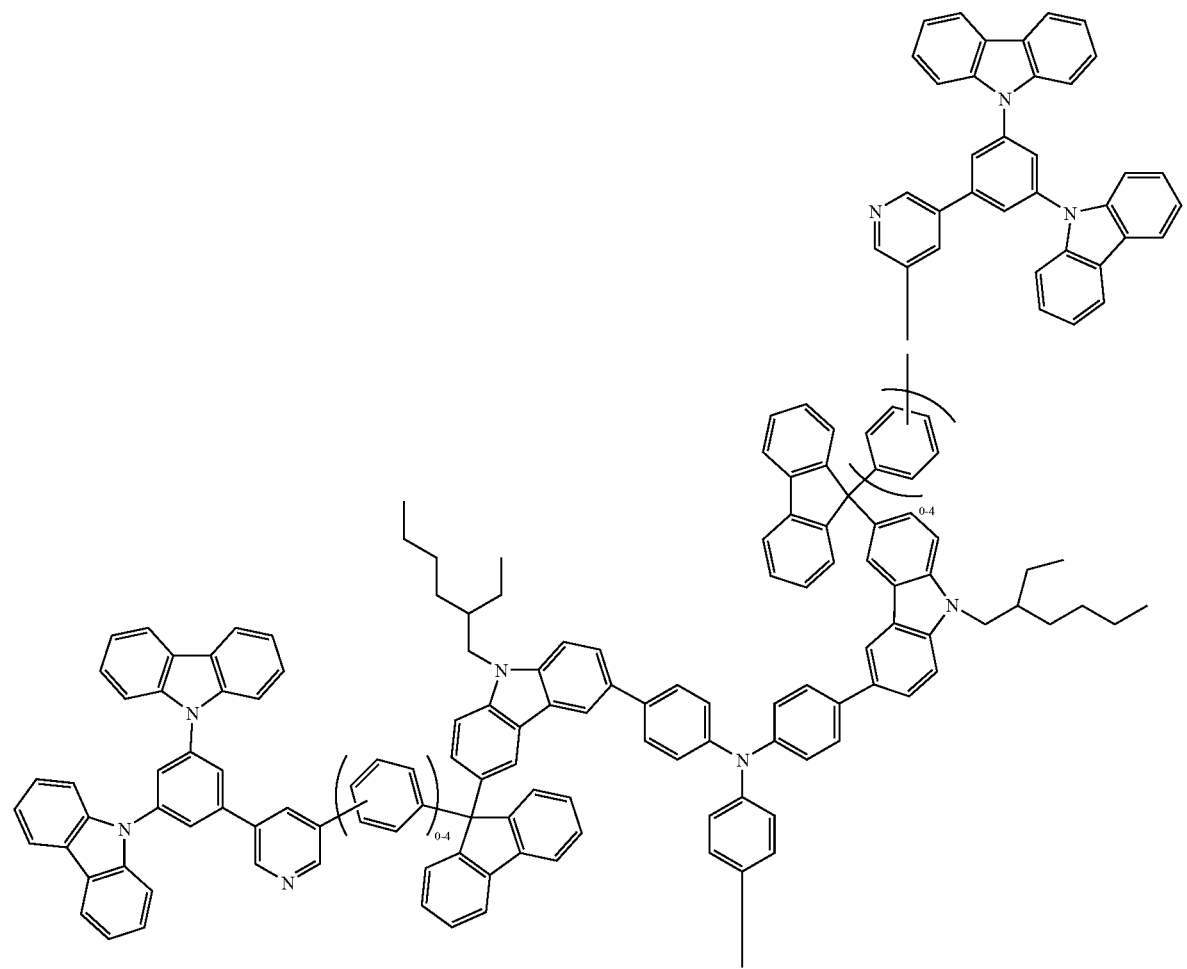

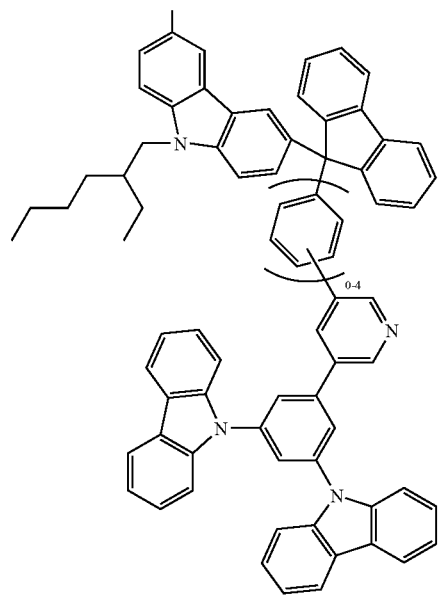
[Chemical Formula 75]
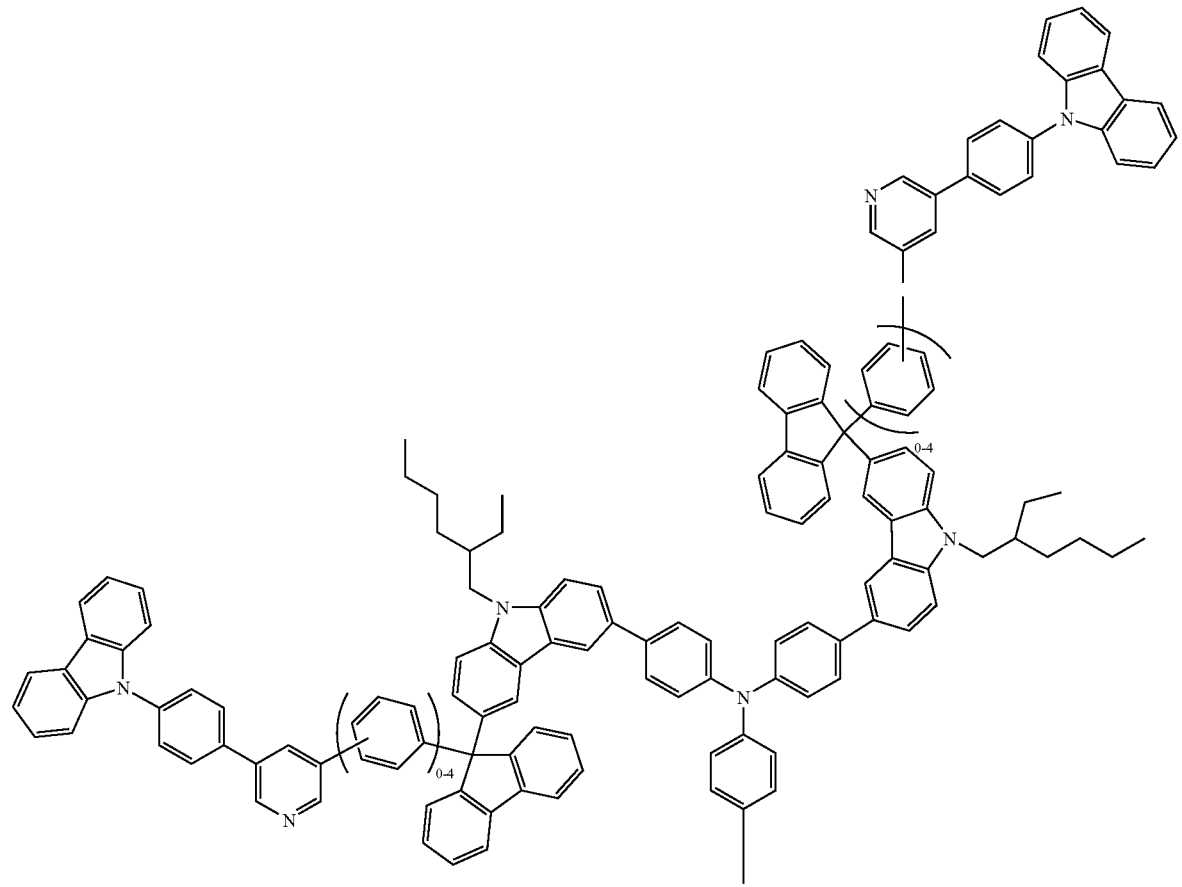

-continued
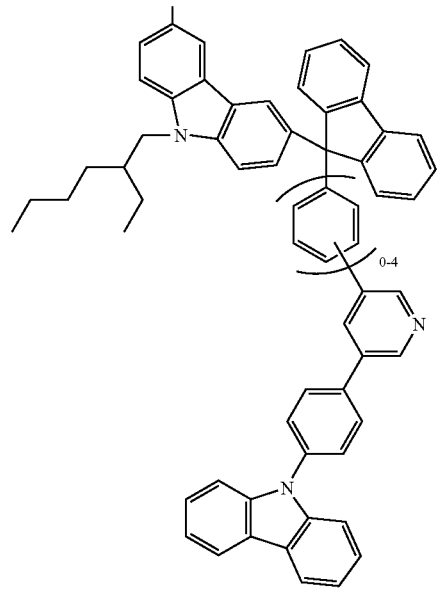
[Chemical Formula 76]
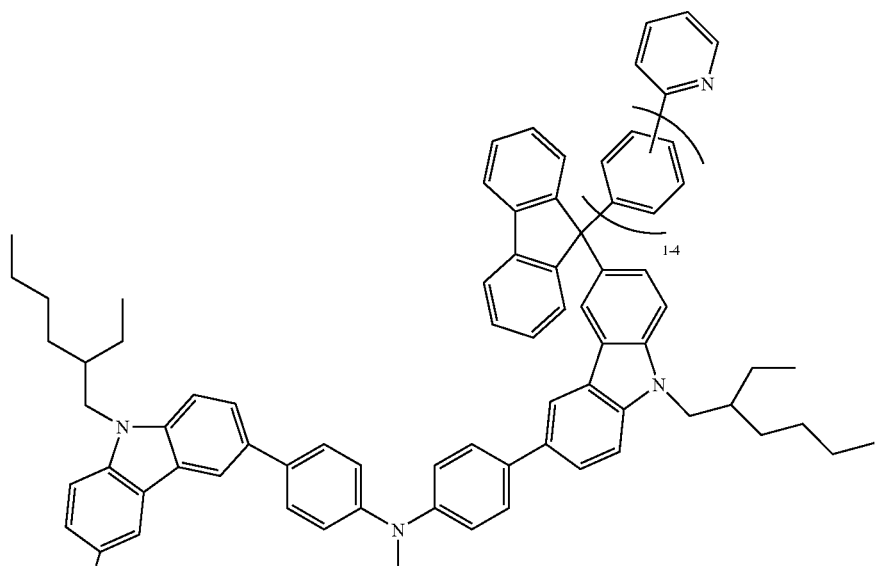

107
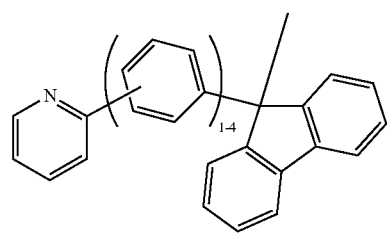
-continued
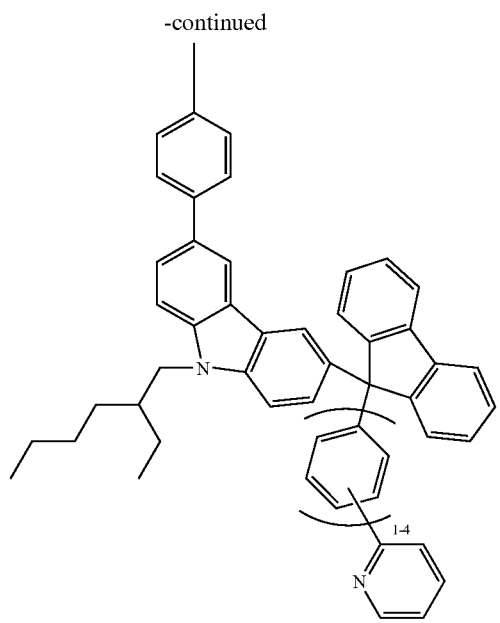
[Chemical Formula 77]
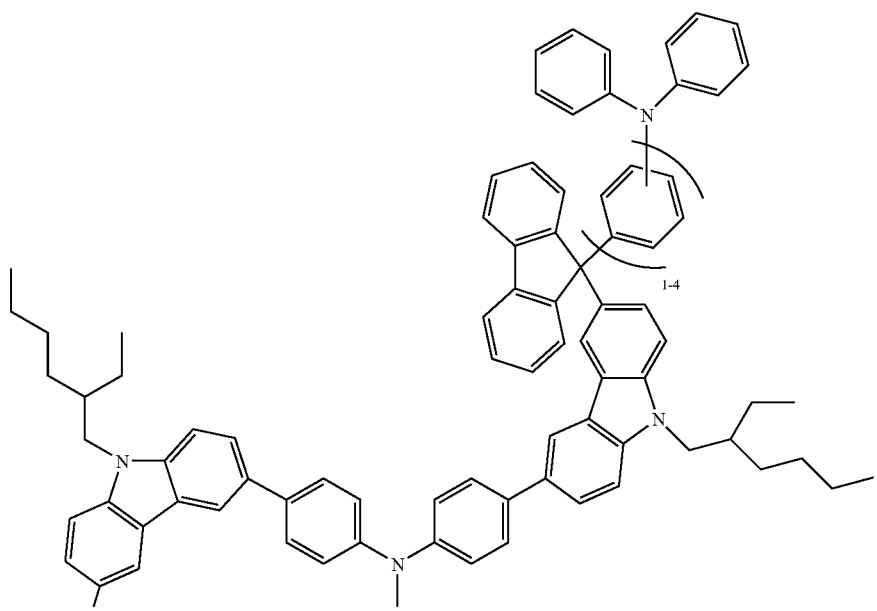

-continued
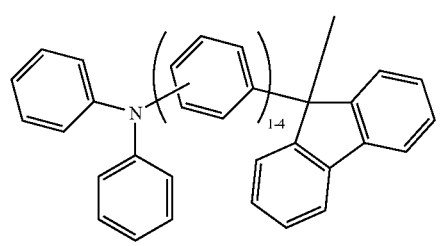
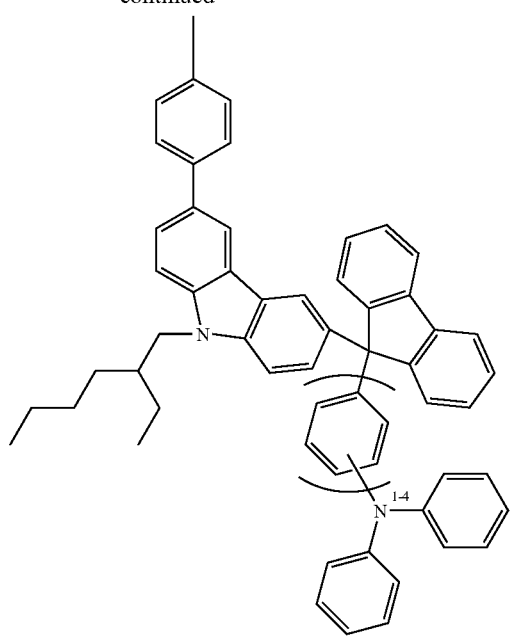
[Chemical Formula 78]
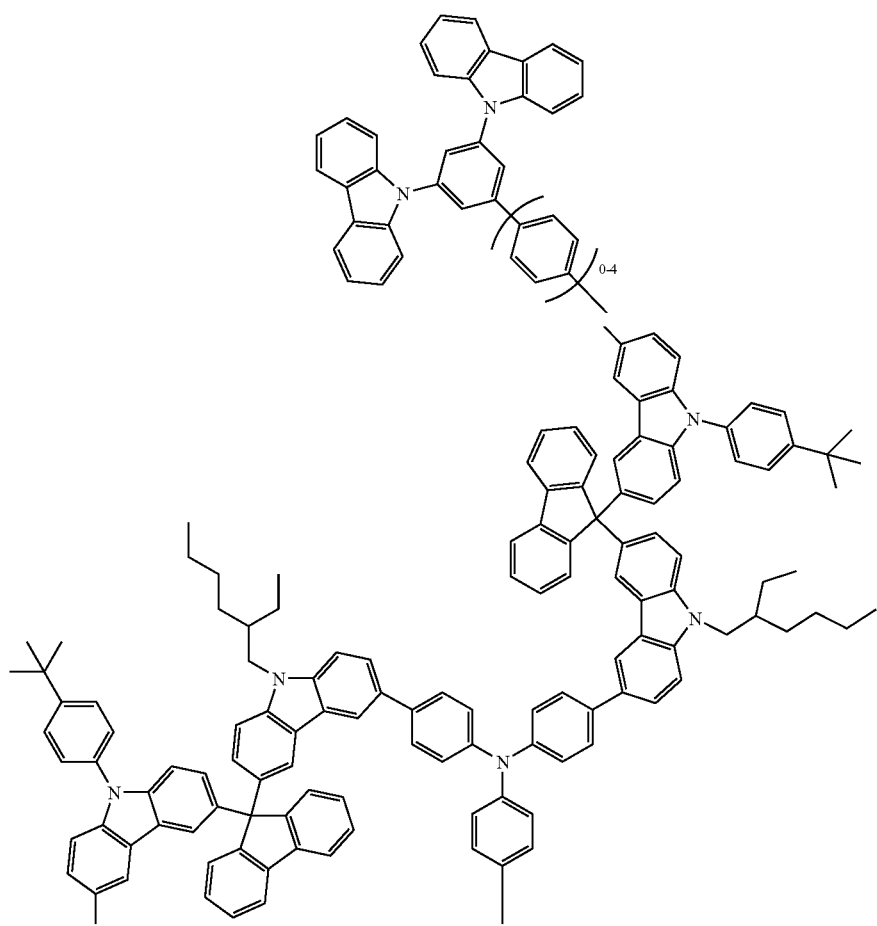

111
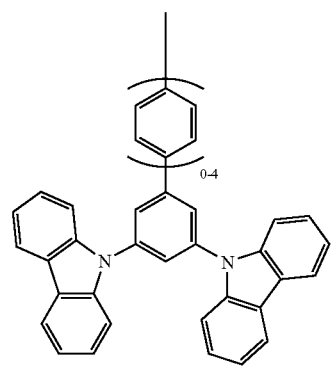
-continued
112
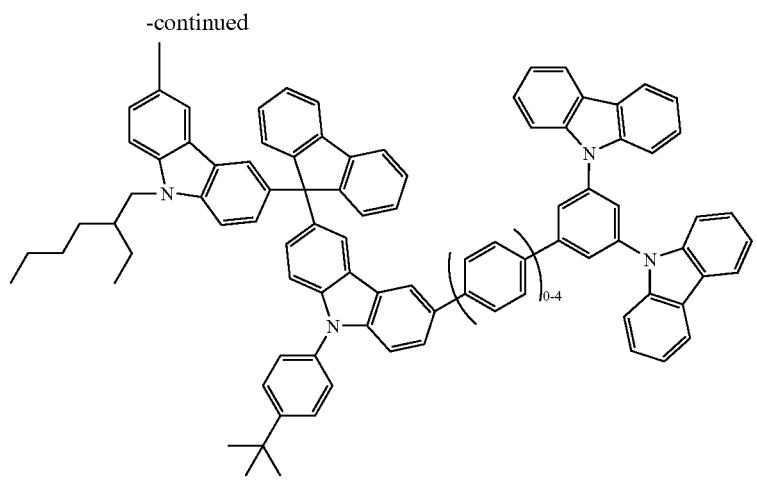
[Chemical Formula 79]
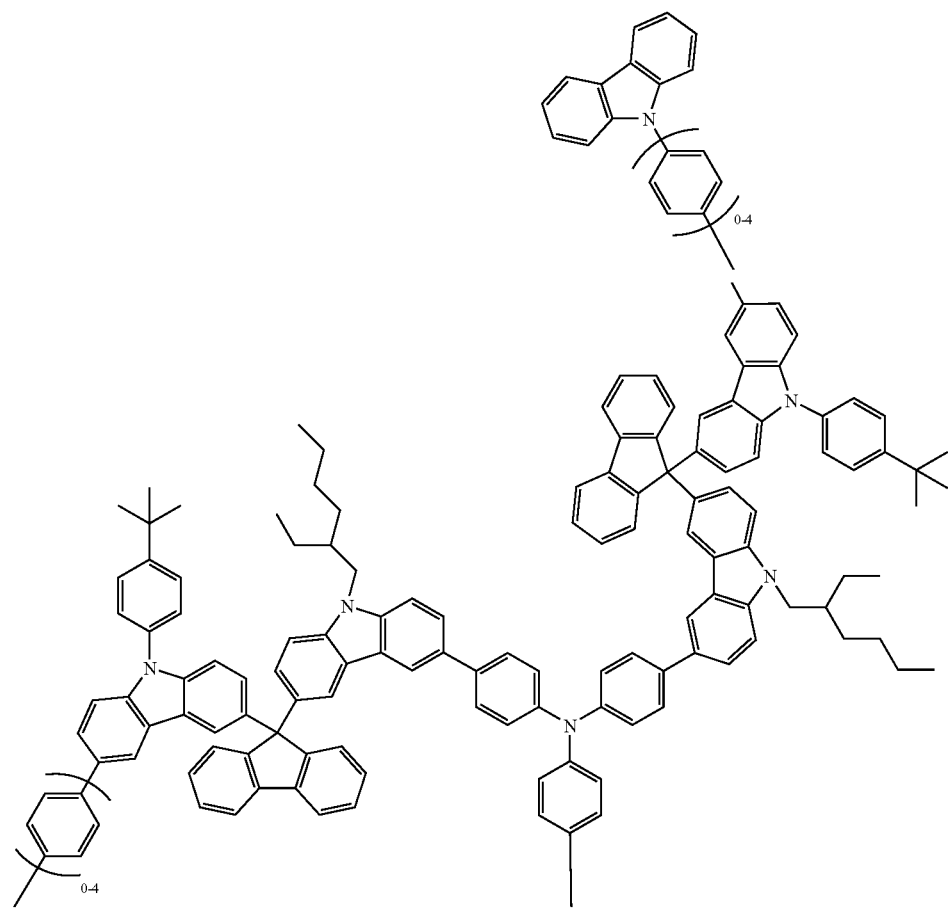

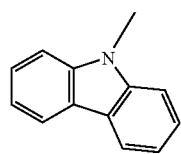
-continued
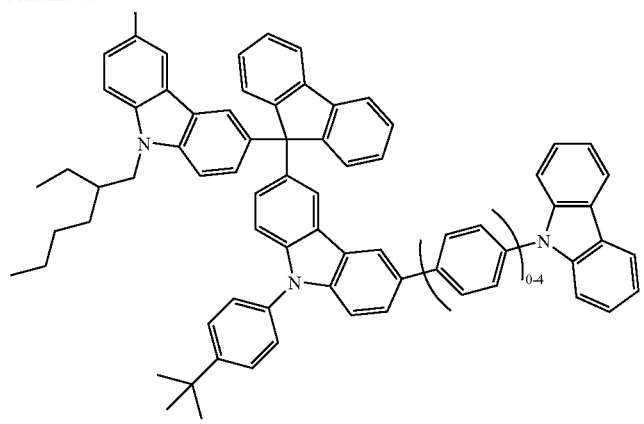
[Chemical Formula 80]
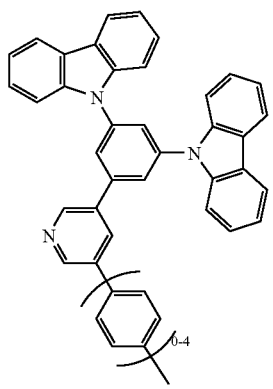
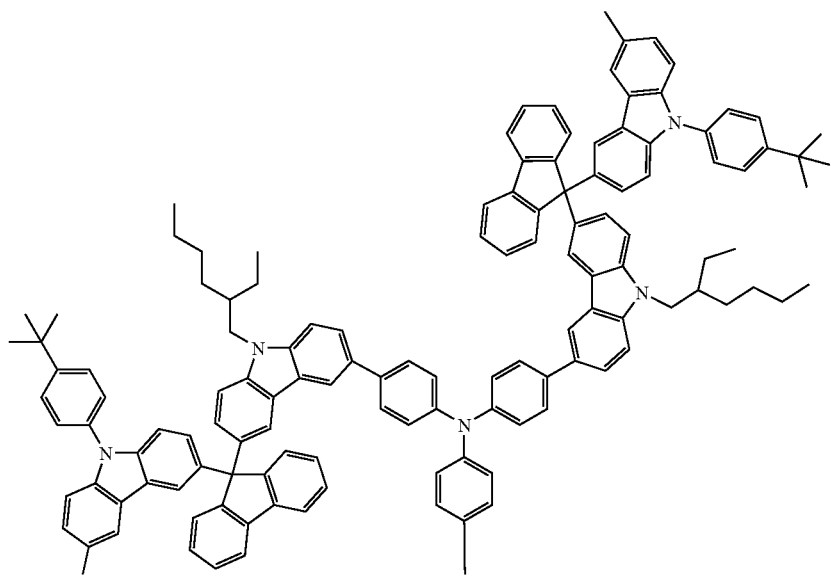

115
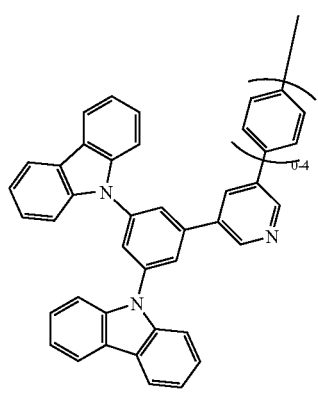
116
-continued
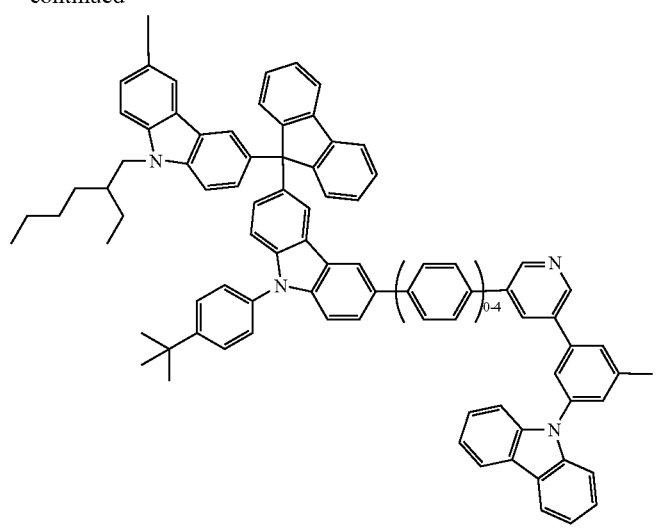
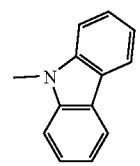
[Chemical Formula 81]
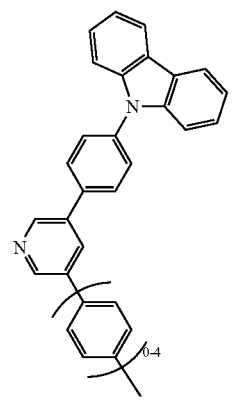

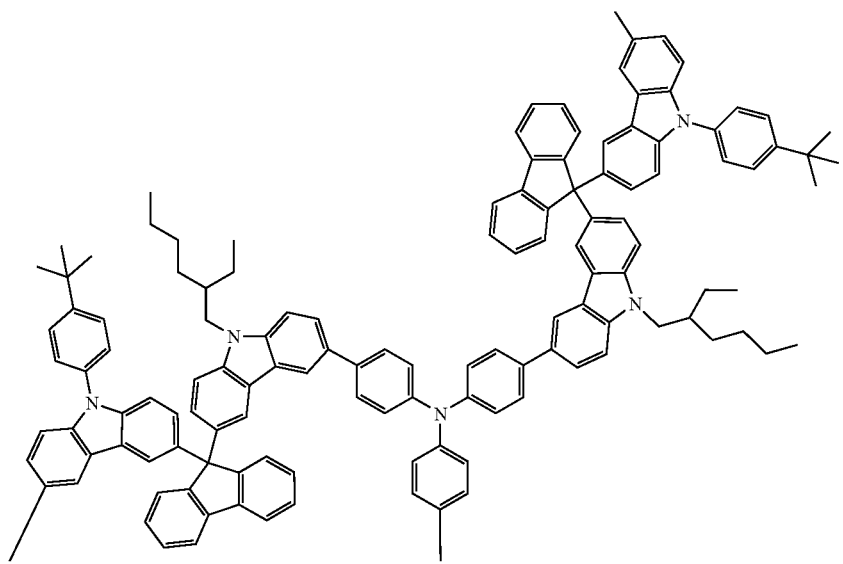
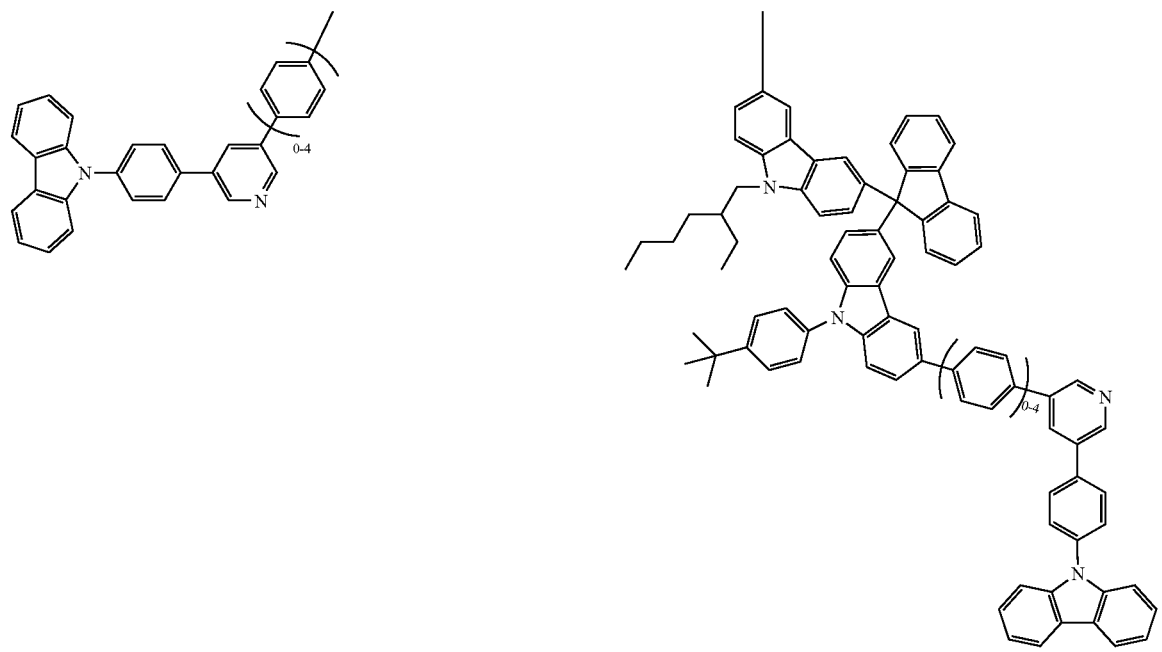
[Chemical Formula 82]
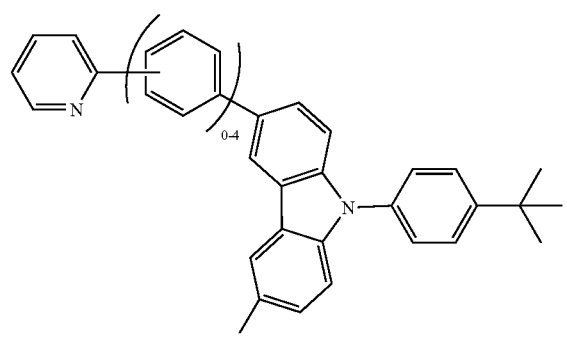

-continued
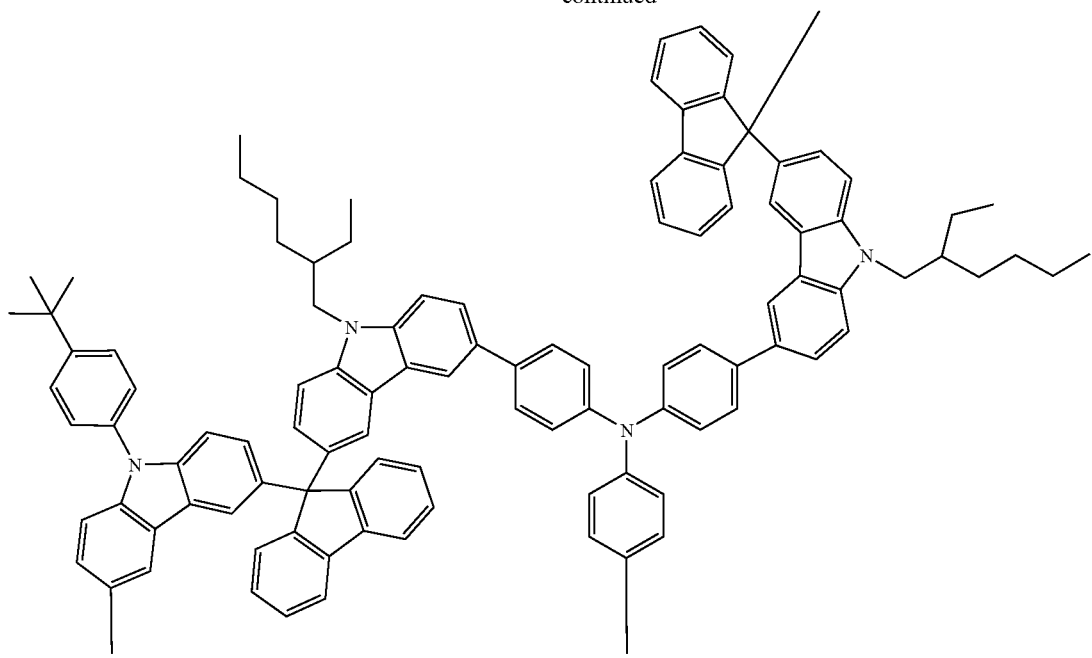
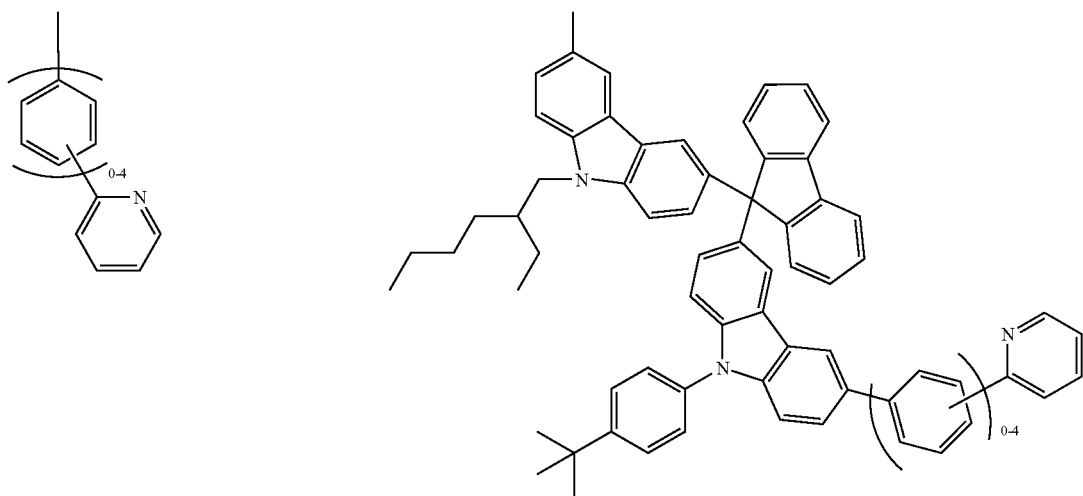
[Chemical Formula 83]
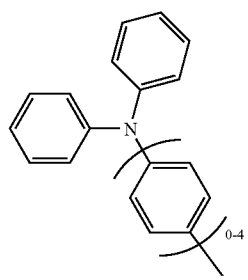

121 122
-continued
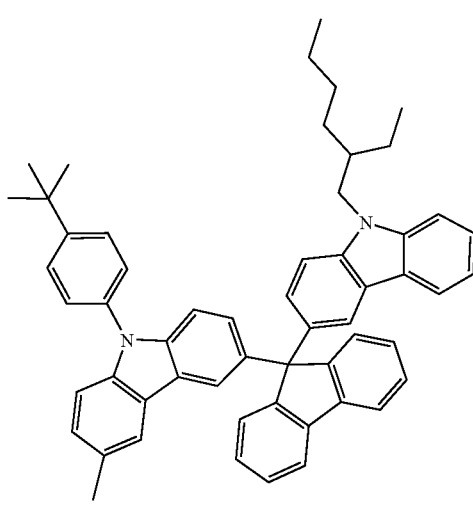
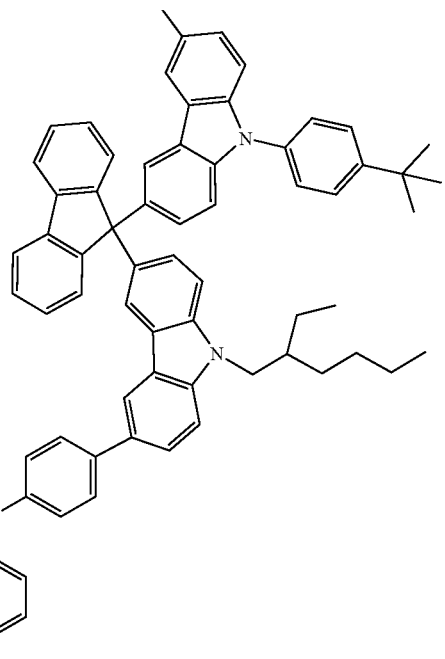
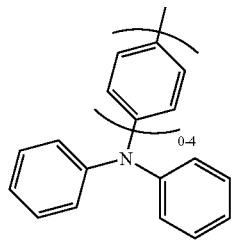
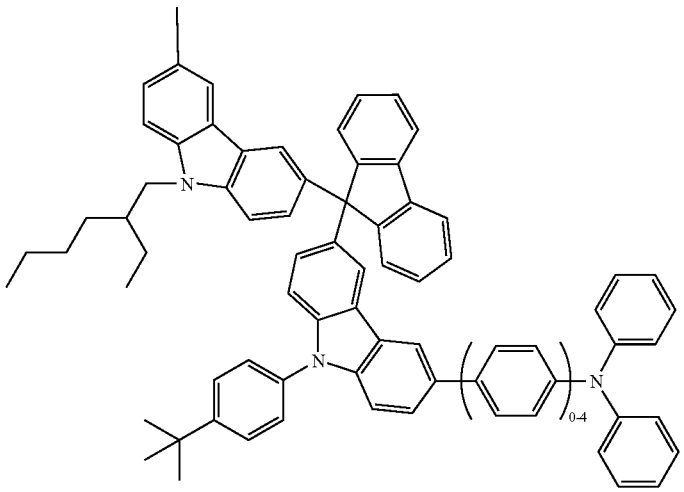
[Chemical Formula 84]
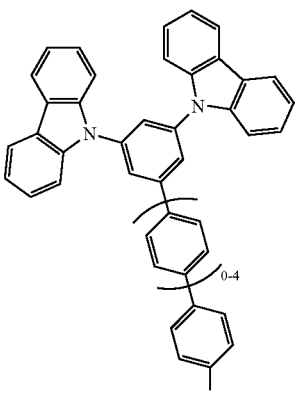

-continued
123
124
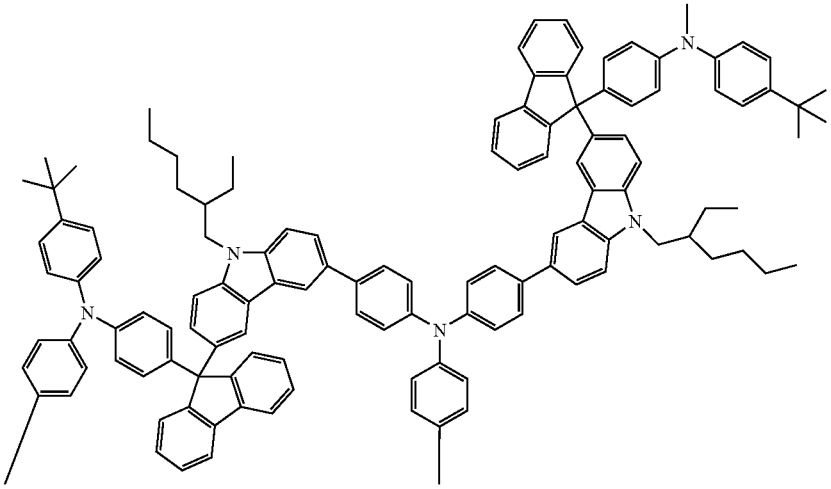
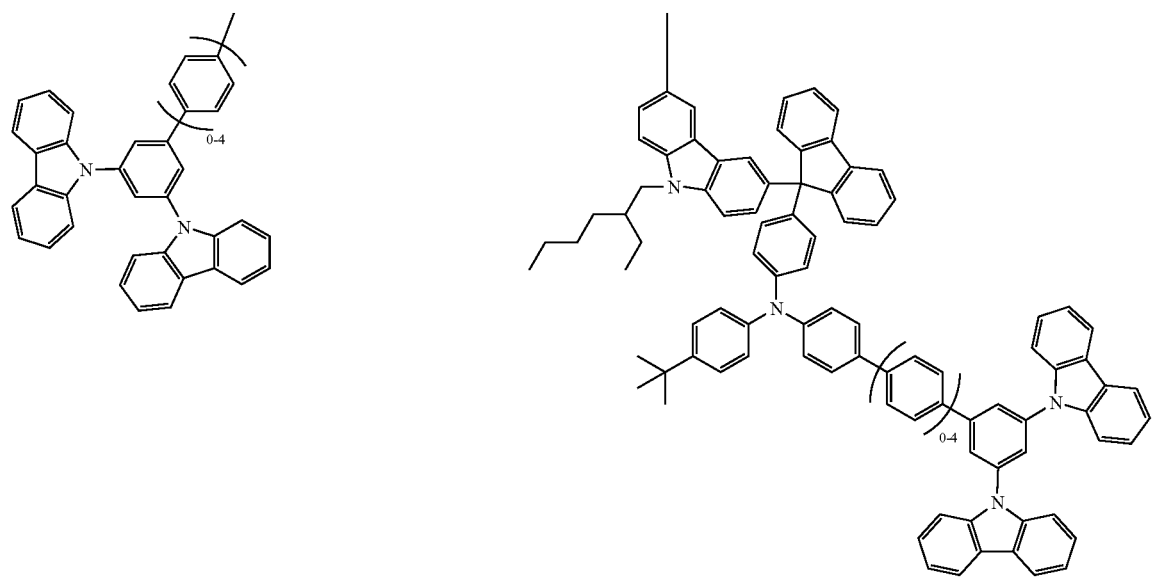
[Chemical Formula 85]
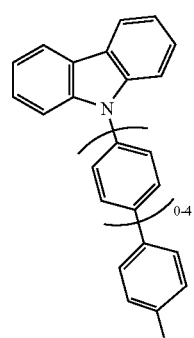

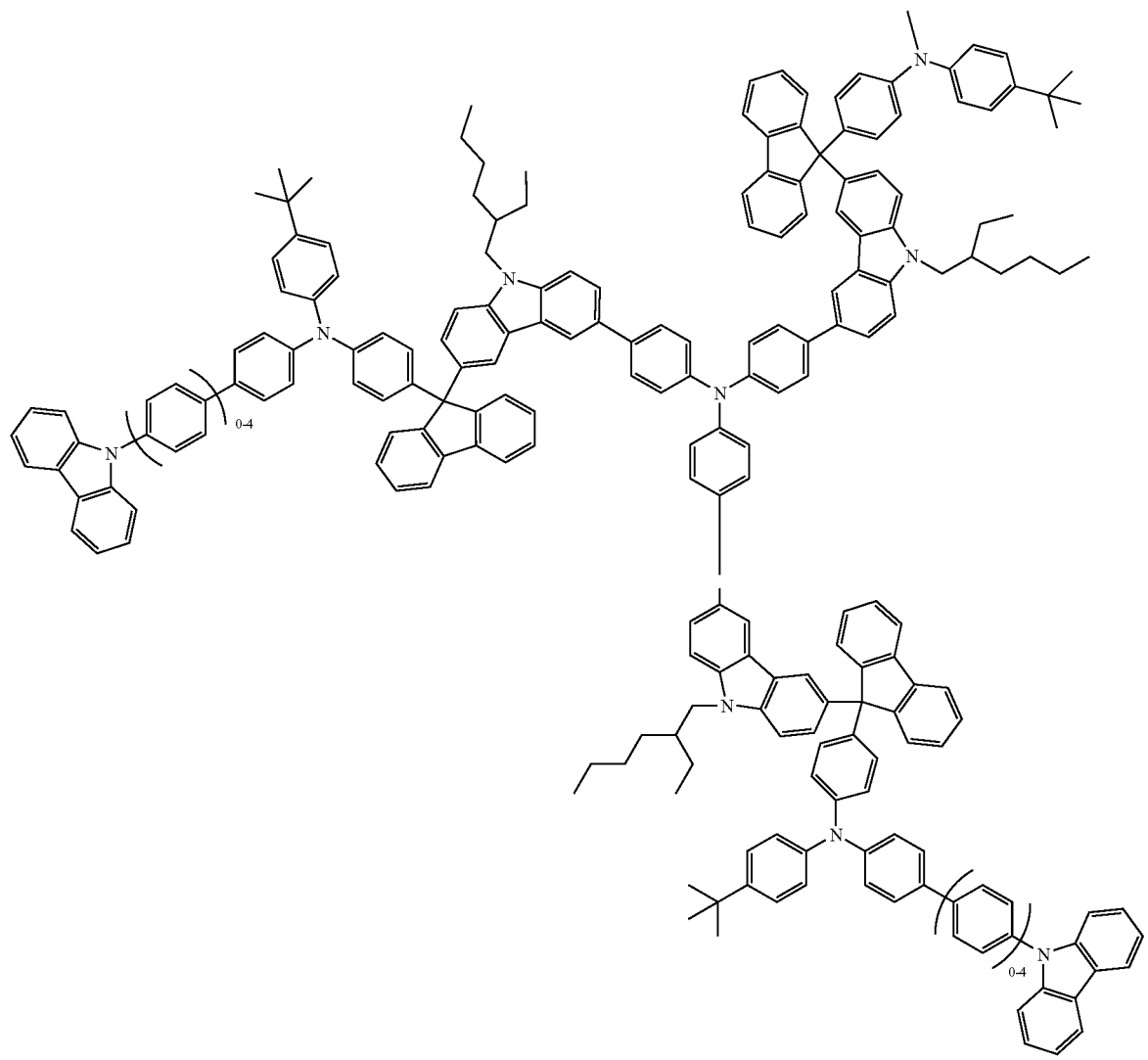
[Chemical Formula 86]
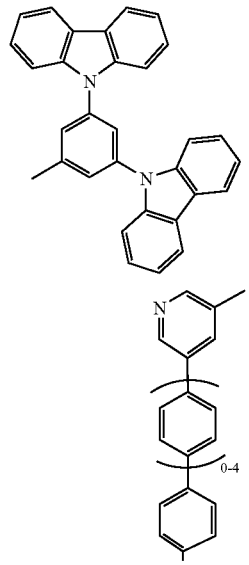

-continued
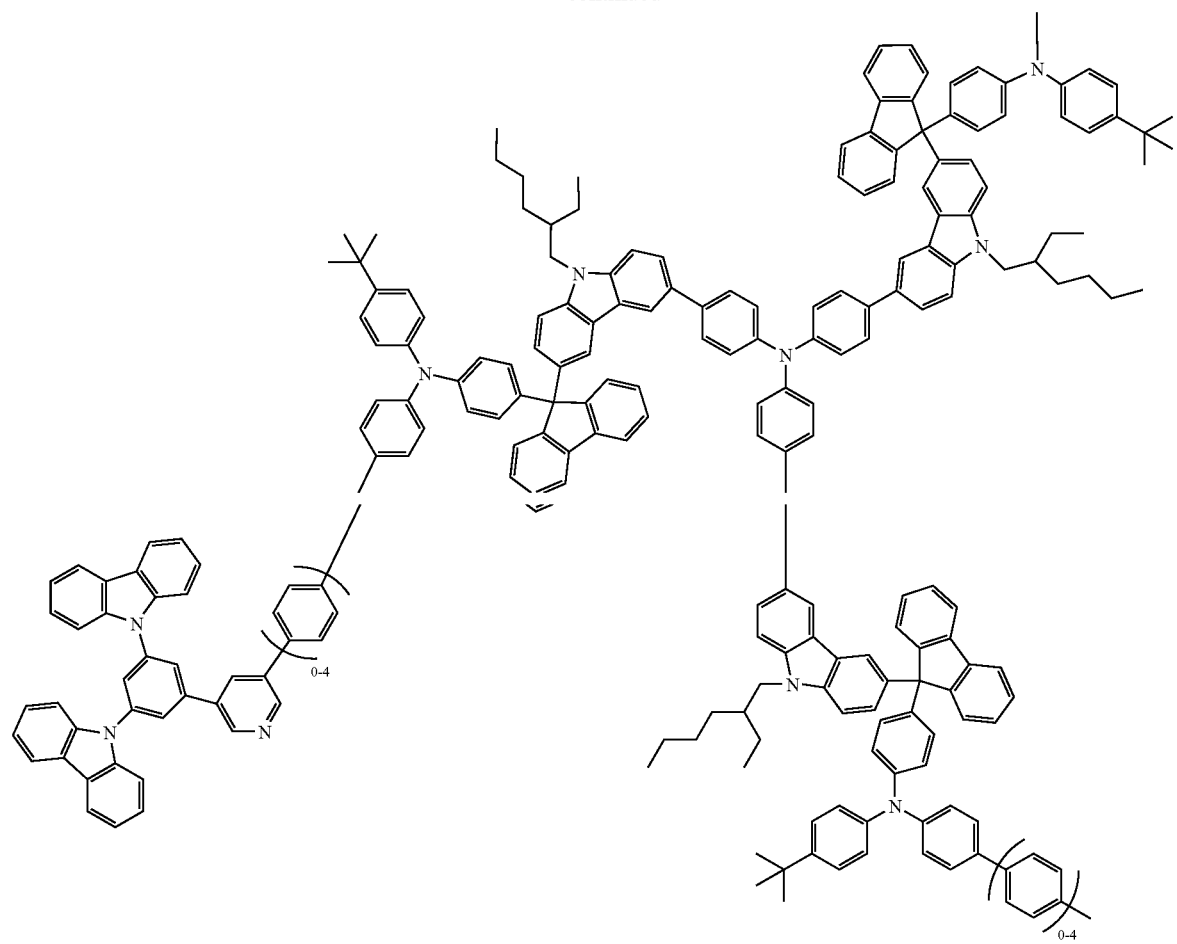
[Chemical Formula 87]
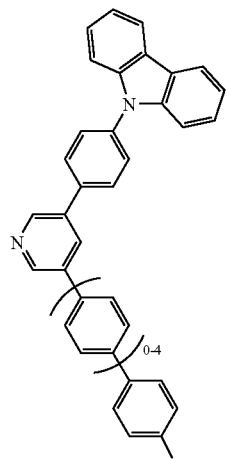

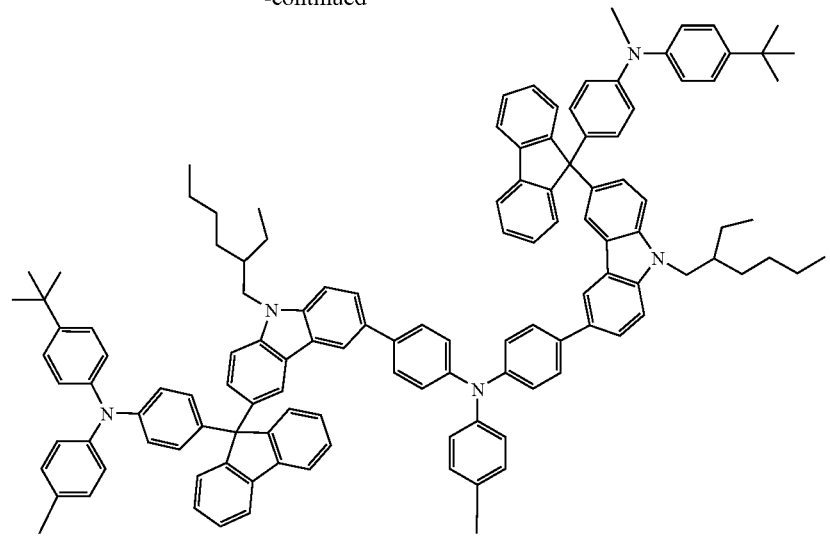
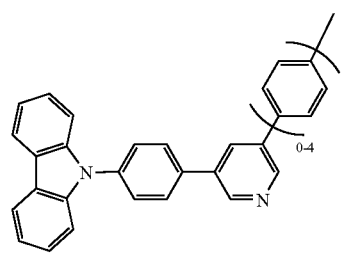
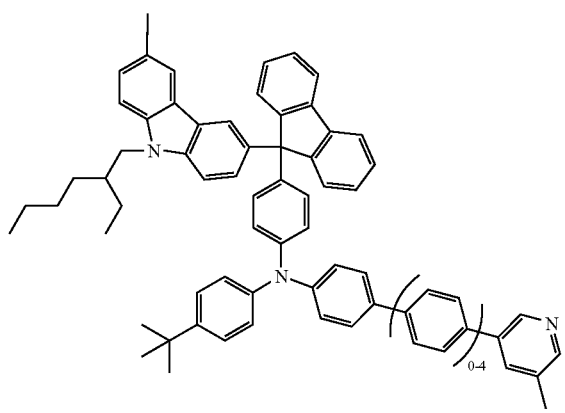
[Chemical Formula 88]
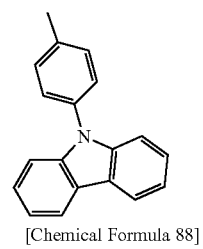
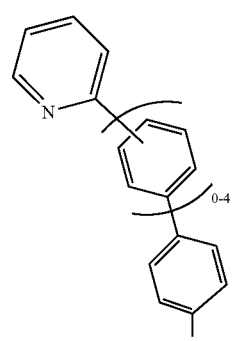

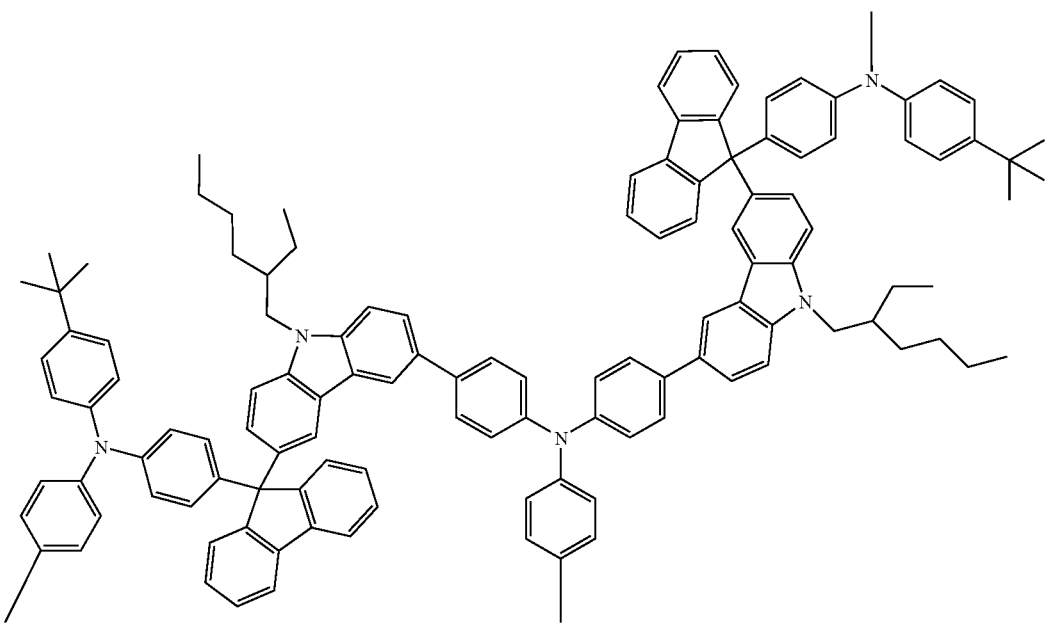
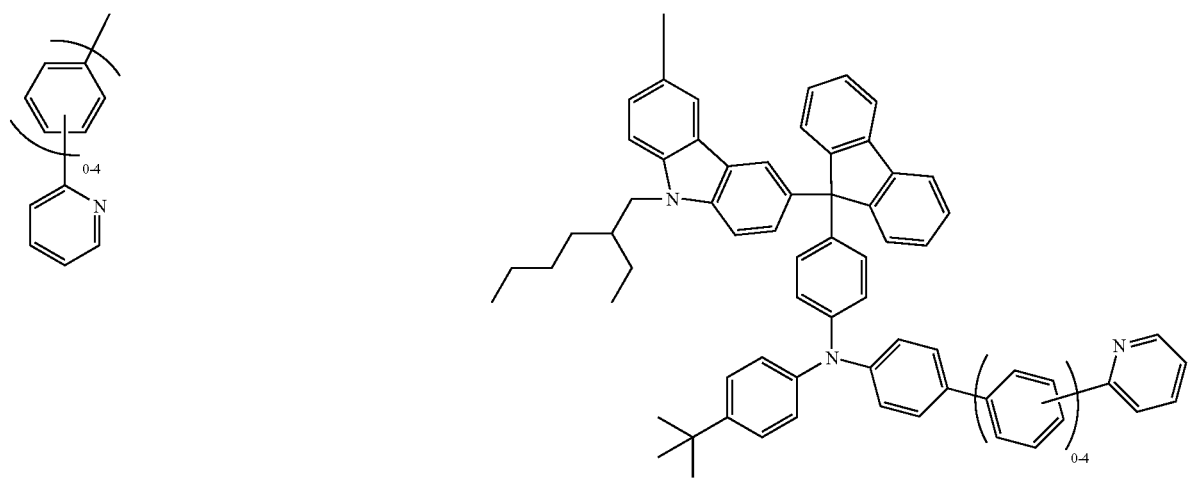
[Chemical Formula 89]
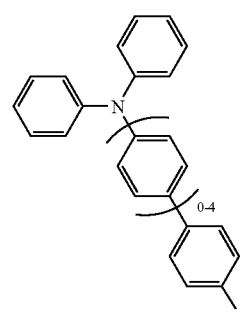

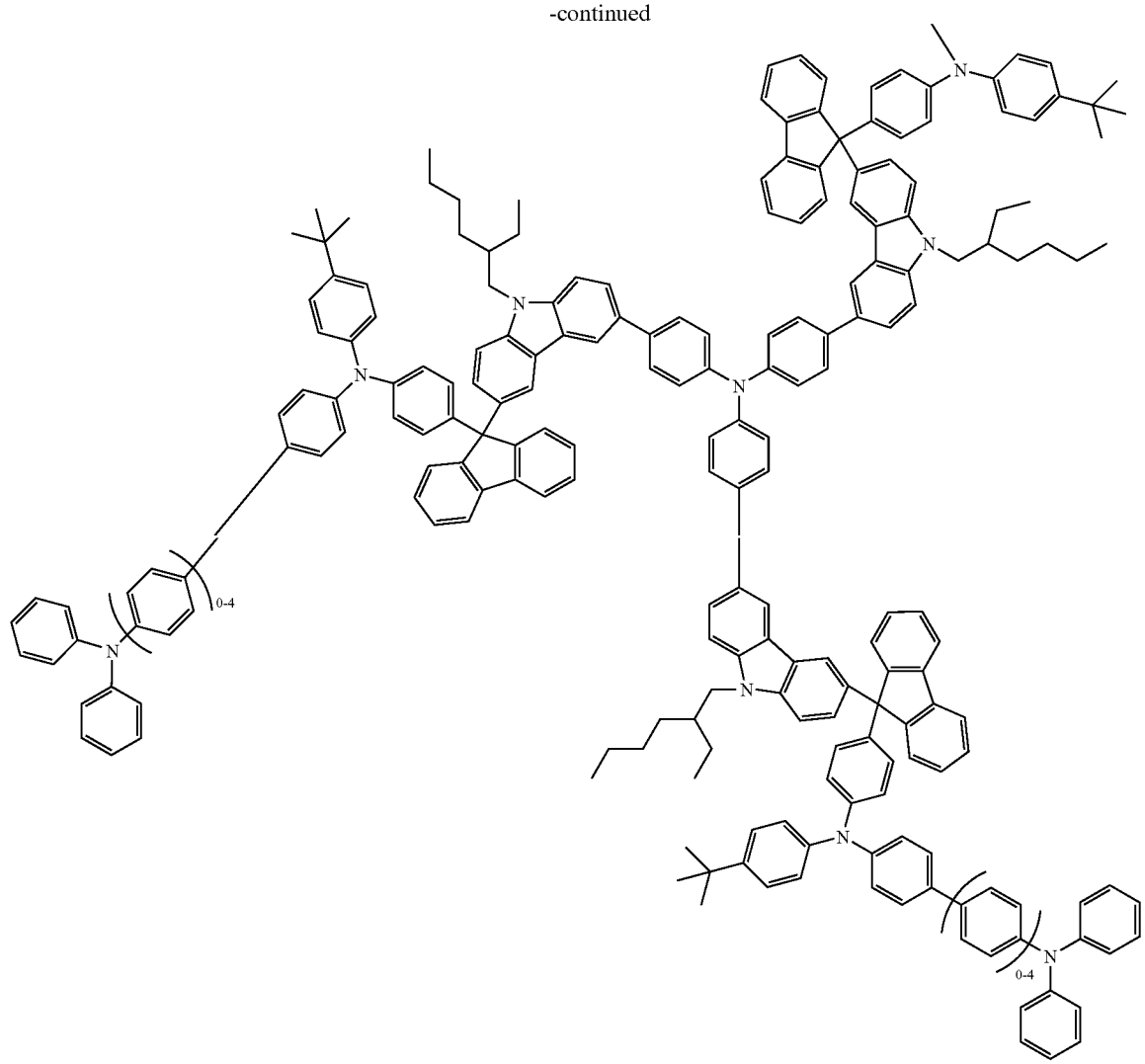
The compound represented by the above Formula 4 may be compounds represented by the following Chemical Formulae 90 to 107.
[Chemical Formula 90]
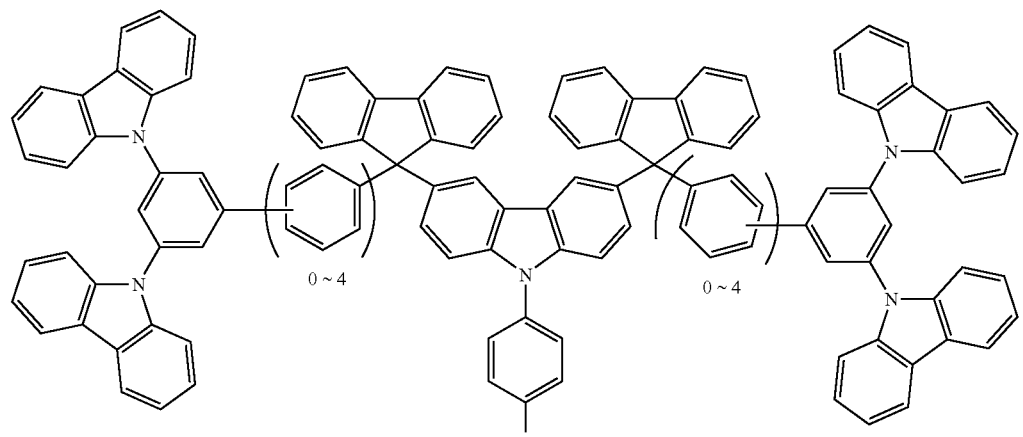

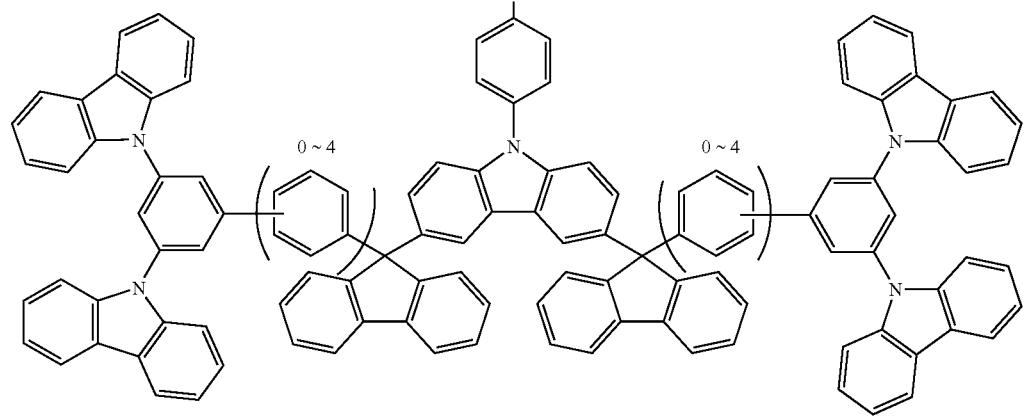
[Chemical Formula 91]
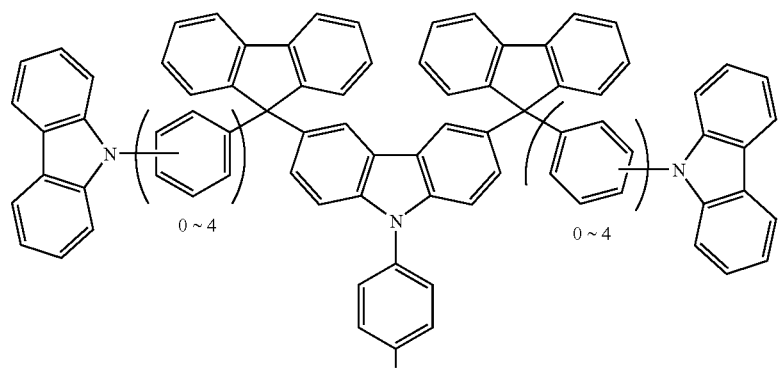
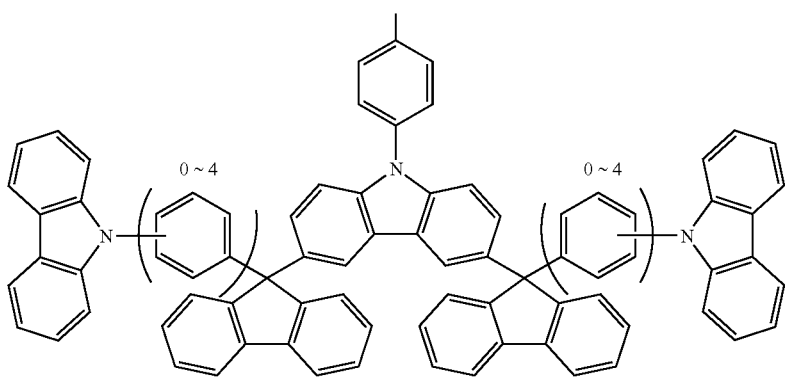

[Chemical Formula 92]
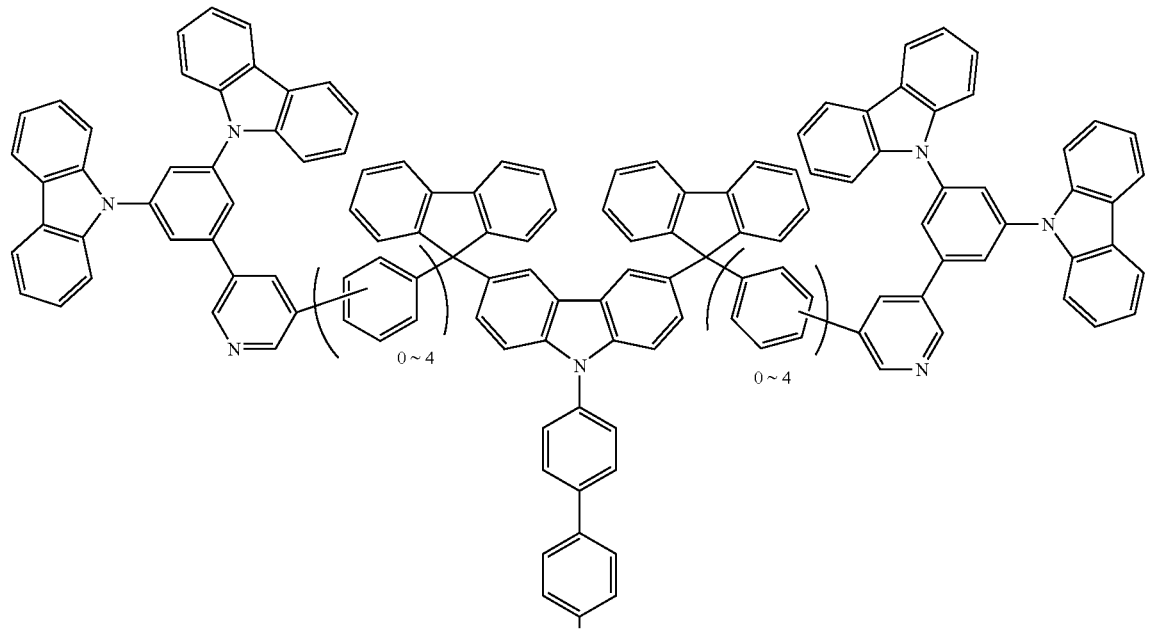
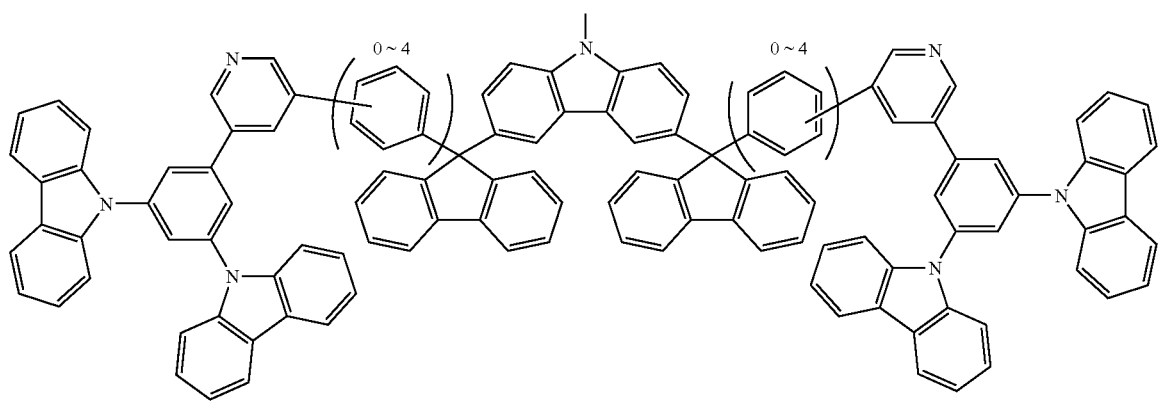

[Chemical Formula 93]
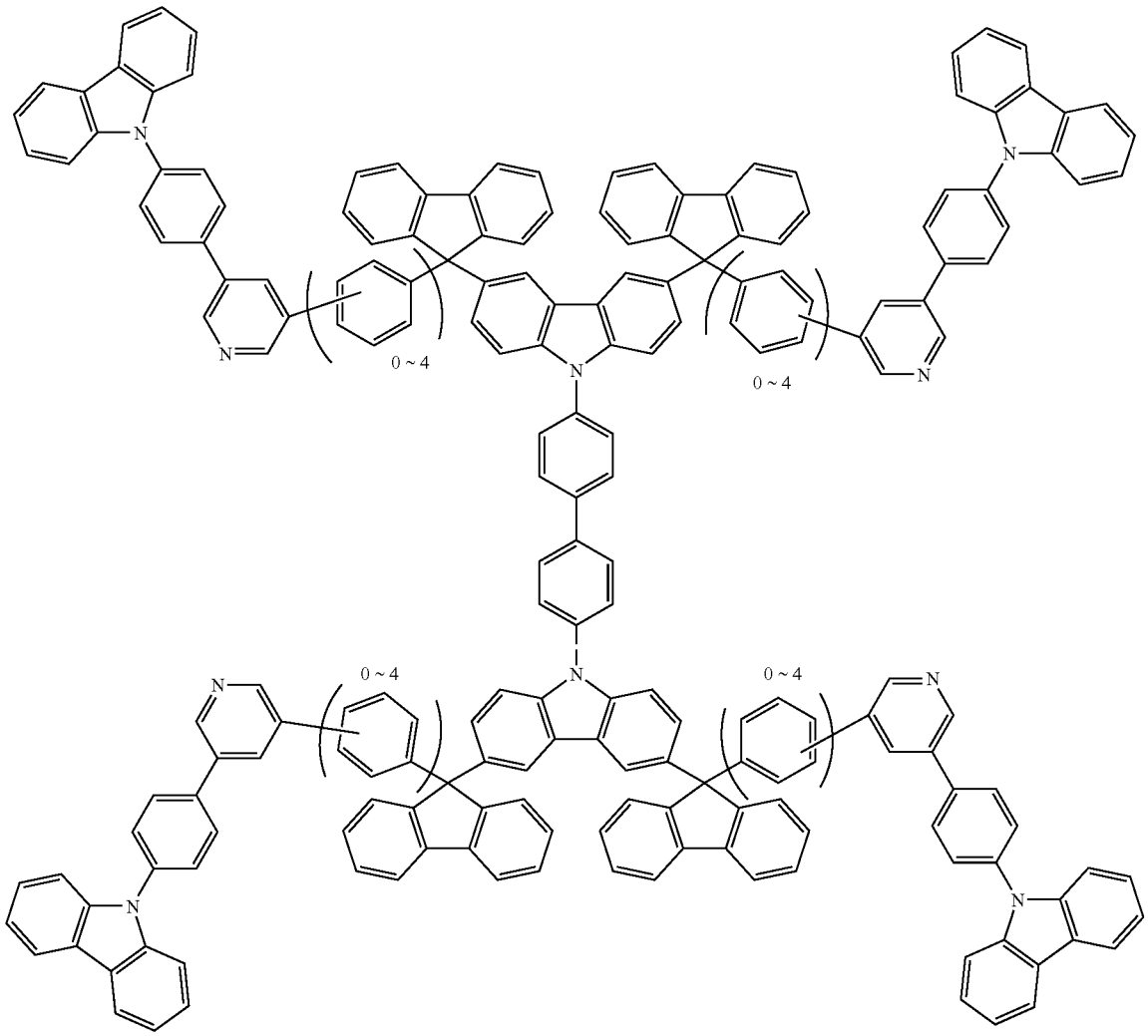
[Chemical Formula 94]
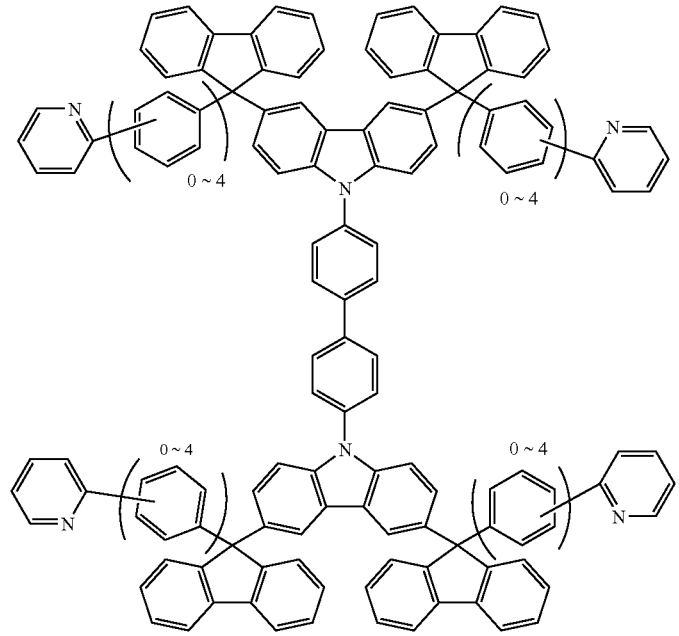

-continued
[Chemical Formula 95]
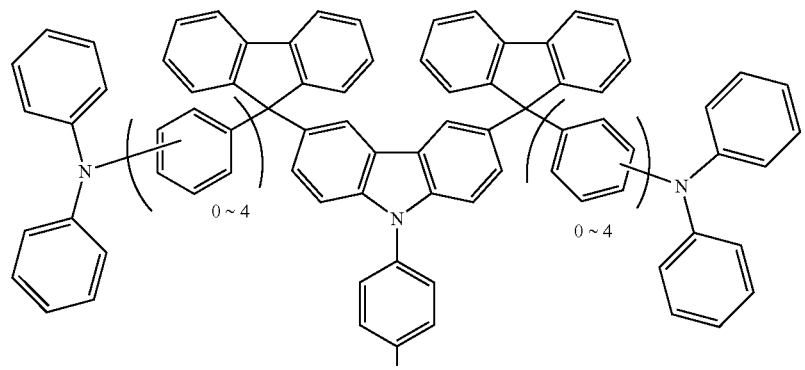
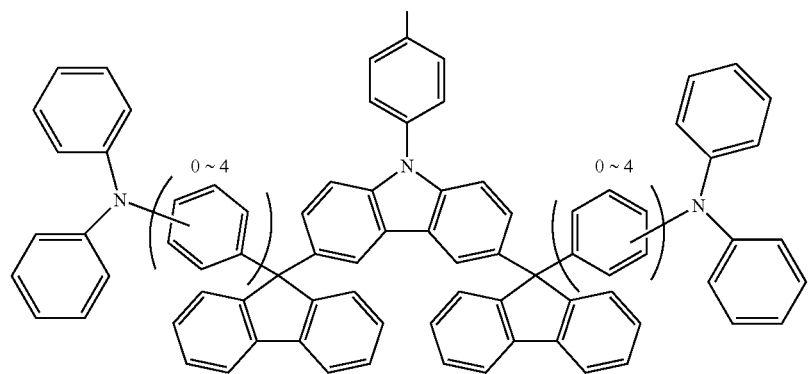
[Chemical Formula 96]
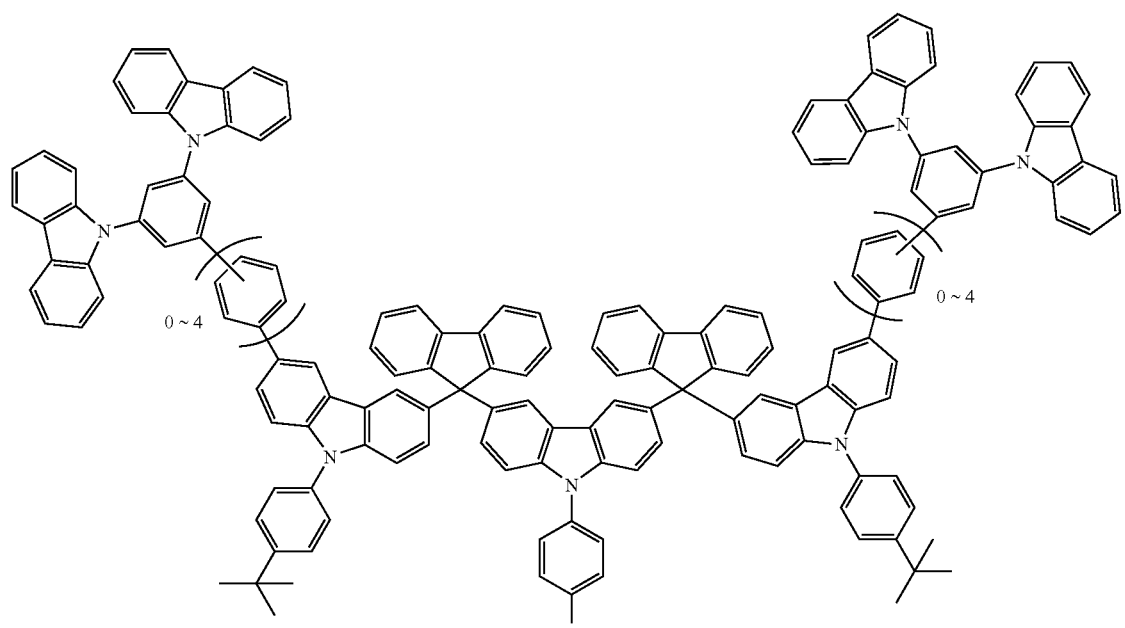

-continued
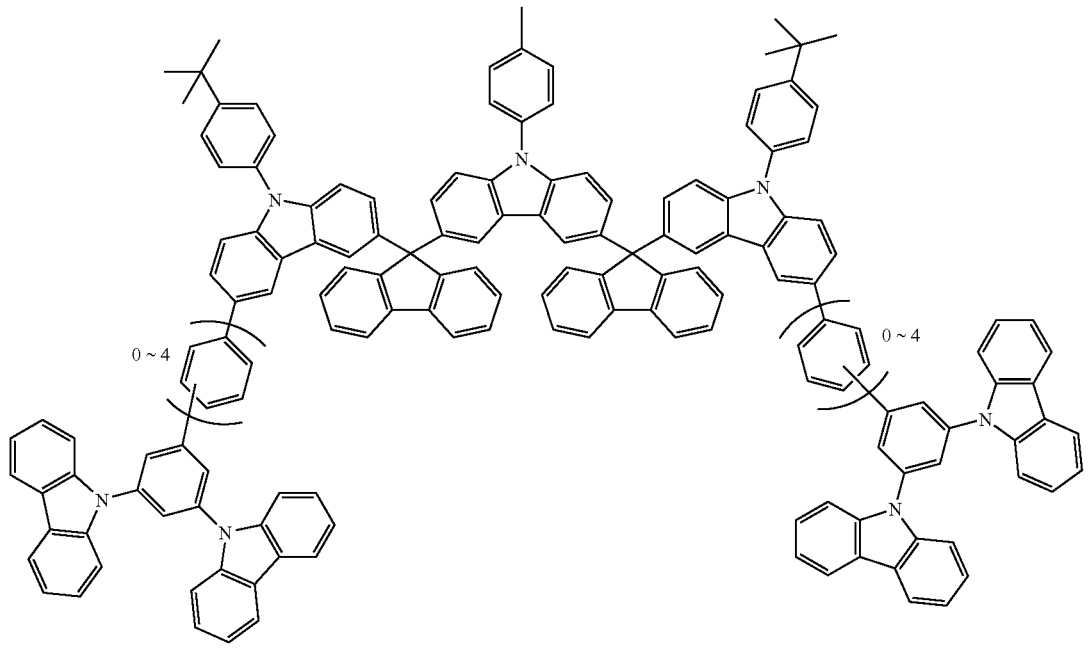
[Chemical Formula 97]
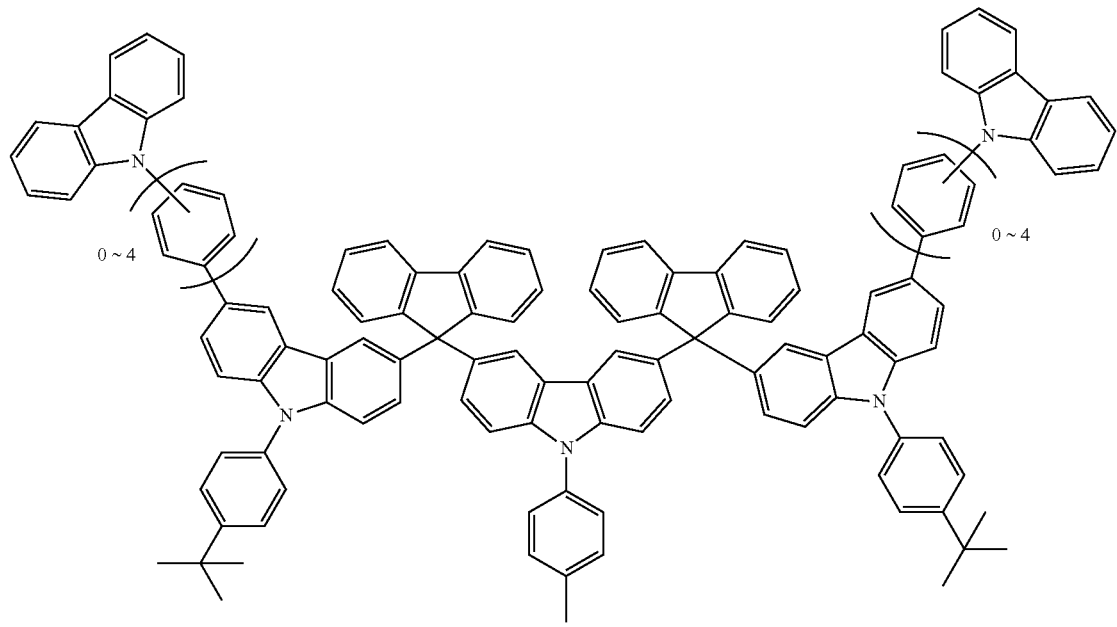

-continued
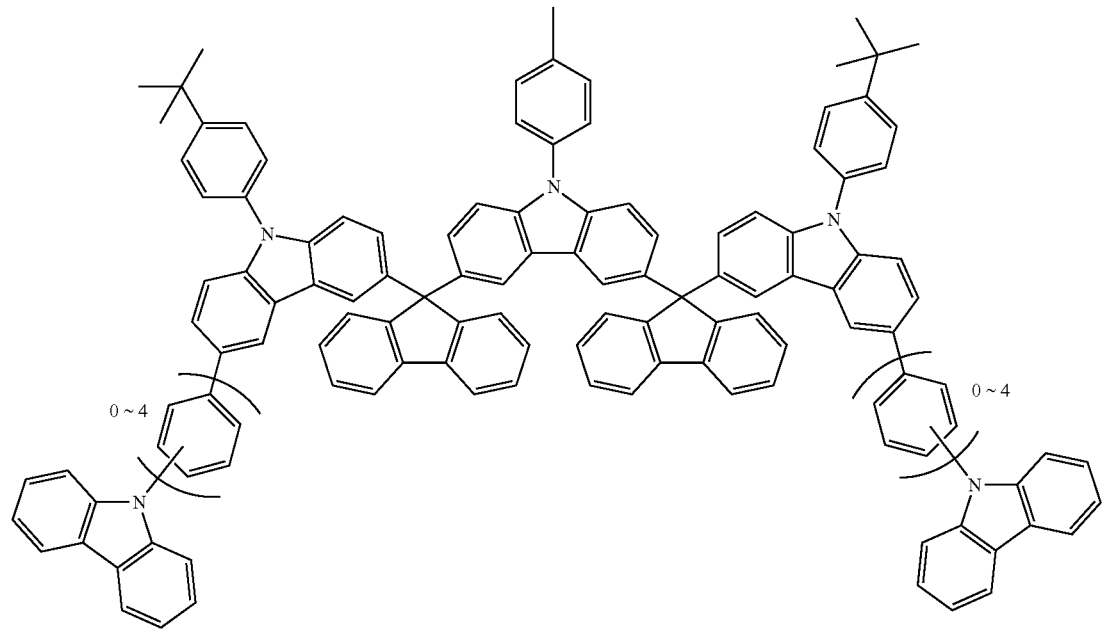
[Chemical Formula 98]
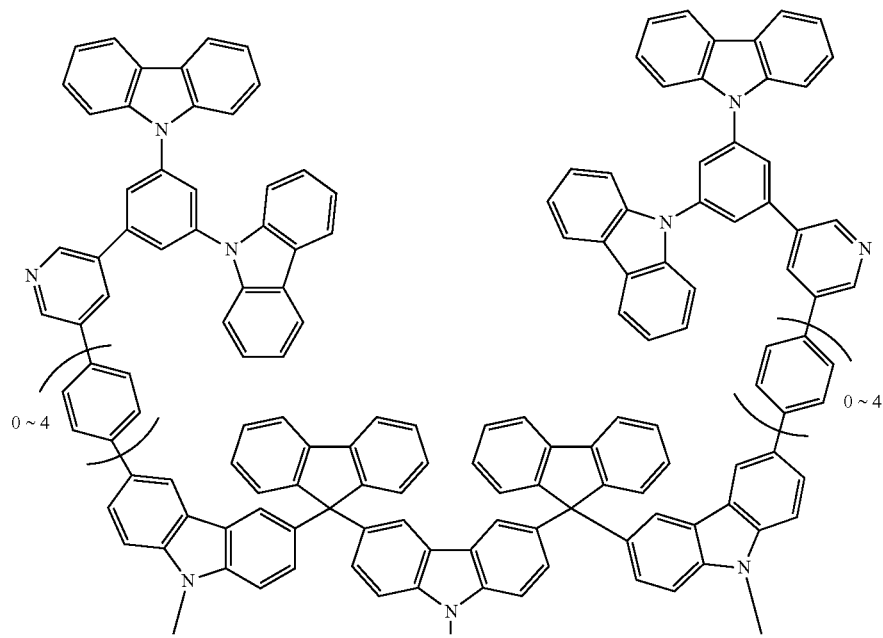

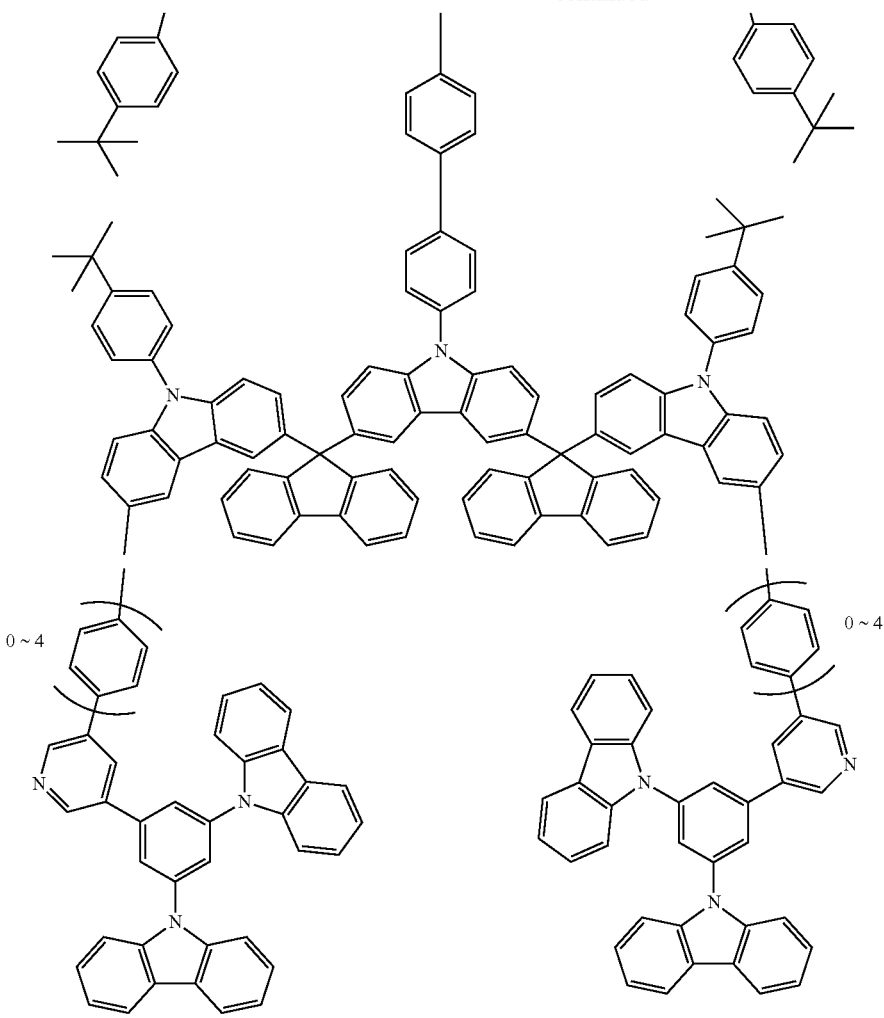
[Chemical Formula 99]
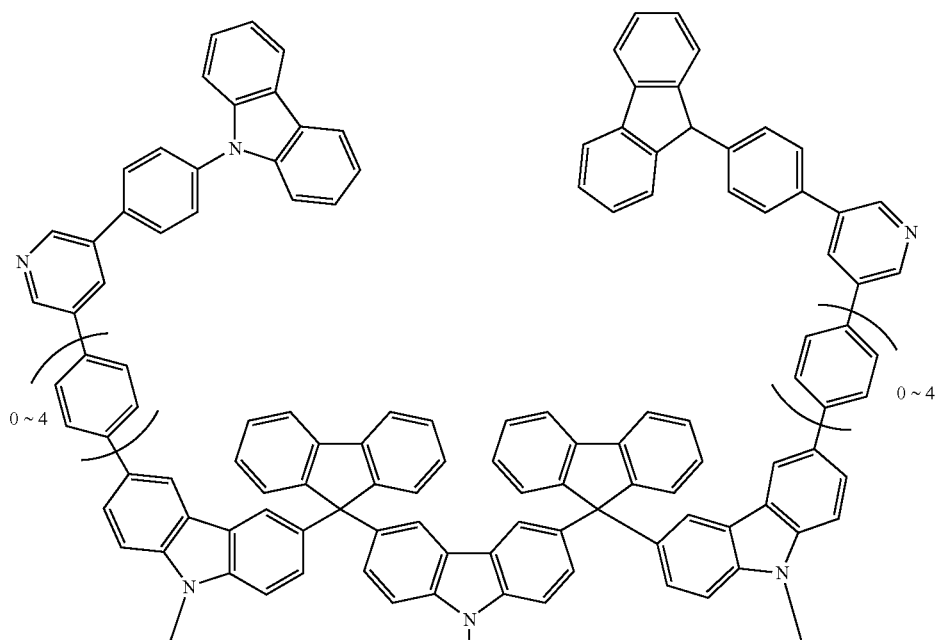

-continued
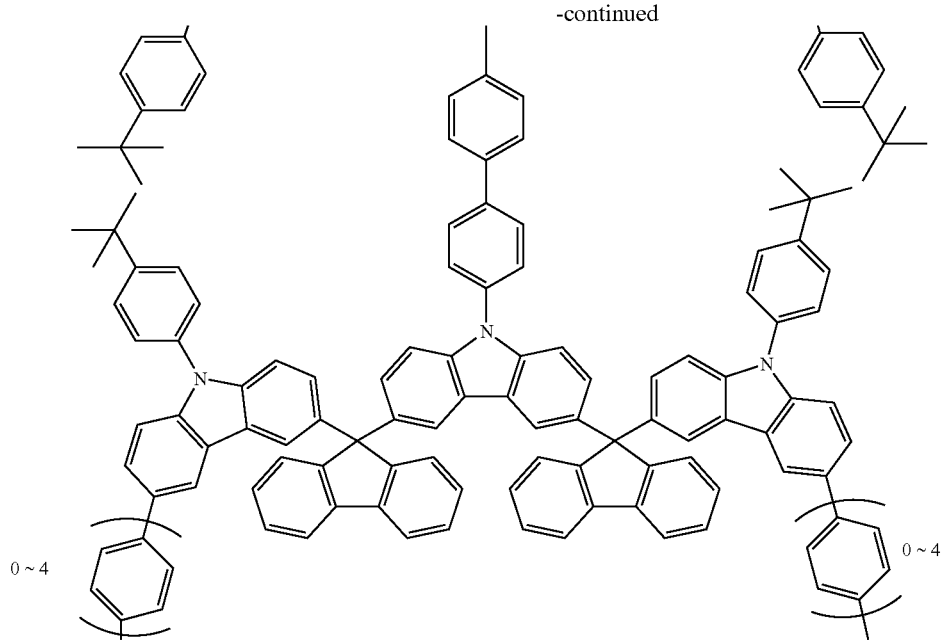
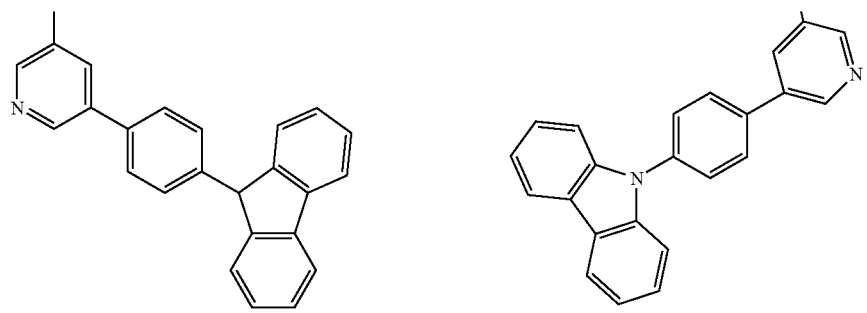
[Chemical Formula 100]
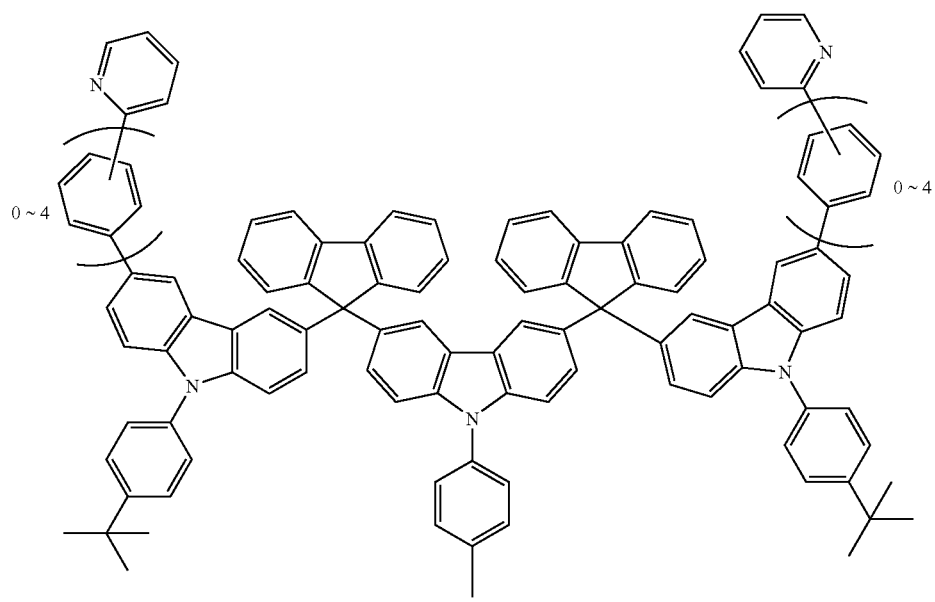

-continued
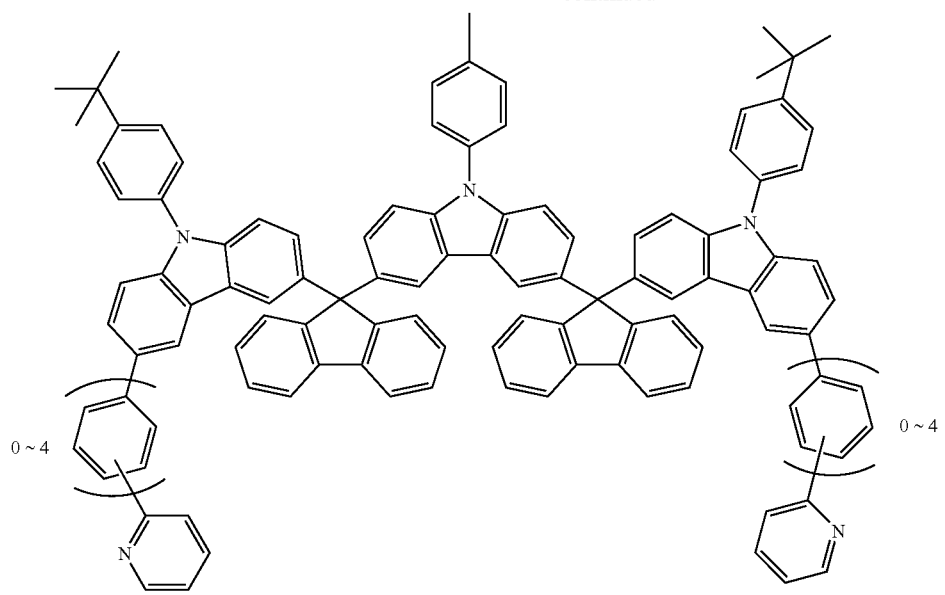
[Chemical Formula 101]
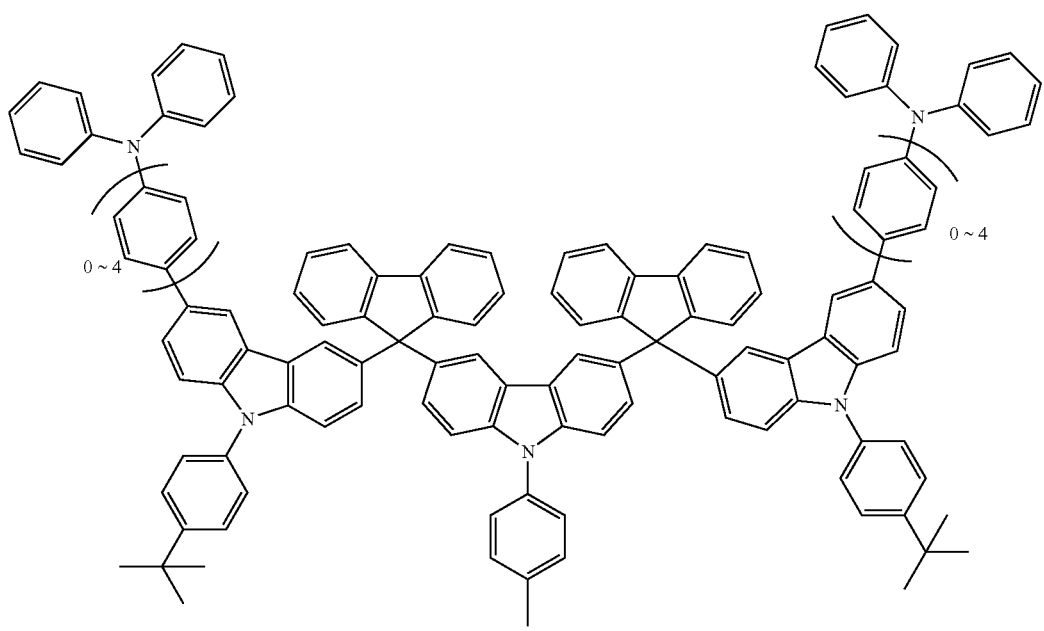

-continued
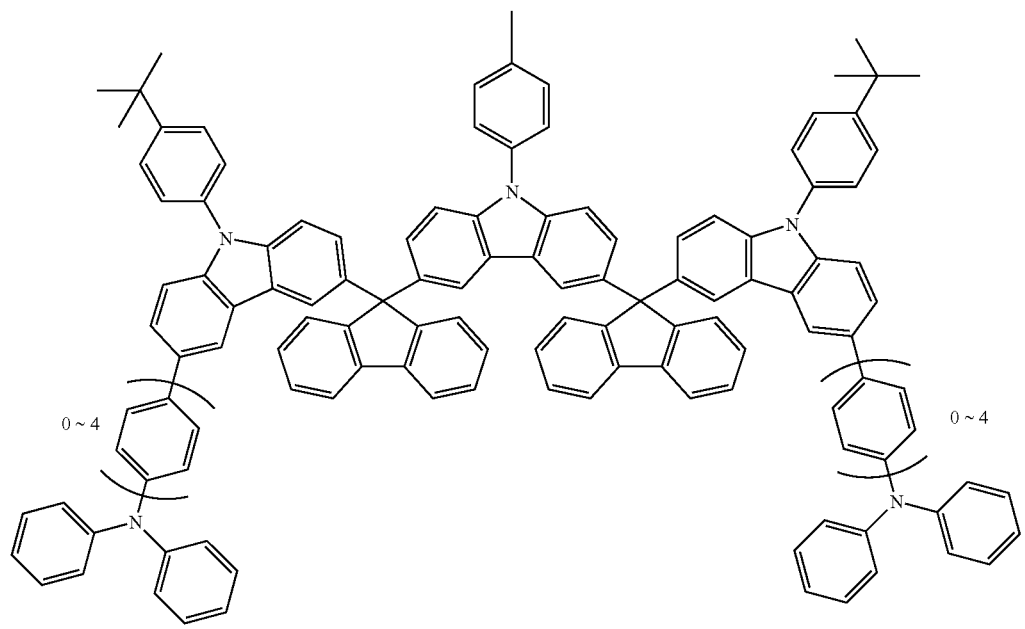
[Chemical Formula 102]
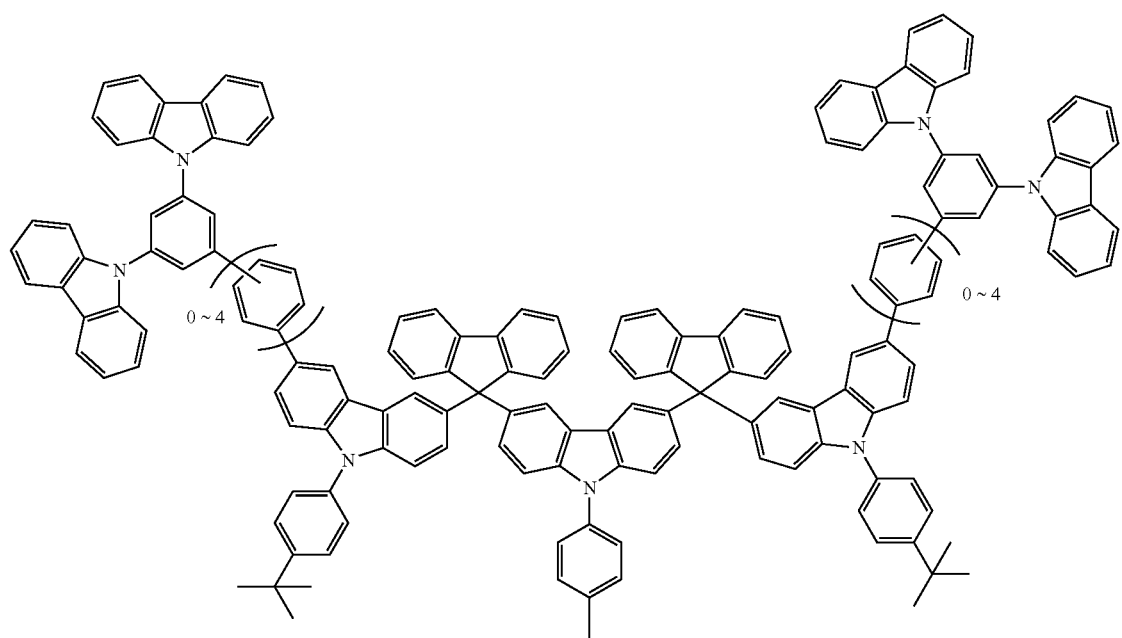

-continued
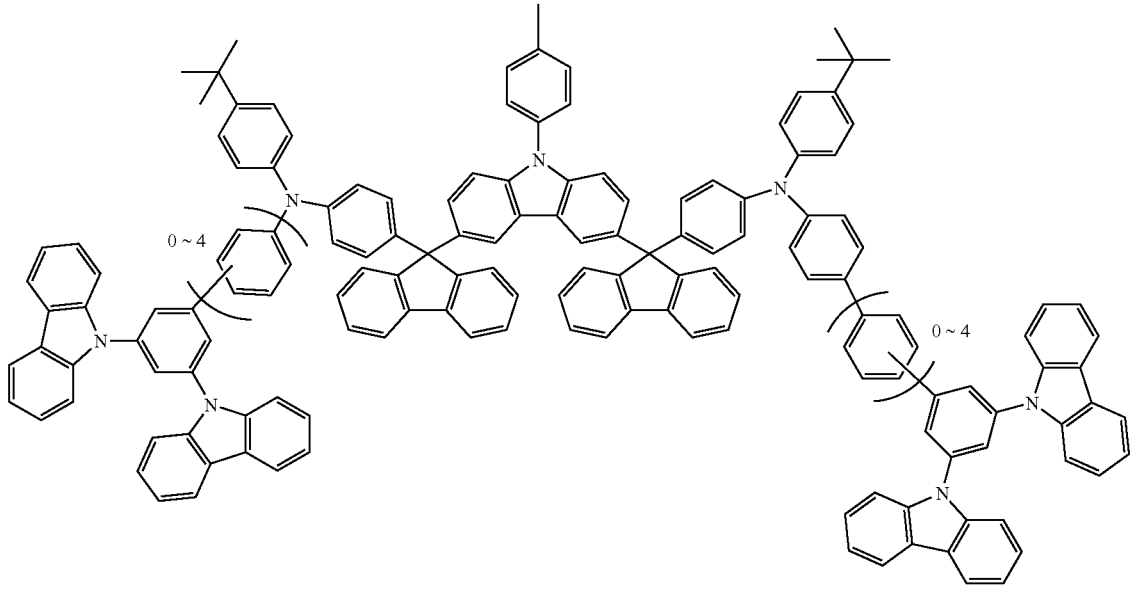
[Chemical Formula 103]
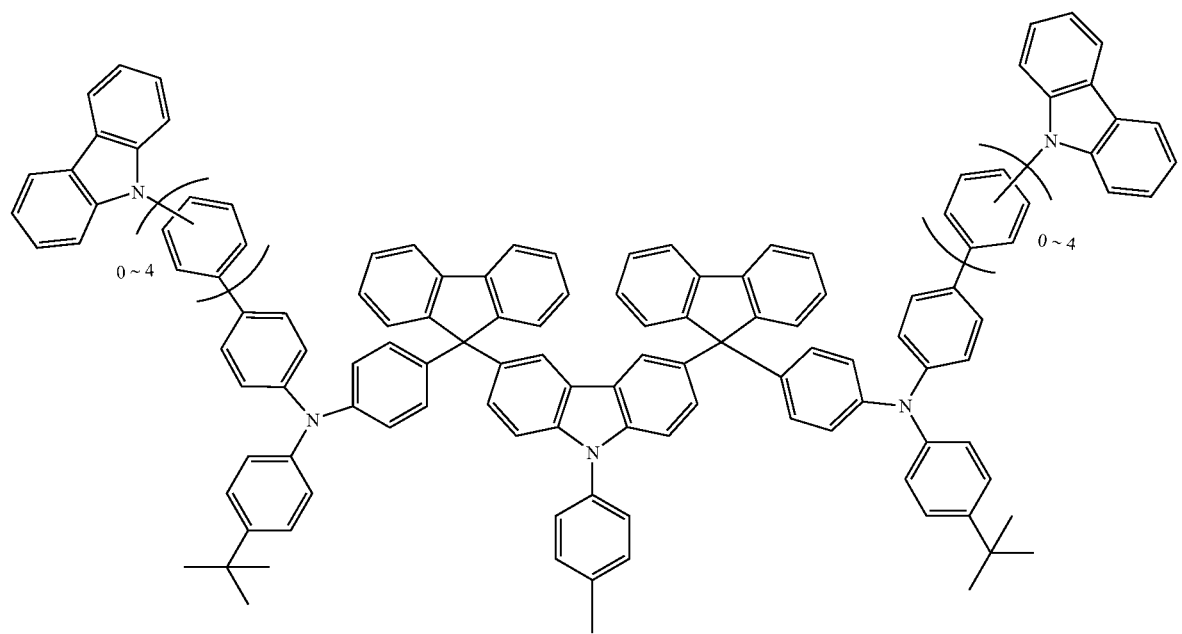

-continued
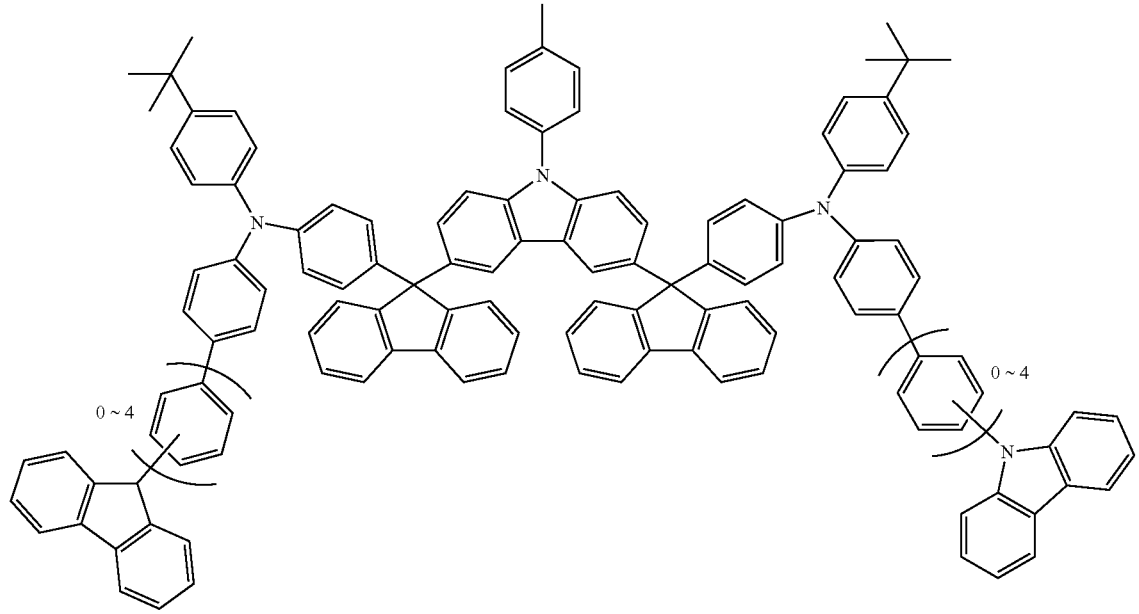
[Chemical Formula 104]
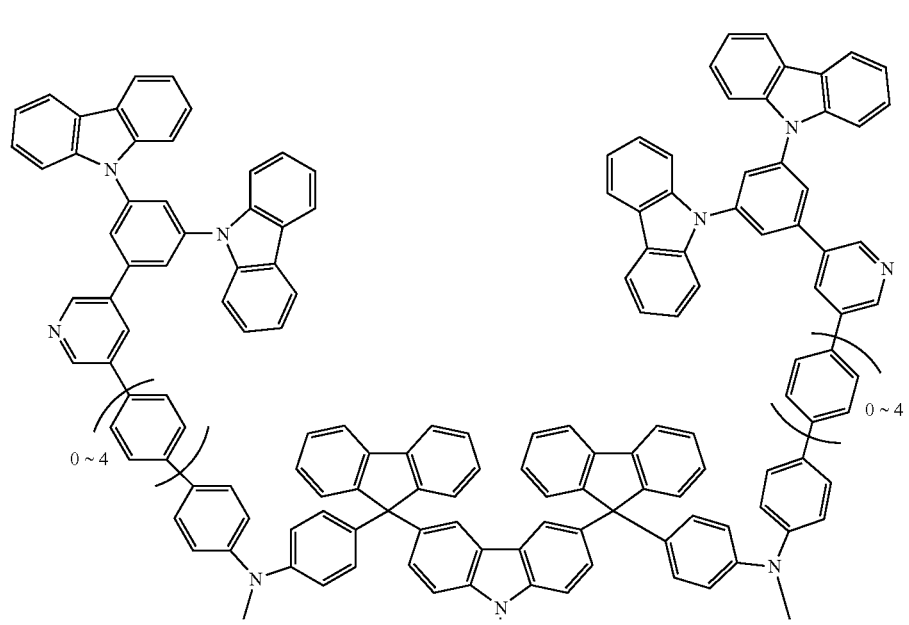

-continued
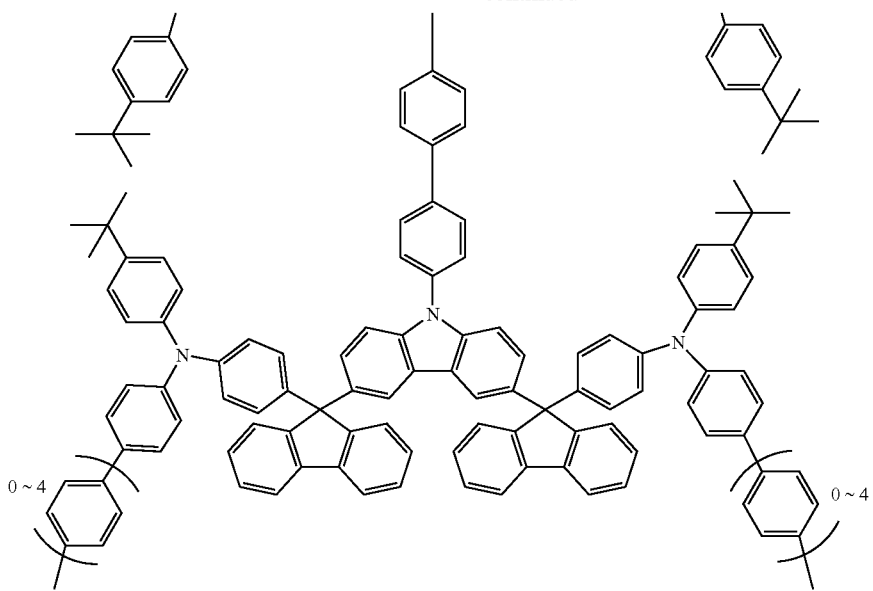
[Chemical Formula 105]
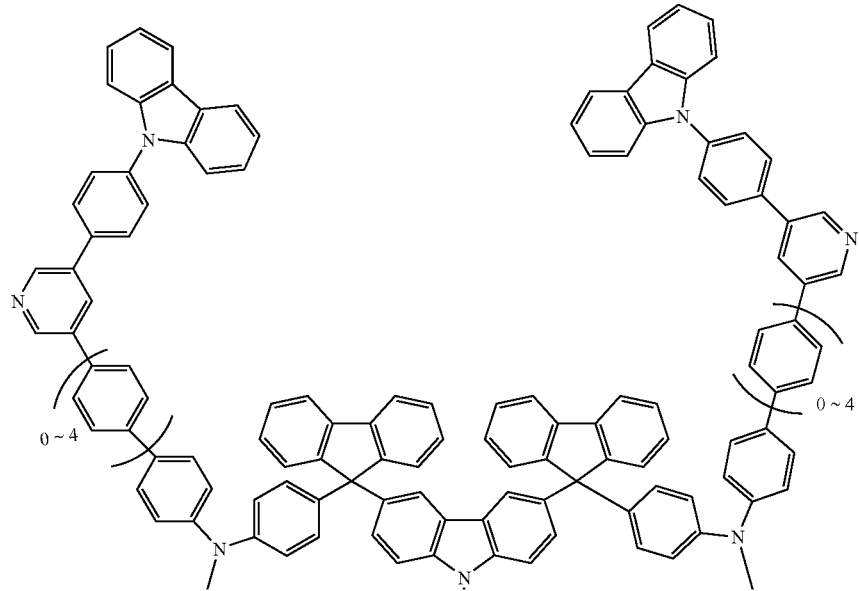

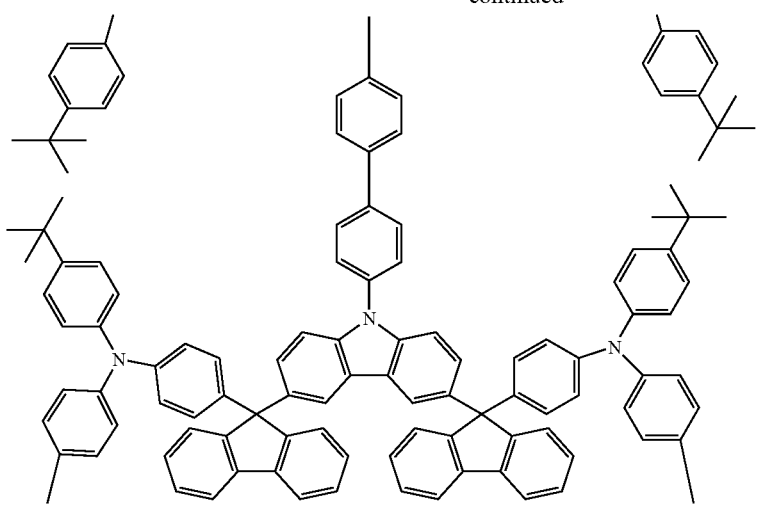
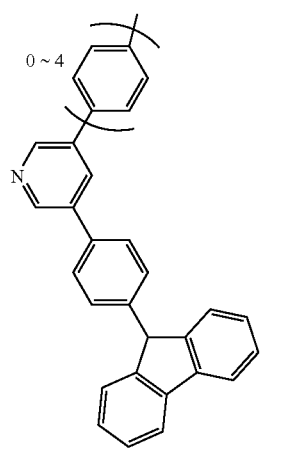
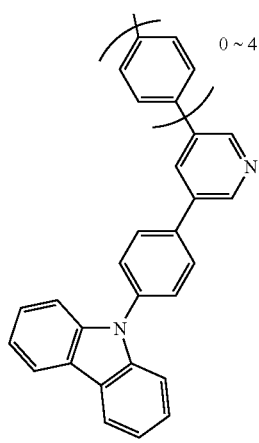
[Chemical Formula 106]
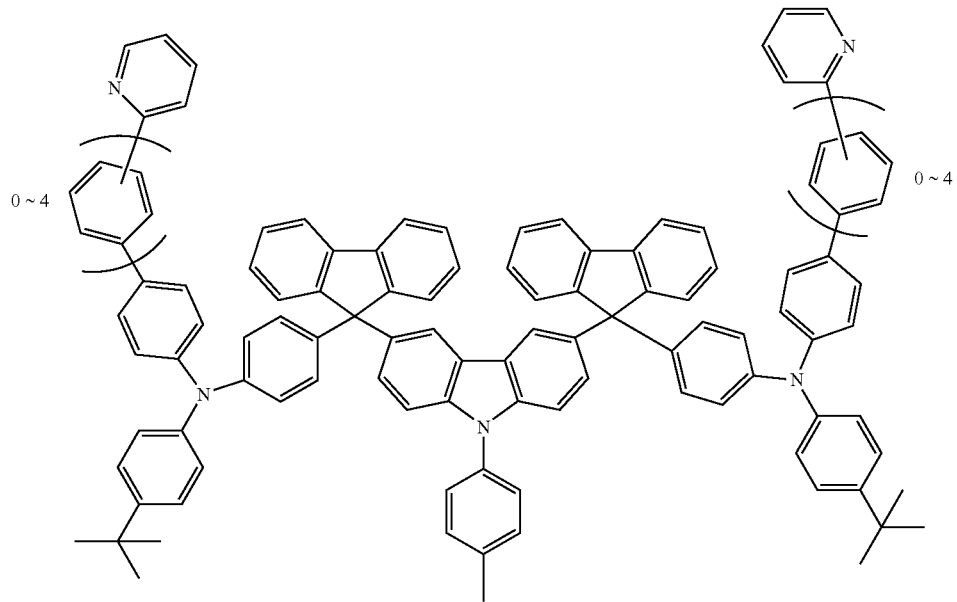

-continued
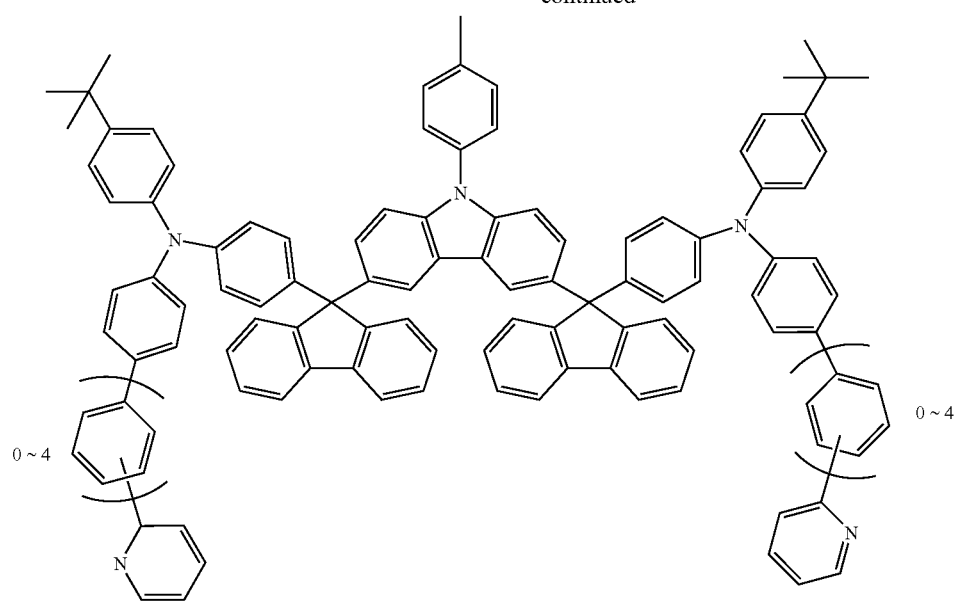
[Chemical Formula 107]
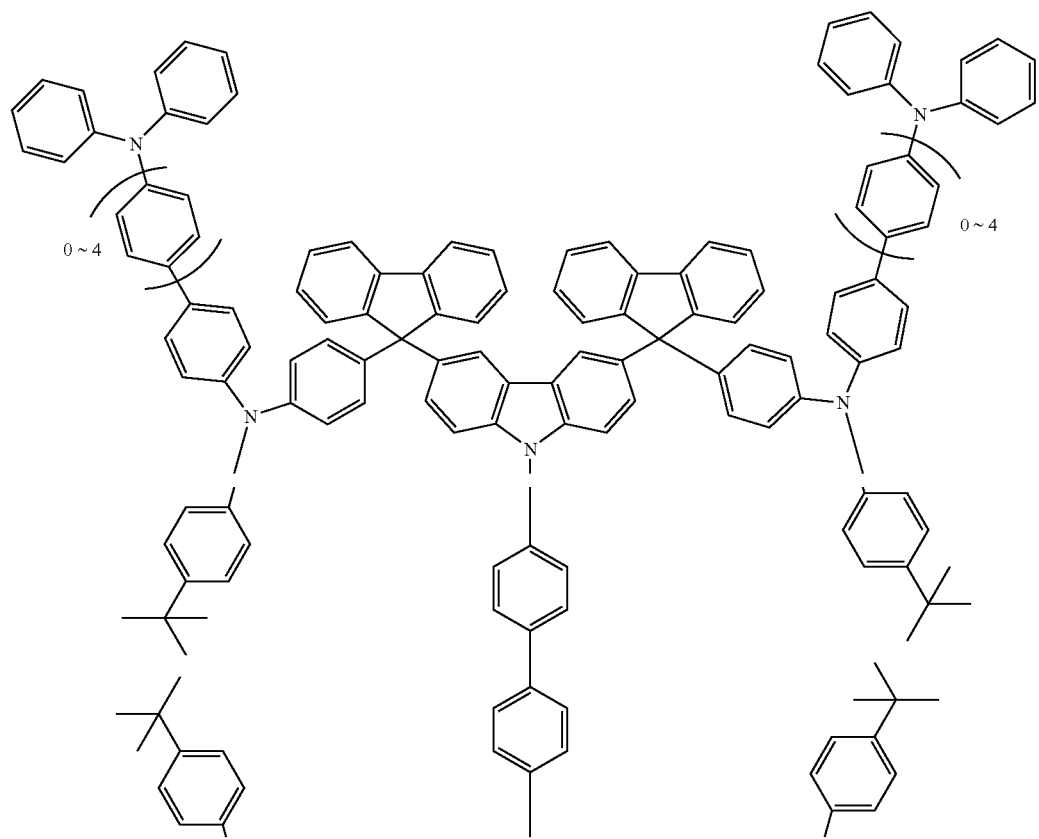

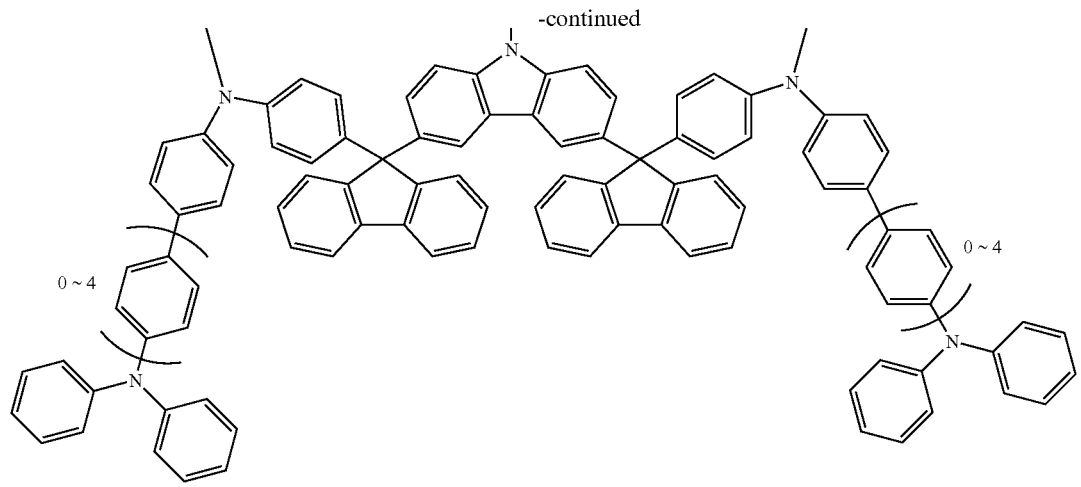
The compound represented by the above Formula 5 may be compounds represented by the following Chemical Formulae 108 to 125.
[Chemical Formula108]
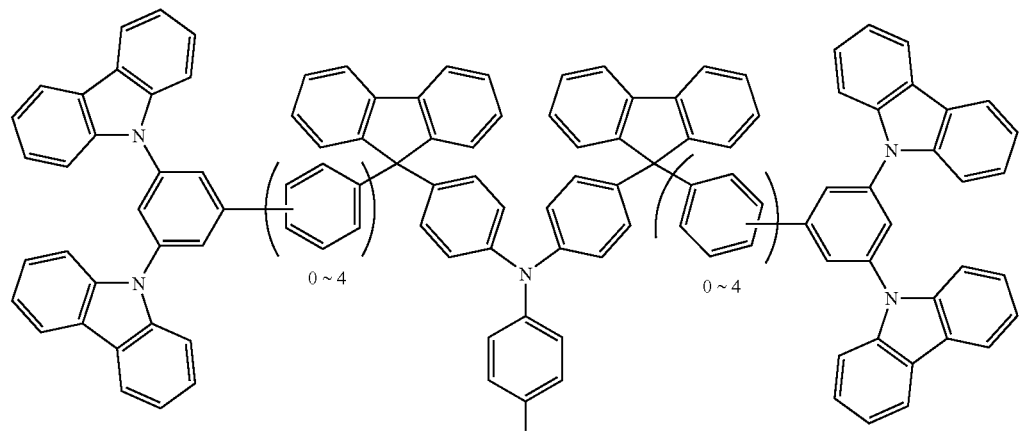
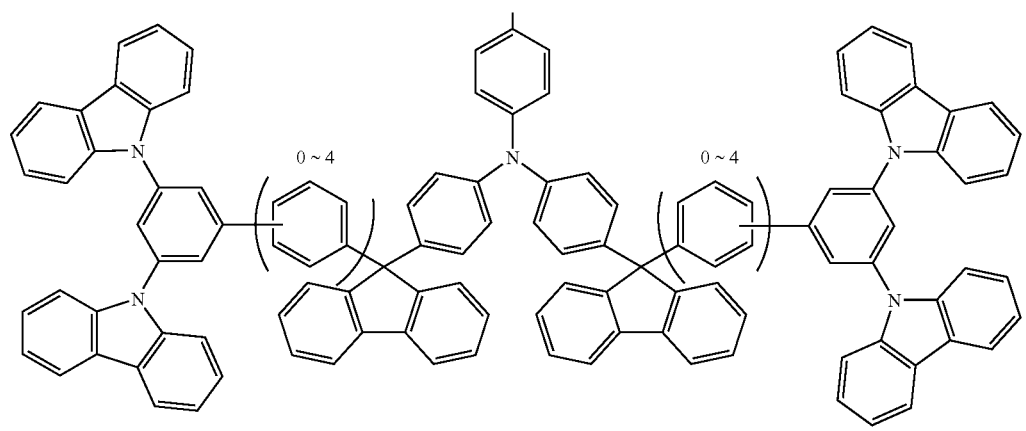

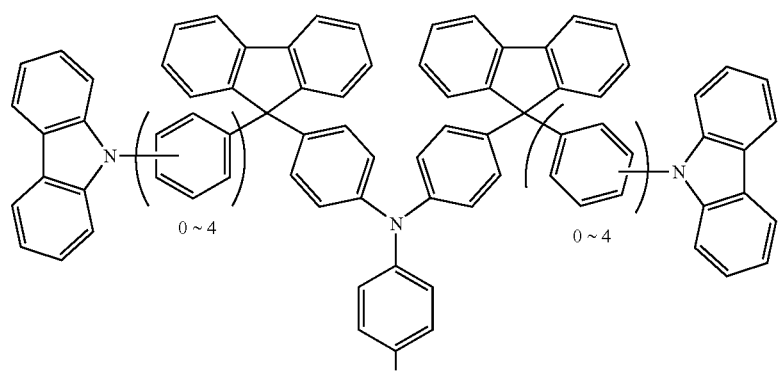
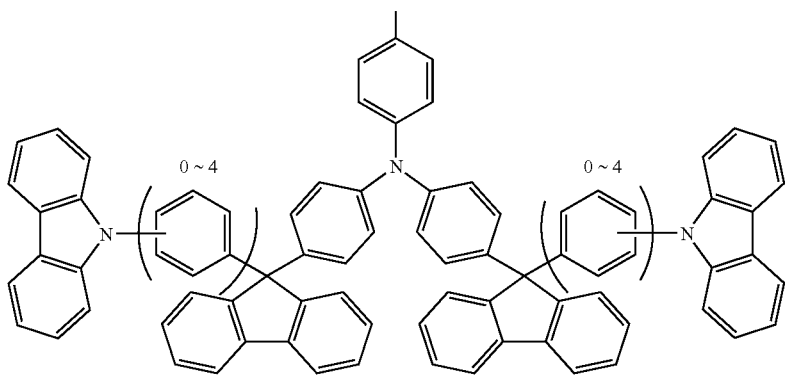
[Chemical Formula 109]
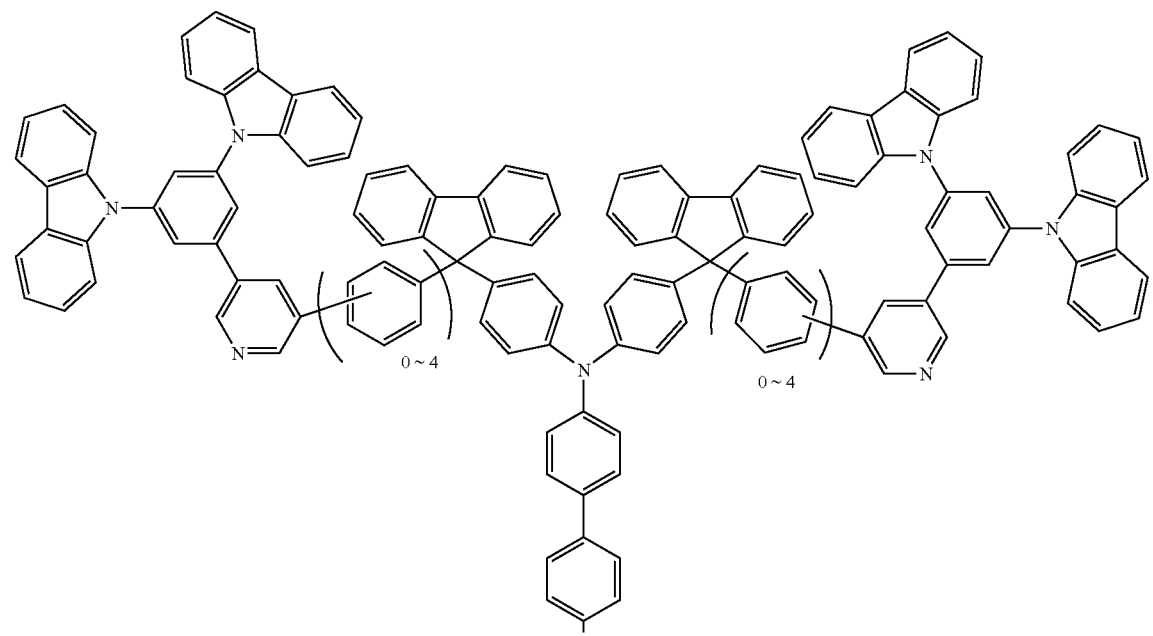
[Chemical Formula 110]

-continued
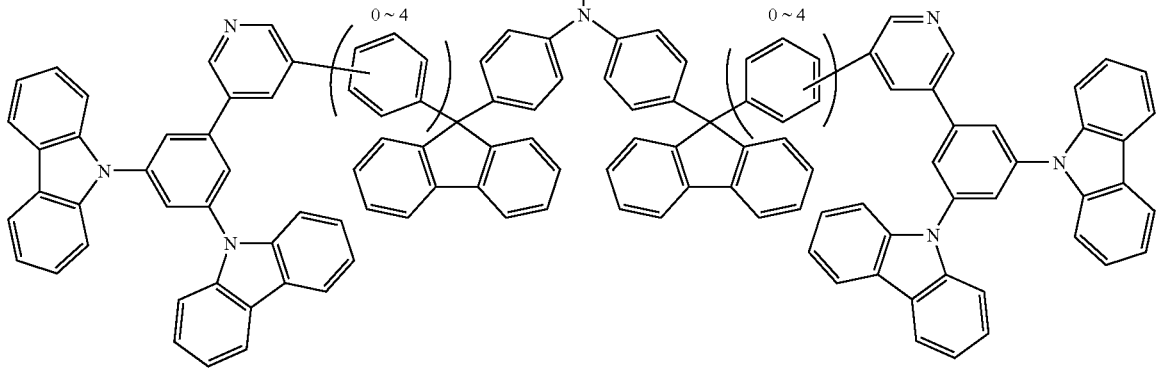
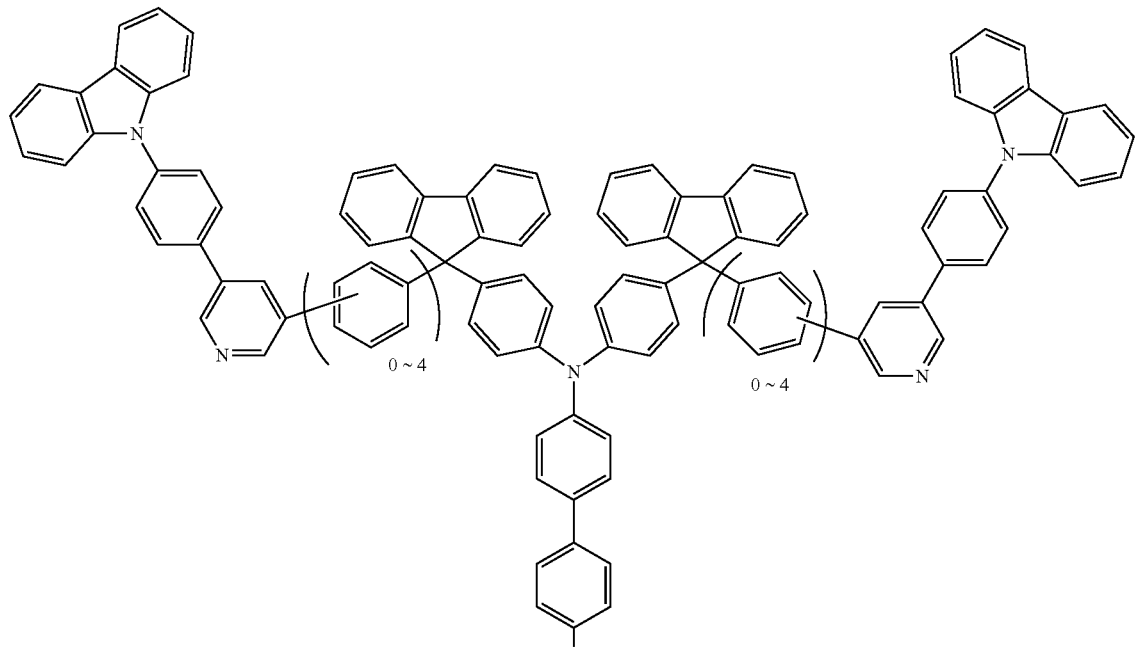
[Chemical Formula 111]
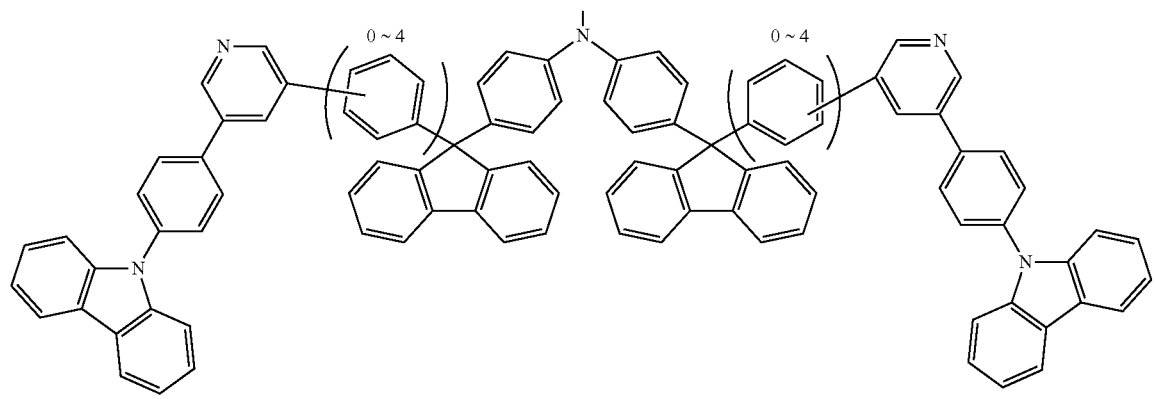

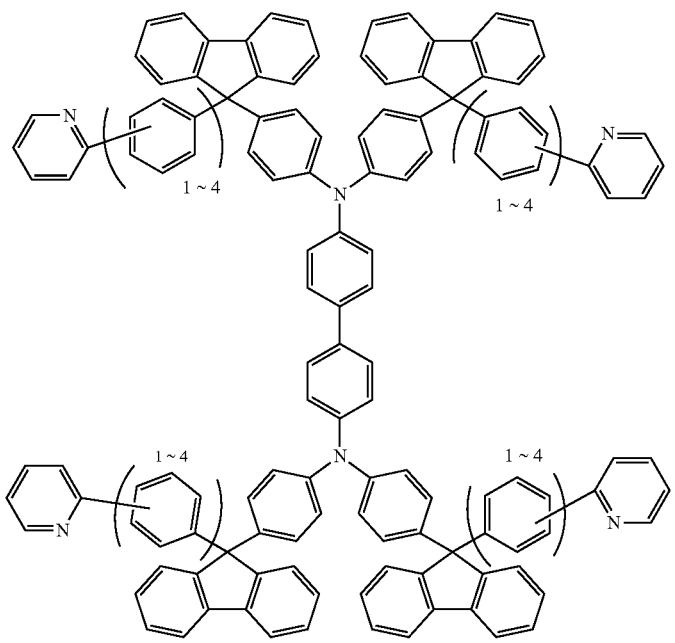
[Chemical Formula 112]
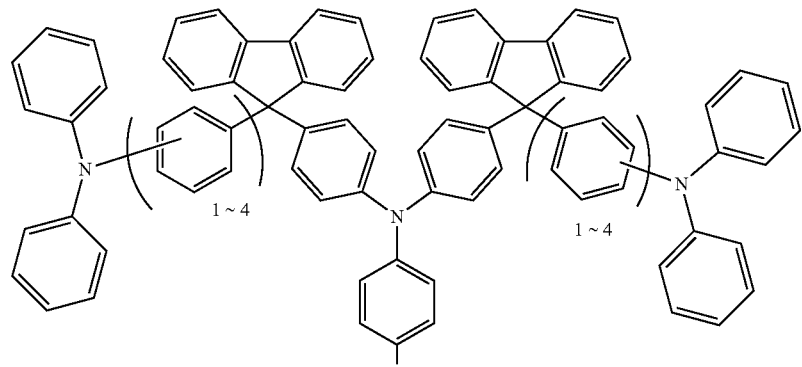
[Chemical Formula113]
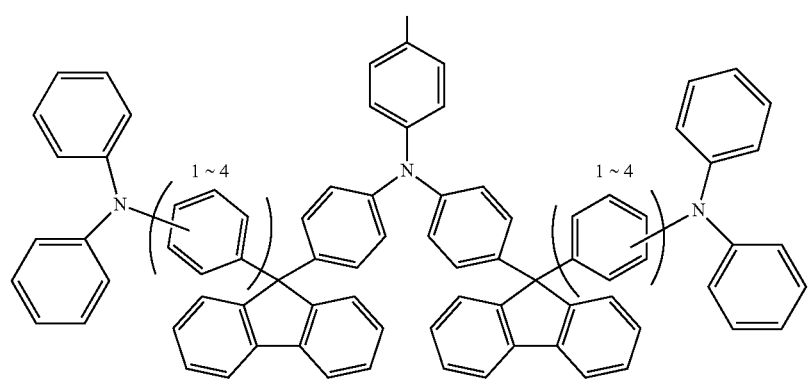

[Chemical Formula 114]
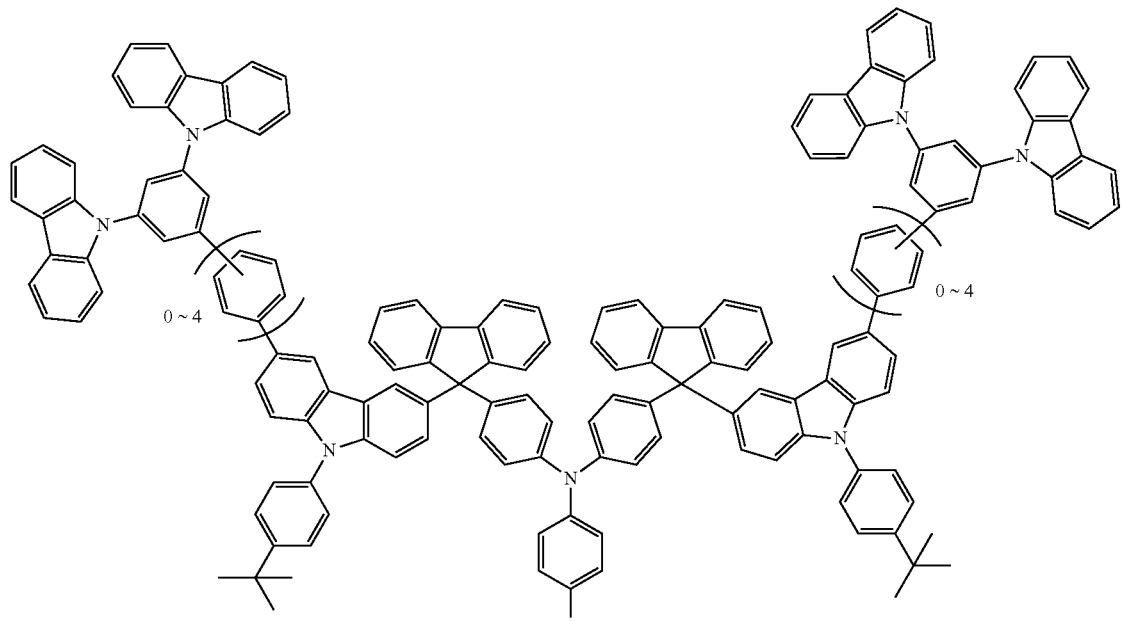
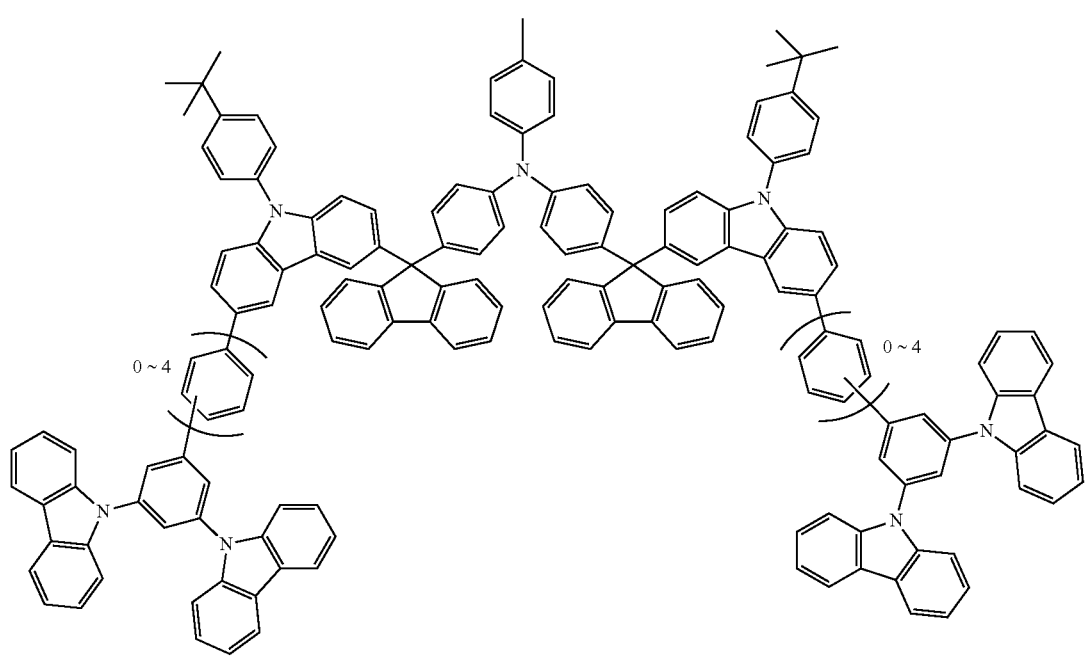

[Chemical Formula 115]
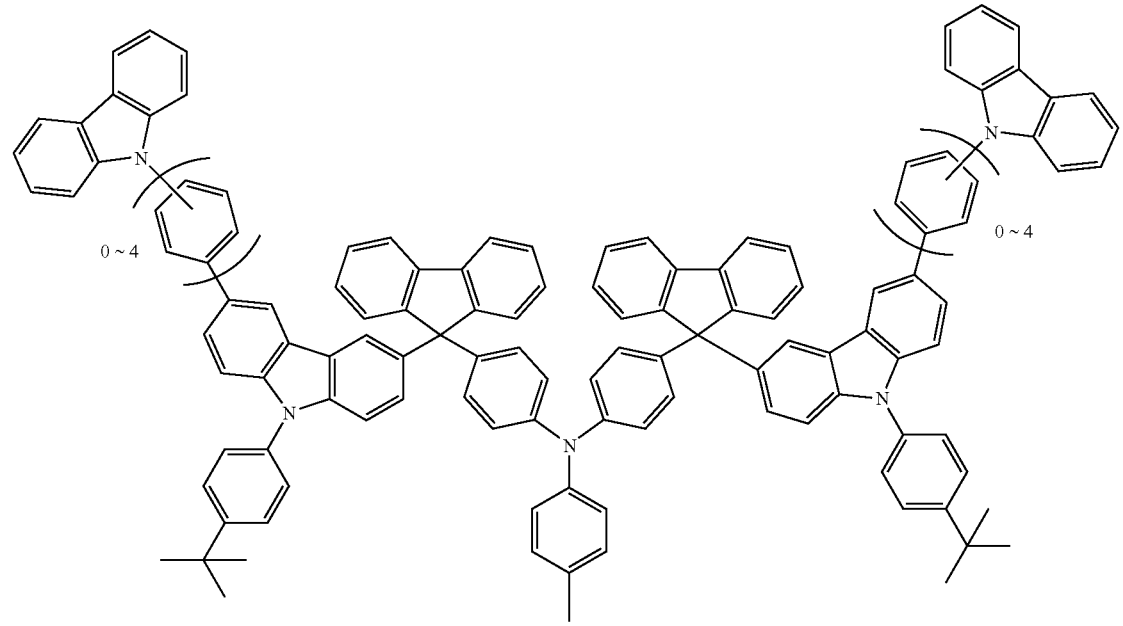
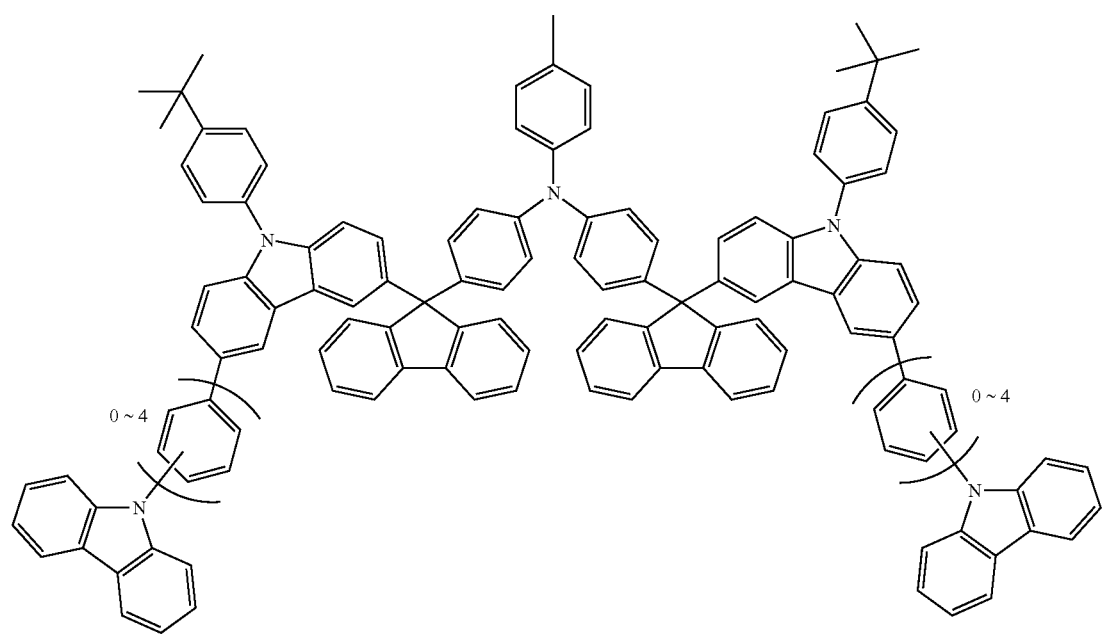

-continued
[Chemical Formula 116]
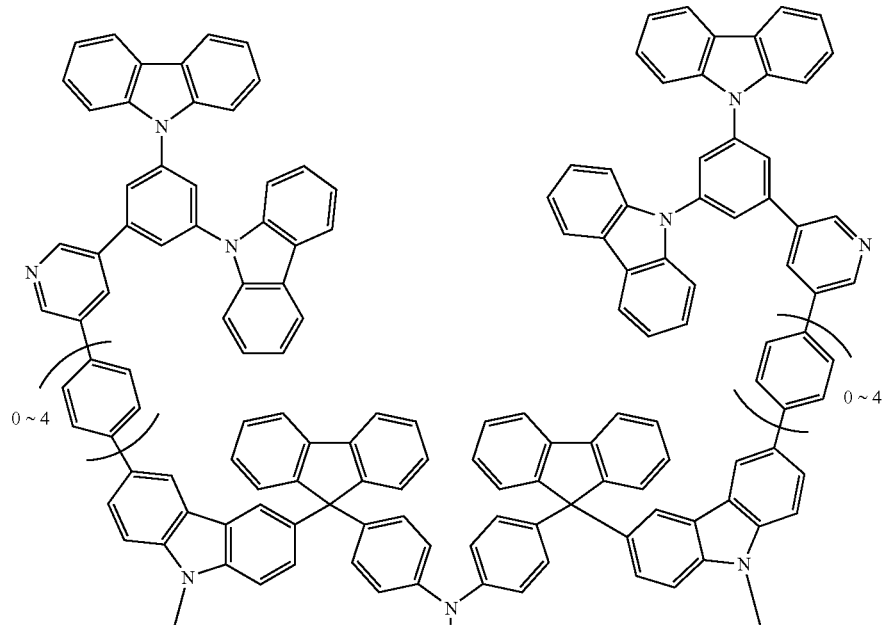
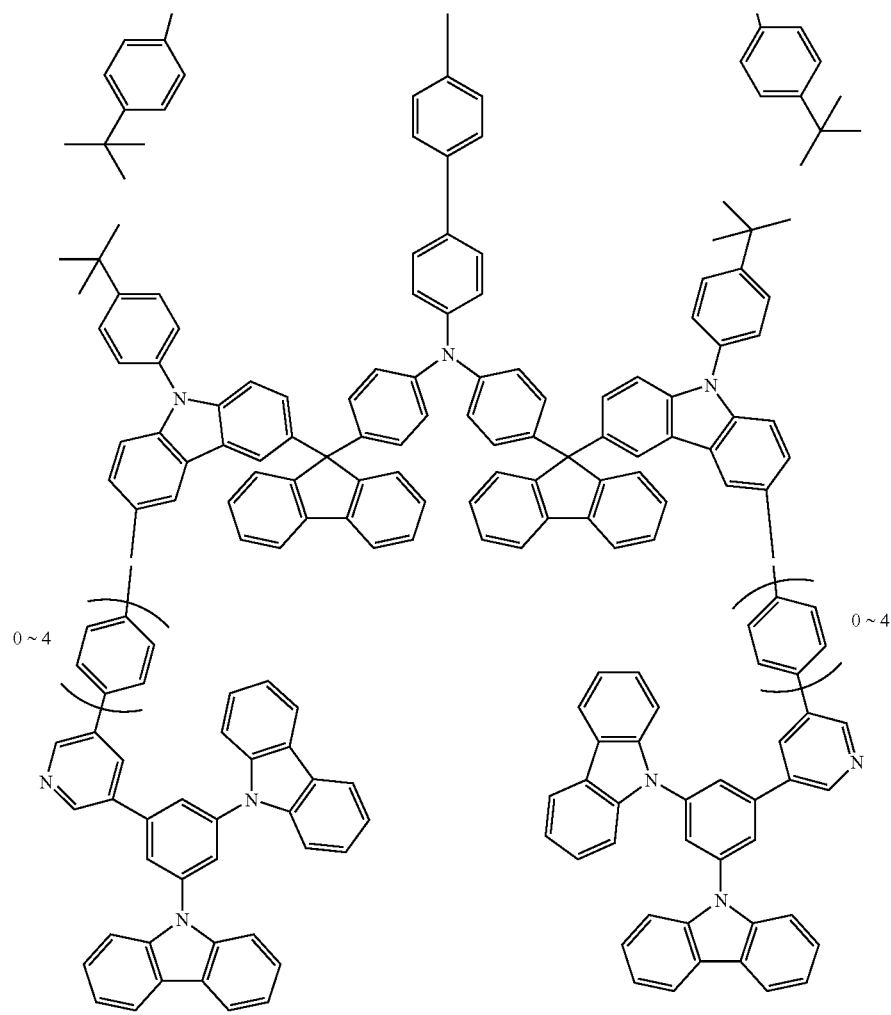

[Chemical Formula 117]
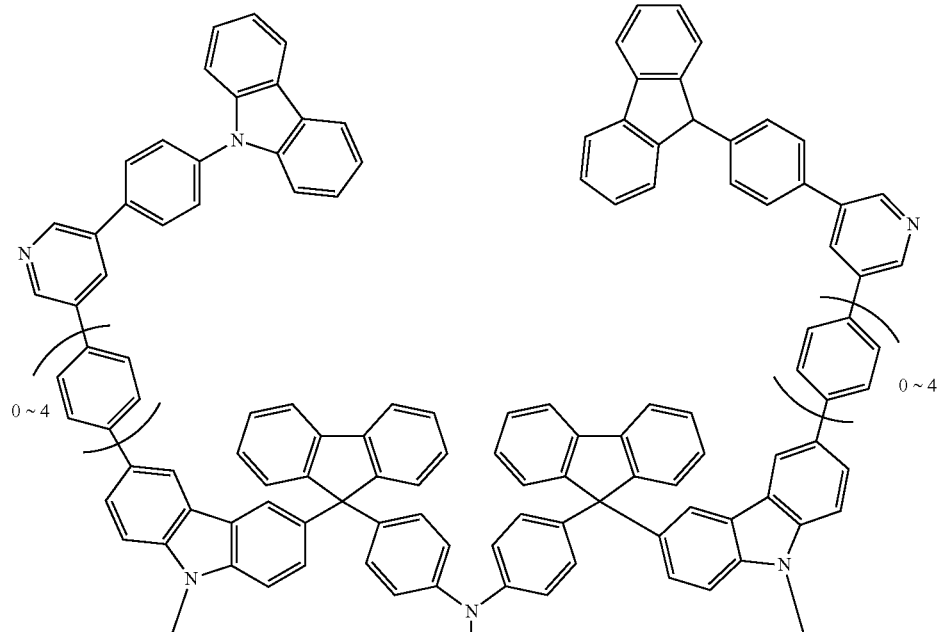
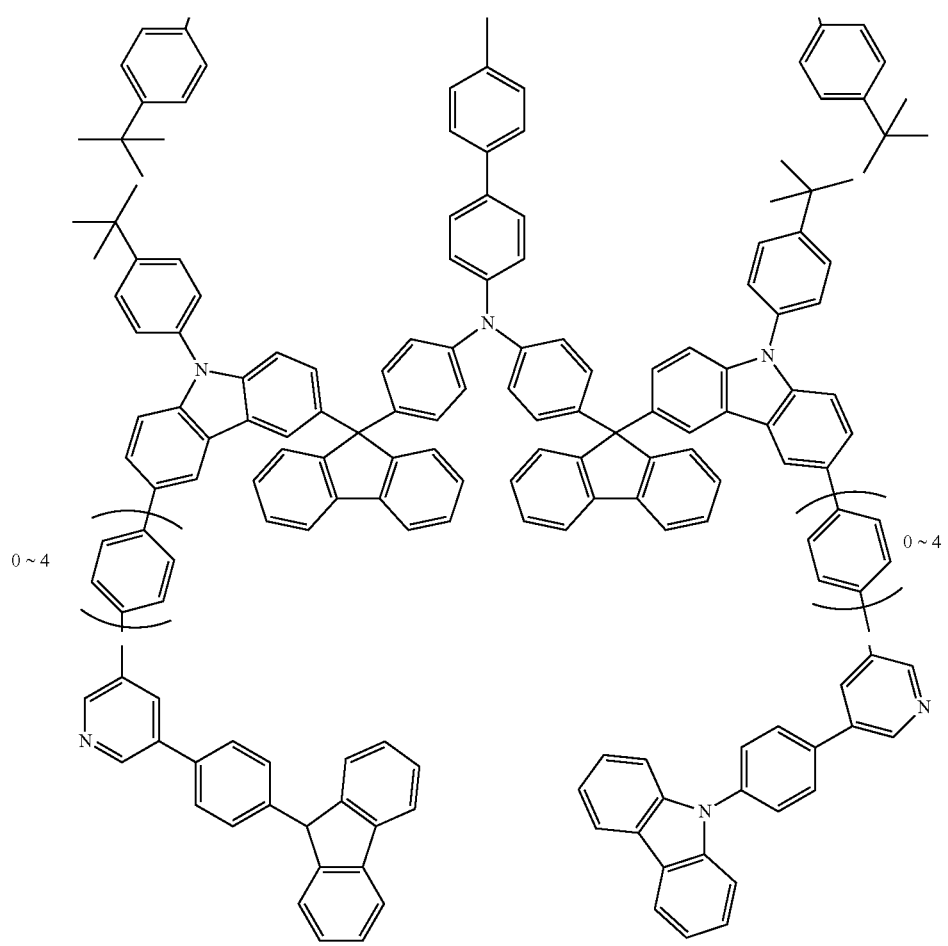

[Chemical Formula 118]
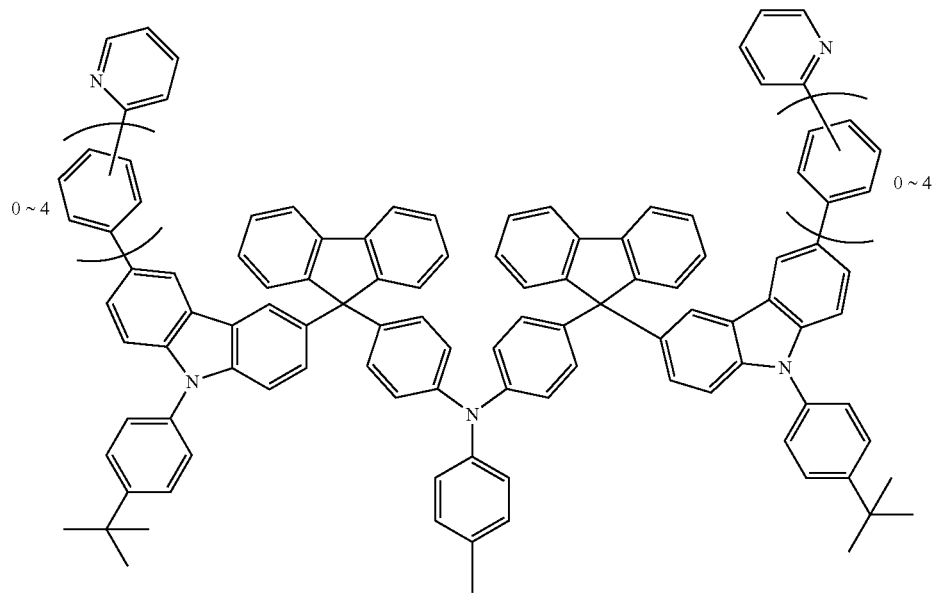
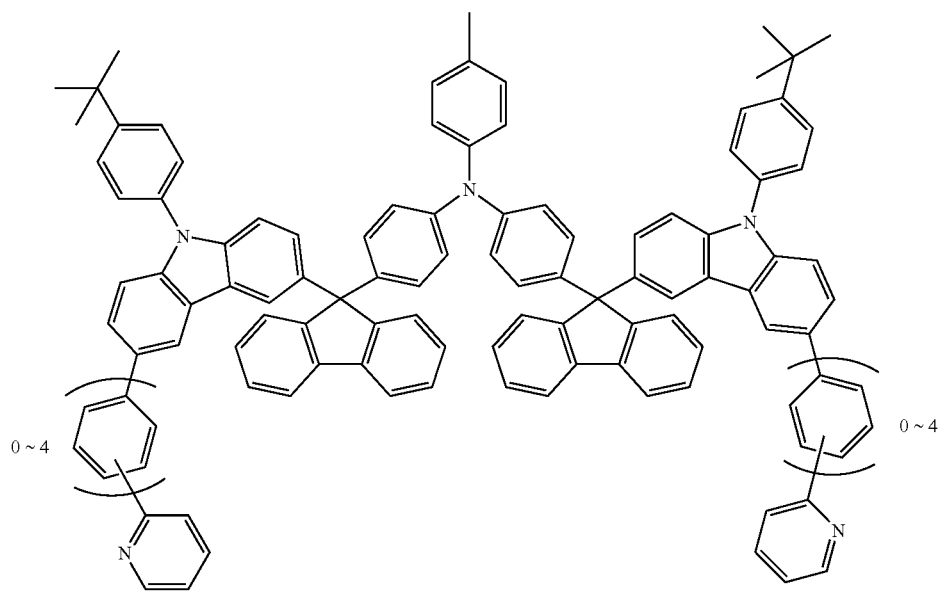

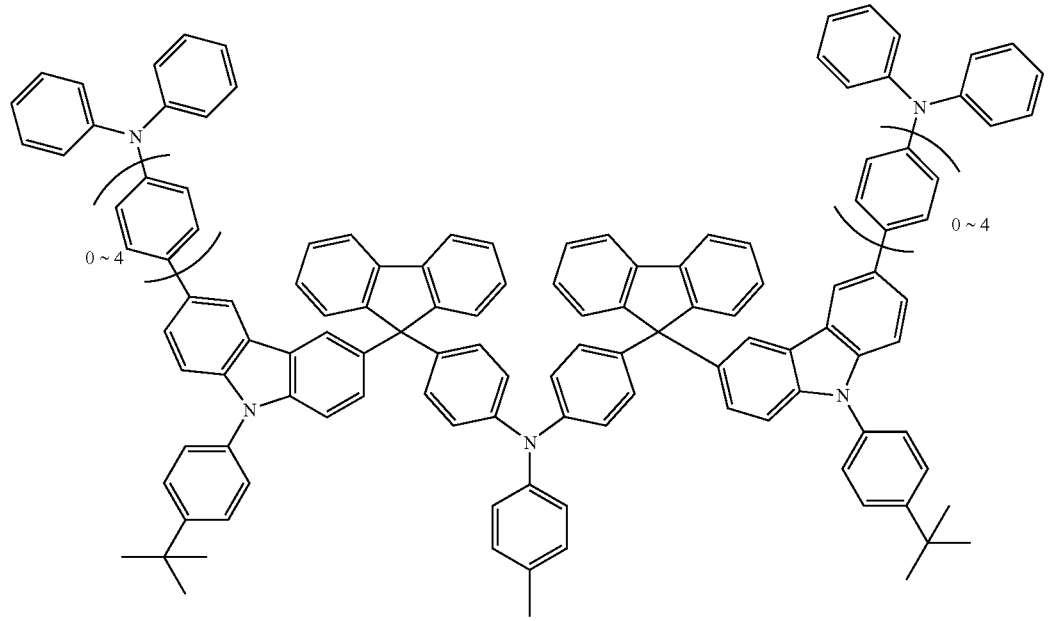
[Chemical Formula 119]
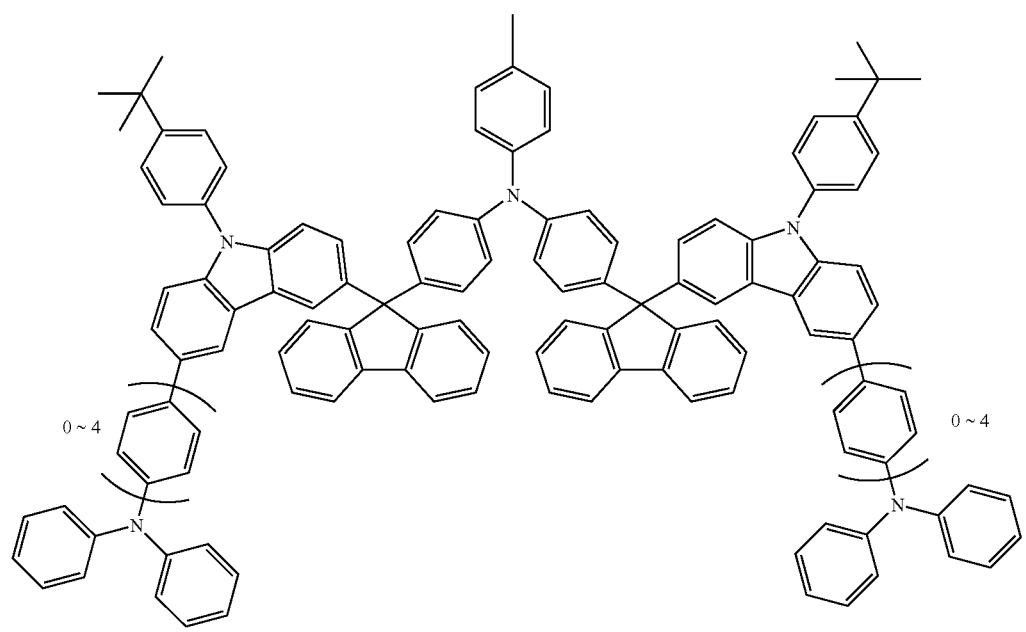

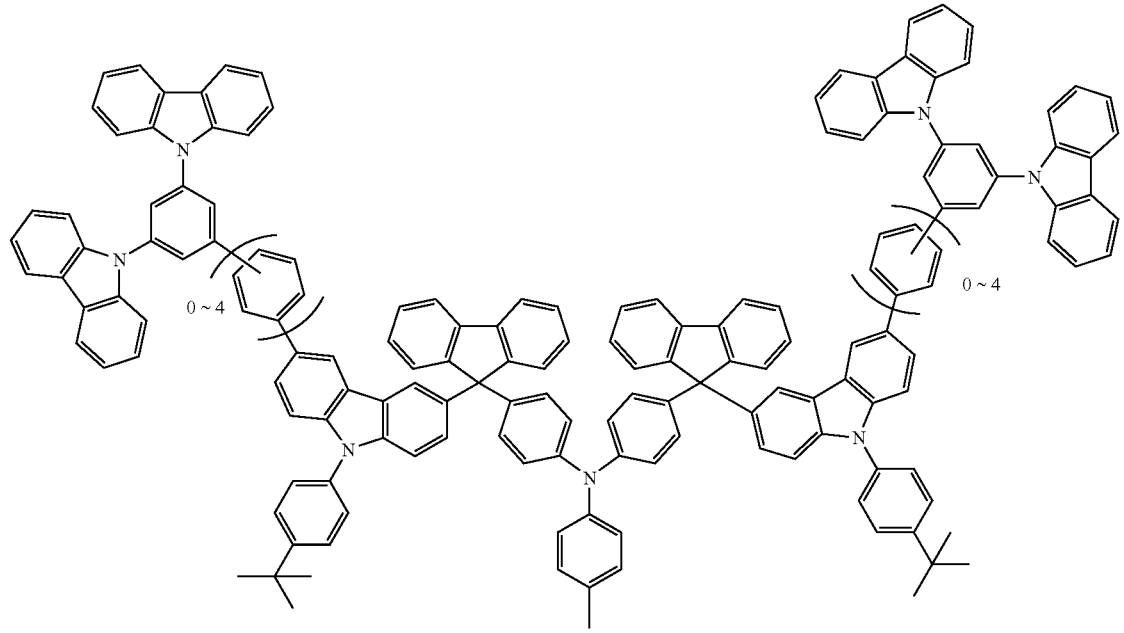
[Chemical Formula 120]
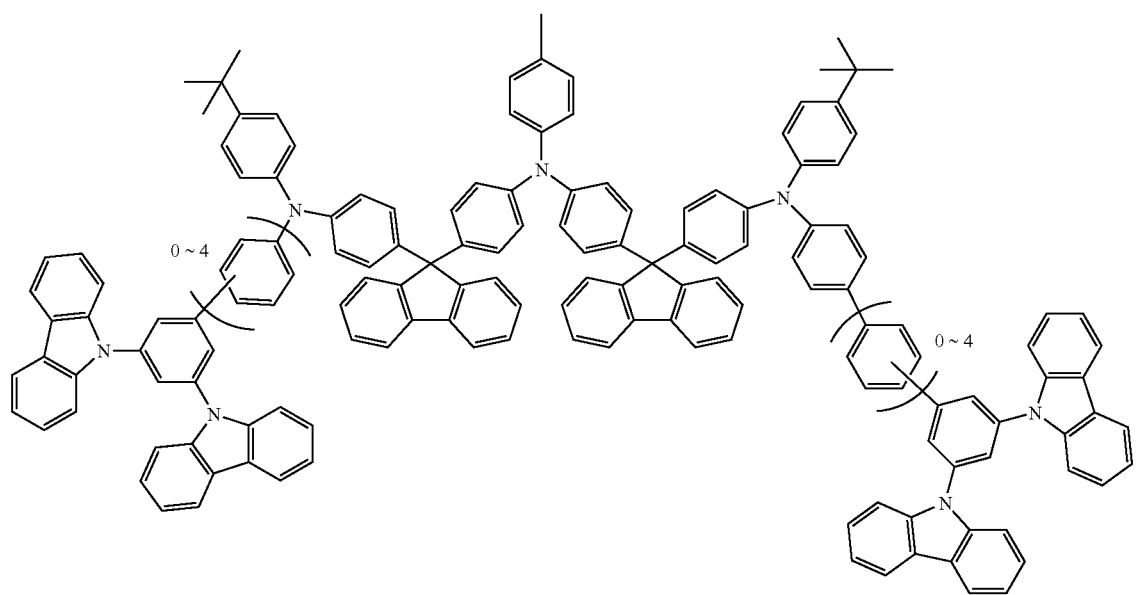

[Chemical Formula 121]
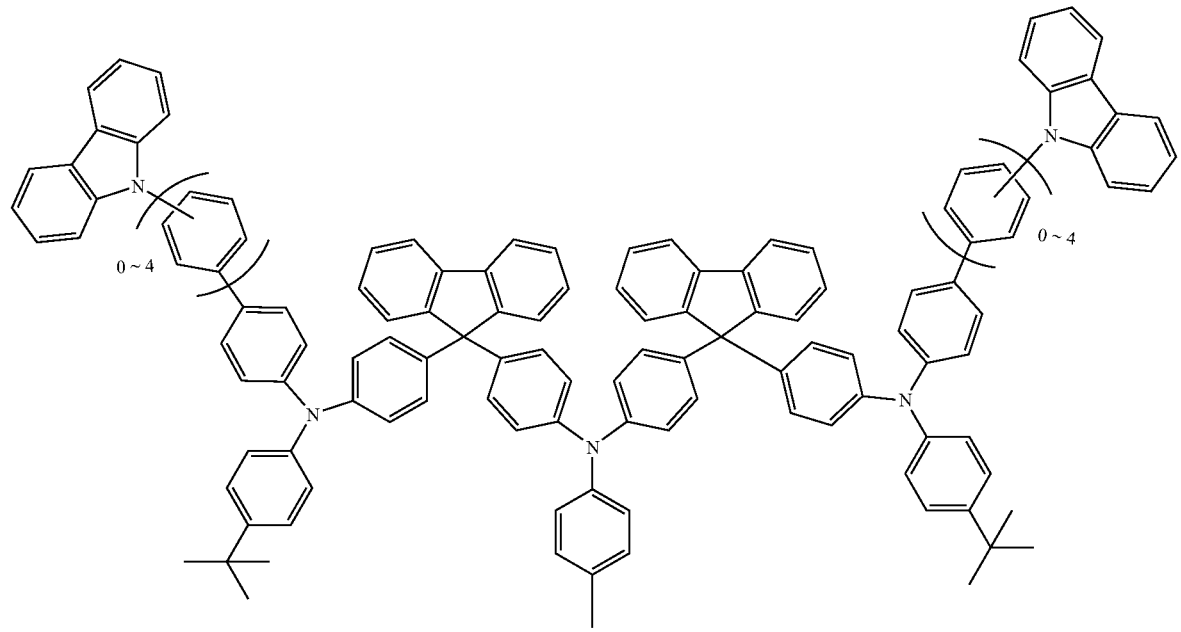
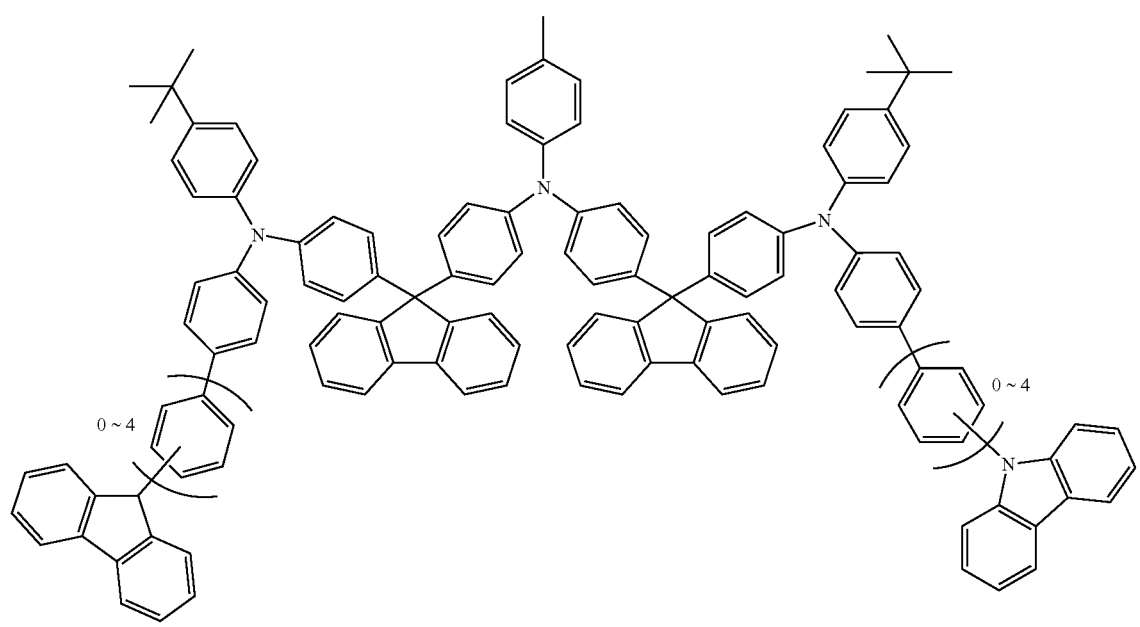

-continued
[Chemical Formula 122]
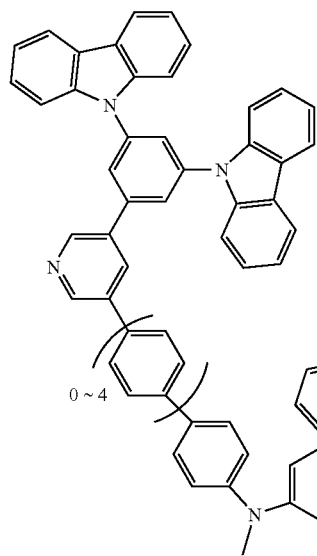
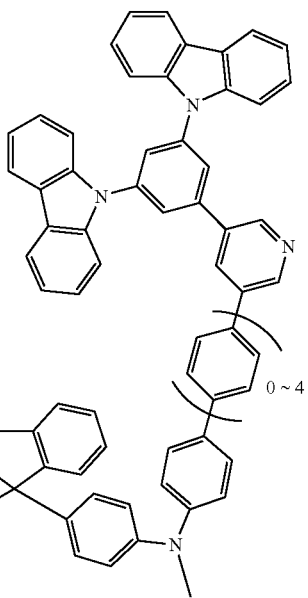
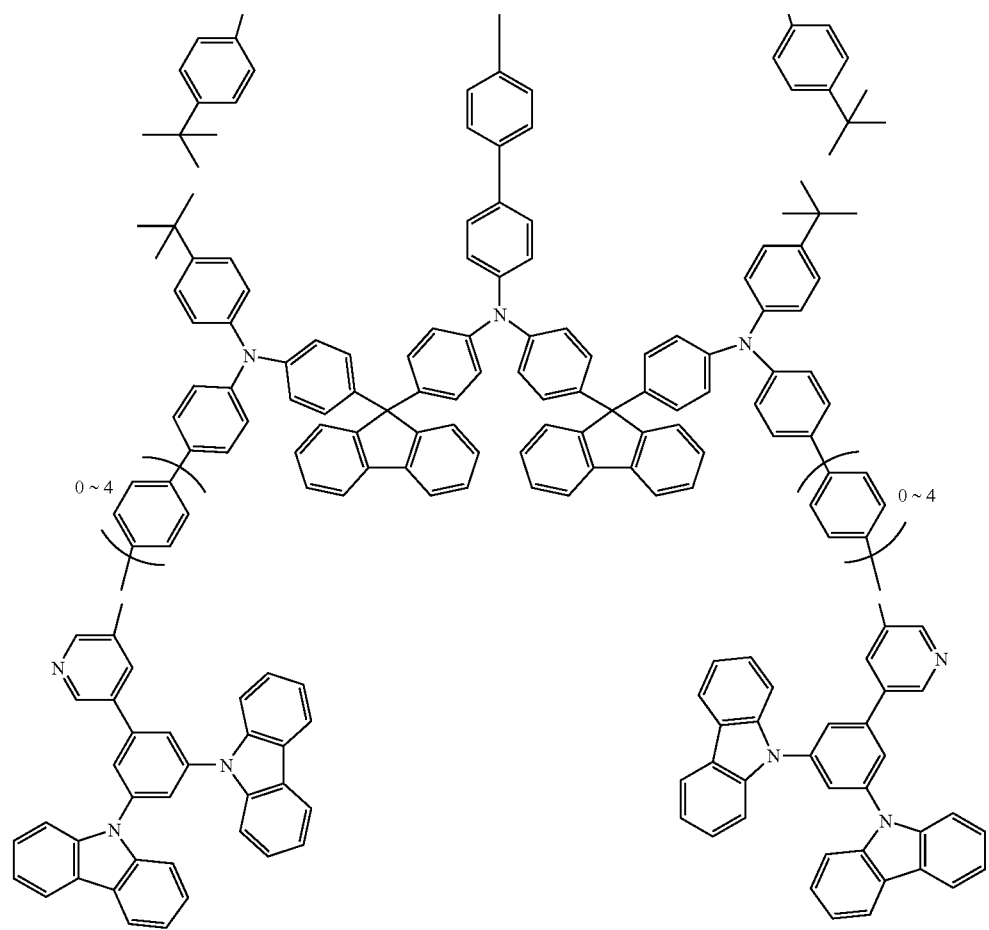

191
192
-continued
[Chemical Formula 123]
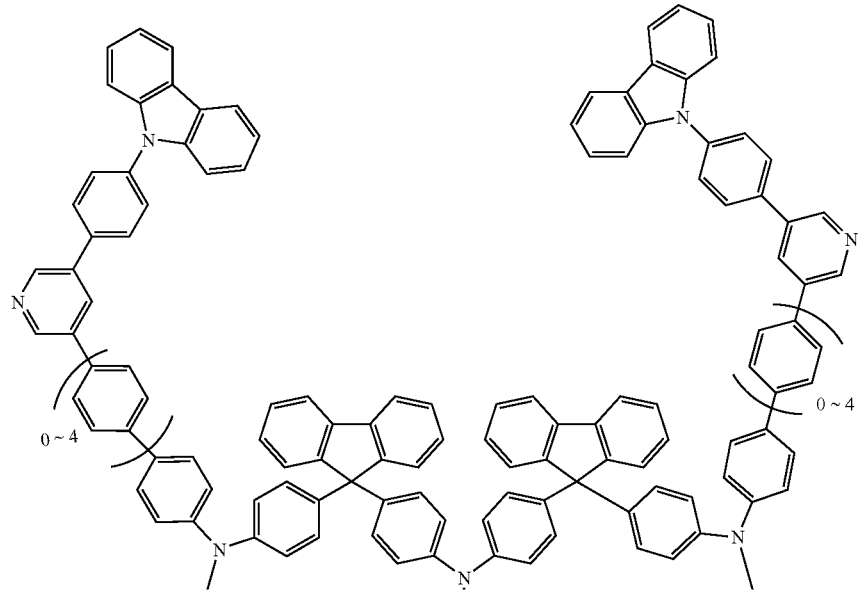
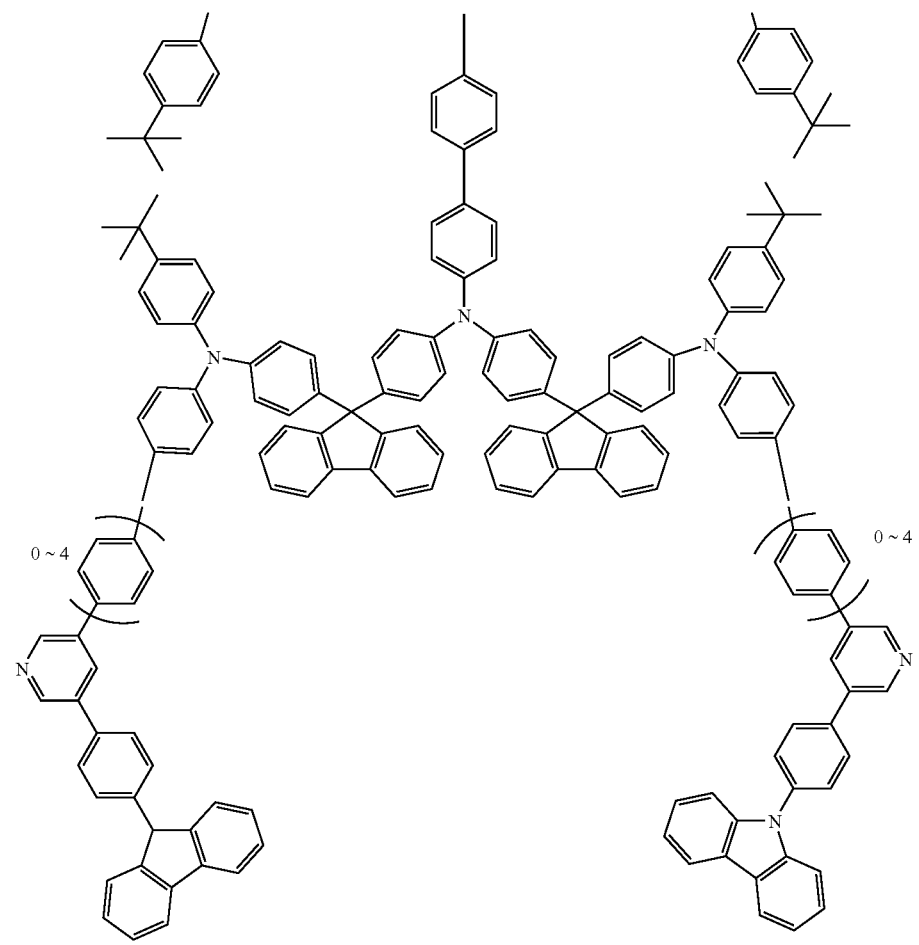

[Chemical Formula 124]
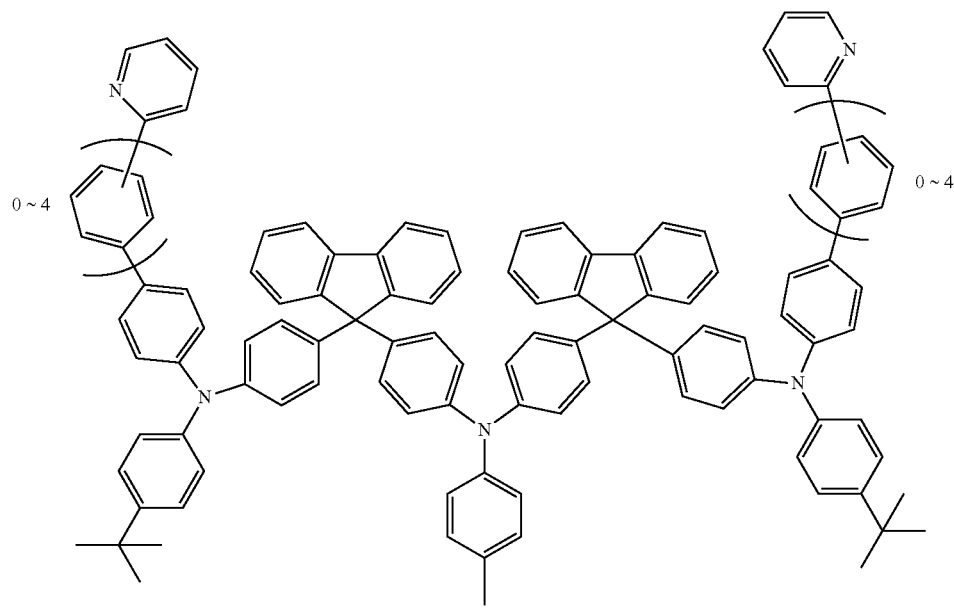
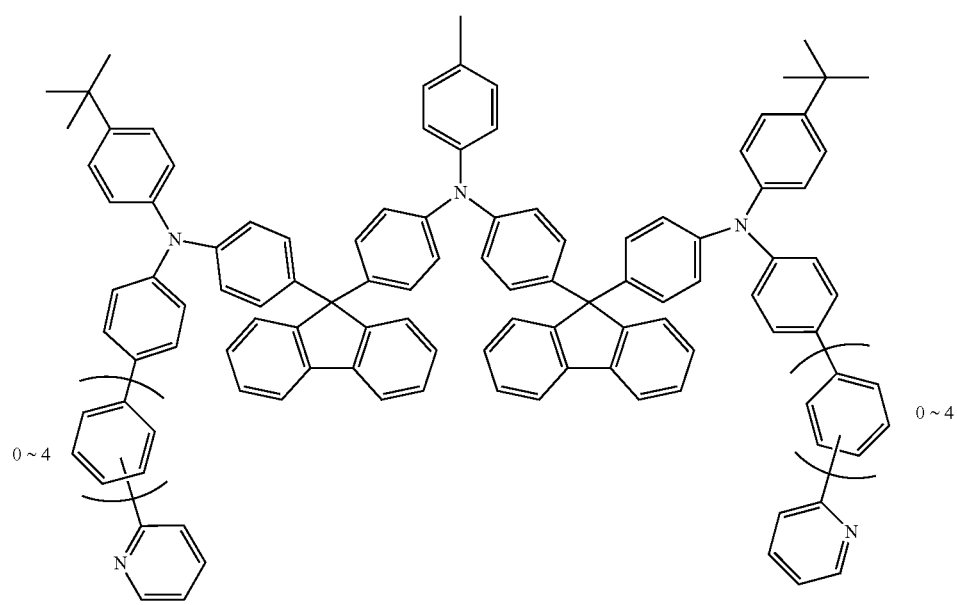

[Chemical Formula 125]

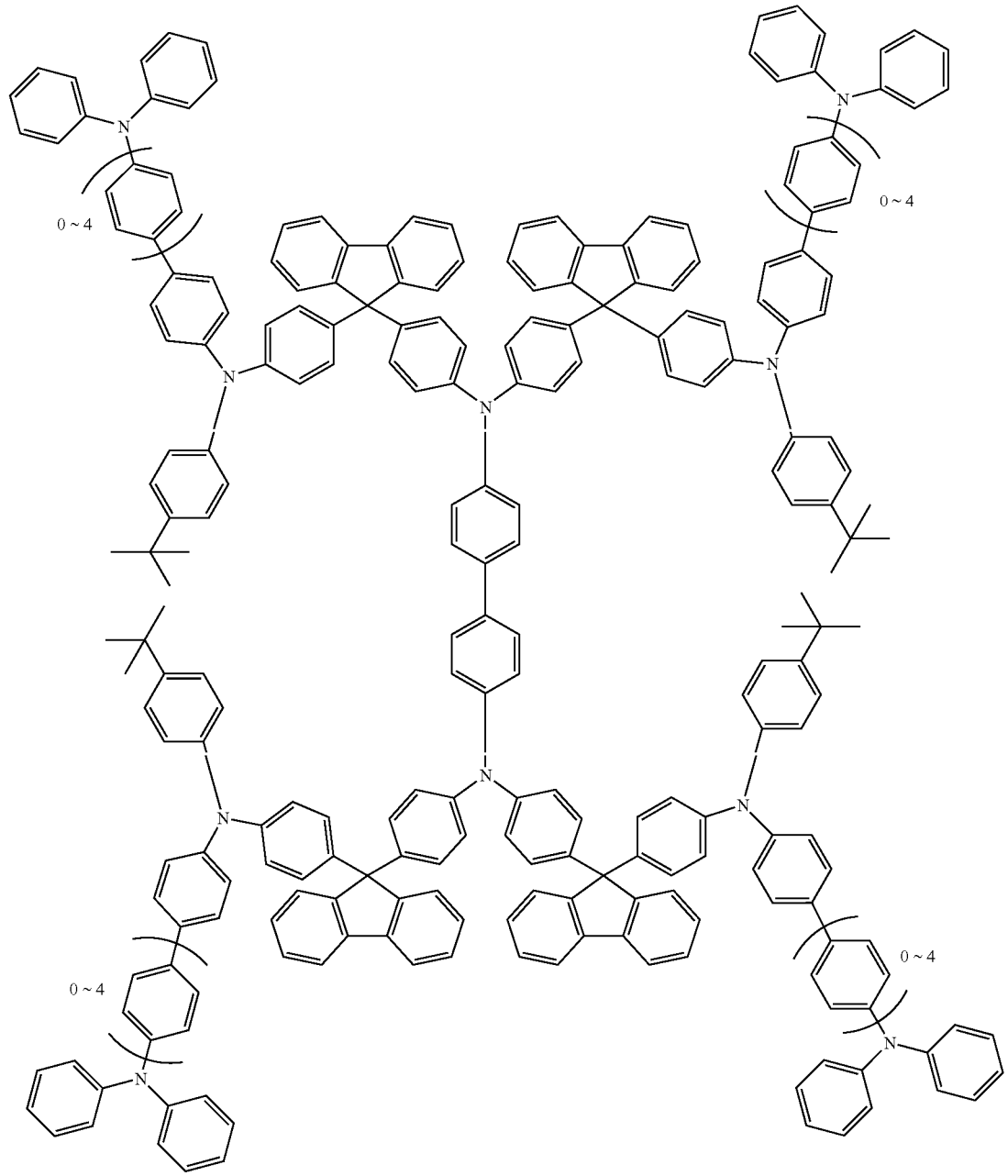

The Chemical Formulae 36 to 53 are examples of Chemical Formula 1, the Chemical Formulae 54 to 71 are examples of Chemical Formula 2, the Chemical Formulae 72 to 89 are examples of Chemical Formula 3, the Chemical Formulae 90 to 107 are examples of Chemical Formula 4, and the Chemical Formulae 108 to 125 are examples of Chemical Formula 5.

The compounds where $X_1$ to $X_{32}$ are N in the above Chemical Formulae 1, 2, 3, 4, and 5 are not particularly represented.

The organic compounds may be prepared using a generally-used preparation method of organic compounds without limitation. In one embodiment, the preparation method may be Yamamoto reactions, Suzuki reactions, Stille reactions, Ullman reactions, or so on.

Reaction temperatures, reaction solvents, and reaction times of the preparation method can be adjusted to provide the above organic compounds.

Another embodiment of the present invention provides an organic photoelectric device that includes an organic layer including the above-described organic compounds between a pair of electrodes In one embodiment, the organic photoelectric device may be an organic light emitting diode.

The organic layer may be an emission layer, a hole injection layer (HIL), a hole transport layer (HTL), an electron transport layer (ETL), an electron injection layer (EIL), an interlayer, and a hole blocking layer. In another embodiment, the emission layer is appropriate for the organic layer.

The organic photoelectric device may further selectively include an interlayer, a hole transport layer (HTL), and an electron transport layer (ETL) as well as a basic device structure of anode/emission layer/cathode.

FIG. 1 is a cross-sectional schematic view of the organic photoelectric device 1 according to one embodiment. FIG. 1 shows an organic photoelectric device including a substrate 11, an anode 12, a hole transport layer (HTL) 13, an emission layer 14, an electron transport layer (ETL) 15, and a cathode 16.

Referring to FIG. 1, the organic photoelectric device may be fabricated using the organic compounds as follows.

First, an anode 12 material is coated on an upper side of the substrate 11.

The substrate 11 is a glass substrate or a transparent plastic substrate having excellent general transparence, face smoothness, handling ease, and water repellency.

The anode 12 material may include transparent and highly conductive indium tin oxide (ITO), tin oxide ($SnO_2$), zinc oxide (ZnO), or so on.

Then, a hole transport layer (HTL) 13 is disposed on the anode 12 using vacuum deposition, sputtering, or spin coating, and an emission layer 14 is disposed on the hole transport layer (HTL) 13 using vacuum deposition, or a solution coating method such as spin coating, Inkjet printing, and so on.

An electron transport layer (ETL) 15 is disposed between the emission layer 14 and a cathode 16.

The emission layer 14 has a thickness ranging from 5 nm to 1 μm, and preferably 10 to 500 nm, and the hole transport layer (HTL) 13 and electron transport layer (ETL) 15 respectively have a thickness ranging from 10 to 10,000 Å.

The electron transport layer (ETL) 15 is formed using vacuum deposition, sputtering, or spin coating of generally-used electron transport layer (ETL) 15 materials.

The hole transport layer (HTL) 13 and electron transport layer (ETL) 15 play roles of efficiently transporting a carrier to the emission layer 14 to heighten light emitting recombination in the emission layer 14.

The hole transport layer (HTL) 13 material includes, but is not limited to, poly (3,4-ethylenedioxy-thiophene) (PEDOT) doped with poly(styrenesulfonic acid) (PSS), and N,N'-bis(3-methylphenyl)-N,N-diphenyl-[1,1'-biphenyl]-4,4'-diamine (TPD).

The electron transport layer (ETL) 15 material includes, but is not limited to, aluminum trihydroxyquinoline ($Alq_3$), a 1,3,4-oxadiazole derivative such as 2-(4-biphenylyl-5-phenyl-1,3,4-oxadiazole (PBD), a quinoxaline derivative such as 1,3,4-tris[(3-phenyl-6-trifluoromethyl)quinoxalin-2-yl]benzene (TPQ), and a triazole derivative.

The organic compound may be mixed with a phosphorescent light emitting organic compound. The phosphorescent organic compound may be a phosphorescent light emitting organic metal complex from its triplet state, and is preferably a metal complex of at least one group VIII metal ion according to the periodic table of Gregor Johann Mendel. The group VIII metal ion includes a metal ion selected from the group consisting of Fe, Co, Ni, Ru, Rh, Pd, Os, Ir, and Pt, and is preferably Ir or Pt.

Examples of the metal complex may be represented by the following Chemical Formulae 126 to 128, but are not limited thereto.

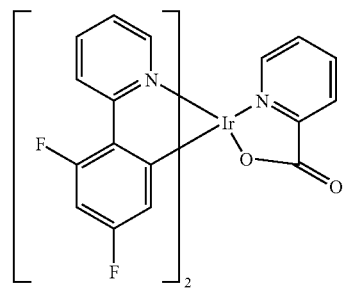

[Chemical Formula 126]

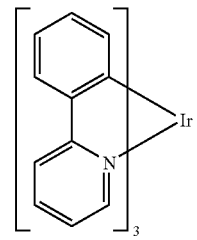

[Chemical Formula 127]

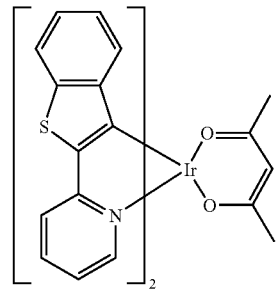

[Chemical Formula 128]

When the organic layer including the organic compound is formed using a solution coating, another low molecular host material can be included along with the organic compound. Examples of the low molecular host material include the compounds of the following Chemical Formulae 129 to 132, but are not limited thereto.

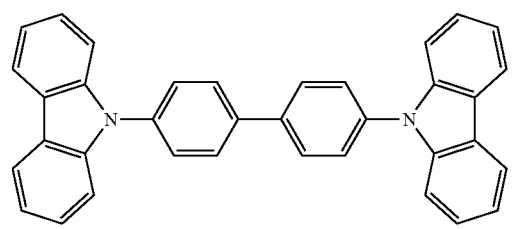

[Chemical Formula 129]

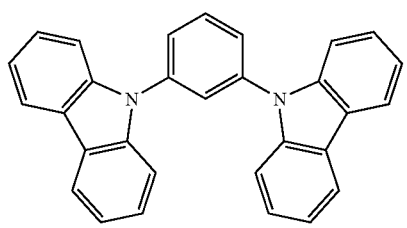

[Chemical Formula 130]

[Chemical Formula 131]

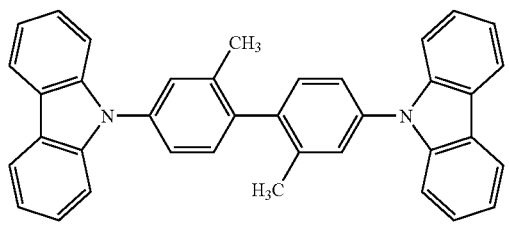

[Chemical Formula 132]

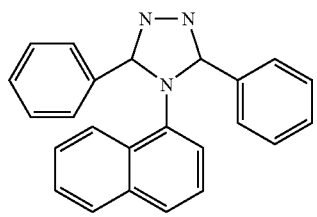

The organic compound may be used by mixing with polymers having conjugated double bonds such as fluorine-based polymers, polyphenylenevinylene-based polymers, and polyparaphenylene-based polymers, and also by mixing with binder resins.

The binder resins may include polyvinylcarbazole (PVK), polycarbonate, polyester, polyan arylate, polystyrene, acryl polymers, methacryl polymers, polybutyral, polyvinylacetal, diallylphthalate polymers, phenol resins, epoxy resins, silicone resins, polysulfone resins, or urea resins, and these resins can be used singularly and in combinations.

Selectively, a hole blocking layer may be disposed using vacuum deposition to limit a transport speed of holes into the emission layer 14 and thus to increase recombination opportunity of electrons and holes.

A cathode 16 material is coated on the electron transport layer (ETL) 15. The cathode material may be lithium (Li), magnesium (Mg), calcium (Ca), aluminum (Al), Al:Li, Ba:Li, or Ca:Li having a small work function.

Hereinafter, the embodiments are illustrated in more detail with reference to examples. However, it is understood that the present invention is not limited by these examples.

A person having ordinary skills in this art can sufficiently understand parts of the present invention that are not specifically described.

EXAMPLE 1

Synthesis of M-1

[Reaction Scheme 1]

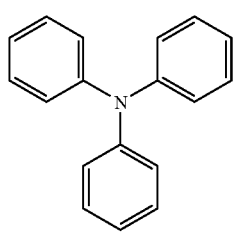

+

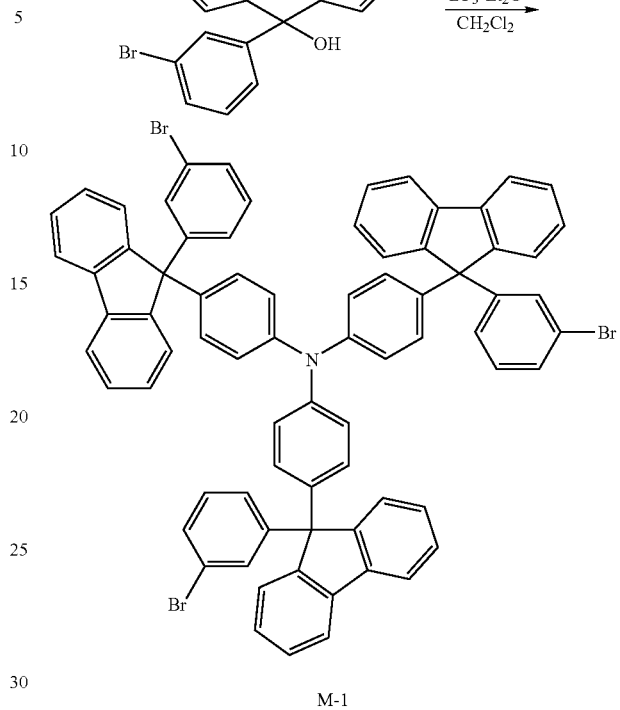

M-1

3.2 g (26 mmol) of 9-(3-bromophenyl)-9-H-fluorene-9-ol and 2.0 g (8.15 mmol) of triphenylamine were dissolved in 60 mL of dichloromethane under a nitrogen atmosphere, and 4 mL of a boron trifluoride diethylether complex ($BF_3 \cdot OEt_2$) was added thereto in a dropwise fashion. The mixture was agitated at room temperature for 12 hours, and 60 mL of water was added thereto, completing the reaction. The reactant was extracted with dichloromethane and washed four times. The extraction solution was dried with anhydrous magnesium sulfate. Then, the solvent was removed from the dried solution under reduced pressure. The resulting product was purified with a silica gel column using a mixed solvent of methylenechloride/hexane in a ratio of 1:2, and then recrystallized with a mixed solvent of methylenechloride/hexane, obtaining 8.6 g (87.7%) of white M-1.

EXAMPLE 2

Synthesis of M-2

[Reaction Scheme 2]

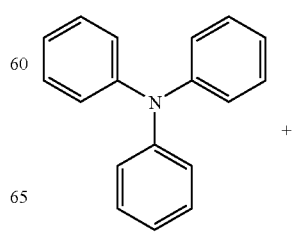

+

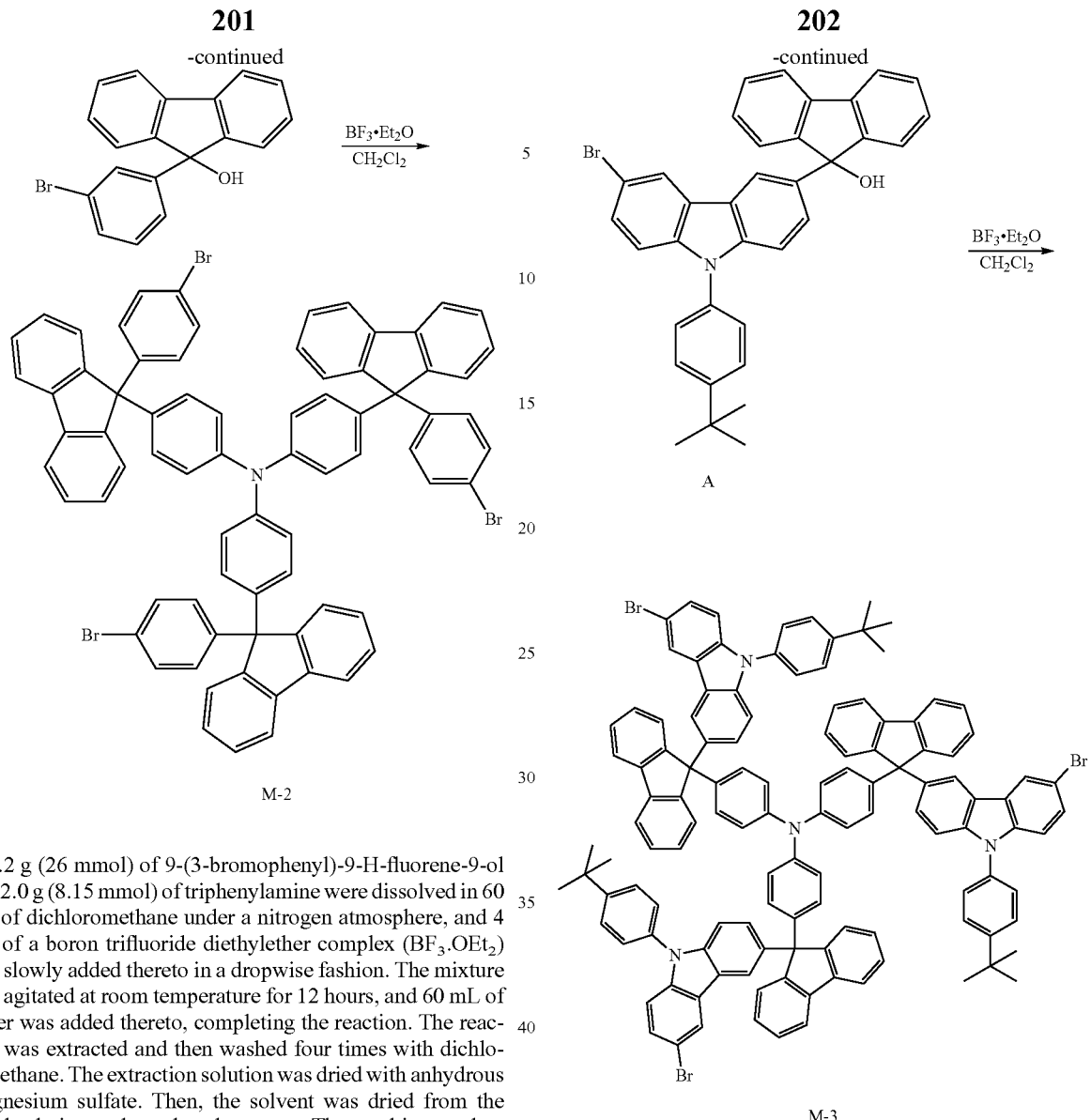

3.2 g (26 mmol) of 9-(3-bromophenyl)-9-H-fluorene-9-ol and 2.0 g (8.15 mmol) of triphenylamine were dissolved in 60 mL of dichloromethane under a nitrogen atmosphere, and 4 mL of a boron trifluoride diethylether complex ($BF_3 \cdot OEt_2$) was slowly added thereto in a dropwise fashion. The mixture was agitated at room temperature for 12 hours, and 60 mL of water was added thereto, completing the reaction. The reactant was extracted and then washed four times with dichloromethane. The extraction solution was dried with anhydrous magnesium sulfate. Then, the solvent was dried from the dried solution under reduced pressure. The resulting product was purified with a silica gel column using a mixed solvent of methylenechloride/hexane in a ratio of 1:2, and then recrystallized with a mixed solvent of methylenechloride/hexane, preparing 8.0 g (81.6%) of white M-2.

EXAMPLE 3

Synthesis of M-3

[Reaction Scheme 3]

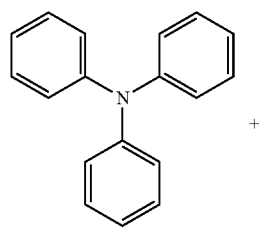

7.28 g (13 mmol) of an A material (9-(9-(4-tert-butylphenyl)-3-bromo-9H-carbazol-6-yl)-9H-fluorene-9-ol) and 1.0 g (4.07 mmol) of triphenylamine were dissolved in 50 mL of dichloromethane under a nitrogen atmosphere, and 2 mL of a boron trifluoride diethylether complex ($BF_3 \cdot OEt_2$) was added thereto in a dropwise fashion. The mixture was agitated at room temperature for 12 hours, and 50 mL of water was added thereto, completing the reaction. The reactant was extracted and washed four times with dichloromethane. The extraction solution was dried with anhydrous magnesium sulfate. Then, the solvent was removed from the dried solution under reduced pressure and purified with a silica gel column using a mixed solvent of methylenechloride/hexane in a ratio of 2:3, obtaining 6.5 g (85.5%) of white M-3.

EXAMPLE 4
Synthesis of CISH-1
[Reaction Scheme 4]
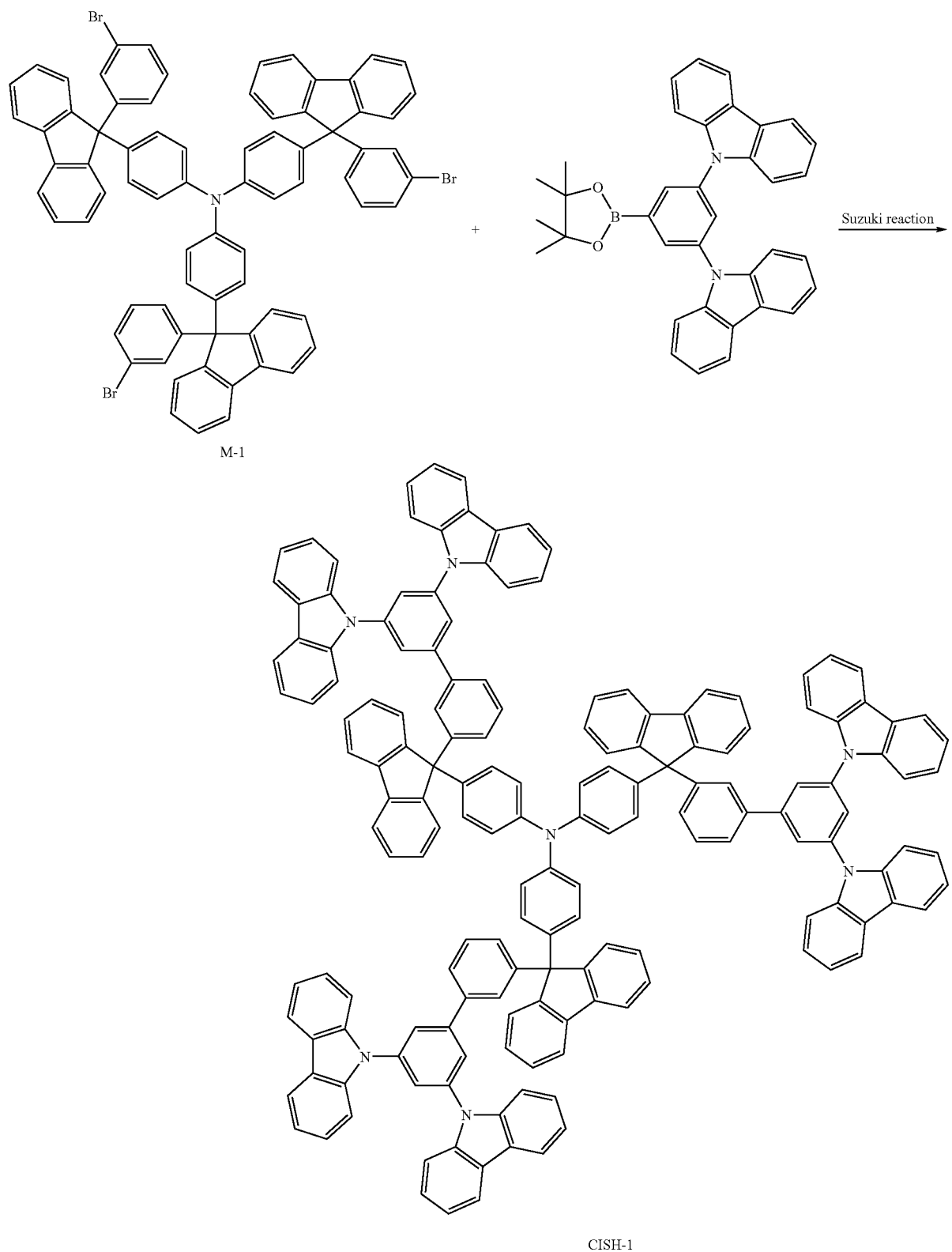

1.0 g (0.83 mmol) of M-1, 2.22 g (4.15 mmol) of (3-(9H-carbazole-9-yl)-5-(4,4,5,5-tetramethyl-1,3,2-dioxaborolan-2-yl)phenyl)-9H-carbazole, and 0.05 g of tetrakistriphenylphosphine palladium were dissolved in 40 mL of tetrahydrofuran (THF) under an argon atmosphere in a 100 ml round flask with a thermometer, a reflux condenser, and an agitator. 20 mL of 20% tetratriethyl ammonium hydroxide was added thereto. The mixture was refluxed for reaction at 75° C. for 48 hours.

When the reaction was complete, the reactant was cooled to room temperature and then extracted with methylenechloride and washed several times.

Then, anhydrous magnesium sulfate was used to remove moisture from the reactant. The resulting product was filtered to remove a solvent.

After removing the solvent, the reactant was purified with a silica gel column using a mixed solvent of methylenechloride/hexane in a ratio of 1:1 and recrystallized in a mixed solvent of acetone/hexane, obtaining 1.54 g (85%) of CISH-1.

EXAMPLE 5

Synthesis of CISH-2

[Reaction Scheme 5]

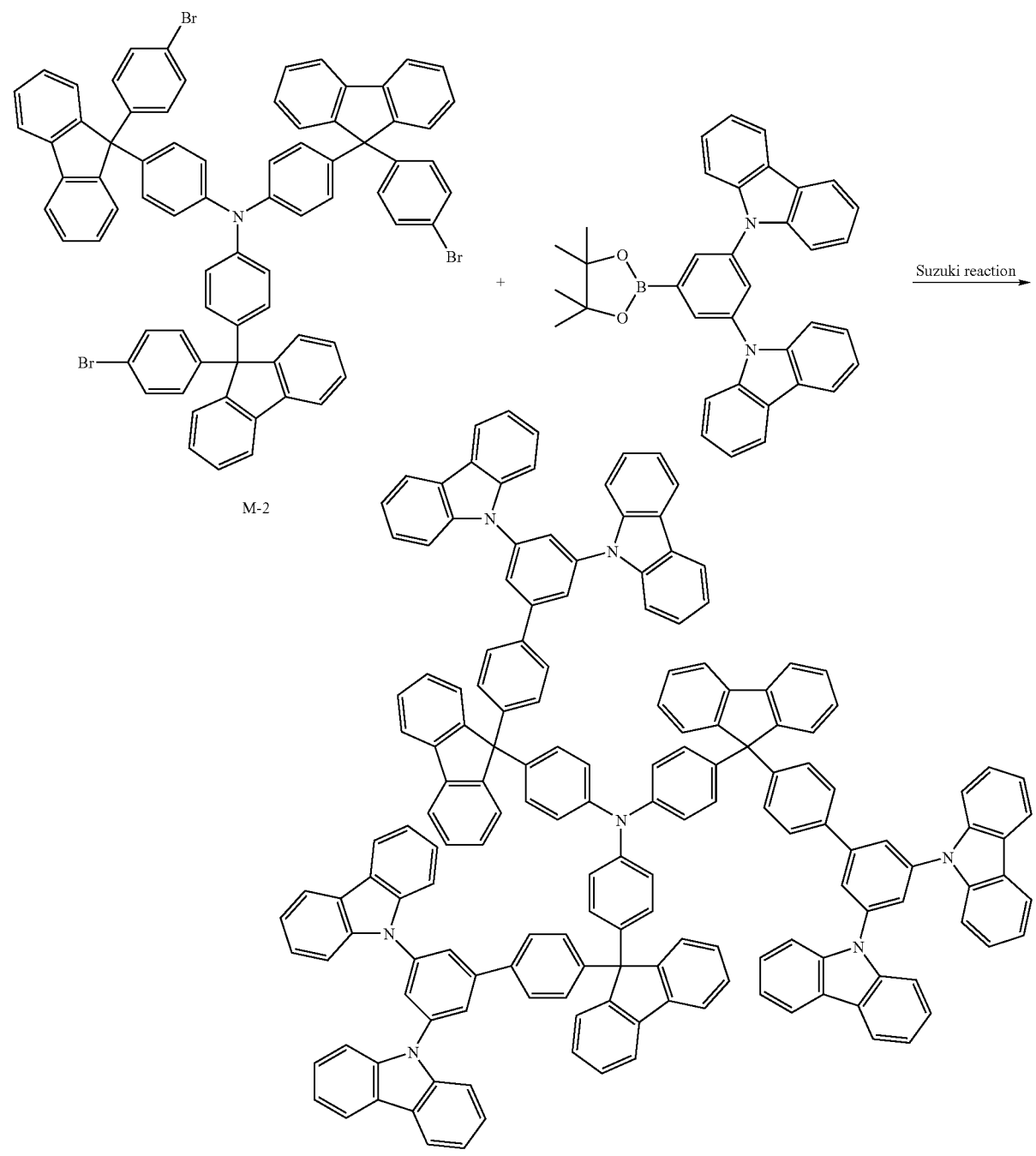

CISH-2

0.8 g (0.66 mmol) of M-2, 1.42 g (2.66 mmol) of (3-(9H-carbazole-9-yl)-5-(4,4,5,5-tetramethyl-1,3,2-dioxaborolan-2-yl)phenyl)-9H-carbazole, and 0.06 g of tetrakistriphenylphosphinepalladium were dissolved in 30 mL of tetrahydrofuran (THE) under an argon atmosphere in a 100 ml round flask with a thermometer, a reflux condenser, and an agitator. Then, 15 mL of 20% tetratriethyl ammonium hydroxide was added thereto and refluxed for reaction at 75° C. for 48 hours.

When the reaction was complete, the reactant was cooled to room temperature, and was then extracted several times with methylenechloride and washed.

Then, anhydrous magnesium sulfate was used to remove moisture from the reactant, which was then filtered to remove a solvent.

The reactant with no solvent was purified through a silica gel column using a mixed solvent of methylenechloride/hexane in a ratio of 1:1, preparing 1.1 g (75.8%) of white CISH-2.

EXAMPLE 6

Synthesis of CISH-3

[Reaction Scheme 6]

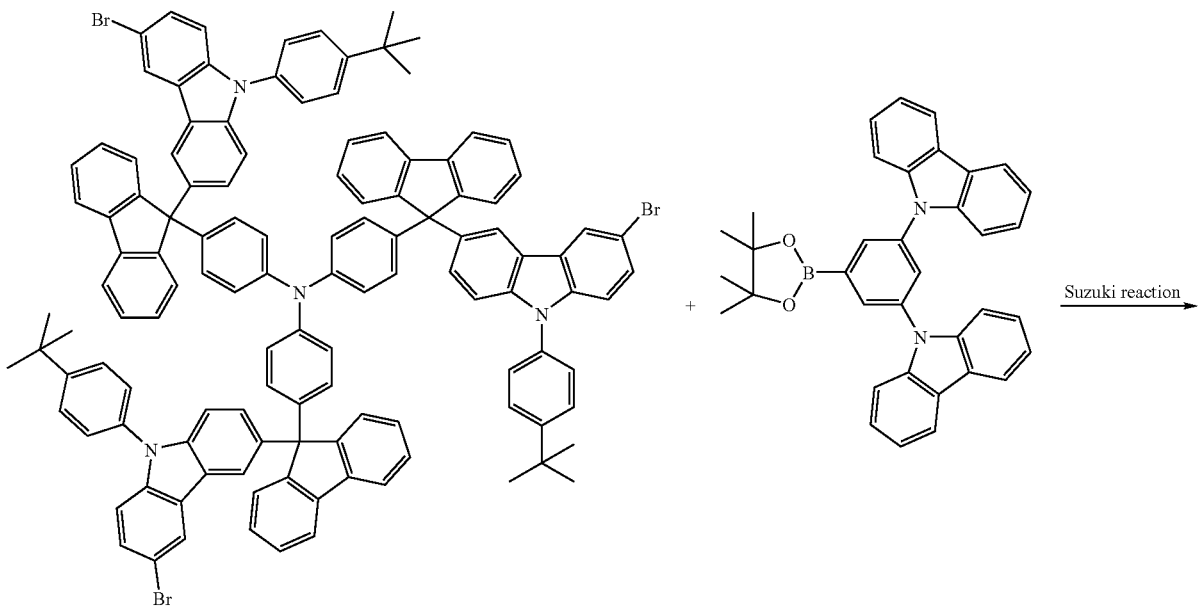

M-3

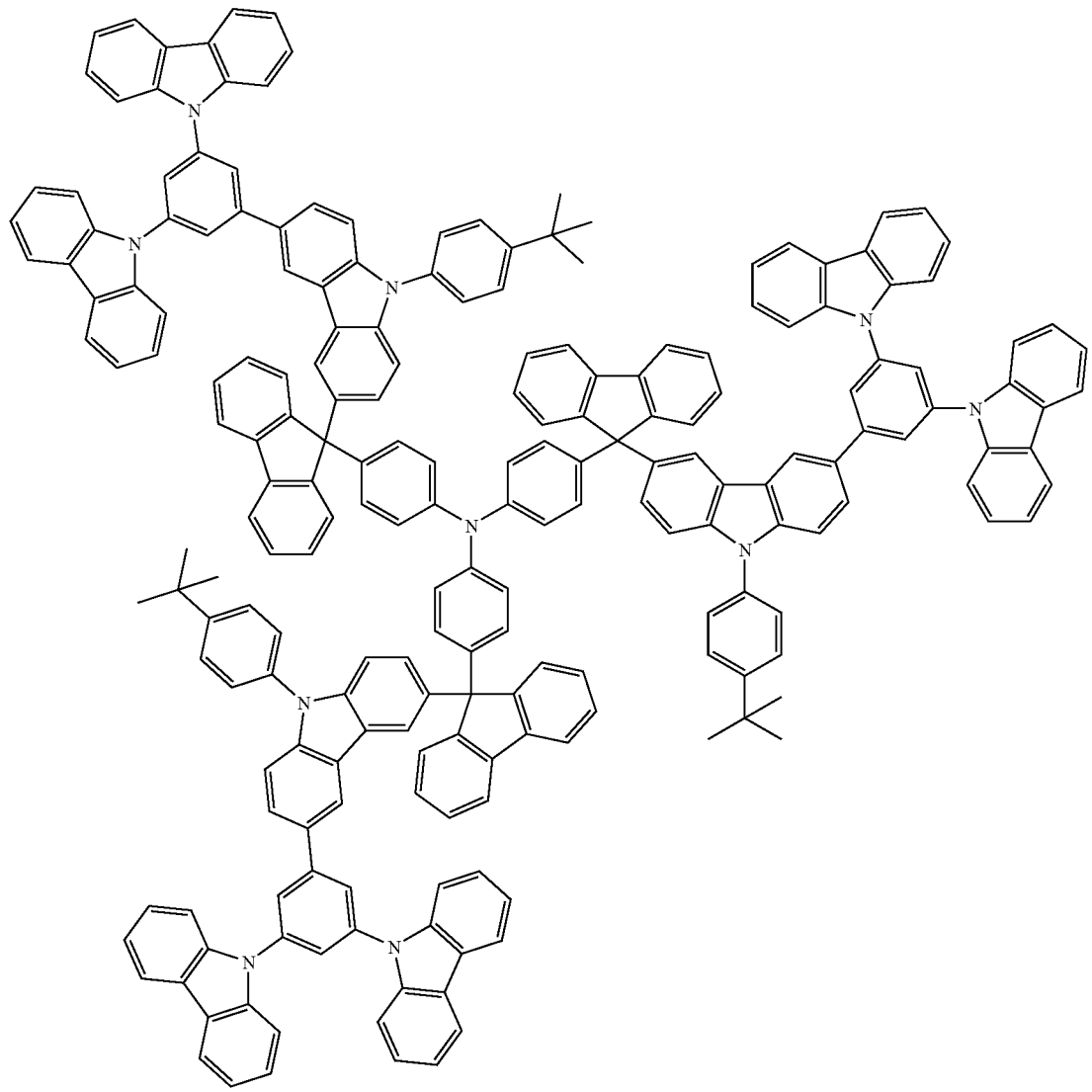
CISH-3

1.0 g (0.53 mmol) of M-3, 1.03 g (1.92 mmol) of (3-(9H-carbazole-9-yl)-5-(4,4,5,5-tetramethyl-1,3,2-dioxaborolan-2-yl)phenyl)-9H-carbazole, and 0.05 g of tetrakistriphenylphosphine palladium were dissolved in 30 mL of tetrahydrofuran (THF) under an argon atmosphere in a 100 ml round flask with a thermometer, a reflux condenser, and an agitator, and 15 mL of 20% tetratriethyl ammonium hydroxide was added thereto. The resulting mixture was refluxed at 75° C. for 48 hours.

When the reaction was complete, the reactant was cooled to room temperature, and was then extracted several times with methylenechloride and washed with water.

Then, anhydrous magnesium sulfate was used to remove moisture from the washed reactant. The resulting product was filtered to remove the solvent.

The reactant with no solvent was purified through a silica gel column using a mixed solvent of methylenechloride/hexane in a ratio of 1:1 and recrystallized in acetone, preparing 0.8 g (52.6%) of white CISH-3.

EXAMPLE 7

Synthesis of CISH-4

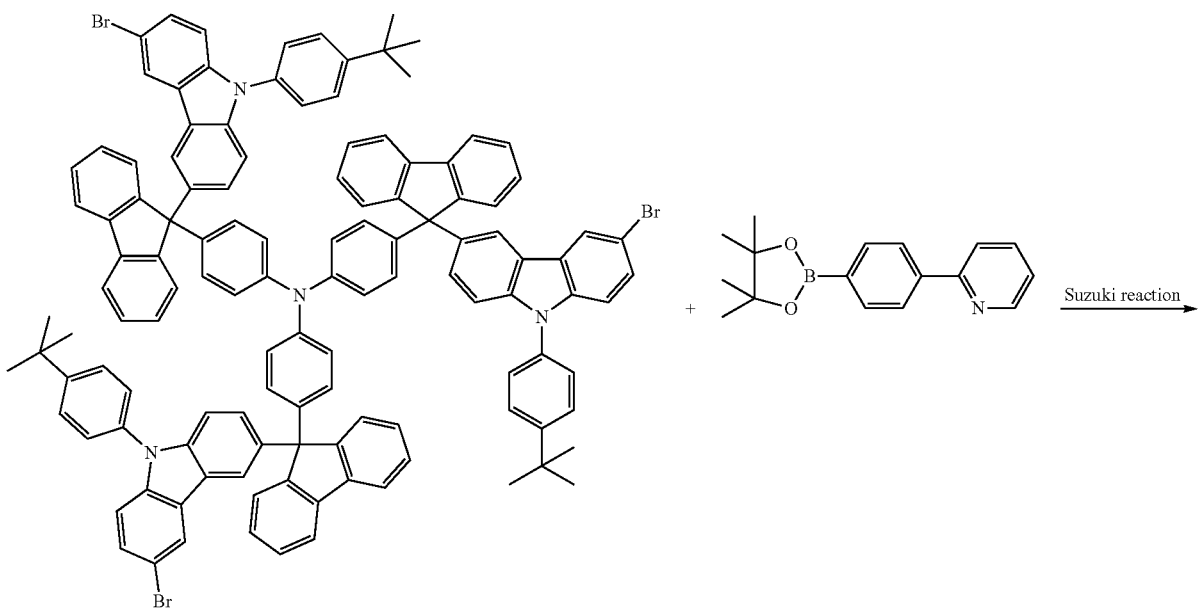

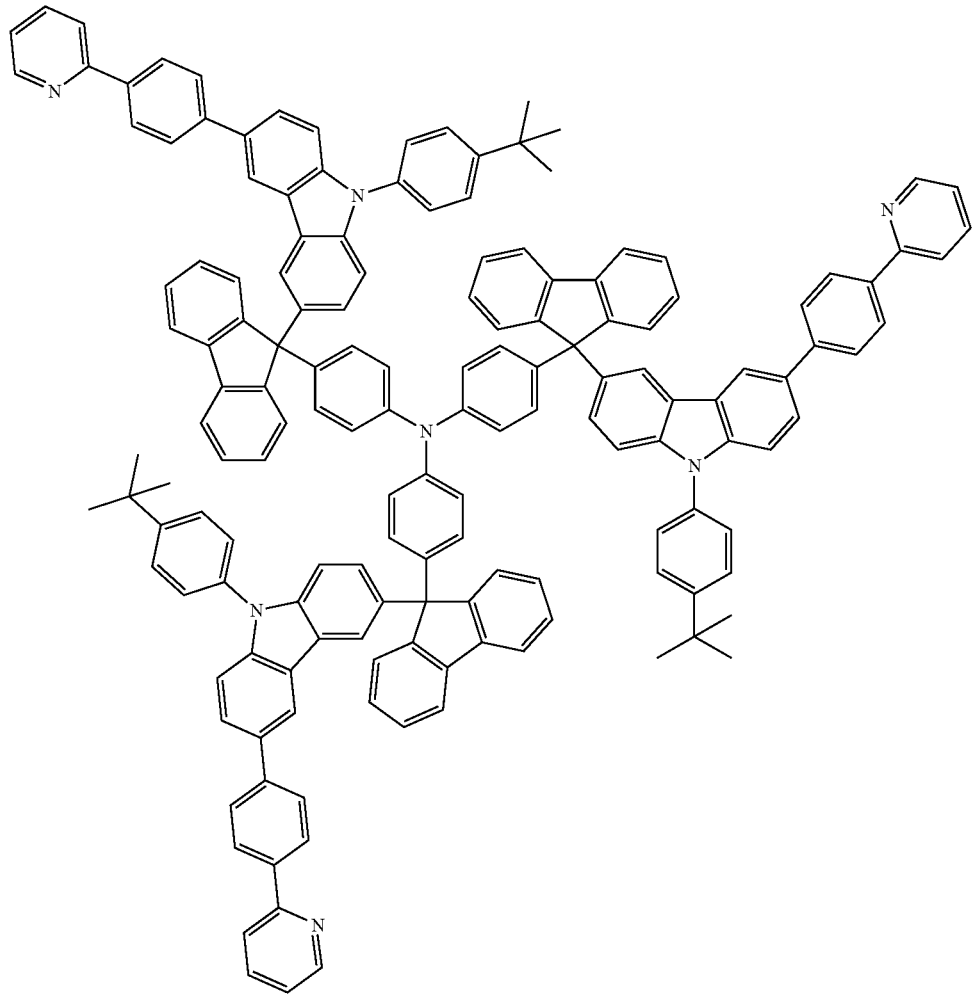
CISH-4

1.2 g (0.64 mmol) of M-3, 0.72 g (2.57 mmol) of 1-(4-(4, 4,5,5-tetramethyl-1,3,2-dioxaboran-2-yl)phenyl)pyridine, and 0.05 g of tetrakistriphenylphosphine palladium were dissolved in 30 mL of tetrahydrofuran (THF) under an argon atmosphere in a 250 ml round flask with a thermometer, a reflux condenser, and an agitator. 15 mL of 20% tetratriethyl ammonium hydroxide was added thereto. The resulting mixture was refluxed for reaction at 75° C. for 48 hours.

When the reaction was complete, the reactant was cooled to room temperature, and was then extracted several times with methylenechloride and washed with water.

Then, anhydrous magnesium sulfate was used to remove moisture from the washed reactant. The resulting product was filtered to remove the solvent.

The reactant with no solvent was purified through a silica gel column using a mixed solvent of methylenechloride/methanol in a ratio of 9:1 and recrystallized by a mixed solvent of methylenechloride/ethylacetate in a ratio of 94:6, obtaining 0.7 g (52.2%) of white CISH-4.

EXAMPLE 8

Synthesis of CISH-5

[Reaction Scheme 8]

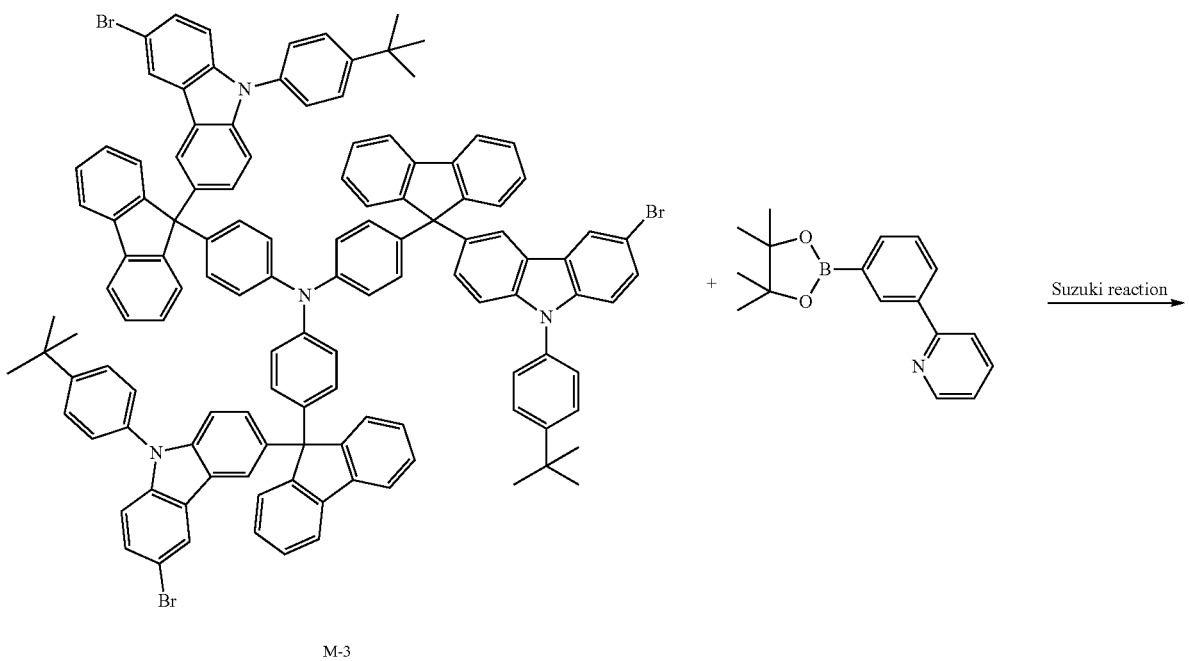

M-3

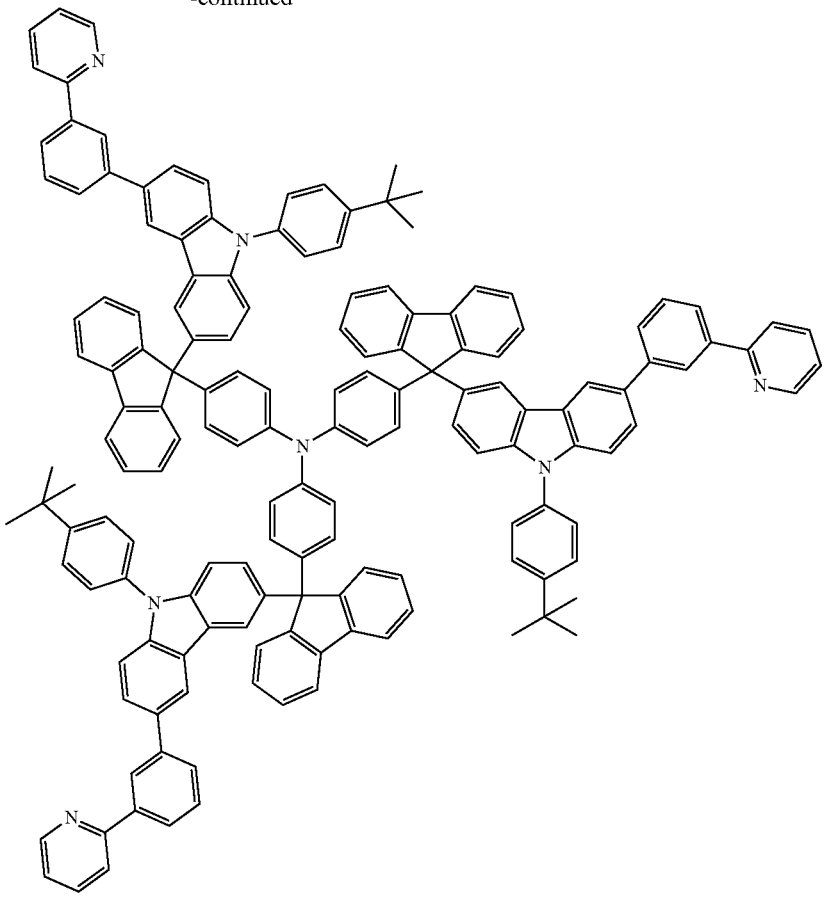

CISH-5

1.2 g (0.64 mmol) of M-3, 0.72 g (2.57 mmol) of 1-(3-(4,4,5,5-tetramethyl-1,3,2-dioxaborolan-2-yl)phenyl)pyridine, and 0.05 g of tetrakistriphenylphosphine palladium were dissolved in 30 mL of tetrahydrofuran (THF) under an argon atmosphere in a 250 ml round flask with a thermometer, a reflux condenser, and an agitator. 15 mL of 20% tetratriethyl ammonium hydroxide was added thereto. The resulting mixture was refluxed for reaction at 75° C. for 48 hours.

When the reaction was complete, the reactant was cooled to room temperature, and was then extracted several times with methylenechloride and washed with water.

Then, moisture was removed from the washed reactant using anhydrous magnesium sulfate. The resulting product was filtered to remove a solvent.

The solvent was purified through a silica gel column using a mixed solvent of methylenechloride/methanol in a ratio of 9:1 and recrystallized with a mixed solvent of methylenechloride/ethylacetate in a ratio of 94:6, obtaining 0.8 g (59.7%) of white CISH-5.

EXAMPLE 9
Synthesis of CISH-6
[Reaction Scheme 9]
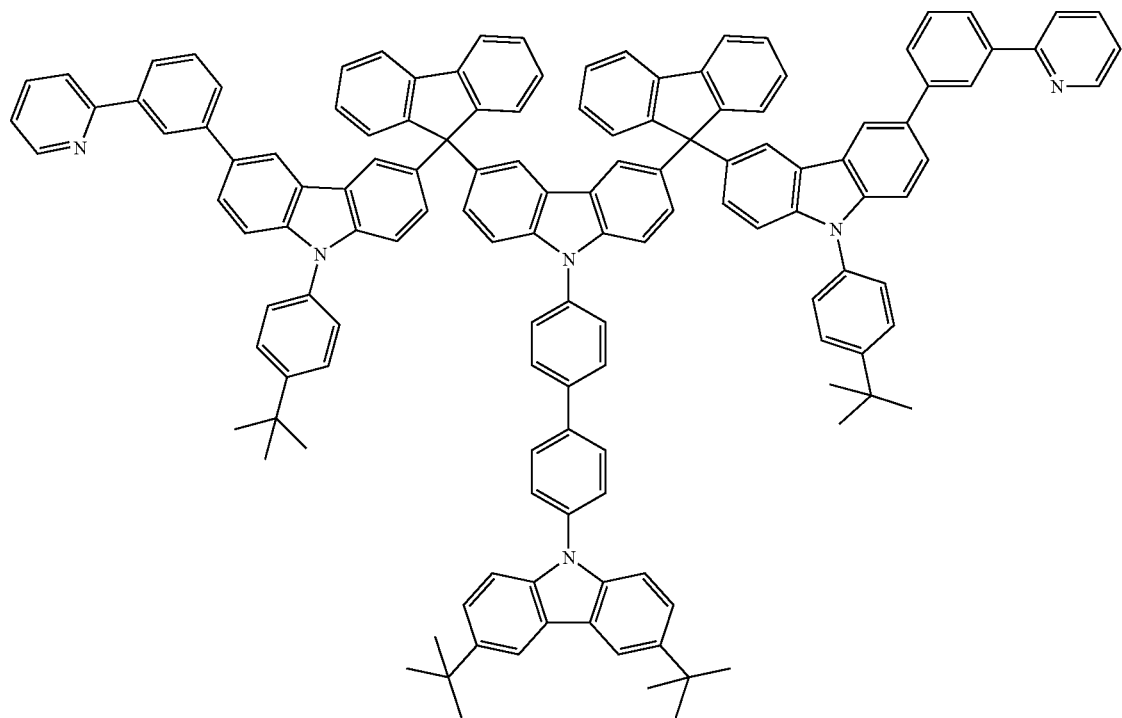

The Synthesis of CISH-6, which is shown above in Scheme 9, may be performed in a manner analogous to that of CISH-5 in Scheme 8 above using a Suzuki reaction.
EXAMPLE 10
Synthesis of CISH-7
[Reaction Scheme 10]
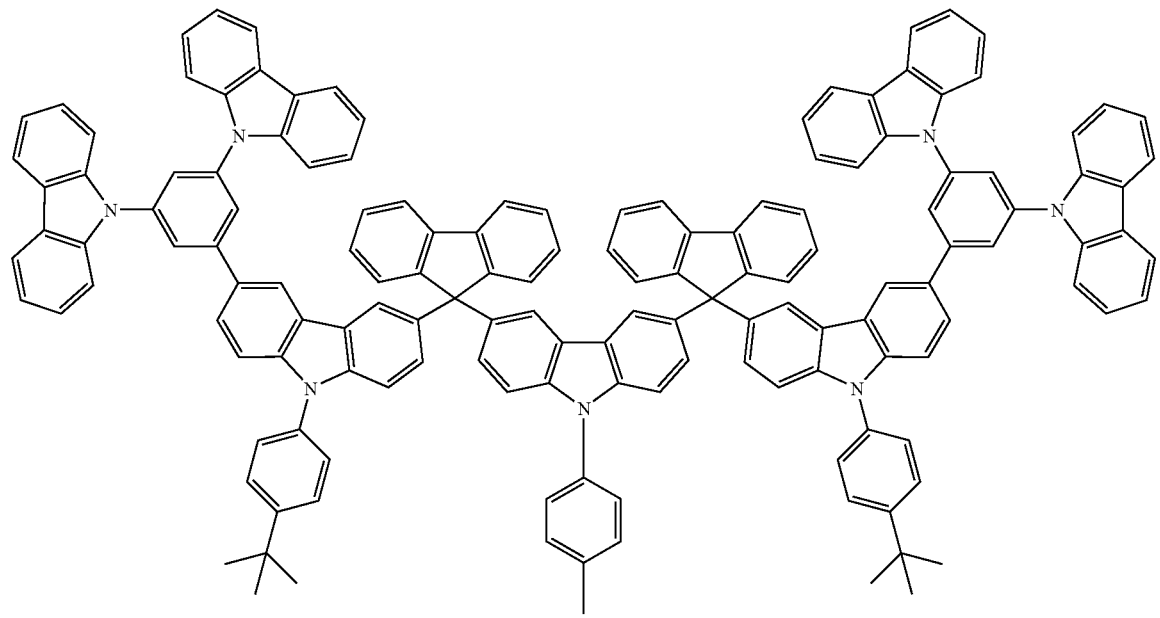
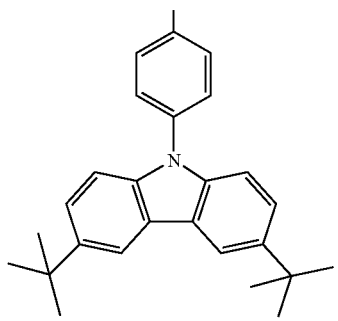

The Synthesis of CISH-7, which is shown above in Scheme 10, may be performed in a manner analogous to that of CISH-5 in Scheme 8 above using a Suzuki reaction.

COMPARATIVE EXAMPLE 1

Synthesis of 4,4-N,N-dicarbazolebiphenyl (CBP)

[Reaction Scheme 11]

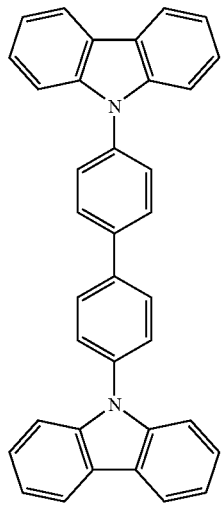

The Synthesis of CBP (4,4-N,N'-dicarbazole biphenyl, used in Comparative Example 1) is well-known, or CBP may be purchased commercially.

Performance Evaluation of Organic Compounds

Figure 2:
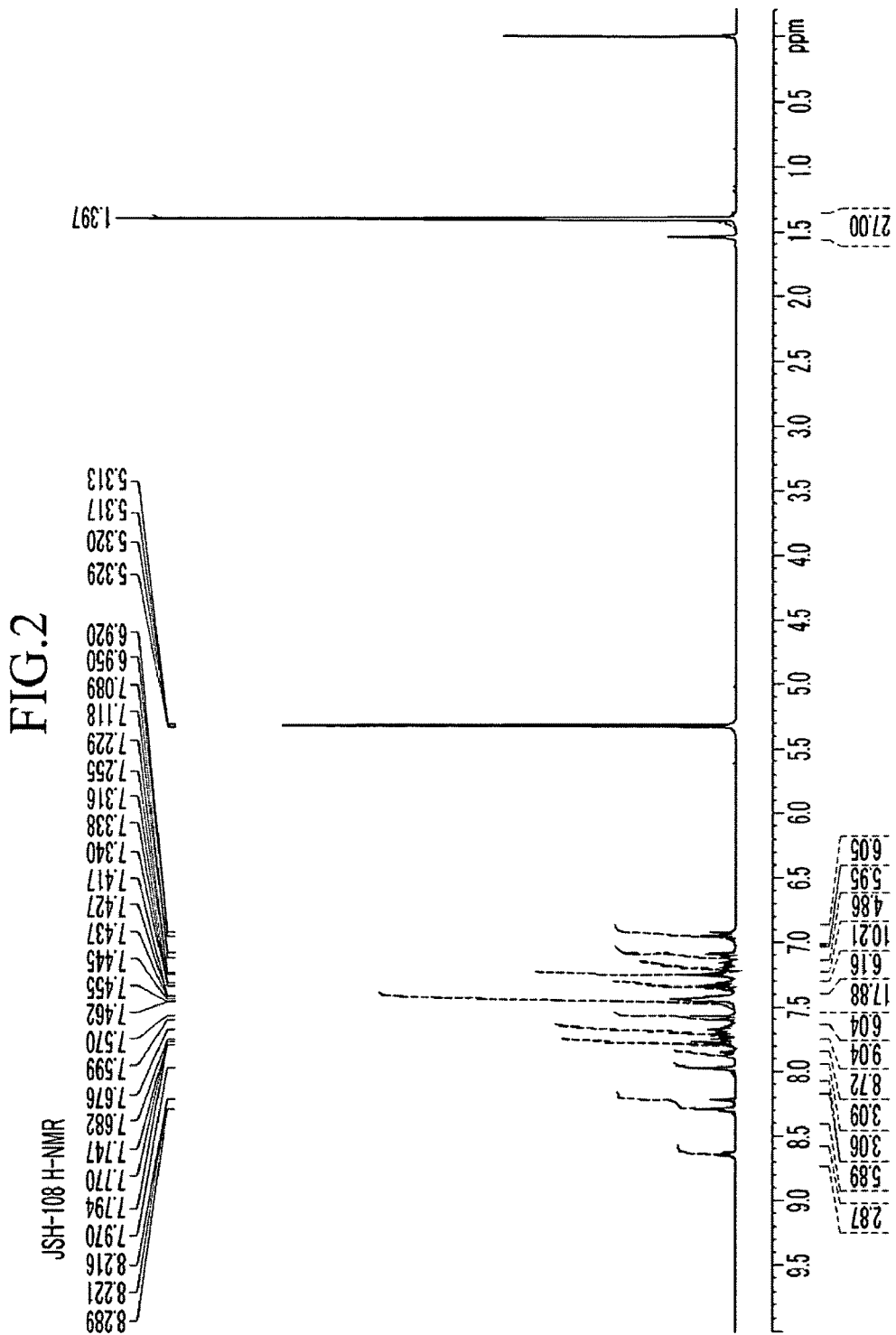
FIG. 2 shows a $^1$H-NMR spectrum of the organic compound according to Example 8.

The CISH-5 of Example 8 was measured regarding $^1$H-NMR using a Bruker 300MHz®. The result is shown in FIG. 2. Referring to FIG. 2, the organic compound of Example 8 was identified as CISH-5. Referring to FIG. 2, the organic compound of Example 8 was identified as CISH-5.

Figure 3:
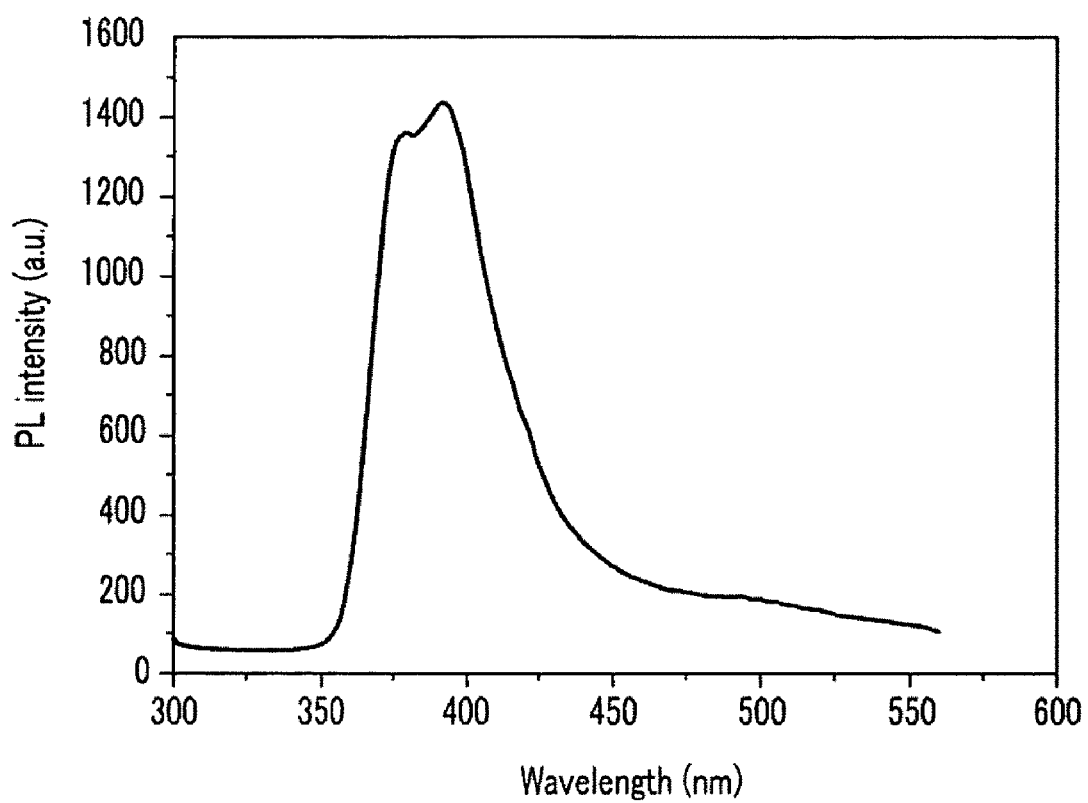
FIG. 3 is a graph showing photoluminescence (PL) wavelength of the organic compound according to Example 8.

The CISH-5 was coated on a glass substrate to form a thin film. The film was measured regarding photoluminescence (PL) wavelength by using a HITACHI F-4500®. The result is shown in FIG. 3. Referring to FIG. 3, the CISH-5 made into a thin film had a maximum light emitting wavelength at 391 nm.

Preparation of Organic Photoelectric Device

EXAMPLE 11

Preparation of a Device Using Example 7

An ITO substrate was used as an anode, and poly(3,4-ethylene dioxy-thiophene) (PEDOT) was formed by spin-coating on the substrate.

Next, an emission layer was formed through spin-coating on the surface of the PEDOT by doping Ir(mppy)$_3$ as a dopant in CISH-7 in an amount of 6 to 7 wt %.

Then, a 50 Å-thick hole blocking layer was formed on the emission layer by vacuum-depositing BAlq.

Then, a 200 Å thick electron transport layer (ETL) was formed on top of the emission layer by vacuum-depositing Alq$_3$.

Finally, an organic photoelectric device was completed by sequentially vacuum-depositing LiF 10 Å and Al 1000 Å on top of the electron transport layer (ETL) to fabricate a cathode.

PVK was used as a polymer host for a comparison reference device structure.

Herein, an evaluation device structure included Al 1000 Å/LiF 10 Å/Alq$_3$ 200 Å/BAlq 50 Å/EML(CISH-2+Ir (mppy)$_3$)/PEDOT/ITO 1500 Å, while the comparison reference device structure included Al 1000 Å/LiF 10 Å/Alq$_3$ 200 Å/BAlq 50 Å/EML(PVK+Ir(mppy)$_3$)/PEDOT/ITO 1500 Å.

EXAMPLE 12

Preparation of a Device Using Example 8

An organic photoelectric device was fabricated using the same method as in Example 11, except that Example 8 was used instead of Example 7.

EXAMPLE 13

Preparation of a Device Using Example 9

An organic photoelectric device was fabricated using the same method as in Example 11, except that Example 9 was used instead of Example 7.

EXAMPLE 14

Preparation of a Device Using Example 10

An organic photoelectric device was fabricated using the same method as in Example 11, except that Example 10 was used instead of Example 7.

COMPARATIVE EXAMPLE 2

Preparation of a Device Using Comparative Example 1

An organic photoelectric device was fabricated using the same method as in Example 11, except that Comparative Example 1 was used instead of Example 7.

Performance Measurement of Organic Photoelectric Devices

The organic photoelectric device of Example 11 was measured regarding luminance change and efficiency change depending on voltage change. The results are respectively shown in FIGS. 4 and 5.

In addition, the organic photoelectric devices of Examples 7 and 8 were measured regarding a threshold voltage, a driving voltage at 1000 nit, current efficiency, and electric power efficiency. The results are shown in the following Table 1.

TABLE 1

| | | | At 1000 nit | | |
| --- | --- | --- | --- | --- | --- |
| Device | Organic compound | Threshold Voltage (V) | Driving Voltage (V) | Current Efficiency (cd/A) | Electric power efficiency lm/W |
| Green | Example 11 | 4.8 | 9.4 | 11.12 | 3.72 |
| | Example 12 | 5.0 | 9.8 | 11.78 | 3.77 |

Figure 4:
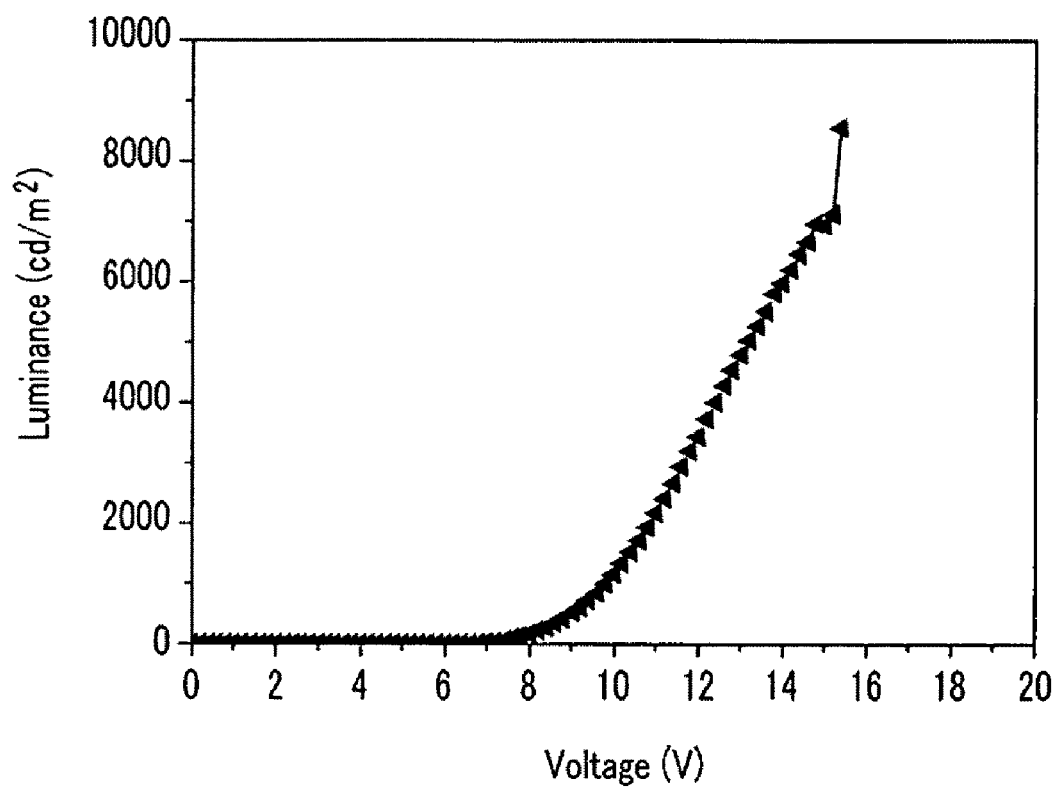
FIG. 4 is a graph showing voltage-luminance of the organic photoelectric device including the organic compound according to Example 8.
Figure 5:
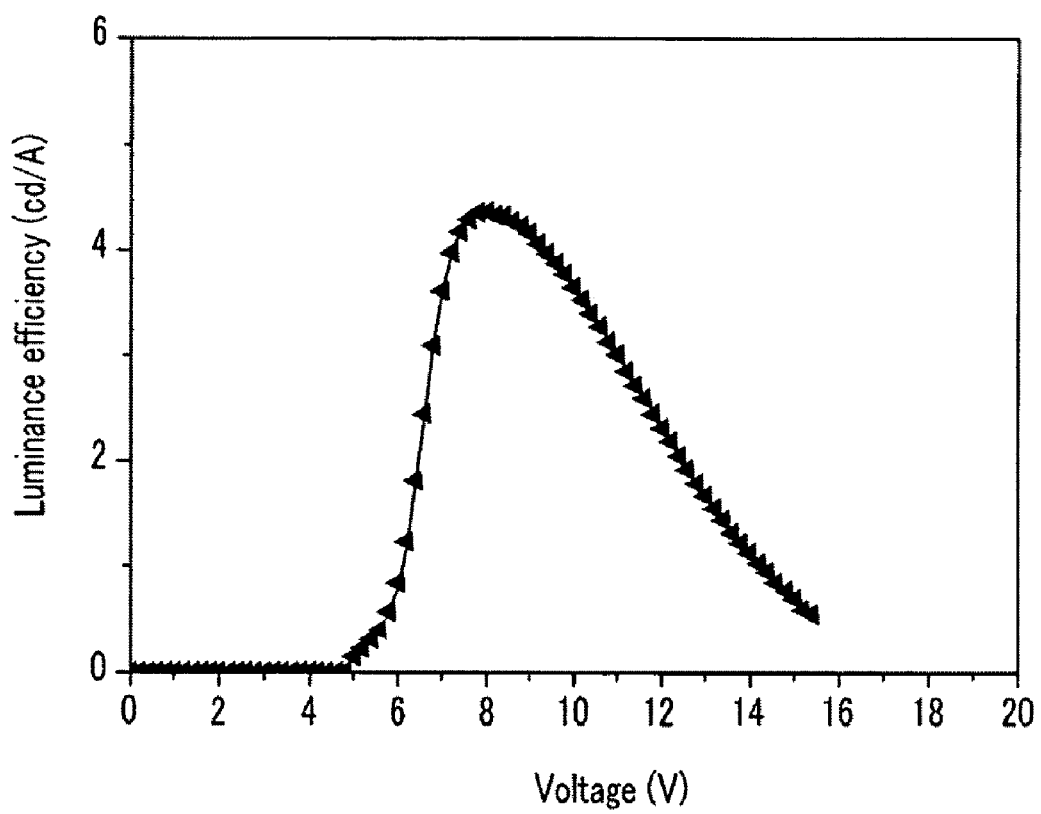
FIG. 5 is a graph showing voltage-efficiency of the organic photoelectric device including the organic compound according to Example 8.

Referring to FIGS. 4 and 5 and Table 1, the organic compound of the present invention was found to be useful as a host material for an organic photoelectric device.

Measurement of Characteristic of Compound

Differential scanning calorimetry (DSC) and thermogravimetric analysis (TGA) analyses of the compounds according to Examples 9, 10, and Comparative Example 1 were performed, and the glass transition temperatures, the decomposition temperatures, the melting points, and the triplet energy levels were compared.

Figure 6A:
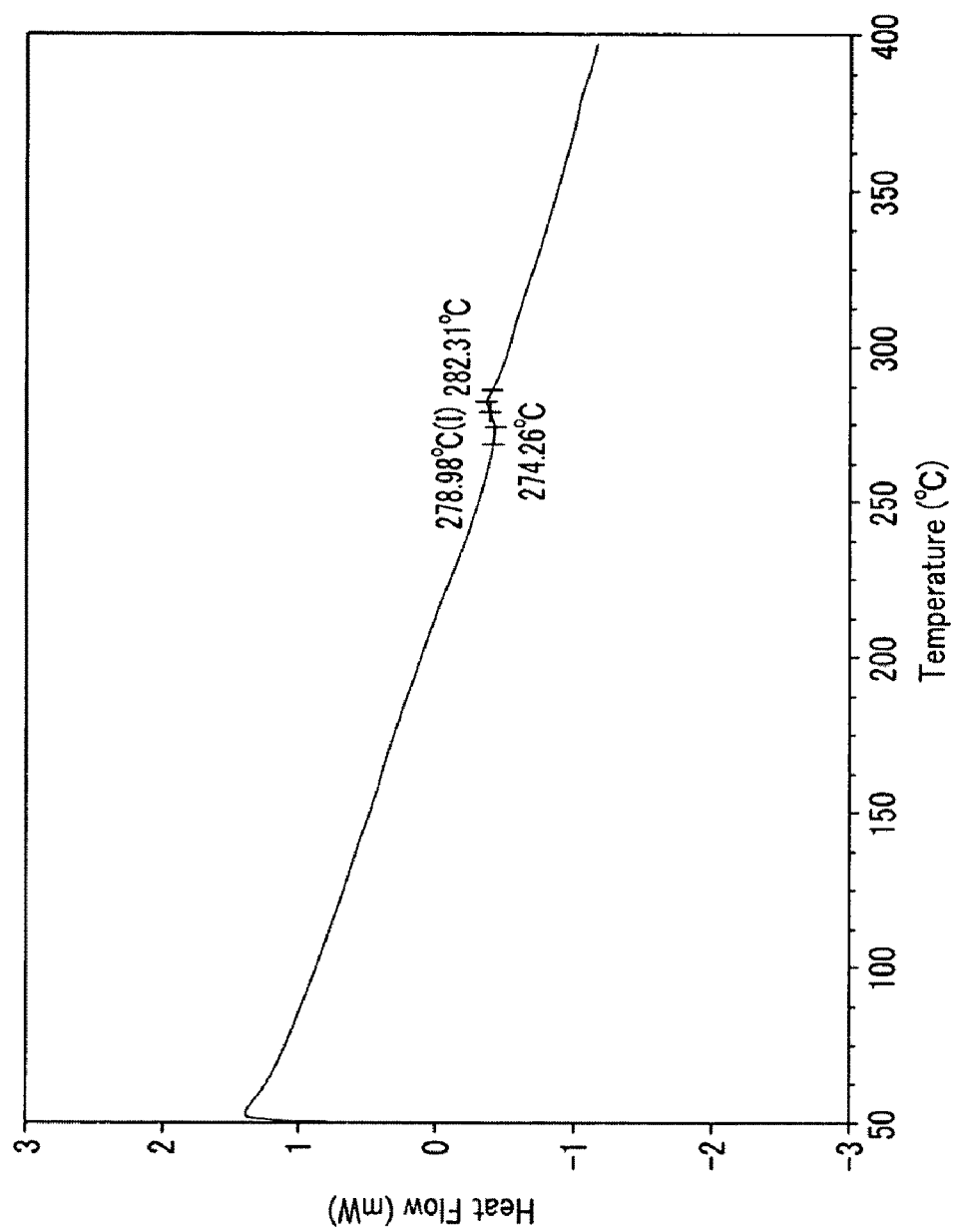
FIG. 6a is a data of Differential Scanning Calorimetry (DSC) according to Example 9.
Figure 6B:
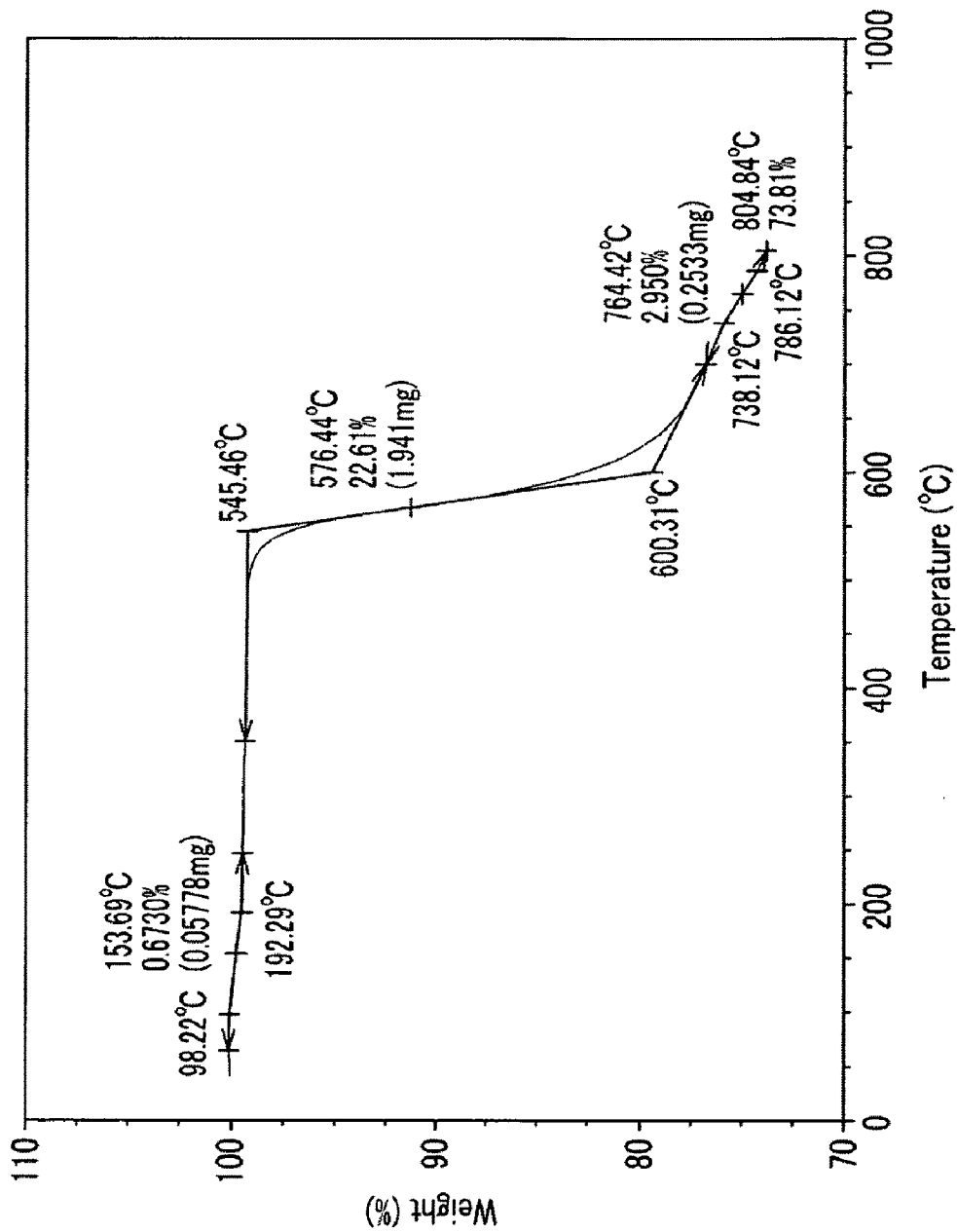
FIG. 6b is a data of Thermogravimetric Analysis (TGA) according to Example 9.

FIG. 6A shows the result of DSC of Example 9, and FIG. 6B shows the result of a TGA of Example 9.

Figure 7A:
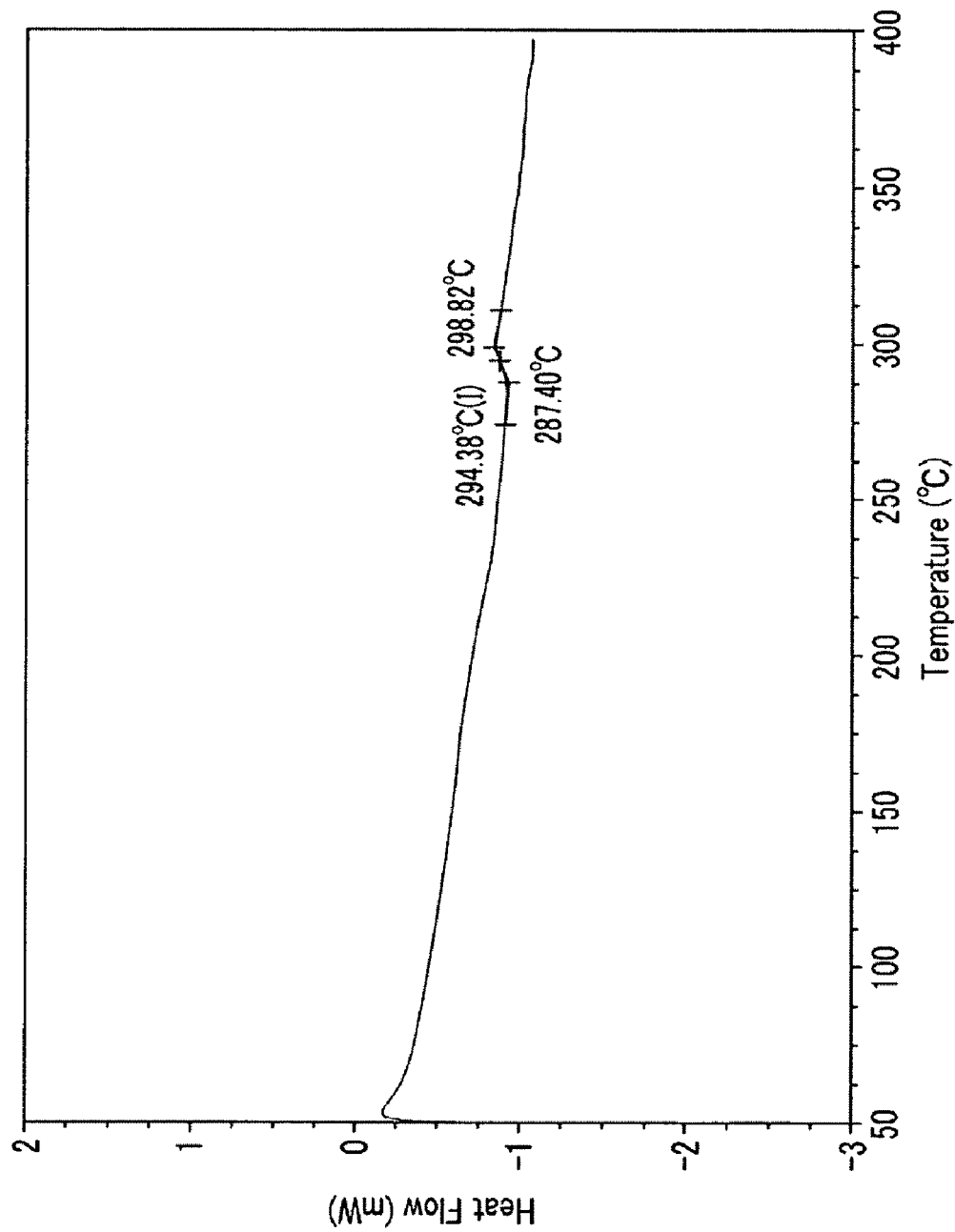
FIG. 7a is a data of DSC according to Example 10.
Figure 7B:
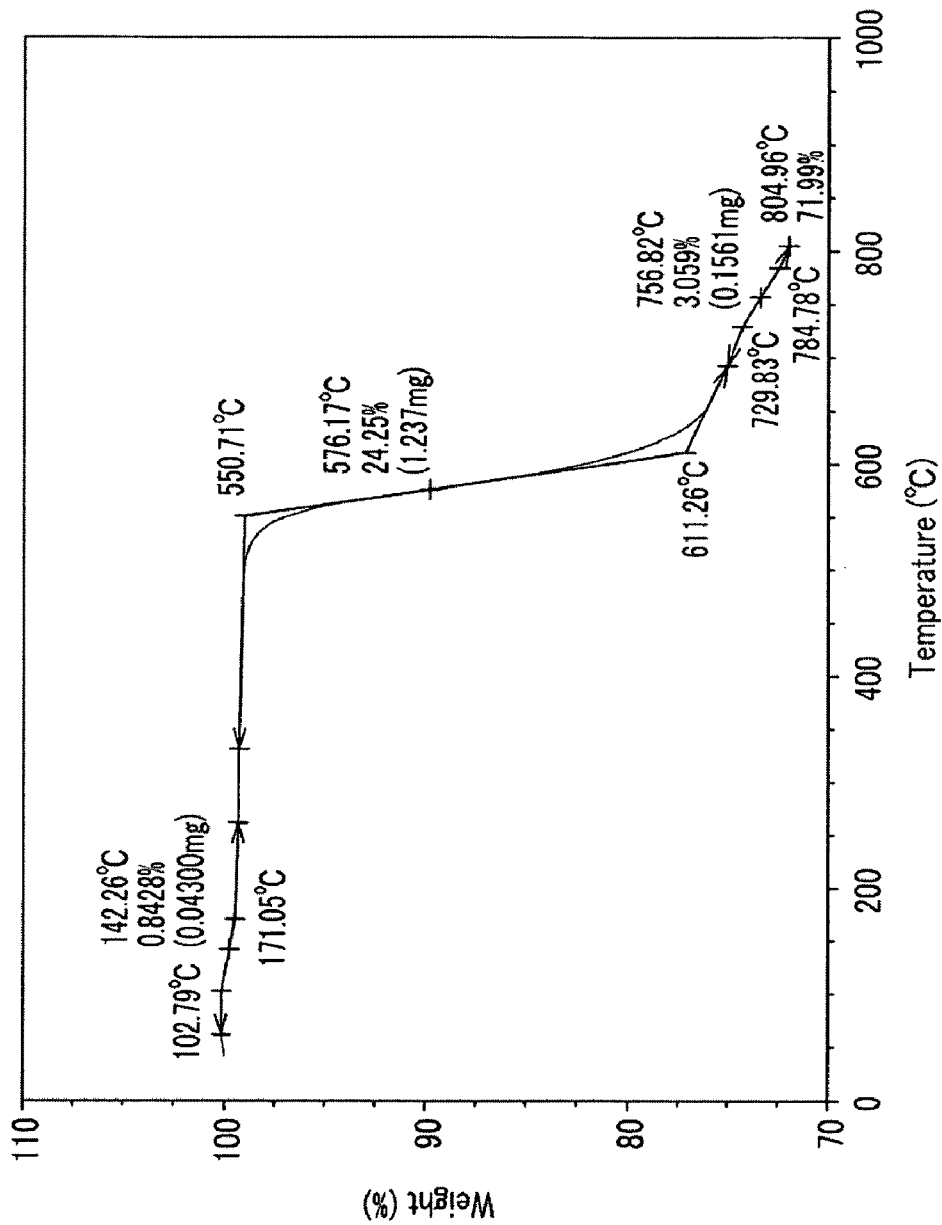
FIG. 7b is a data of TGA according to Example 10.

FIG. 7A shows the result of DSC of Example 10, and FIG. 7B shows the result of a TGA of Example 10.

The results of FIGS. 6A, 6B, 7A, and 7B are as shown in the following Table 2.

TABLE 2

| Material | Tg (° C.) | Tm (° C.) | Td (° C.) | T1 |
|---|---|---|---|---|
| Comparative Example 1 | N.D. | 282 | 392 | 2.65 |
| Example 9 | 278 | N.D. | 545 | 2.63 |
| Example 10 | 294 | N.D. | 550 | 2.63 |

Tg: glass transition temperature
Tm: melting point
Td: decomposition temperature
T1: Triplet energy level
N.D.: Not determined As shown in the Table 2, thermal properties of CBP according to Comparative Example 1 are well known to a person of ordinary skill in the art.

When a fluorenyl group is directly linked to CBP at the $9^{th}$ position of the fluorenyl group, thermal stabilities may be improved compared with CBP of Comparative Example 1 without a change of triplet energy level (T1).

Comparing the decomposition temperatures of Table 2, Examples 9 and 10 have remarkably higher temperatures than CBP of Comparative Example 1. Further, while they have excellent thermal stability, their triplet energy levels (T1) do not change.

Evaluation of Solubility

The compounds of Comparative Example 1 and Examples 7 and 9 were used to fabricate emission layers of an organic photoelectric device through a solution process, and the surface of the fabricated emission layers were evaluated through an atomic force microscope (AFM).

Figure 8A:
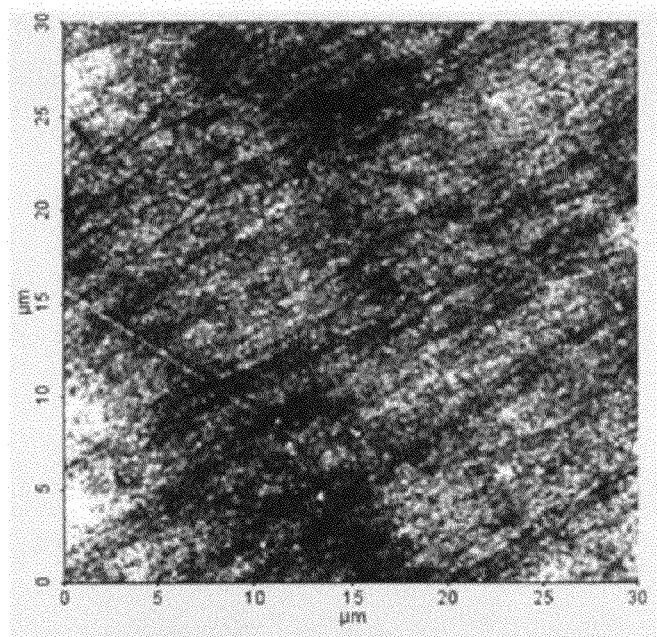
FIG. 8a is a topography photo related to a surface of an emission layer according to Comparative Example 1.
Figure 8B:
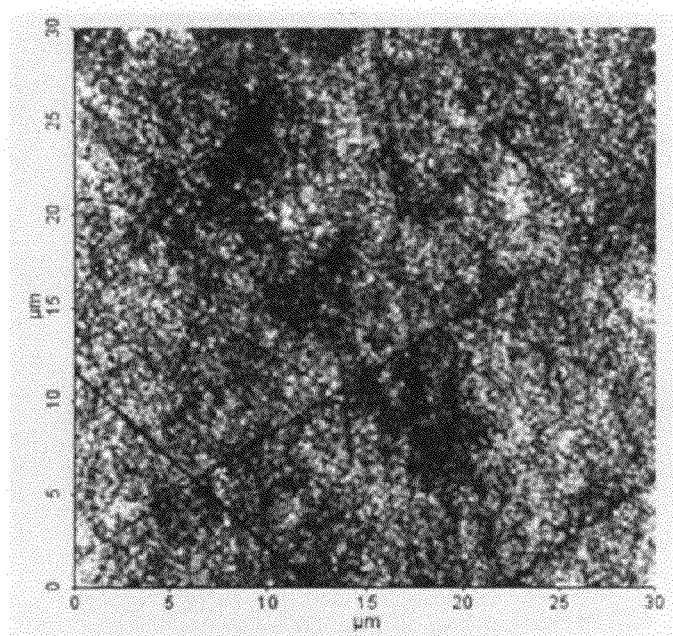
FIG. 8b is a topography photo related to a surface of an emission layer according to Example 9.
Figure 8C:
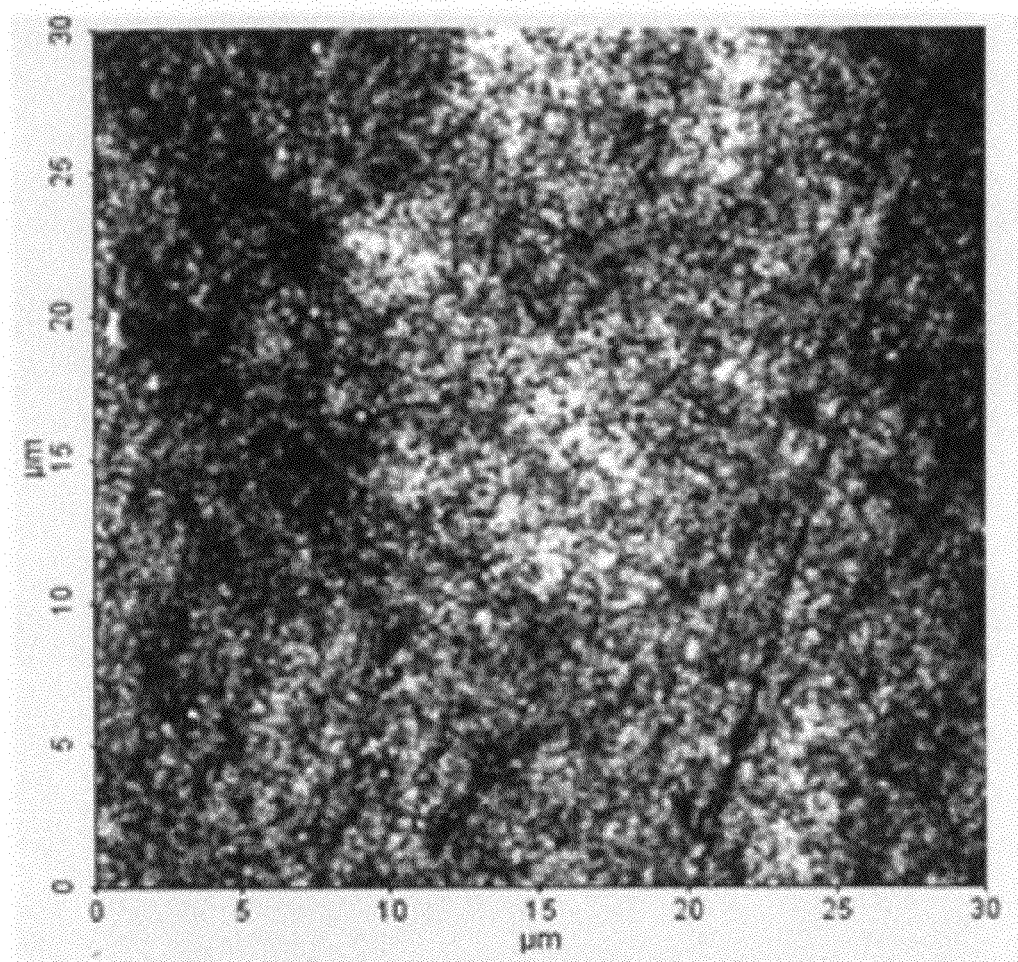
FIG. 8c is a topography photo related to a surface of an emission layer according to of Example 10.

FIG. 8A is a topography image of an emission layer according to Comparative Example 1, FIG. 8B is a topography image of an emission layer according to Example 9, and FIG. 8C is a topography image of an emission layer according to Example 10.

Rq refers to surface roughness measured by AFM.

TABLE 3

| Compound | Rq (nm) |
|---|---|
| Comparative Example 1 | 0.727 |
| Example 9 | 0.471 |
| Example 10 | 0.571 |

As shown in Table 3, when emission layers are fabricated through a solution process using the compounds, then a low surface roughness, Rq is obtained indicating that the compounds of Examples 9 and 10 are suitable materials of an organic photoelectric device for a solution process.

Crystallinity of a material affects surface roughness. The compound of Comparative Example 1 that is well known to a person of ordinary skill in the art provides an emission layer having bad surface roughness due to crystallization of a compound through a solution process.

As shown in Table 2, Examples 9 and 10 including a fluorenyl group compared with Comparative Example 1 have an increased glass transition temperature (Tg), and do not undergo recrystallization after a solution process by preventing their crystallization. Therefore, as shown in Table 3, the surface roughness of the emission layers including compounds according to Examples 9 and 10 is low.

When the surface roughness increases, the device characteristics remarkably decrease, which is well known to a person of ordinary skill in the art.

Therefore, the organic photoelectric devices fabricated using the compounds according to Examples 9 and 10 may have excellent device characteristics compared to the organic photoelectric device fabricated using CBP of Comparative Example 1.

Evaluation of Optical Characteristics of Organic Photoelectric Device

Optical characteristics of the organic photoelectric devices according to Examples 13, 14, and Comparative Example 2 were evaluated.

Figure 9A:
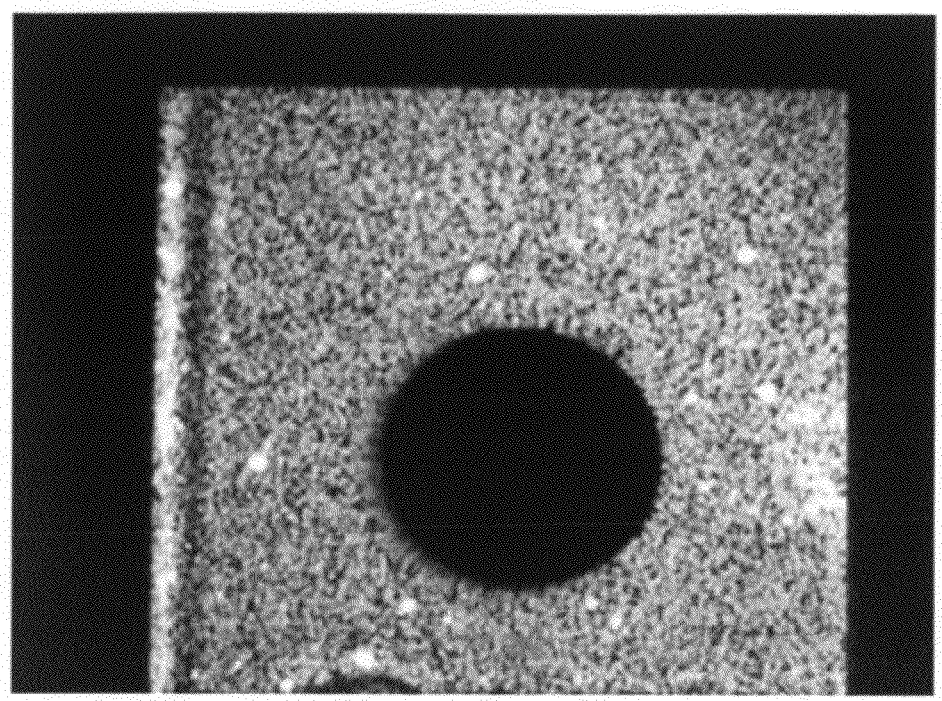
FIG. 9a is a luminous photo according to Comparative Example 2.
Figure 9B:
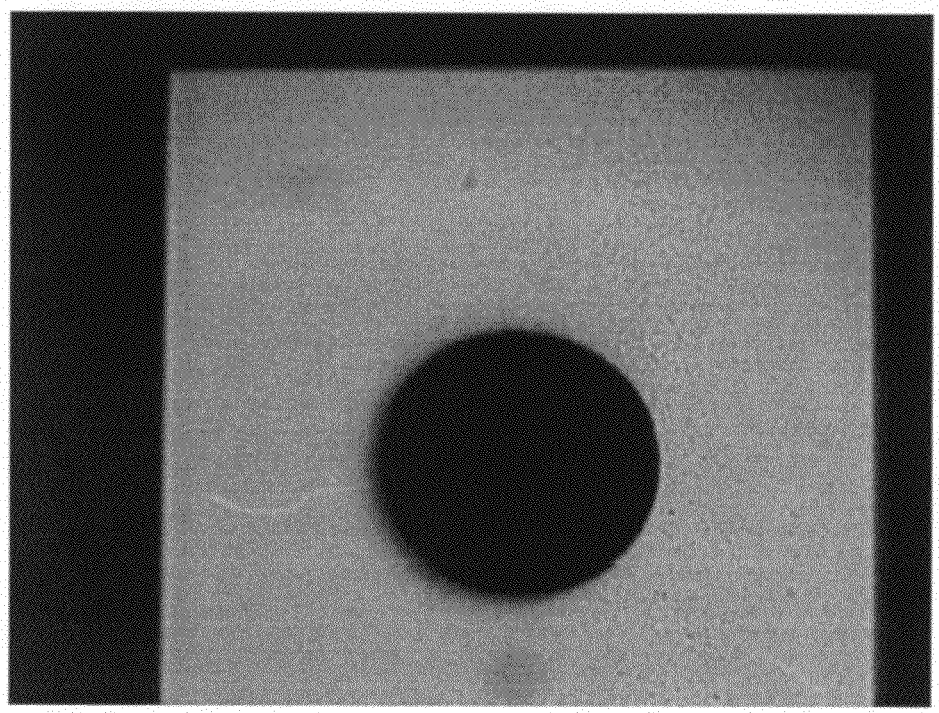
FIG. 9b is a luminous photo according to Example 13.
Figure 9C:
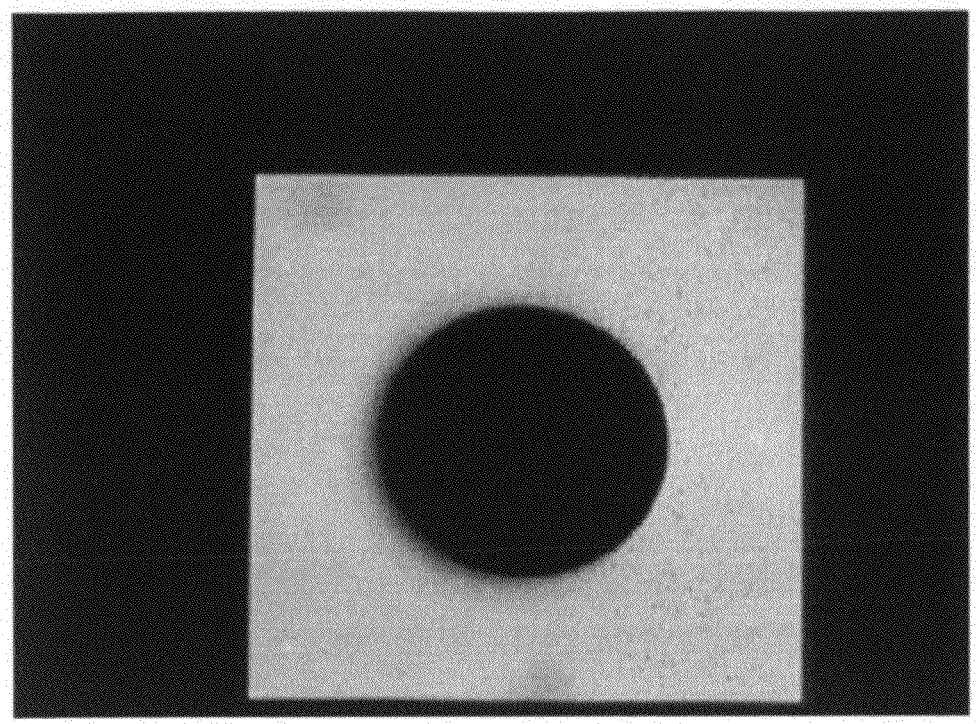
FIG. 9c is a luminous photo according to Comparative Example 14.

FIG. 9A is a green light emission photograph of the device of Comparative Example 2, FIG. 9B is a light emission photograph of the device of Example 13, and FIG. 9C is a light emission photograph of the device of Example 14.

As shown in the photographs of FIGS. 9A to 9C, when the compound of Comparative Example 1 (CBP) that is a compound of the emission layer of Comparative Example 2 is mixed with a dopant during a solution process to provide a thin film, it is easily recrystallized during thin film conditions due to a small molecular weight and a rigid structure.

The recrystallization of a host used for an emission layer does not provide uniform light emission, and shortens the lifetime of a device.

The devices of Examples 13 and 14 using the compounds of Examples 9 and 10 show very uniform light emission. Therefore, recrystallization is remarkably decreased.

The present invention is not limited to the embodiments illustrated with the drawings and table, but can be fabricated into various modifications and equivalent arrangements included within the spirit and scope of the appended claims by a person who is ordinarily skilled in this field. Therefore, the aforementioned embodiments should be understood to be exemplary but not limiting the present invention in any way.

What is claimed is:

1. An organic compound selected from compounds represented by the following Chemical Formulae 1, A, 4, and 5:

[Chemical Formula 1]

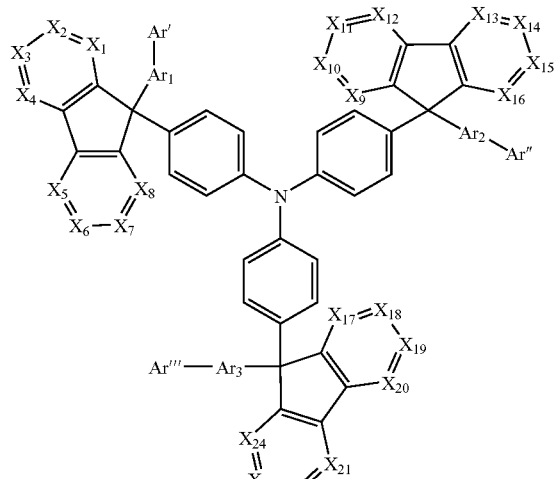

[Chemical Formula A]

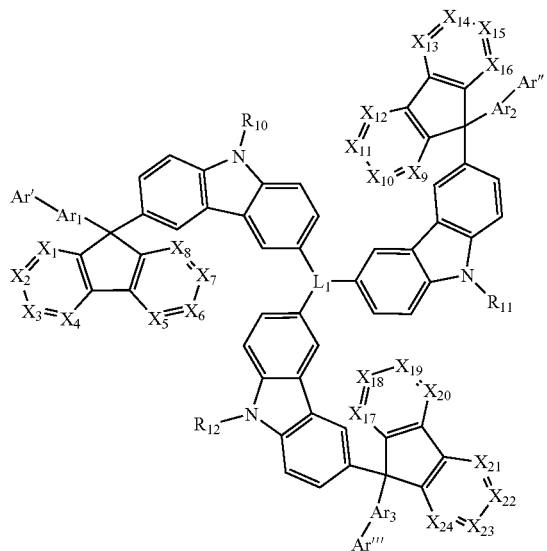

[Chemical Formula 4]

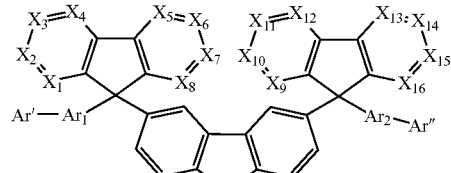

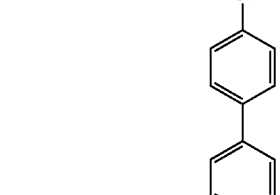

[Chemical Formula 5]

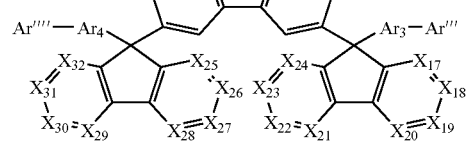

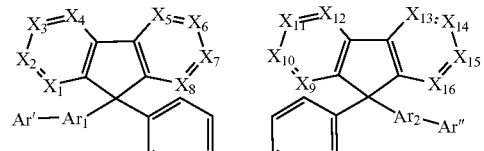

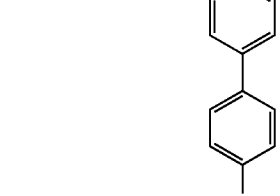

wherein, in the above Chemical Formulae 1, A, 4, and 5, $X_1$ to $X_{32}$ are the same or different, and are independently selected from CR' and N, $Ar_1$ to $Ar_4$ are the same or different, and are independently selected from a single bond, a substituted or unsubstituted C6 to C30 arylene group, and a substituted or unsubstituted C2 to C30 heteroarylene group, Ar' to Ar'''' are the same or different, and are independently selected from a substituted or unsubstituted C6 to C30 aryl group and a substituted or unsubstituted C2 to C30 heteroaryl group, and $L_1$ is a substituent represented by the following Chemical Formulae A-1 or A-2,

[Chemical Formula A-1]

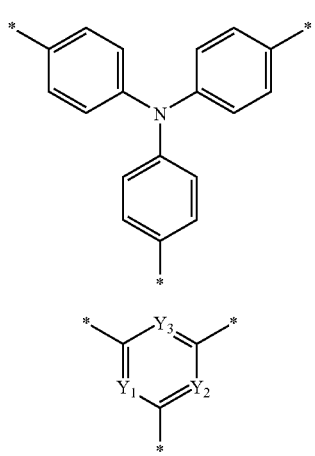

[Chemical Formula A-2]

wherein $Y_1$ to $Y_3$ are the same or different, and are independently selected from CR" and N, and R', R", and $R_{10}$ to $R_{12}$ are the same or different, and are independently selected from hydrogen, a halogen, a cyano group, a hydroxyl group, an amino group, a nitro group, a carboxyl group, a substituted or unsubstituted C1 to C20 alkyl group, a substituted or unsubstituted C2 to C20 alkenyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C2 to C20 heterooxy group, a substituted or unsubstituted C3 to C40 silyloxy group, a substituted or unsubstituted C1 to C20 acyl group, a substituted or unsubstituted C2 to C20 alkoxy carbonyl group, a substituted or unsubstituted C2 to C20 acyloxy group, a substituted or unsubstituted C2 to C20 acylamino group, a substituted or unsubstituted C2 to C20 alkoxy carbonyl amino group, a substituted or unsubstituted C7 to C20 acyloxy carbonyl amino group, a substituted or unsubstituted C1 to C20 sulfamoyl amino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocycloalkyl thiol group, a substituted or unsubstituted C1 to C20 ureide group, a substituted or unsubstituted C1 to C20 phosphoric acid amide group, and a substituted or unsubstituted C3 to C40 silyl group.

2. The organic compound of claim 1, wherein, $Ar_1$ to $Ar_4$ are the same or different, and are independently selected from a substituted or unsubstituted carbazolyl group, a substituted or unsubstituted arylamine group, a substituted or unsubstituted phenyl group, a substituted or unsubstituted tolyl group, a substituted or unsubstituted naphthyl group, a substituted or unsubstituted stilbene group, a substituted or unsubstituted fluorenyl group, a substituted or unsubstituted anthracenyl group, a substituted or unsubstituted terphenyl group, a substituted or unsubstituted pyrenyl group, a substituted or unsubstituted diphenyl anthracenyl group, a substituted or unsubstituted dinaphthylanthracenyl group, a substituted or unsubstituted pentacenyl group, a substituted or unsubstituted bromophenyl group, a substituted or unsubstituted hydroxyphenyl group, a substituted or unsubstituted thienyl group, a substituted or unsubstituted pyridyl group, a substituted or unsubstituted azobenzenyl group, and a substituted or unsubstituted ferrocenyl group, and Ar' to Ar"" are the same or different, and are independently selected from a substituted or unsubstituted carbazolyl group, a substituted or unsubstituted arylamine group, a substituted or unsubstituted phenyl group, a substituted or unsubstituted naphthyl group, a substituted or unsubstituted anthracenyl group, a substituted or unsubstituted fluorene group, a substituted or unsubstituted thiophene group, a substituted or unsubstituted pyrrole group, a substituted or unsubstituted pyridine group, a substituted or unsubstituted aryloxadiazole group, a substituted or unsubstituted triazole group, and a substituted or unsubstituted arylsilane group.

3. The organic compound of claim 1, wherein,

Ar' to Ar"" are the same or different, and are independently selected from the substituents represented by the following Chemical Formulae 6 to 35:

[Chemical Formula 6]

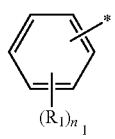

[Chemical Formula 7]

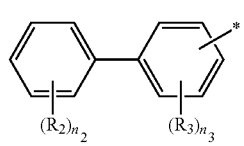

[Chemical Formula 8]

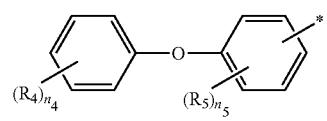

[Chemical Formula 9]

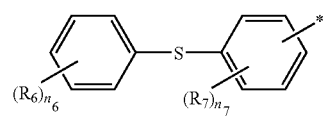

[Chemical Formula 10]

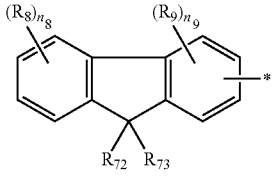

[Chemical Formula 11]

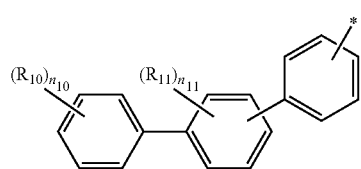

[Chemical Formula 12]

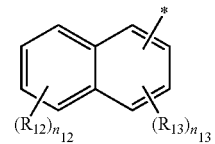

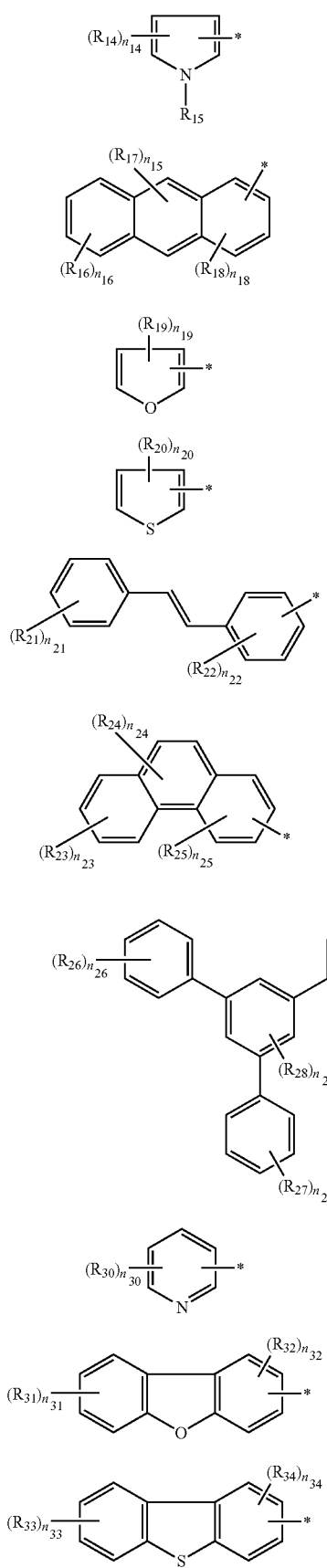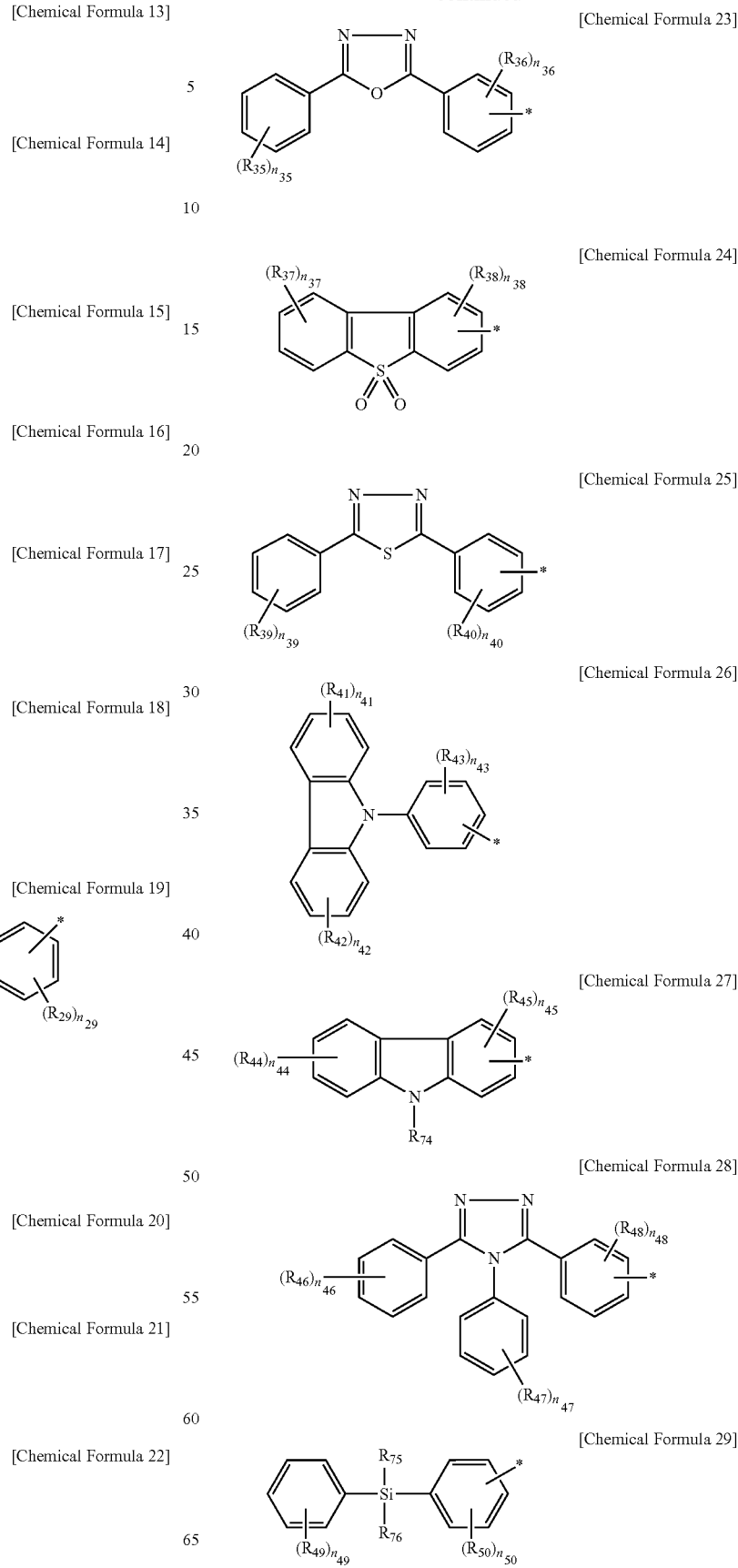

233
-continued

[Chemical Formula 30]

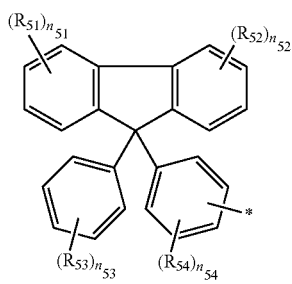

[Chemical Formula 31]

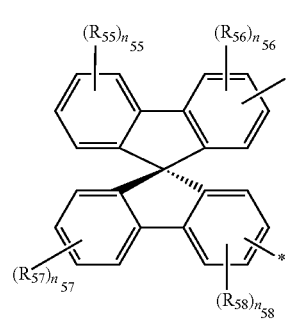

[Chemical Formula 32]

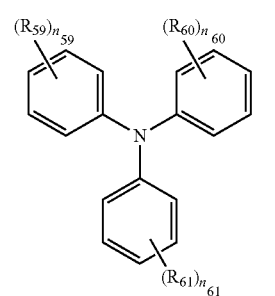

[Chemical Formula 33]

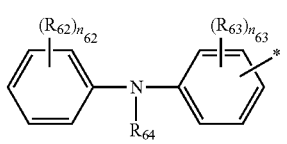

[Chemical Formula 34]

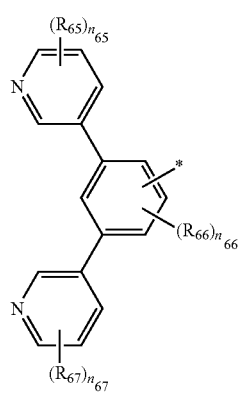

234
-continued

[Chemical Formula 35]

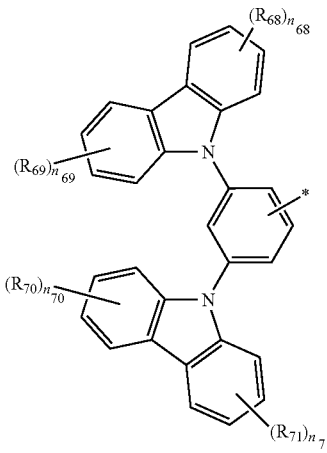

wherein, in the above Chemical Formulae 6 to 35, $R_1$ to $R_{76}$ are the same or different, and are independently selected from a halogen, a cyano group, a hydroxyl group, an amino group, a nitro group, a carboxyl group, a substituted or unsubstituted C1 to C20 alkyl group, a substituted or unsubstituted C2 to C20 alkenyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C2 to C20 heterooxy group, a substituted or unsubstituted C3 to C40 silyloxy group, a substituted or unsubstituted C1 to C20 acyl group, a substituted or unsubstituted C2 to C20 alkoxy carbonyl group, a substituted or unsubstituted C2 to C20 acyloxy group, a substituted or unsubstituted C2 to C20 acylamino group, a substituted or unsubstituted C2 to C20 alkoxy carbonyl amino group, a substituted or unsubstituted C7 to C20 acyloxy carbonyl amino group, a substituted or unsubstituted C1 to C20 sulfamoyl amino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocycloalkyl thiol group, a substituted or unsubstituted C1 to C20 ureide group, a substituted or unsubstituted C1 to C20 phosphoric acid amide group, and a substituted or unsubstituted C3 to C40 silyl group, $n_1, n_2, n_4, n_6, n_{10}, n_{21}, n_{26}, n_{27}, n_{35}, n_{39}, n_{46}, n_{47}, n_{49}, n_{53}, n_{59}, n_{61}$, and $n_{62}$ are integers ranging from 0 to 5, $n_3, n_5, n_7, n_8, n_{11}, n_{12}, n_{16}, n_{22}, n_{23}, n_{29}, n_{30}, n_{31}, n_{33}, n_{36}, n_{37}, n_{40}, n_{41}$ to $n_{44}, n_{48}, n_{50}$ to $n_{52}, n_{54}, n_{55}, n_{57}, n_{60}, n_{63}, n_{65}, n_{67}, n_{68}, n_{69}, n_{70}$, and $n_{71}$ are integers ranging from 0 to 4, $n_9, n_{13}, n_{14}, n_{18}, n_{19}, n_{20}, n_{25}, n_{28}, n_{32}, n_{34}, n_{38}, n_{45}, n_{56}, n_{58}$, and $n_{66}$ are integers ranging from 0 to 3, and $n_{15}$ and $n_{24}$ are integers ranging from 0 to 2.

4. The organic compound of claim 1, wherein,

Ar' to Ar'''' are the same or different, and are independently selected from the substituents represented by the following Chemical Formulae B-1 to B-9:

[Chemical Formula B-1]
[Chemical Formula B-2]
[Chemical Formula B-3]
[Chemical Formula B-4]
[Chemical Formula B-5]
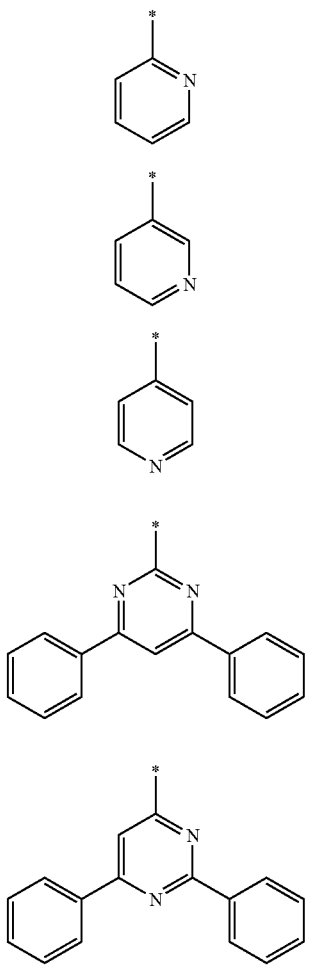
[Chemical Formula B-6]
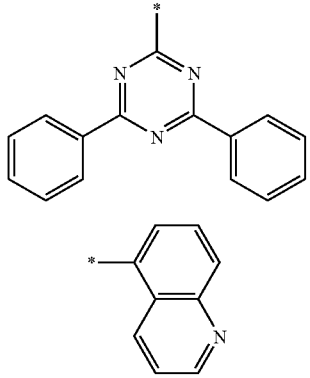
[Chemical Formula B-7]
[Chemical Formujla B-8]
[Chemical Formula B-9]
5. The organic compound of claim 1, wherein at least one of $X_4$, $X_5$, $X_{12}$, $X_{13}$, $X_{20}$, $X_{21}$, $X_{28}$, and $X_{29}$ is N.
6. An organic compound represented by the following Chemical Formulae 2 or 3:
[Chemical Formula 2]
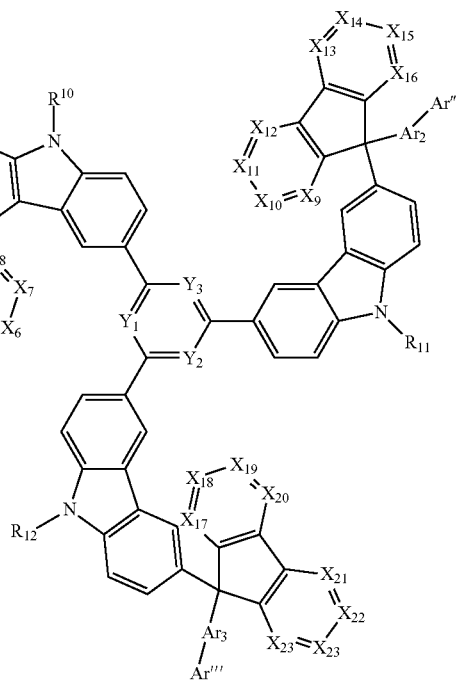

[Chemical Formula 3]

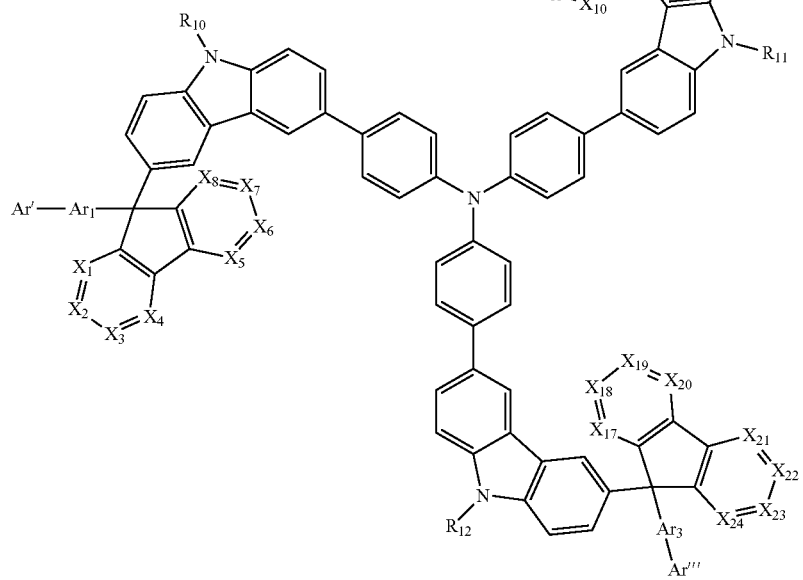

wherein, in the above Chemical Formulae 2 and 3,
$X_1$ to $X_{24}$ are the same or different, and are independently selected from CR' and N,
$Y_1$ to $Y_3$ are the same or different, and are independently selected from CR" and N,
$Ar_1$ to $Ar_3$ are the same or different, and are independently selected from a single bond, a substituted or unsubstituted C6 to C30 arylene group, and a substituted or unsubstituted C2 to C30 heteroarylene group,
Ar' to Ar''' are the same or different, and are independently selected from a substituted or unsubstituted C6 to C30 aryl group and a substituted or unsubstituted C2 to C30 heteroaryl group, and
R', R", and $R_{10}$ to $R_{12}$ are the same or different, and are independently selected from hydrogen, a halogen, a cyano group, a hydroxyl group, an amino group, a nitro group, a carboxyl group, a substituted or unsubstituted C1 to C20 alkyl group, a substituted or unsubstituted C2 to C20 alkenyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C2 to C20 heterooxy group, a substituted or unsubstituted C3 to C40 silyloxy group, a substituted or unsubstituted C1 to C20 acyl group, a substituted or unsubstituted C2 to C20 alkoxy carbonyl group, a substituted or unsubstituted C2 to C20 acyloxy group, a substituted or unsubstituted C2 to C20 acyl amino group, a substituted or unsubstituted C2 to C20 alkoxy carbonyl amino group, a substituted or unsubstituted C7 to C20 aryloxy carbonyl amino group, a substituted or unsubstituted C1 to C20 sulfamoyl amino group, a substituted or unsubstituted C1 to C20 sulfonyl group, a substituted or unsubstituted C1 to C20 alkylthio group, a substituted or unsubstituted C6 to C20 arylthio group, a substituted or unsubstituted C1 to C20 heterocycloalkyl thiol group, a substituted or unsubstituted C1 to C20 ureide group, a substituted or unsubstituted C1 to C20 phosphoric acid amide group, and a substituted or unsubstituted C3 to C40 silyl group.

7. The organic compound of claim 6, wherein,
$Ar_1$ to $Ar_3$ are the same or different, and are independently selected from a single bond, a substituted or unsubstituted carbazolyl group, a substituted or unsubstituted arylamine group, a substituted or unsubstituted phenyl group, a substituted or unsubstituted tolyl group, a substituted or unsubstituted naphthyl group, a substituted or unsubstituted stilbene group, a substituted or unsubstituted fluorene group, a substituted or unsubstituted anthracenyl group, a substituted or unsubstituted terphenyl group, a substituted or unsubstituted pyrenyl group, a substituted or unsubstituted diphenyl anthracenyl group, a substituted or unsubstituted dinaphthyl anthracenyl group, a substituted or unsubstituted pentacenyl group, a substituted or unsubstituted bromophenyl group, a substituted or unsubstituted hydroxyphenyl group, a substituted or unsubstituted thienyl group, a substituted or unsubstituted pyridyl group, a substituted or unsubstituted azobenzenyl group, and a substituted or unsubstituted ferrocenyl group, and
Ar' to Ar''' are the same or different, and are independently selected from a substituted or unsubstituted carbazolyl group, a substituted or unsubstituted arylamine group, a substituted or unsubstituted phenyl group, a substituted or unsubstituted naphthyl group, a substituted or unsubstituted anthracenyl group, a substituted or unsubstituted fluorene group, a substituted or unsubstituted thiophene group, a substituted or unsubstituted pyrrole group, a substituted or unsubstituted pyridine group, a substituted or unsubstituted aryloxadiazole group, a substituted or unsubstituted triazole group, and a substituted or unsubstituted arylsilane group.

8. The organic compound of claim 6, wherein,

Ar' to Ar''' are the same or different, and are independently selected from the substituents represented by the following Chemical Formulae 6 to 35:

[Chemical Formula 6]
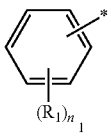

[Chemical Formula 7]
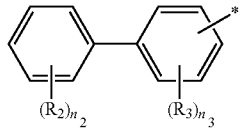

[Chemical Formula 8]
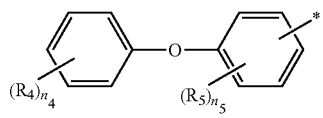

[Chemical Formula 9]
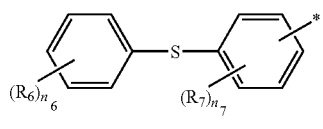

[Chemical Formula 10]
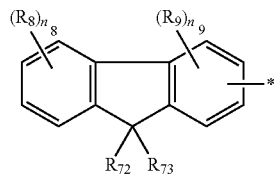

[Chemical Formula 11]
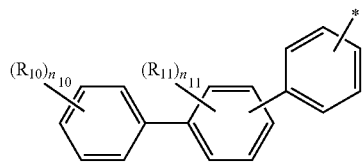

[Chemical Formula 12]
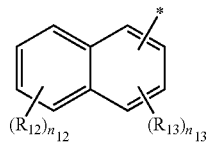

[Chemical Formula 13]
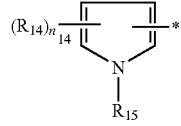

-continued

[Chemical Formula 14]
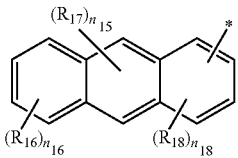

[Chemical Formula 15]
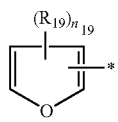

[Chemical Formula 16]
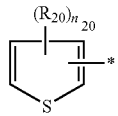

[Chemical Formula 17]
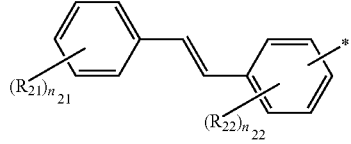

[Chemical Formula 18]
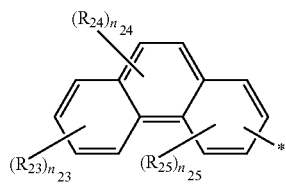

[Chemical Formula 19]
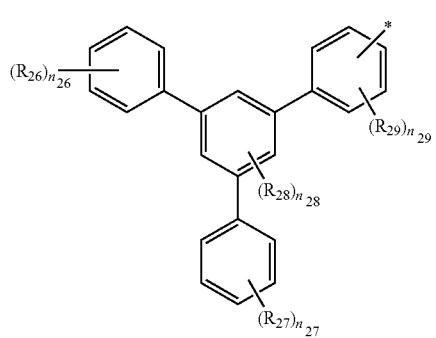

[Chemical Formula 20]
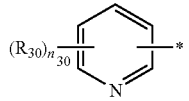

[Chemical Formula 21]
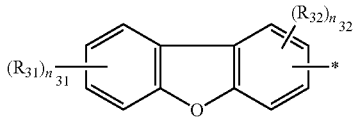

[Chemical Formula 22]
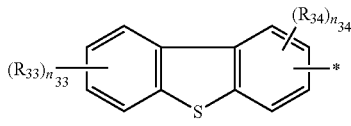

[Chemical Formula 23]
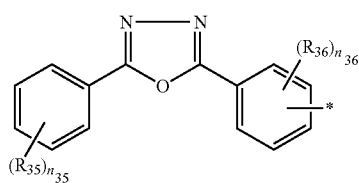
[Chemical Formula 24]
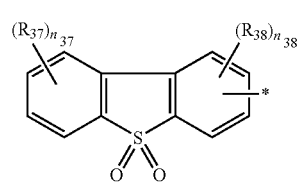
[Chemical Formula 25]
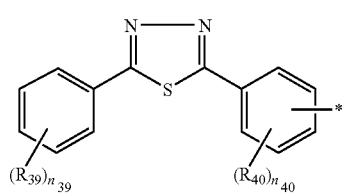
[Chemical Formula 26]
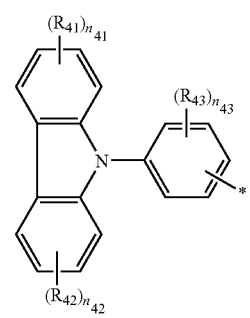
[Chemical Formula 27]
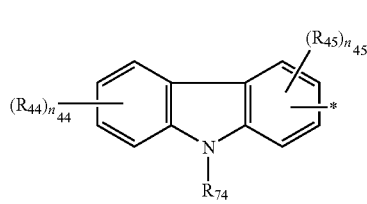
[Chemical Formula 28]
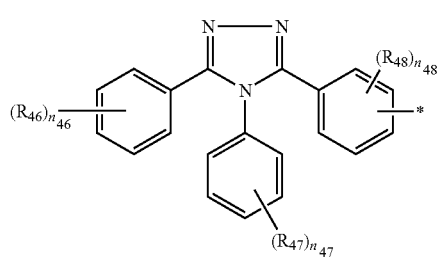
[Chemical Formula 29]
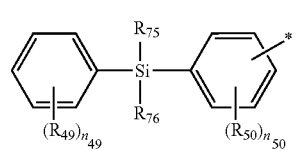
[Chemical Formula 30]
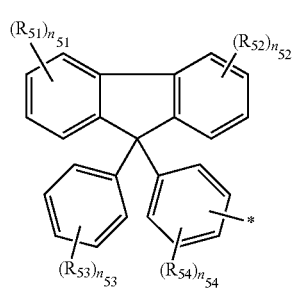
[Chemical Formula 31]
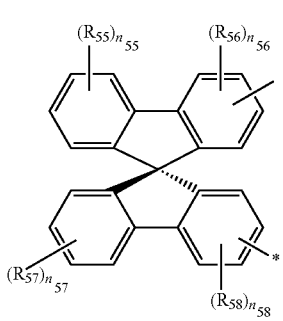
[Chemical Formula 32]
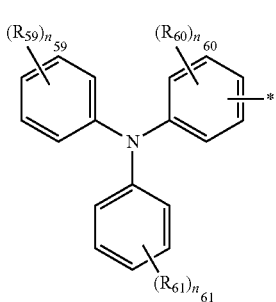
[Chemical Formula 33]
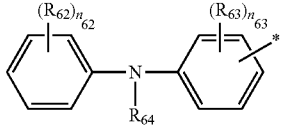
[Chemical Formula 34]
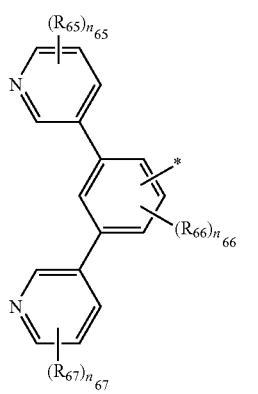

-continued

[Chemical Formula 35]

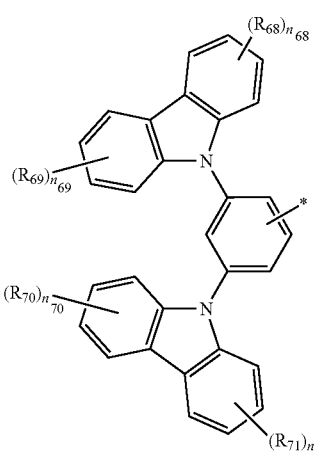

wherein, in the above Chemical Formulae 6 to 35, $R_1$ to $R_{76}$ are independently selected from hydrogen, a halogen, a cyano group, a hydroxyl group, an amino group, a nitro group, a carboxyl group, a substituted or unsubstituted C1 to C20 alkyl group, a substituted or unsubstituted C2 to C20 alkenyl, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C2 to C20 heterooxy group, a substituted or unsubstituted C3 to C40 silyloxy group, a substituted or unsubstituted C1 to C20 acyl group, a substituted or unsubstituted C2 to C20 alkoxy carbonyl group, a substituted or unsubstituted C2 to C20 acyloxy group, a substituted or unsubstituted C2 to C20 acylamino group, a substituted or unsubstituted C2 to C20 alkoxy carbonyl amino group, a substituted or unsubstituted C7 to C20 acyloxy carbonyl amino group, a substituted or unsubstituted C1 to C20 sulfamoyl amino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocycloalkyl thiol group, a substituted or unsubstituted C1 to C20 ureide group, a substituted or unsubstituted C1 to C20 phosphoric acid amide group, and a substituted or unsubstituted C3 to C40 silyl group, $n_1$, $n_2$, $n_4$, $n_6$, $n_{10}$, $n_{21}$, $n_{26}$, $n_{27}$, $n_{35}$, $n_{39}$, $n_{46}$, $n_{47}$, $n_{49}$, $n_{53}$, $n_{59}$, $n_{61}$, and $n_{62}$ are integers ranging from 0 to 5, $n_3$, $n_5$, $n_7$, $n_8$, $n_{11}$, $n_{12}$, $n_{16}$, $n_{22}$, $n_{23}$, $n_{29}$, $n_{30}$, $n_{31}$, $n_{33}$, $n_{36}$, $n_{37}$, $n_{40}$, $n_{41}$ to $n_{44}$, $n_{48}$, $n_{50}$ to $n_{52}$, $n_{54}$, $n_{55}$, $n_{57}$, $n_{60}$, $n_{63}$, $n_{65}$, $n_{67}$, $n_{68}$, $n_{69}$, $n_{70}$, and $n_{71}$ are integers ranging from 0 to 4, $n_9$, $n_{13}$, $n_{14}$, $n_{18}$, $n_{19}$, $n_{20}$, $n_{25}$, $n_{28}$, $n_{32}$, $n_{34}$, $n_{38}$, $n_{45}$, $n_{56}$, $n_{58}$, and $n_{66}$ are integers ranging from 0 to 3, and $n_{15}$ and $n_{24}$ are integers ranging from 0 to 2.

9. The organic compound of claim 6, wherein,

Ar' to Ar''' are the same or different, and are independently selected from the substituents represented by the following Chemical Formulae B-1 to B-9:

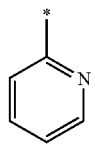

[Chemical Formula B-1]

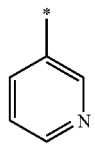

[Chemical Formula B-2]

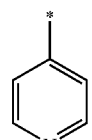

[Chemical Formula B-3]

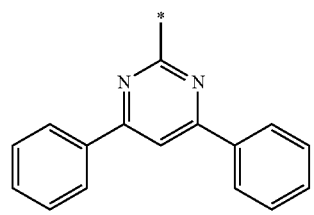

[Chemical Formula B-4]

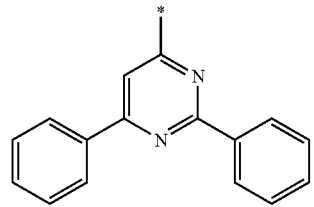

[Chemical Formula B-5]

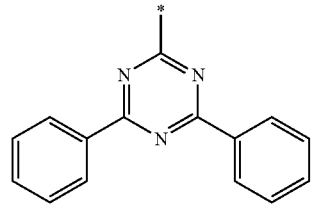

[Chemical Formula B-6]

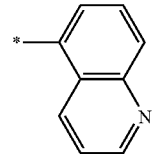

[Chemical Formula B-7]

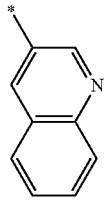

[Chemical Formujla B-8]

-continued

[Chemical Formula B-9]

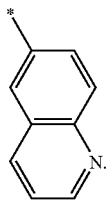

10. The organic compound of claim 6, wherein at least one of $X_4$, $X_5$, $X_{12}$, $X_{13}$, $X_{20}$, $X_{21}$, $X_{28}$, and $X_{29}$ is N.

11. An organic photoelectric device comprising:
an organic layer disposed between a pair of electrodes, wherein the organic layer includes the organic compound of claim 1.

12. An organic photoelectric device of claim 11, wherein the organic layer is an emission layer.

13. An organic photoelectric device of claim 11, wherein the organic layer is selected from a hole injection layer (HIL), a hole transport layer (HTL), a hole blocking film, and a combination thereof.

14. An organic photoelectric device of claim 11, wherein the organic layer is selected from an electron injection layer (EIL), an electron transport layer (ETL), an electron blocking film, and a combination thereof.

* * * * *